United States Patent [19]
Sugai et al.

[11] Patent Number: 6,099,537
[45] Date of Patent: Aug. 8, 2000

[54] MEDICAL TREATMENT INSTRUMENT

[75] Inventors: Toshiya Sugai; Hiroyuki Nagamizu, both of Hachioji; Minoru Tsuruta, Hino; Yoshihito Shimizu; Toshihiko Suzuta, both of Hachioji; Norikiyo Shibata, Yamato; Shinichi Nishigaki, Tokyo; Naoki Uchiyama, Fuchu; Yoshinao Oaki, Hachioji, all of Japan

[73] Assignee: Olympus Optical Co., Ltd., Tokyo, Japan

[21] Appl. No.: 08/805,556

[22] Filed: Feb. 25, 1997

[30] Foreign Application Priority Data

| Feb. 26, 1996 | [JP] | Japan | ................................... 8-037873 |
| Feb. 26, 1996 | [JP] | Japan | ................................... 8-037874 |
| Feb. 26, 1996 | [JP] | Japan | ................................... 8-037875 |
| Feb. 26, 1996 | [JP] | Japan | ................................... 8-038146 |
| Feb. 26, 1996 | [JP] | Japan | ................................... 8-038147 |
| Mar. 12, 1996 | [JP] | Japan | ................................... 8-054798 |
| Mar. 28, 1996 | [JP] | Japan | ................................... 8-074187 |
| May 14, 1996 | [JP] | Japan | ................................... 8-119073 |

[51] Int. Cl.[7] ................................................. A61B 17/10
[52] U.S. Cl. ........................... 606/143; 606/167; 606/205
[58] Field of Search ................................. 606/143, 167, 606/170, 205, 206, 208, 139

[56] References Cited

U.S. PATENT DOCUMENTS

| 5,205,459 | 4/1993 | Brinkerhoff et al. | ................... 227/179 |
| 5,289,963 | 3/1994 | McGarry et al. | ....................... 227/175 |
| 5,307,976 | 5/1994 | Olson et al. | ............................. 227/178 |
| 5,322,055 | 6/1994 | Davidson et al. | .......................... 601/2 |
| 5,381,943 | 1/1995 | Allen et al. | ............................... 227/177 |
| 5,382,255 | 1/1995 | Castro et al. | ............................ 606/143 |
| 5,403,327 | 4/1995 | Thornton et al. | ........................ 606/143 |

FOREIGN PATENT DOCUMENTS

| 0 622 049 A1 | 2/1994 | European Pat. Off. . |
| 7330291 | 12/1973 | Germany . |
| 60-24329 | 7/1985 | Japan . |
| 5-18512 | 3/1993 | Japan . |
| 8-38485 | 2/1996 | Japan . |

*Primary Examiner*—Michael Buiz
*Assistant Examiner*—Daphna Shai
*Attorney, Agent, or Firm*—Morgan, Lewis & Bockius LLP

[57] ABSTRACT

A medical treatment instrument is provided with a treatment section for treating issue, an insertion section which has at one end the treatment section, and an operating section which is provided at the other end of the insertion section, operates the treatment section, and has a fixed portion and a movable portion. The treatment section is actuated by pivoting the movable portion with respect to the fixed portion. The medical treatment instrument is further provided with an actuating main body and a cover. The cover is displaceable between a first position in which the medical treatment instrument is used and a second position in which the inside of the operating section is uncovered.

69 Claims, 90 Drawing Sheets

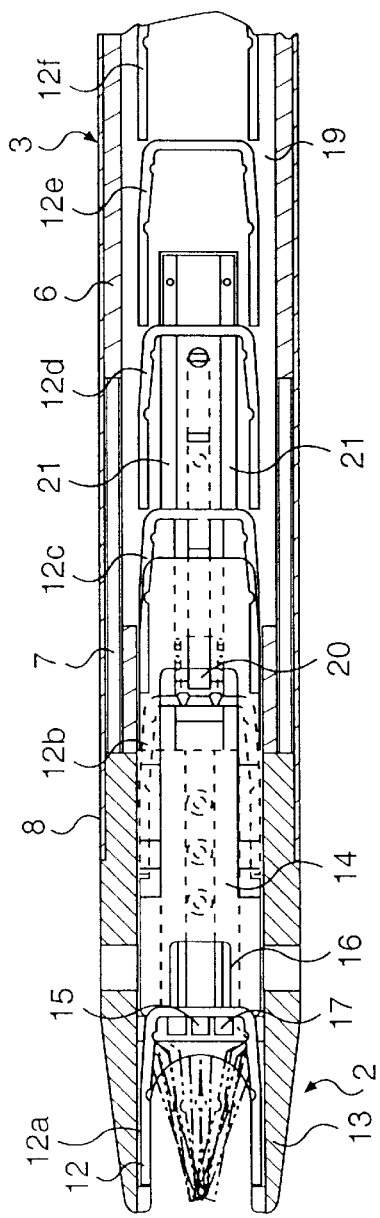
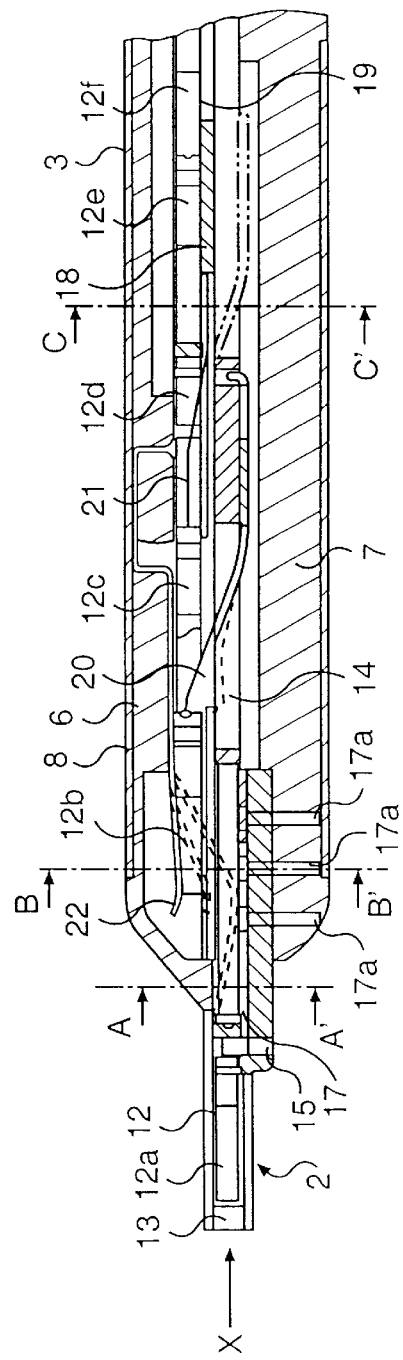
FIG. 2A
FIG. 2B

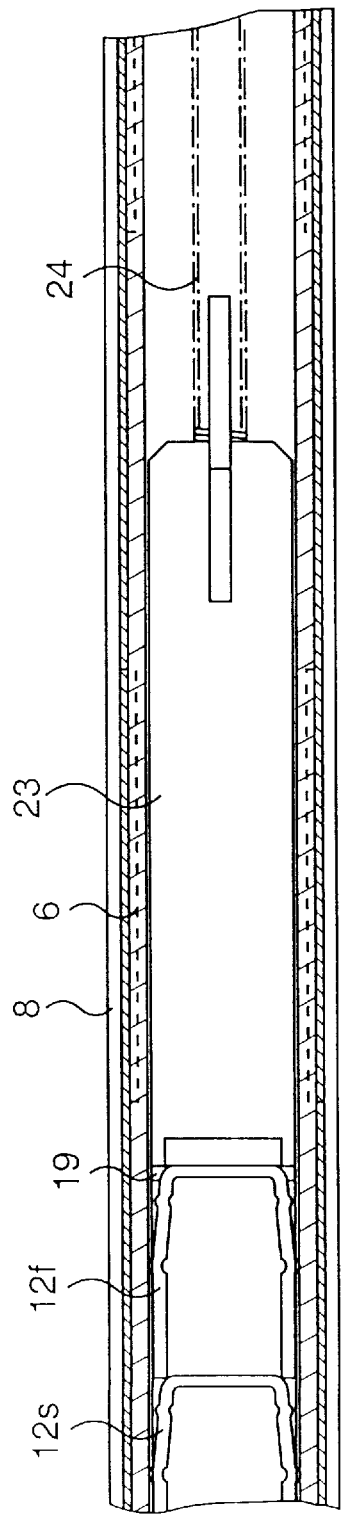
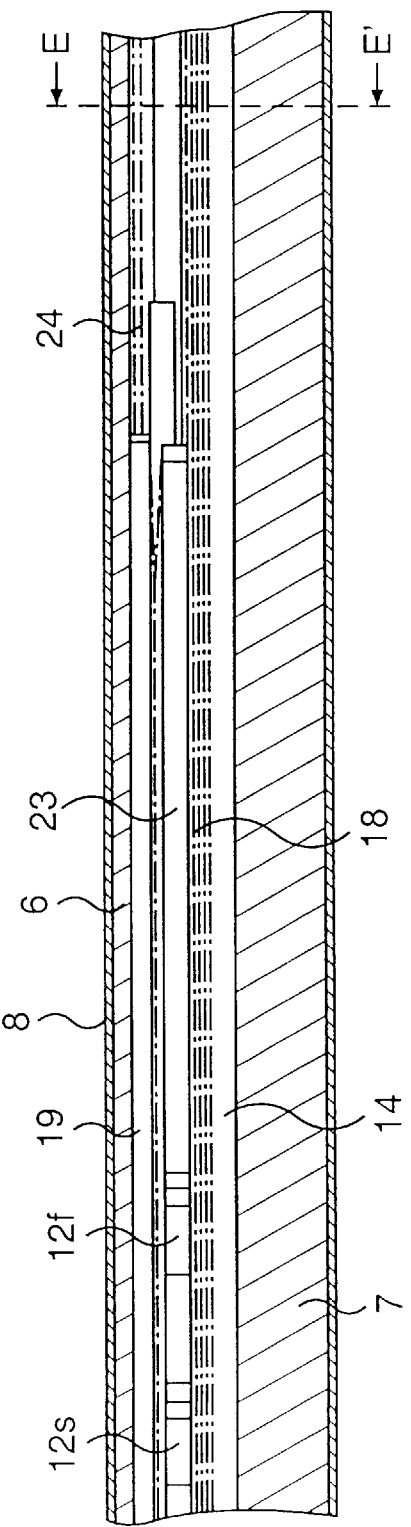
FIG. 7A
FIG. 7B

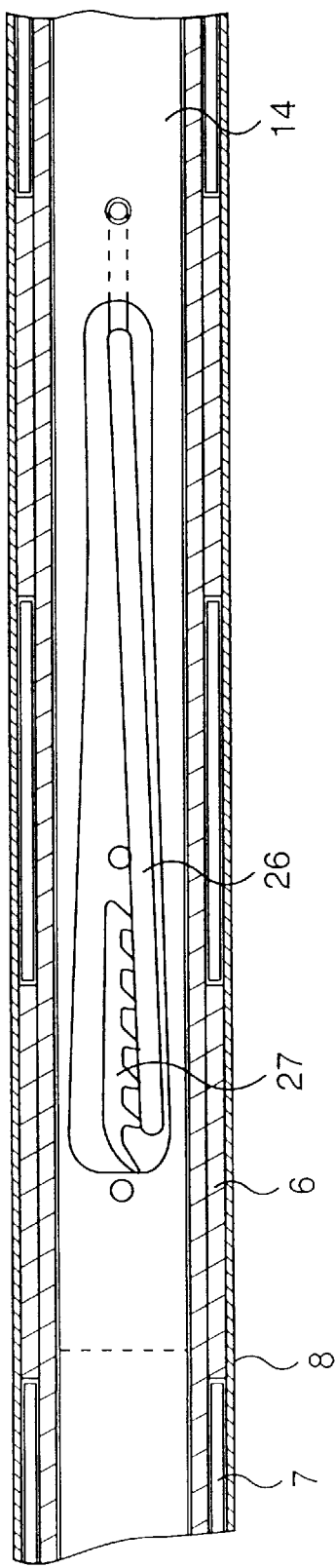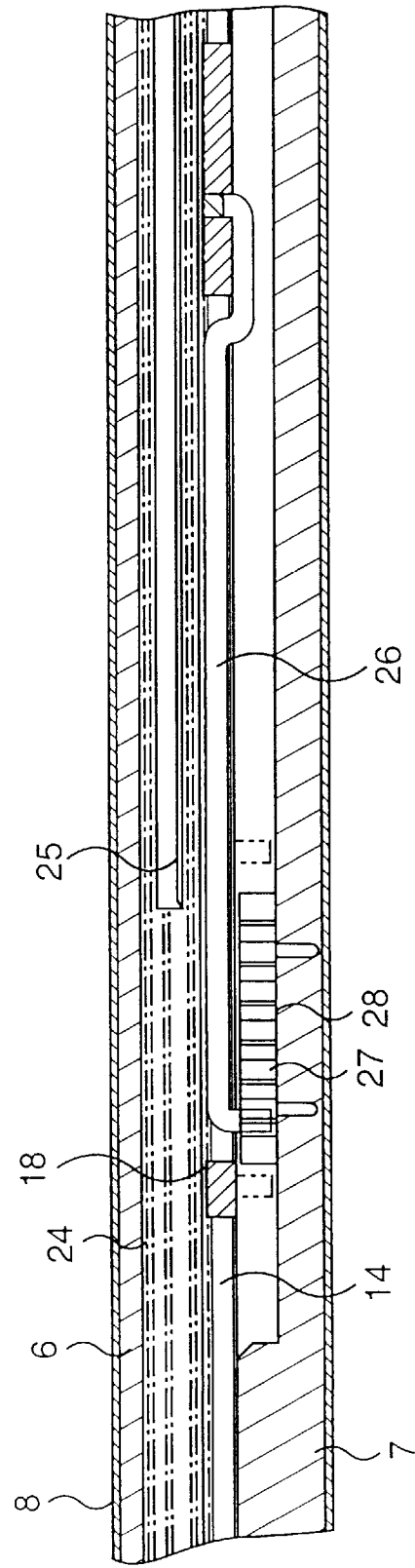
FIG. 8A
FIG. 8B

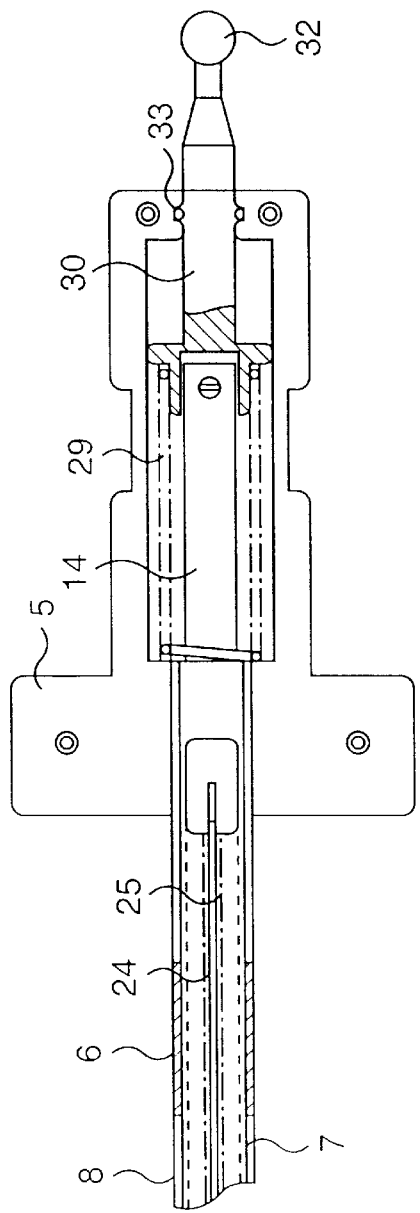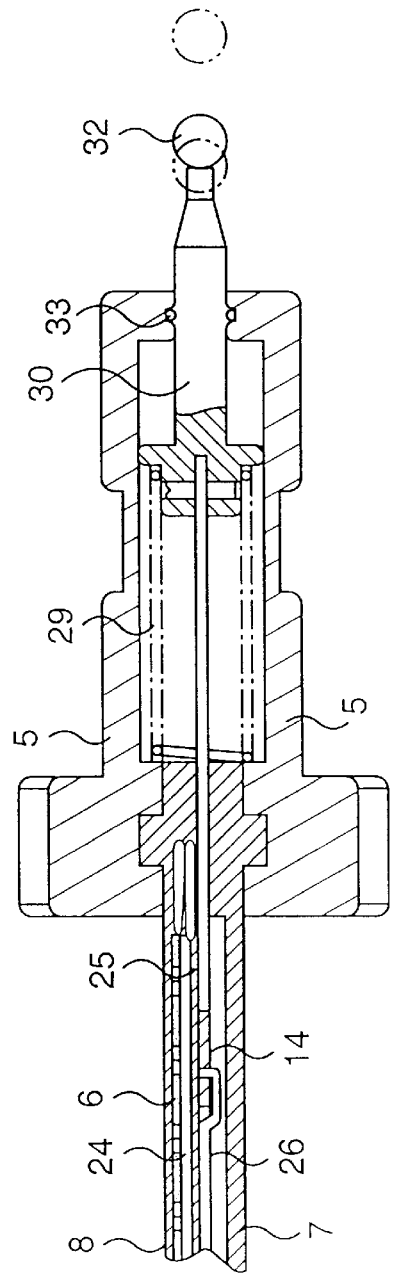

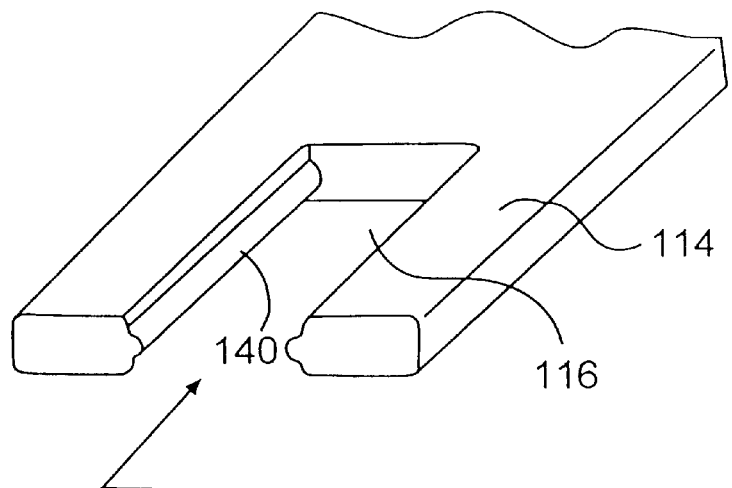
FIG. 34
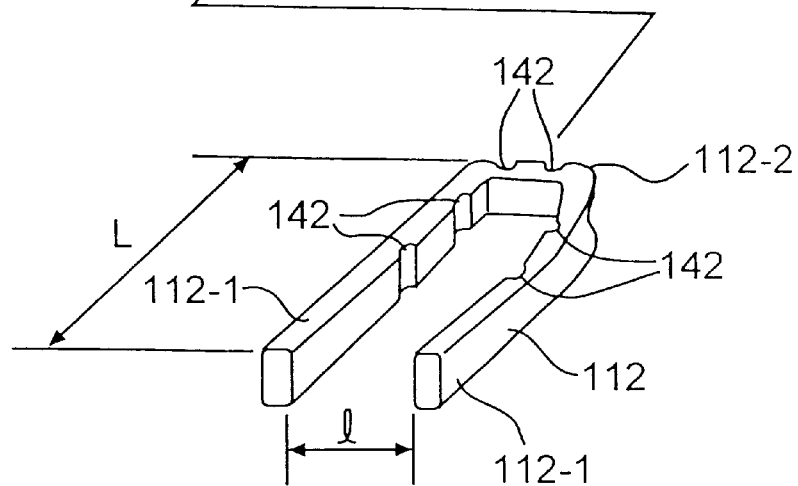
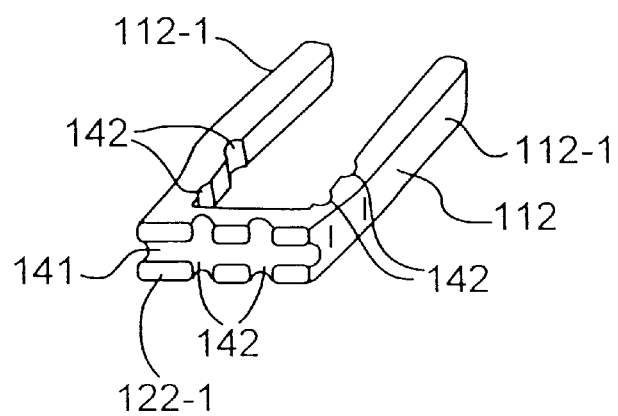
FIG. 35

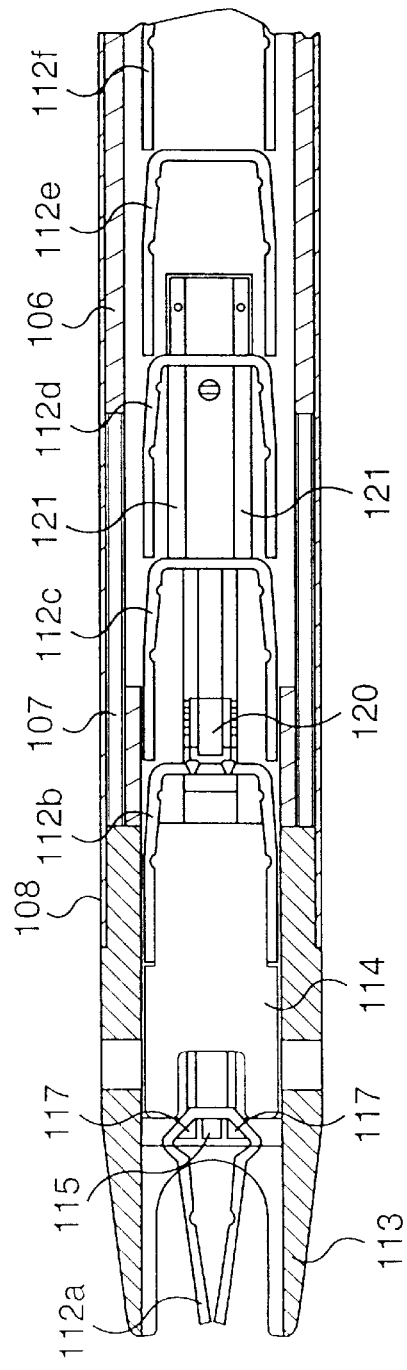
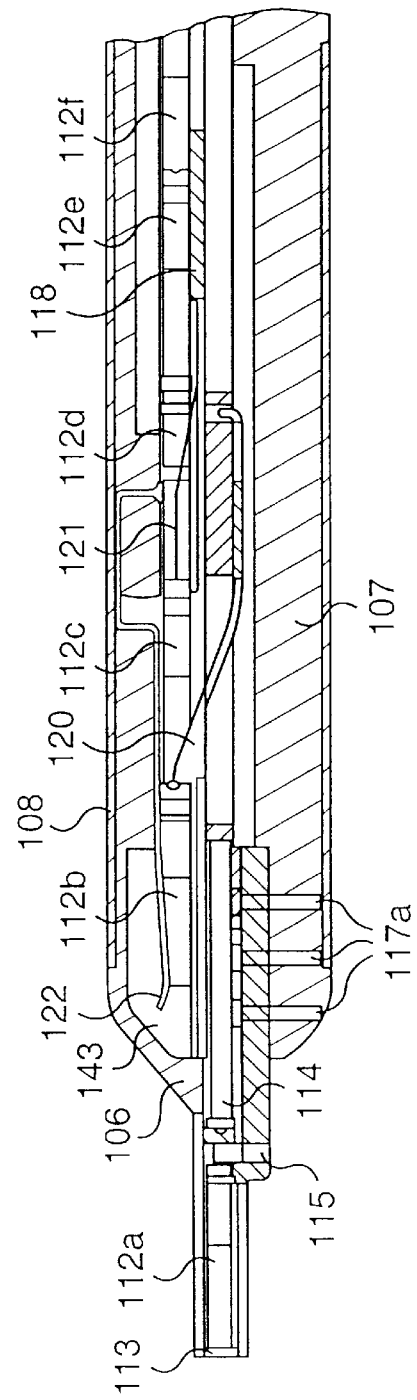
FIG. 38A
FIG. 38B

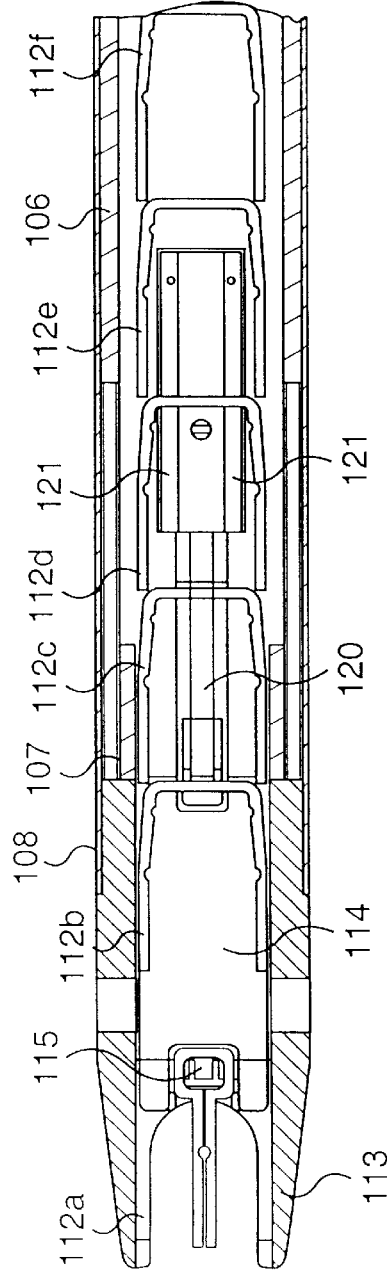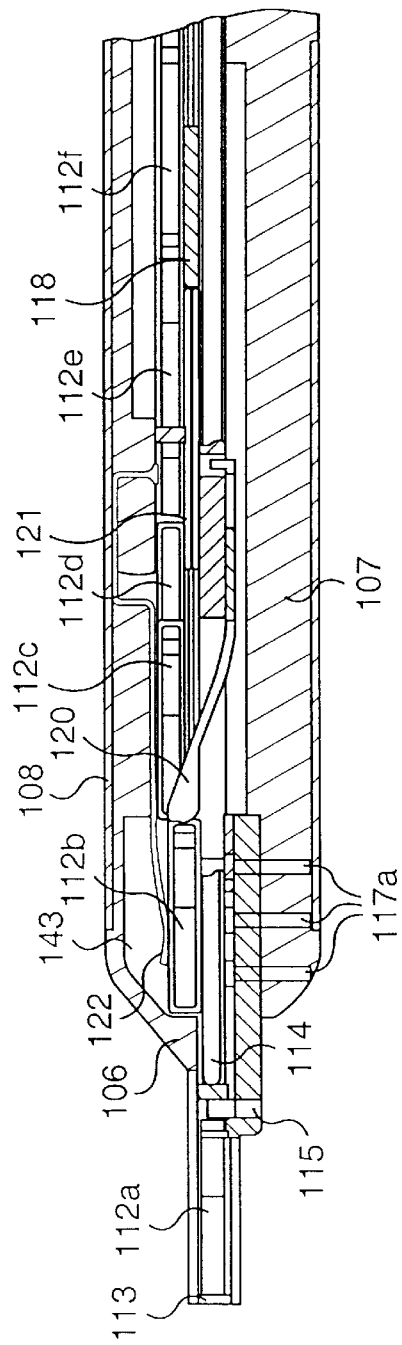
FIG. 40A
FIG. 40B

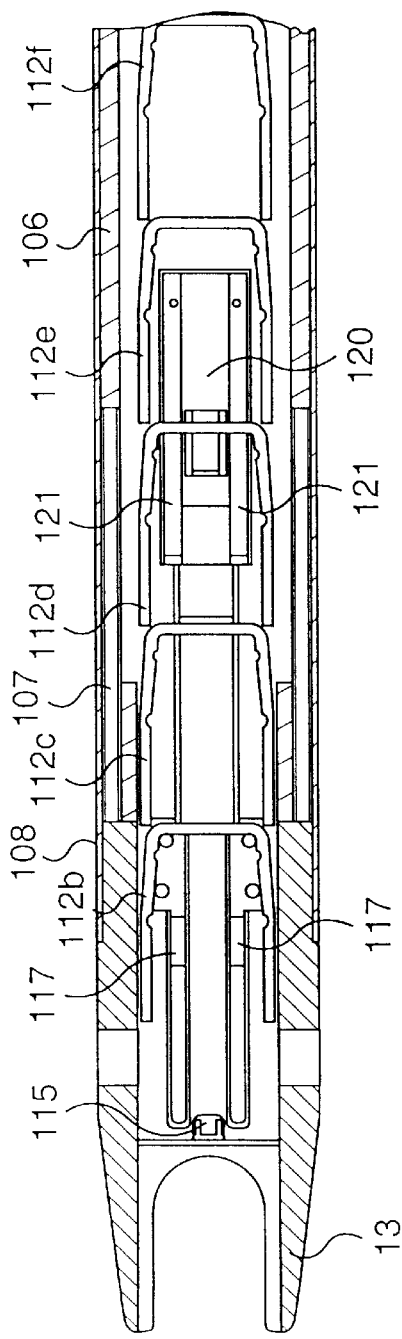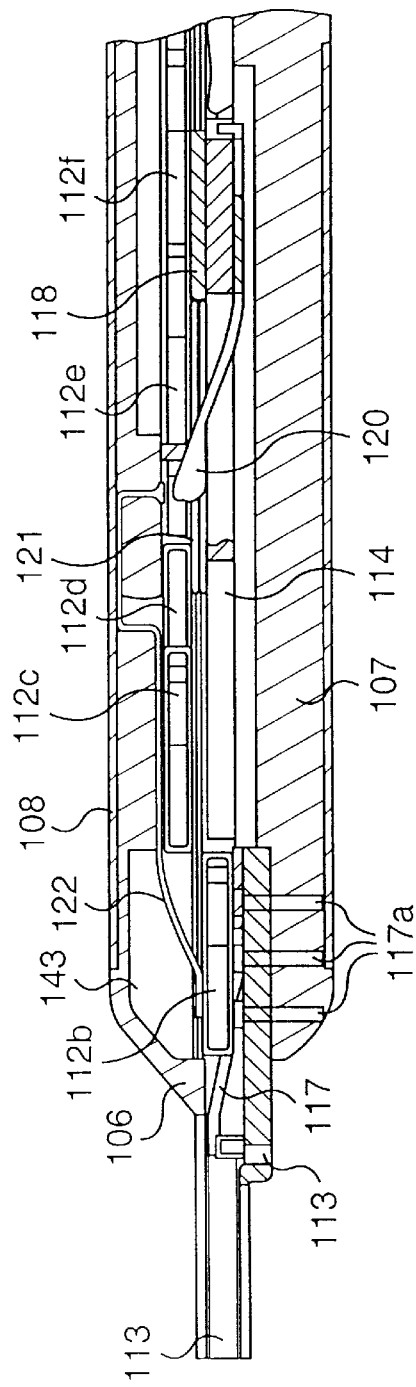
FIG. 41A
FIG. 41B

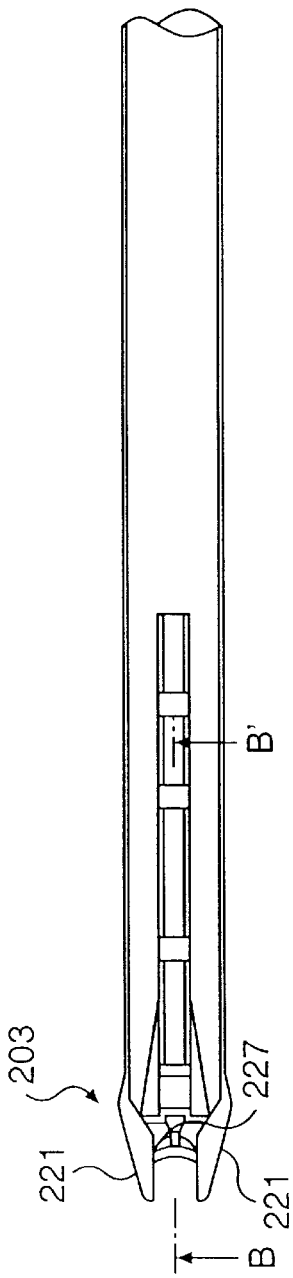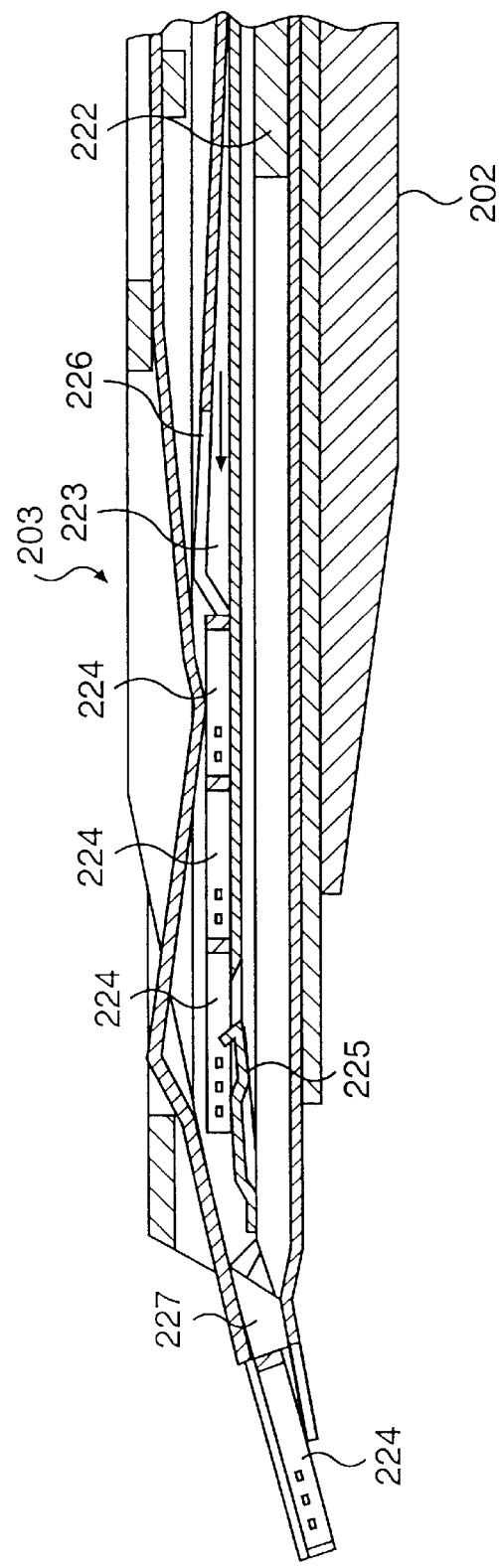

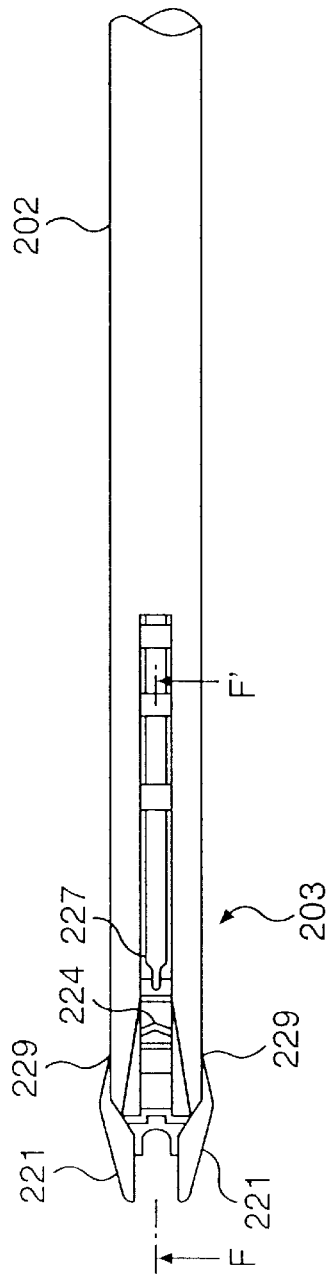
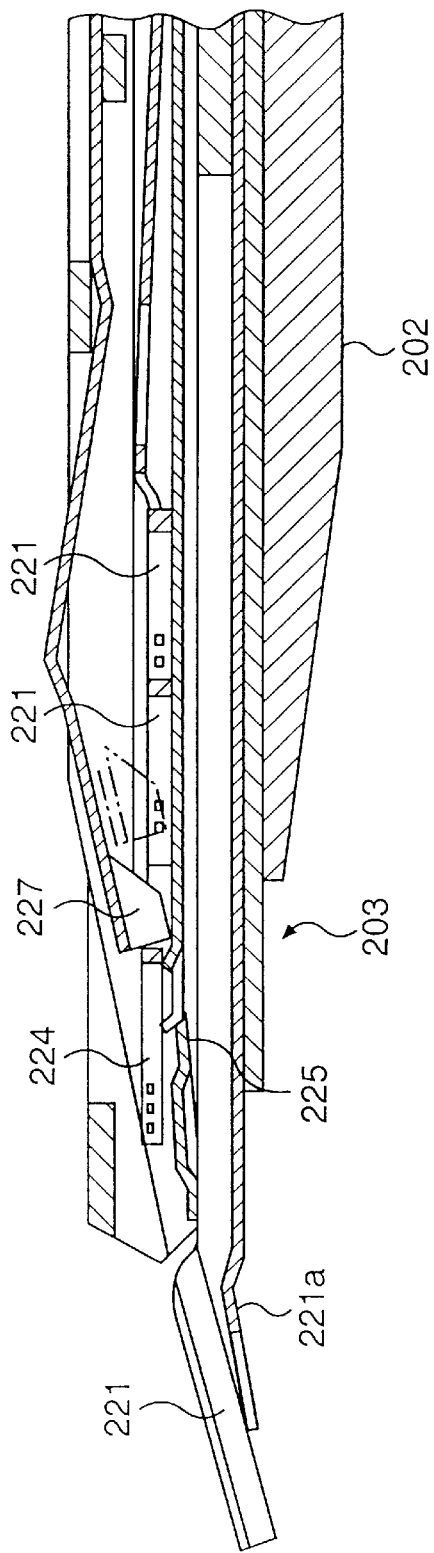

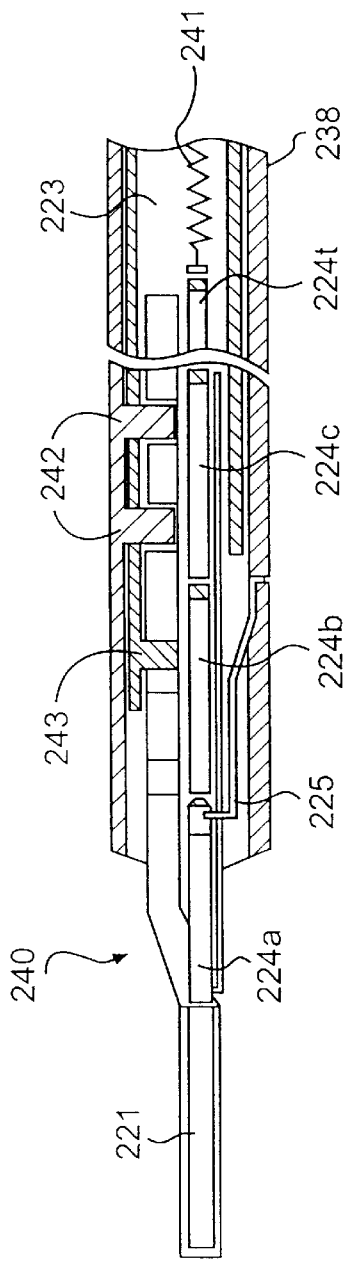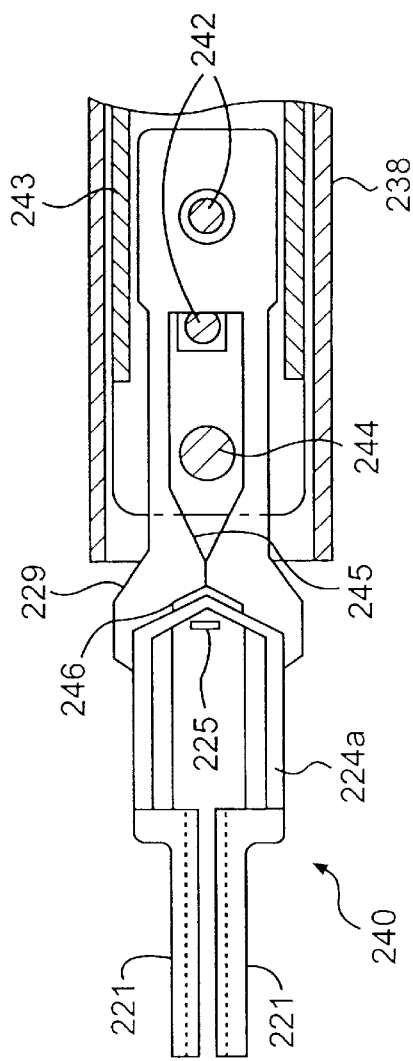
FIG. 70A
FIG. 70B

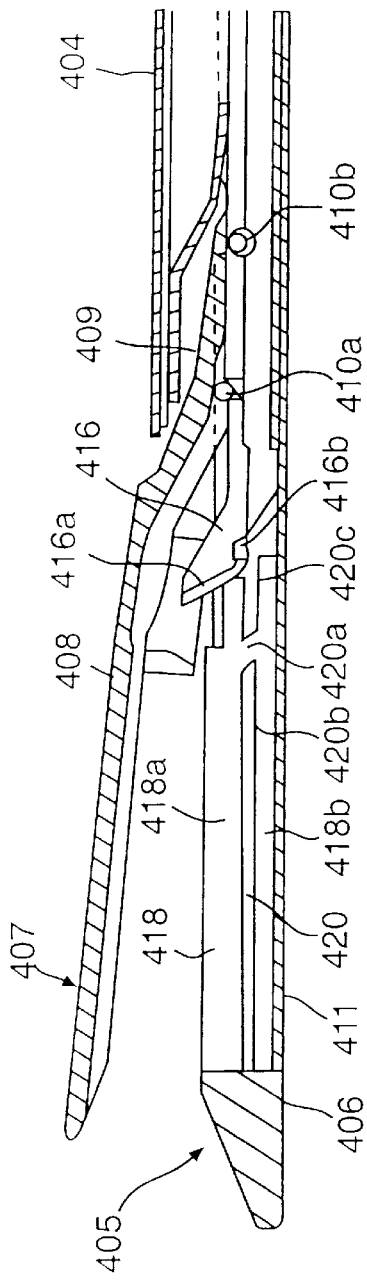
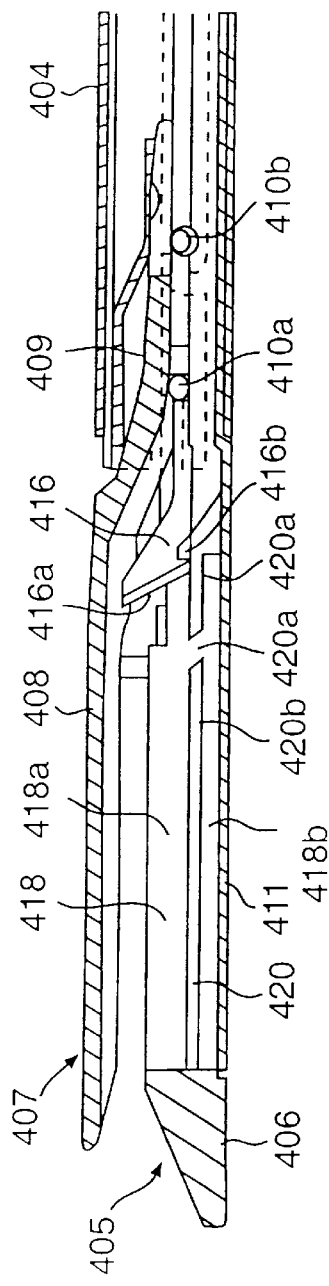
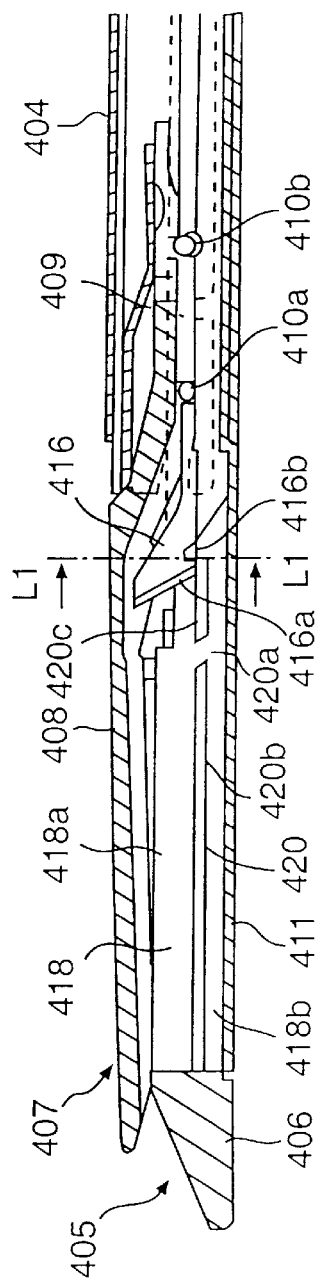
FIG. 99a
FIG. 99b
FIG. 99c

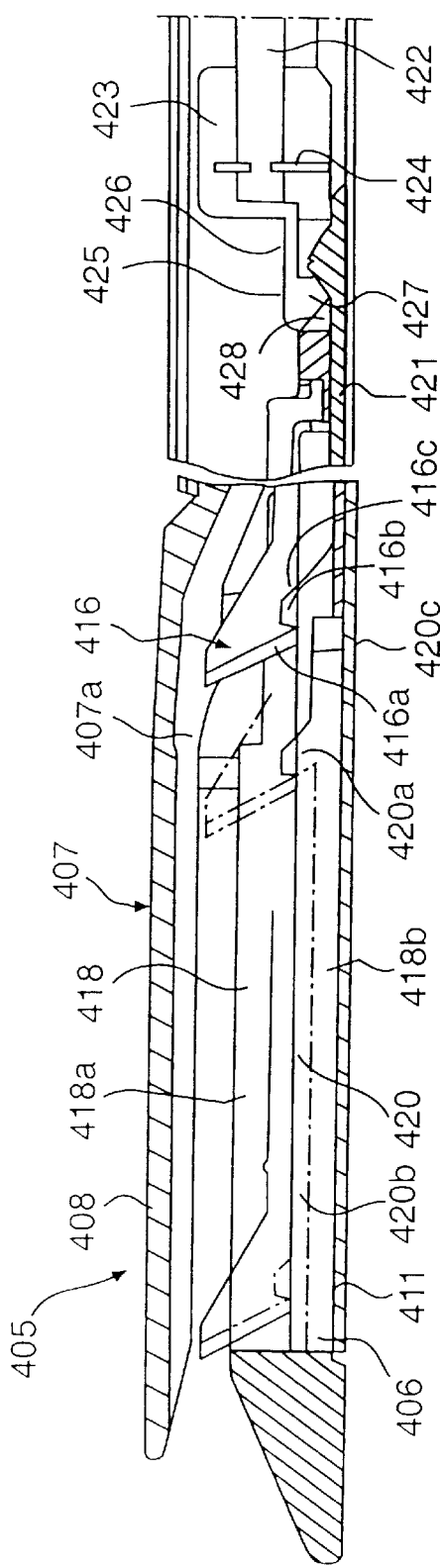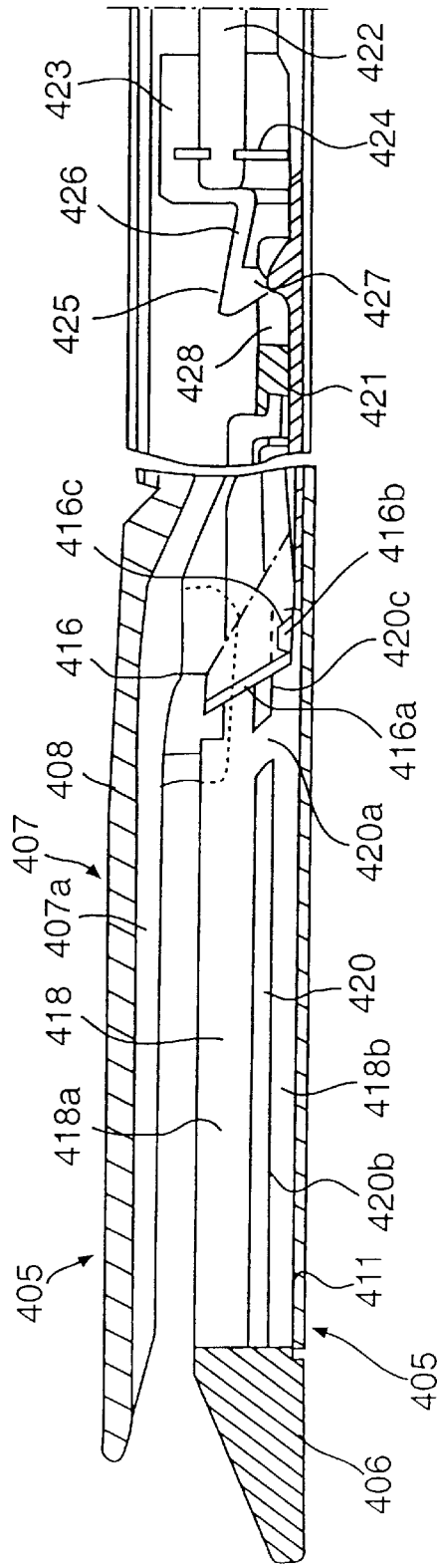

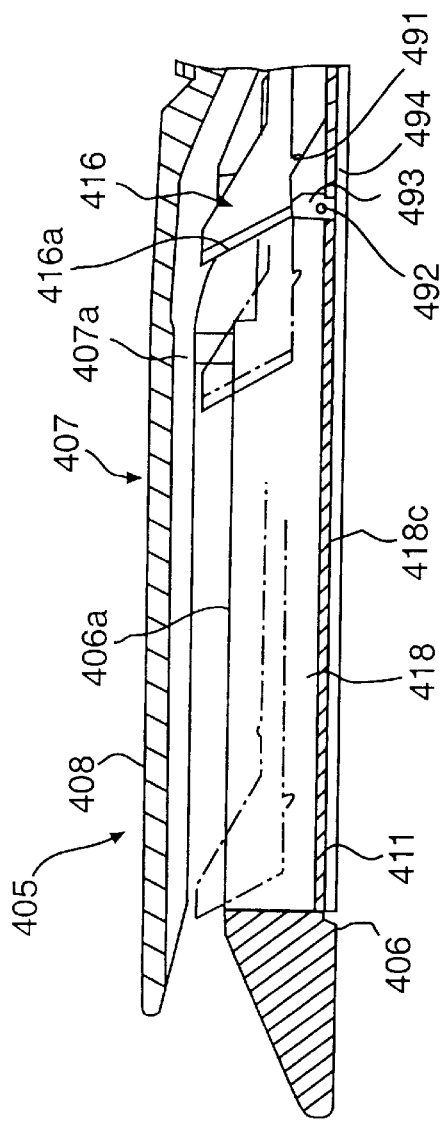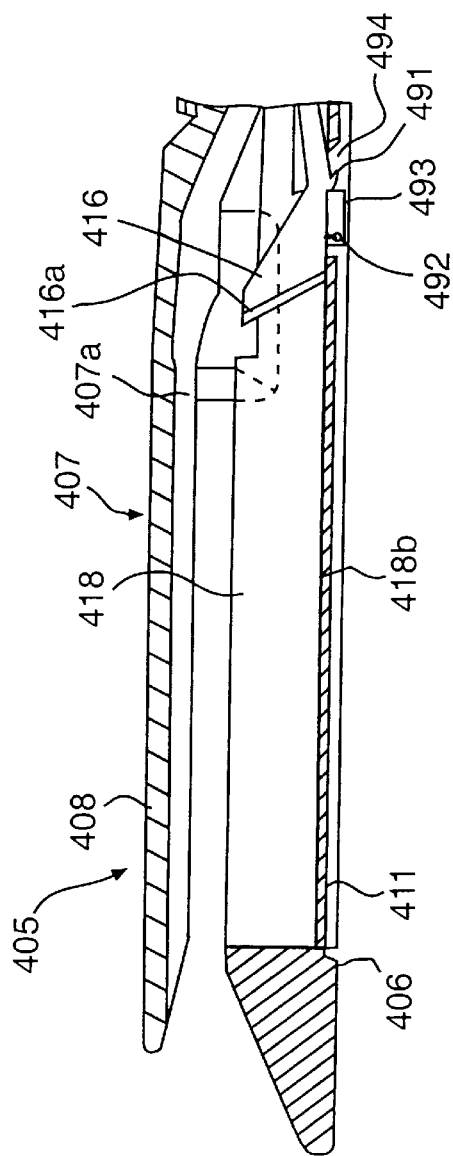

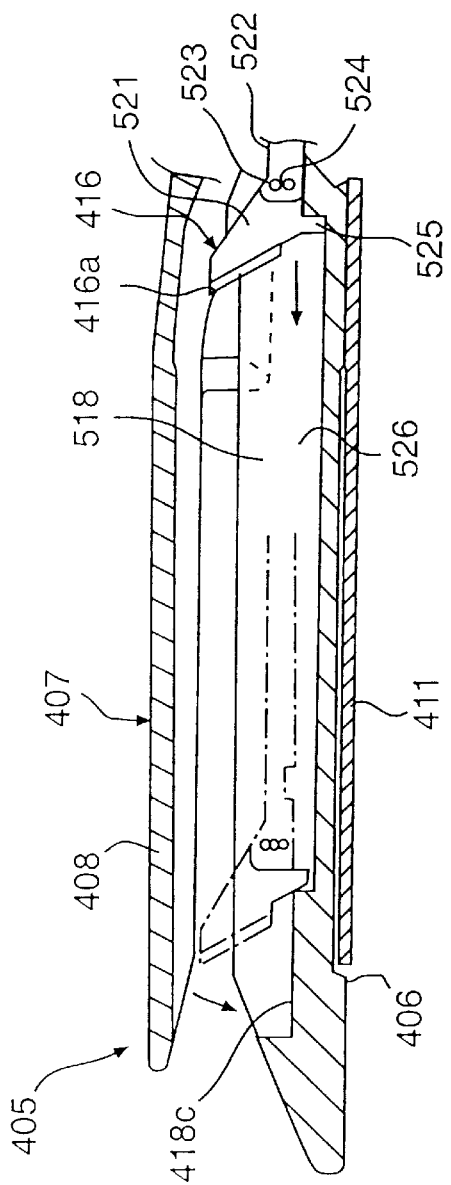
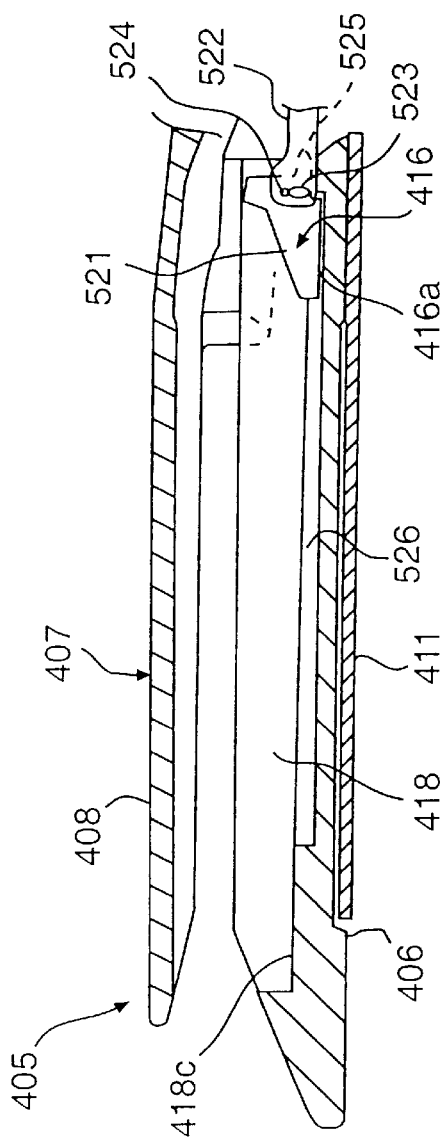
FIG. 109a
FIG. 109b

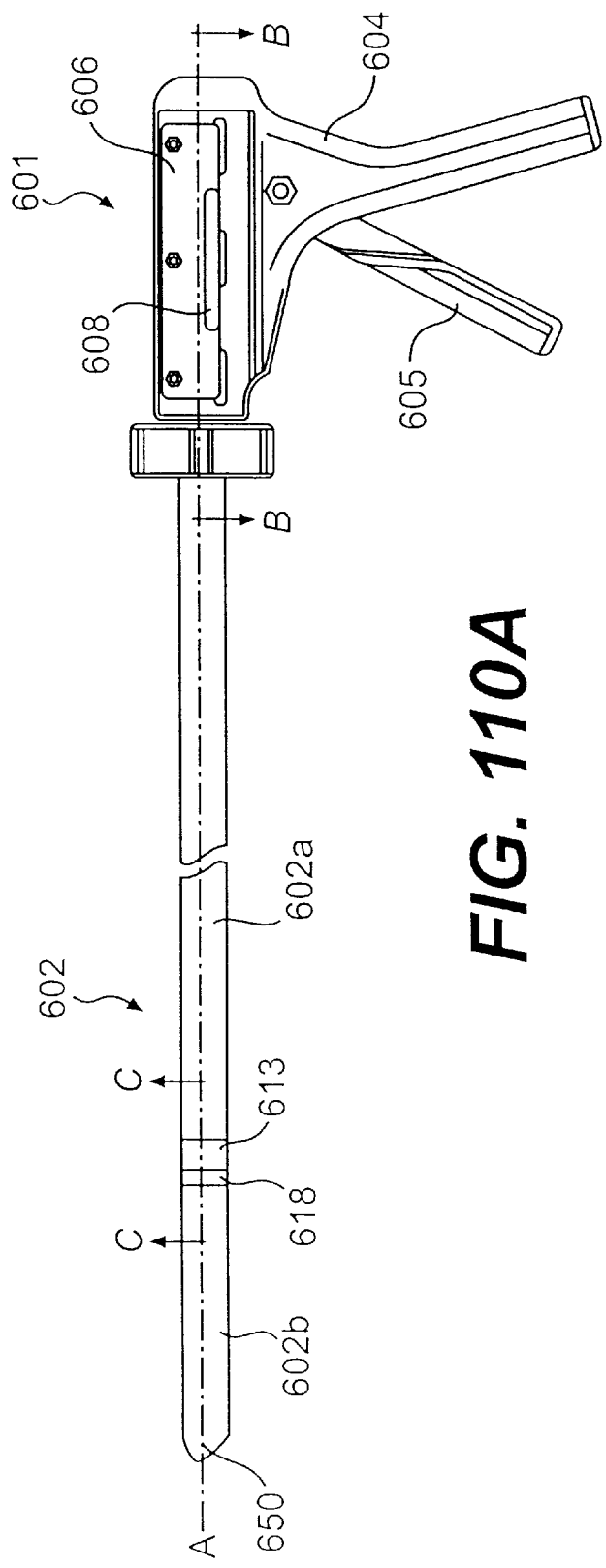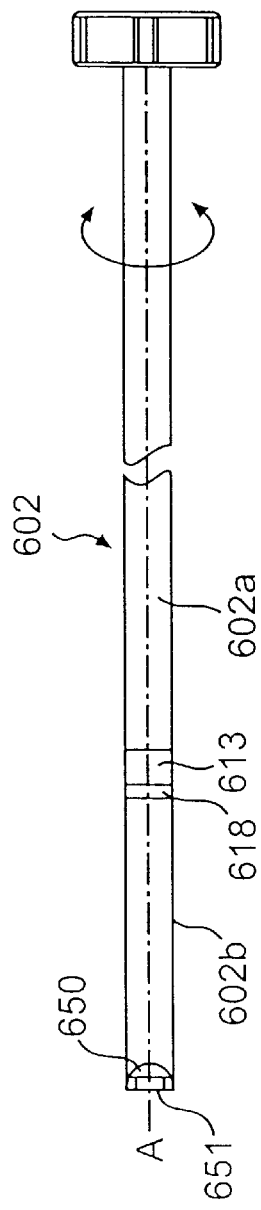
FIG. 110A
FIG. 110B

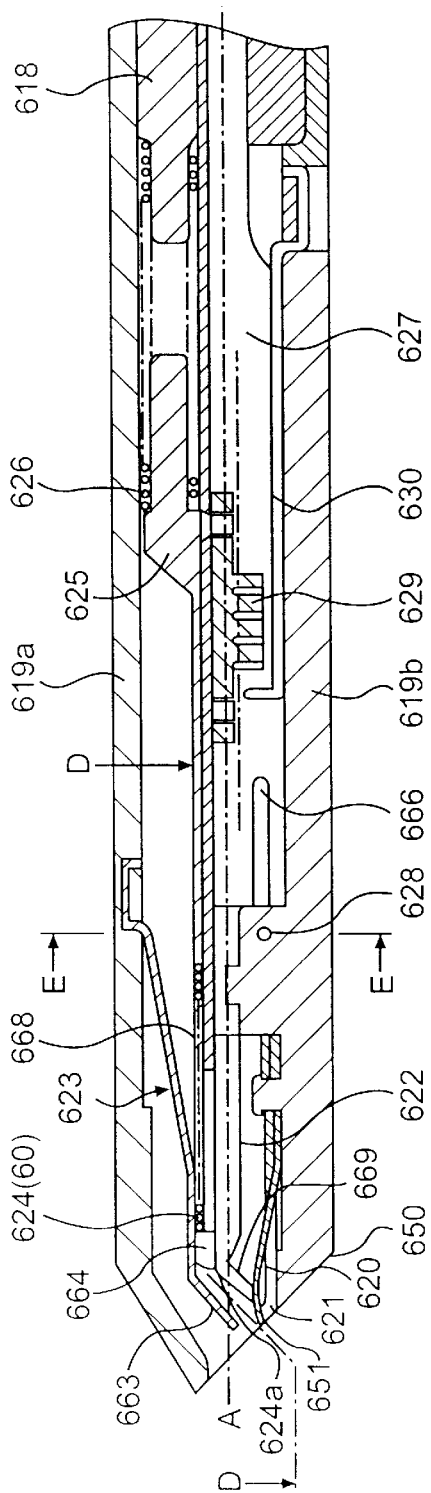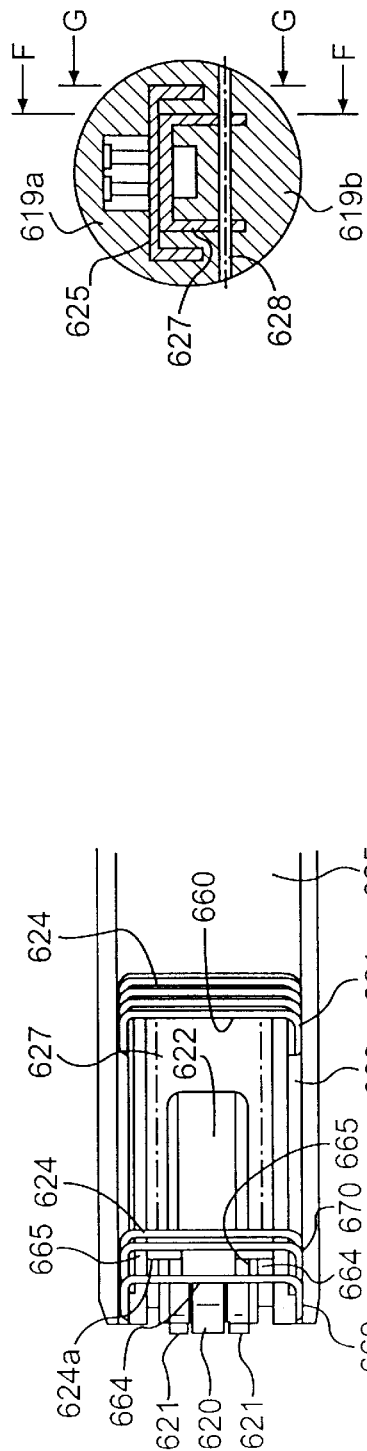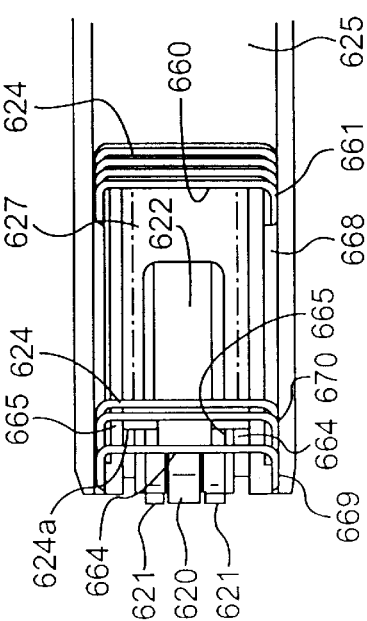

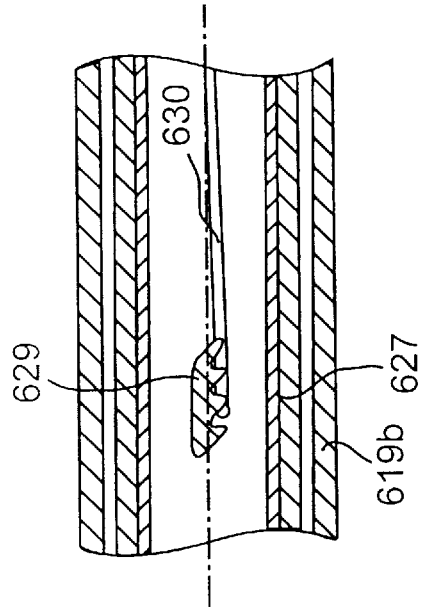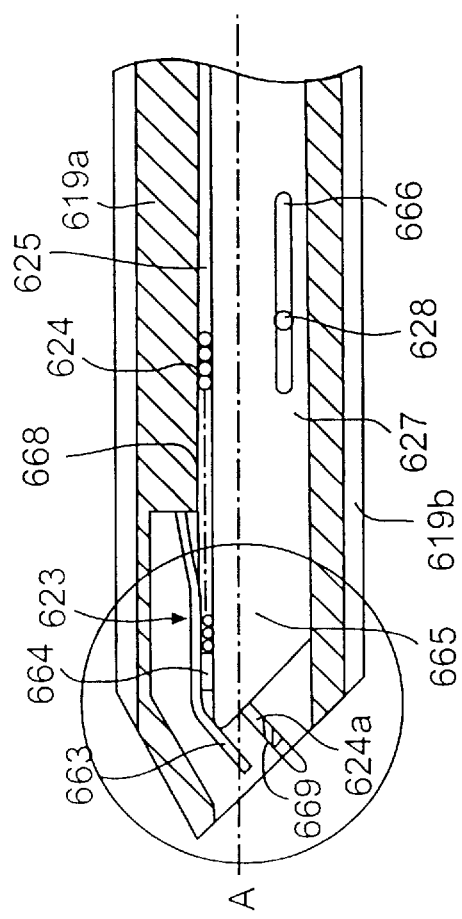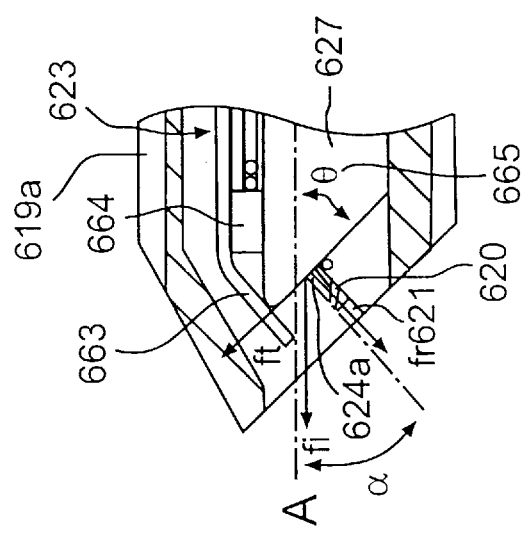
FIG. 123a
FIG. 123b

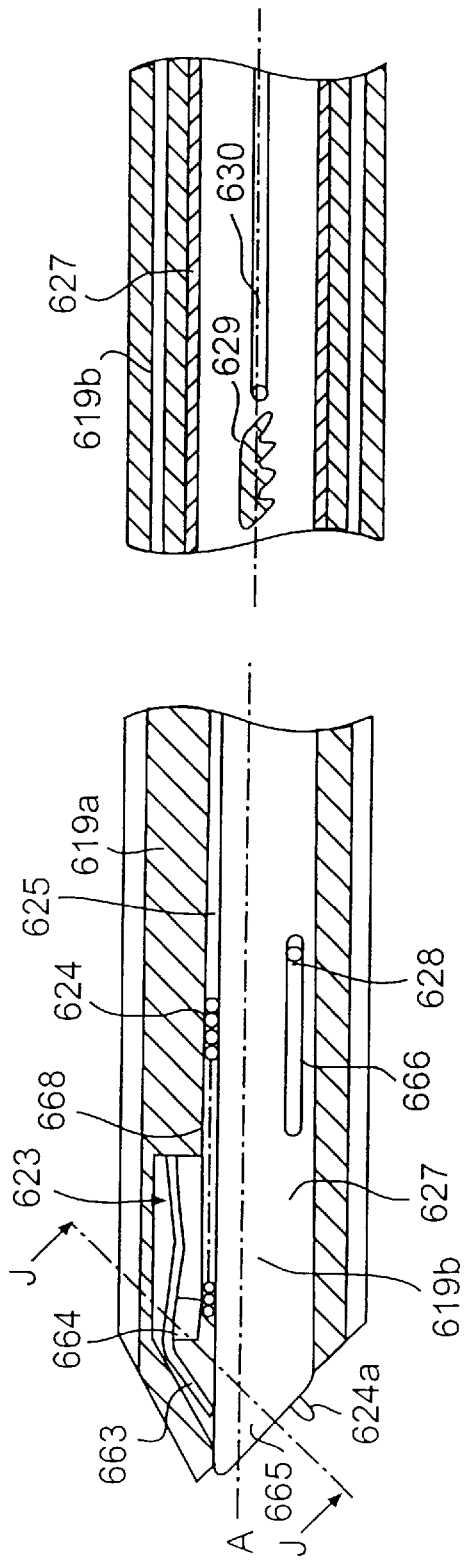
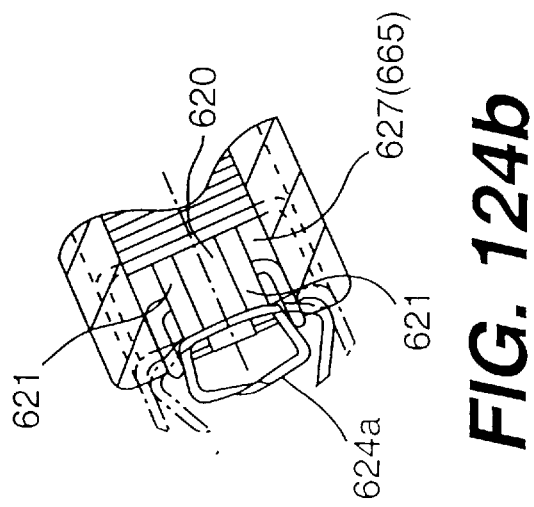
FIG. 124a
FIG. 124b

MEDICAL TREATMENT INSTRUMENT

BACKGROUND OF THE INVENTION

1. Field of the Invention

The present invention relates to a medical treatment instrument used in endoscopy and endoscopic operations and, more particularly, to a cost-saving medical treatment instrument which has a simple mechanism and is capable of being washed and sterilized.

2. Related Art

Of conventional medical treatment instruments used in surgical operations and, more particularly, of the medical treatment instruments for use in endoscopic surgery, the majority of medical treatment instruments, which are generally called forceps, are reusable. The forceps are formed from minute parts, and numerous mechanisms are housed in various portions of the forceps, which in turn results in forceps that are less easily washed and sterilized after they have been used.

To solve such a problem, the main body of the forceps is split into a forceps unit, an insertion section, and an operating section, so as to improve the ease of washing and sterilization of the forceps, as disclosed in; e.g., Japanese Unpublished Patent Application. No. Hei.6-179049 and DE 7330291.

Further, as disclosed in Unexamined Japanese Utility Model Application. No. Hei.5-18512, there is a forceps system which resembles the above-described forceps in structure. This forceps system utilizes a variety of forceps and an operating section in combination. For example, according to Unpublished Japanese Patent Application. No. Hei.6-179049, the forceps and the operating section are joined together by means of a snap fit.

As disclosed in U.S. Pat. Nos. 5,403,327 and 5,382,255, forceps are intended to minimize disposable portions to as small an area as possible by designing an insertion section so as to be capable of being removed from and attached to the operating section. Further, the forceps can be systematically used by preparing a plurality of insertion sections and operating section.

Further, another type of medical treatment instrument is a stapler for stapling tissue as disclosed in U.S. Pat. 5,381,943. There is also a so-called intestine anastomosing instrument. Examined Japanese Utility Model Publication No. Sho. 60-24329 discloses an intestine anastomosing instrument designed so as to permit replacement of a cartridge which incorporates a staple for use with medical treatment instrument device.

Recently, as disclosed in U.S. Pat. No. 5,205,459, totally-disposable intestine anastomosing instruments have become more popular. An automatic suturing instrument is also disclosed in U.S. Pat. No. 5,307,976.

EP 0 622 049 A1 discloses operating section which can use an insertion section for opening purposes and an insertion section for use with an endoscope. Of the medical treatment instruments, there is a medical treatment instrument as disclosed in U.S. Pat. No. 5,322,055 which carries out ultrasonic treatment.

In practice, the medical treatment instruments disclosed in the previously-described Unpublished Japanese Patent Application No. Hei.6-179049, DE 7330291, and Unexamined Utility Model Publication No. Hei.5-18512, require complicated assembling and disassembling operations. For example, the medical treatment instrument disclosed in Unpublished Japanese Patent Application No. Hei.6-179049, which is snap-fitted to the operating section, requires some experience to fit or remove the forceps to or from the operating section with ease. Another method of fitting the forceps to the operating section requires a screwing action, and hence there is a risk of dislodgment of the forceps as a result of rotation of an insertion section. Further, the previously-described methods require longitudinal assembly or disassembly of the insertion section, which is ergonomically uncomfortable for the operator.

Endoscopic forceps are generally designed to enable cauterization of tissue or to stop bleeding by passing a high frequency electric current through the forceps. The drive mechanism of the operating section of the conventional art is exposed to the outside so that it can be washed, sterilized, disassembled, or reassembled. Therefore, the drive mechanism must be coated with an insulating material. The need for coating the drive mechanism with an insulating material further complicates disassembly and assembly of the forceps.

Another medical treatment instrument includes a clip applier used for ligating tissue. A currently-popular disposable clip applier which continuously applies clips, commonly stores multiple clips within an insertion section of the clip applier. These disposable clip appliers are expensive and contribute to an increase in medical expenses. Since this type of clip applier is totally disposed every time it is used, a problem arises in light of a desired reduction in wastes and energy consumption and effective utilization of resources.

The medical treatment instrument disclosed in U.S. Pat. No. 5,403,327 is intended to make the instrument systematically usable. However, this type of medical treatment instrument requires troublesome disassembly and assembly methods. Further, the inside of the drive mechanism of the operating section is not designed such that it can be easily washed and sterilized. Even if the insertion section and the operating section are capable of being disassembled and reassembled, the advantage of assembly and disassembly is not sufficiently utilized because the inside of the drive mechanism of the operating section, which is most difficult to wash and sterilize, still remains difficult to wash and sterilize. The medical treatment instrument disclosed in U.S. Pat. No. 5,382,255 has a similar structure. It should be said that the operating section is not designed with ease of washing and sterilization considered. Therefore, such a medical treatment instrument does not provide any particular advantage when it is used.

There has been a stapler to staple tissue as disclosed in U.S. Pat. No. 5,381,943. However, this stapler is not particularly designed to consider for ease of assembly and disassembly.

The medical treatment instrument disclosed in Examined Japanese Utility Model Publication No. Sho.60-24329 is designed so that the medical treatment instrument cartridge which stores staples can be replaced. Even if the cartridge is replaceable, it is difficult to say that the other portions of the medical treatment instrument are particularly designed in consideration of washing and sterilization. The washing and sterilization of those portions remain difficult.

Since the medical treatment instrument disclosed in U.S. Pat. No. 5,205,459 is totally disposable, it also presents the same problems as those associated with disposable products which have been previously described with reference to the clip applier. In the automatic suturing instrument as disclosed in U.S. Pat. No. 5,307,976, the drive mechanism within the operating section of the automatic suturing instrument is particularly complex. Further, the drive mechanism is housed in the operating section. As a result of this configuration, the drive mechanism cannot be washed and sterilized. For this reason, there is no other alternative but to make the overall automatic suturing instrument disposable. In consequence, the problems associated with disposable products also arise in the automatic suturing instrument.

In EP 0 622 049 A1, there is little chance of sharing an insertion section between an opening operation and an endoscopic operation due to the difference in operation. Further, it cannot be said that the operating section of the insertion section is designed to consider ease of washing and sterilization. Therefore, there are doubts as to the advantageous results of such an operating section.

In the medical treatment instrument as disclosed in U.S. Pat. No. 5,322,055 which carries out ultrasonic treatment, only the ultrasonic transducer is reusable. The other portions of the medical treatment instrument, such as the probe, the operating section, the insertion section, and treatment section, are disposable. Particularly, the complicated internal mechanisms of the operating section, the insertion section, and the treatment section cannot be externally exposed for reasons of structural restrictions and, therefore, are housed. For this reason, the operating section, the insertion section, and the treatment section can be neither washed nor sterilized and, hence, must be disposed. Many parts of the medical treatment instrument must be replaced every time the instrument is used. Consequently, this type of medical treatment instrument also presents the same problems as those associated with the previously-described types of medical treatment instruments.

As described above, regardless of the types of medical treatment instruments, there are not conventional medical treatment instruments having fewer disposable components and reusable components that are easier to wash and sterilize, allow ease of disassembly and assembly, are safe, and allow ease of operation. In addition, there are no conventional medical treatment instruments designed in consideration of systematic use.

SUMMARY OF THE INVENTION

The present invention has been conceived in view of the foregoing drawbacks accompanying the conventional arts. A first object of the present invention is to provide a medical treatment instrument which enables cost cutting, a reduction in wastes and energy waste, insurance of safety when it is used, ease of use, and improving ease of washing and sterilization by increasing the number of reusable members.

A second object of the present invention is to provide a medical treatment instrument capable of ensuring suturing and ligation of tissue.

A third object of the present invention is to provide an applier having a simple and safe mechanism.

A fourth object of the present invention is to provide a medical treatment instrument capable of increasing the number of suturing and ligating tools to be stored in an applier by reducing the size of them.

A fifth object of the present invention is to provide a medical treatment instrument which is capable of feeding another clip to the jaws by storing energy in clip feed member when a clip applier returns to its original state after having attached one clip to tissue, and by discharging the stored energy to feed another clip when the clip applier has fully returned to its original state. In the medical treatment instrument, the clip feeding and the jaw closing are operated manually, and the energy is stored during these operation.

A sixth object of the present invention is to provide a clip applier main unit which has a simple structure and loads the jaws with clips from above, wherein the jaws normally housed in the clip applier project only when attaching a clip to tissue.

A seventh object of the present invention is to provide a medical treatment instrument capable of increasing the ligating force of a resilient clip when it is in its original state.

An eighth object of the present invention is to provide a medical treatment instrument capable of preventing faulty operations by feeding a staple at an angle with respect to the longitudinal direction of an insertion section using a simple action.

A ninth object of the present invention is to provide a medical treatment instrument capable of simultaneously carrying out grasping and excising operations when tissue is excised and of switching the state of the tissue grasped by jaws in an excisable state and an unexcisable state.

A tenth object of the present invention is to provide a medical treatment instrument capable of preventing the released jaws from coming into contact with tissue.

To achieve these objects, the present invention provides a medical treatment instrument comprising:

a treatment section for treating tissue;

an insertion section which has the treatment section provided at a distal end and guides the treatment section into tissue;

an operating section which is provided at the proximal end of the insertion section and actuates the treatment section;

a drive mechanism disposed in the operating section for driving the treatment section; and a cover which is provided on the operating section, able to be opened and closed, which sheathes the drive mechanism.

As a result of housing the drive mechanism therein, and of sheathing the drive mechanism with the cover, fingers and hands are prevented from touching the drive mechanism. Further, it is possible to wash and sterilize the thus-housed drive mechanism by opening or removing the cover.

BRIEF DESCRIPTION OF THE DRAWINGS

FIG. 2A is a longitudinal plan view of attaching section of the first embodiment, FIG. 2B is a longitudinal side view of the attaching section shown in FIG. 2A;

FIG. 7 is a longitudinally cross-sectional view of storage section of the applier of the first embodiment;

FIG. 8 is a longitudinally cross-sectional view of a ratchet mechanism of the applier of the first embodiment;

FIG. 10A is a longitudinal plan view of the side of an insertion section facing operating section of the first embodiment;

FIG. 10B is a longitudinal side view of the side of the insertion section facing the operating section shown in FIG. 10A;

FIG. 34 is a exploded view of a pusher and a suturing and ligating instrument of a thirteenth embodiment of the present invention;

FIG. 35 is a perspective view of the suturing and ligating instrument of the thirteenth embodiment;

FIGS. 38A and 38B are longitudinally cross-sectional plan and side views showing the operation of the applier of the thirteenth embodiment;

FIGS. 40A and 40B are longitudinally cross-sectional plan and side views showing the operation of the applier of the thirteenth embodiment;

FIGS. 41A and 41B are longitudinally cross-sectional plan and side views showing the operation and the applier of the thirteenth embodiment;

FIG. 53A is a plan view of attaching section of the eighteenth embodiment when it is in a first operating state;

FIG. 53B is a longitudinally cross-sectional view of the attaching section taken across line B–B' when it is in the first operating state;

FIG. 63A is a plan view showing the operating section of the nineteenth embodiment when it is in the course of returning to its initial state;

FIG. 63B is a longitudinally cross-sectional view of the operating section of the nineteenth embodiment taken across line F–F';

FIG. 70A is a longitudinally cross-sectional view of attaching section of a twenty-second embodiment when it is in an initial state;

FIG. 70B is a longitudinally cross-sectional plan view of the attaching section of the twenty-second embodiment;

FIG. 99A is a longitudinally cross-sectional view of the anvil of the suturing instrument of the twenty-eighth embodiment when it is open;

FIG. 99B is a longitudinally cross-sectional view of the anvil of the suturing instrument of the twenty-eighth embodiment when it is in an closing state;

FIG. 99C is a longitudinally cross-sectional view of the anvil of the suturing instrument of the twenty-eighth embodiment when it is closed;

FIG. 101A is a longitudinally cross-sectional view of the chief elements of jaws of the suturing instrument according to the twenty-eighth embodiment when a cutter of the jaws is switched to an excisable state;

FIG. 101B is a longitudinally cross-sectional view of the chief elements of the jaws of the twenty-eighth embodiment when it is switched to an unexcisable state;

FIG. 102B is a perspective view showing a stop member of a double-stapling preventive mechanism and a joint rod of the twenty-eighth embodiment while they are jointed together;

FIG. 103 is a longitudinally cross-sectional view of the suturing instrument of the twenty-eighth embodiment when an anvil open-close lever and a stapling lever are respectively retained in open positions;

FIG. 104 is an exploded perspective view of the chief elements of a suturing instrument of a twenty-ninth embodiment;

Figure 106A:
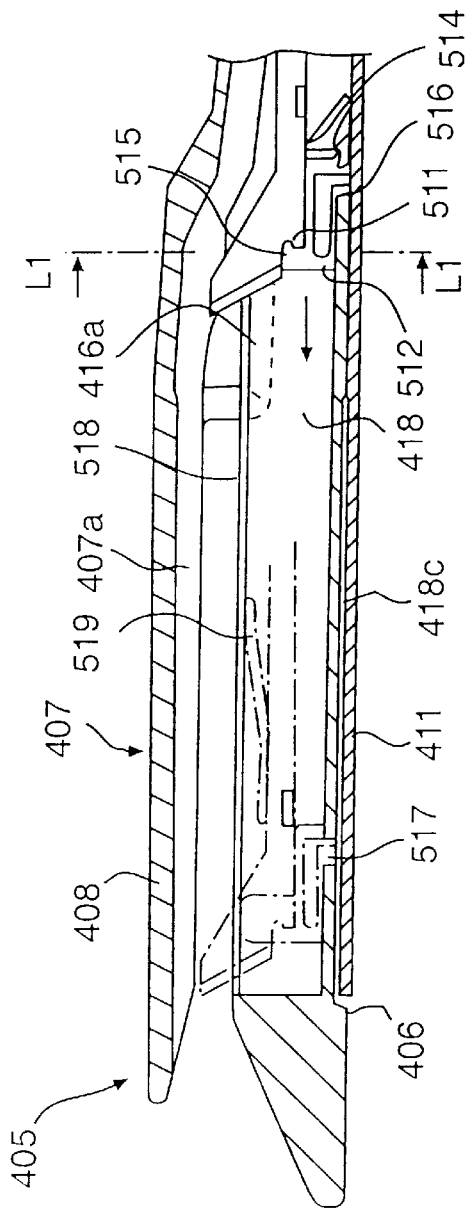
Figure 106B:
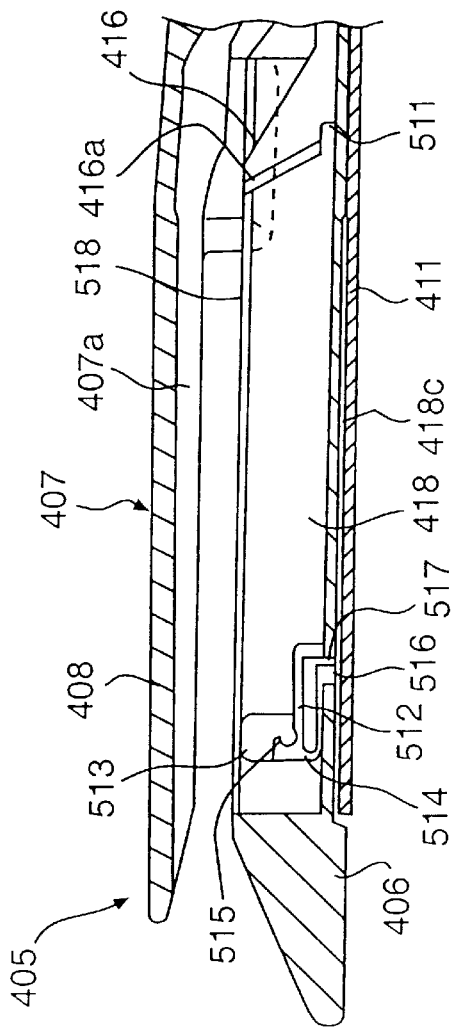
Figure 107:
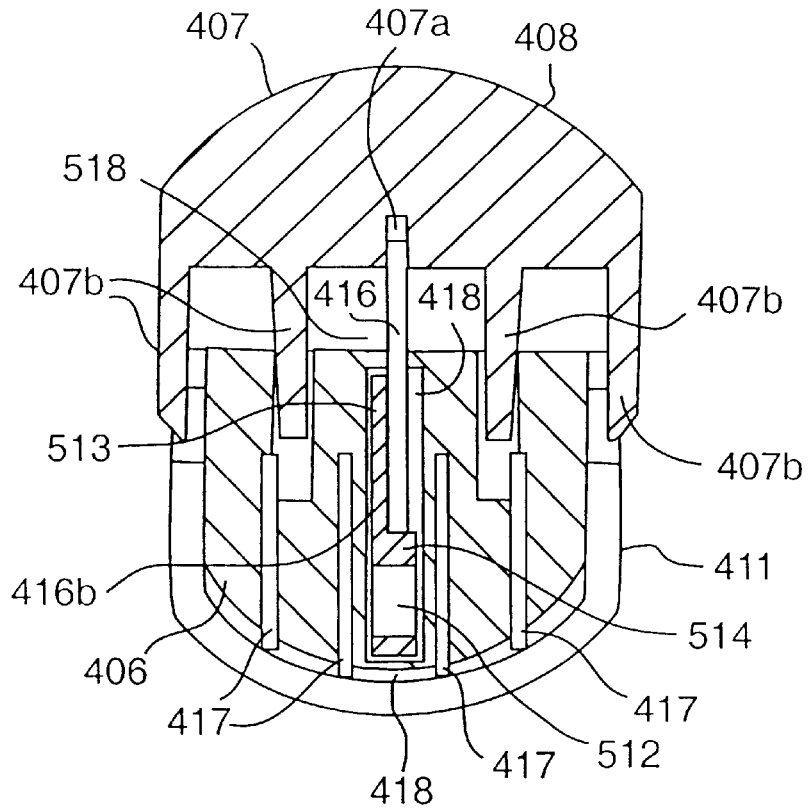
Figure 108:
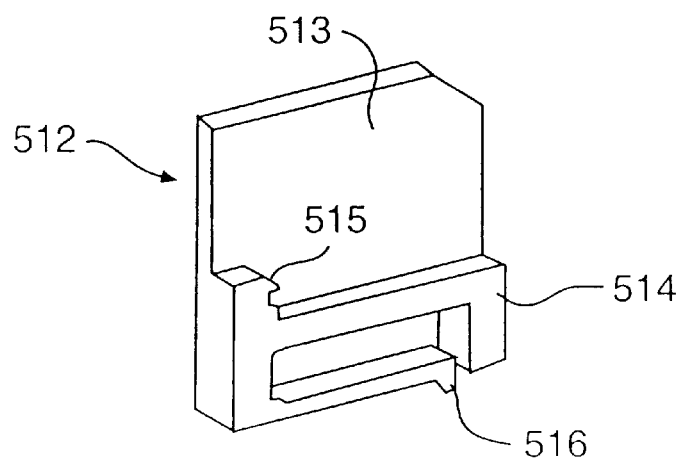
Figure 111:
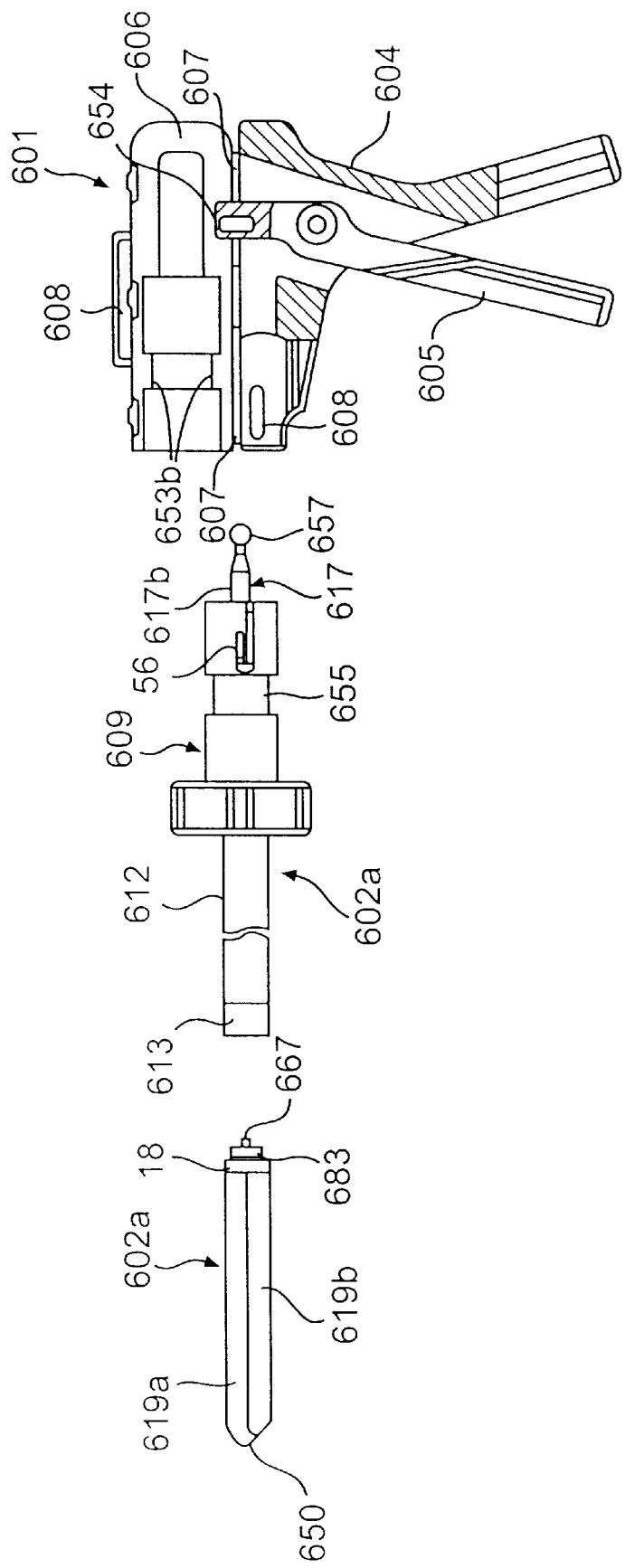
Figure 112:
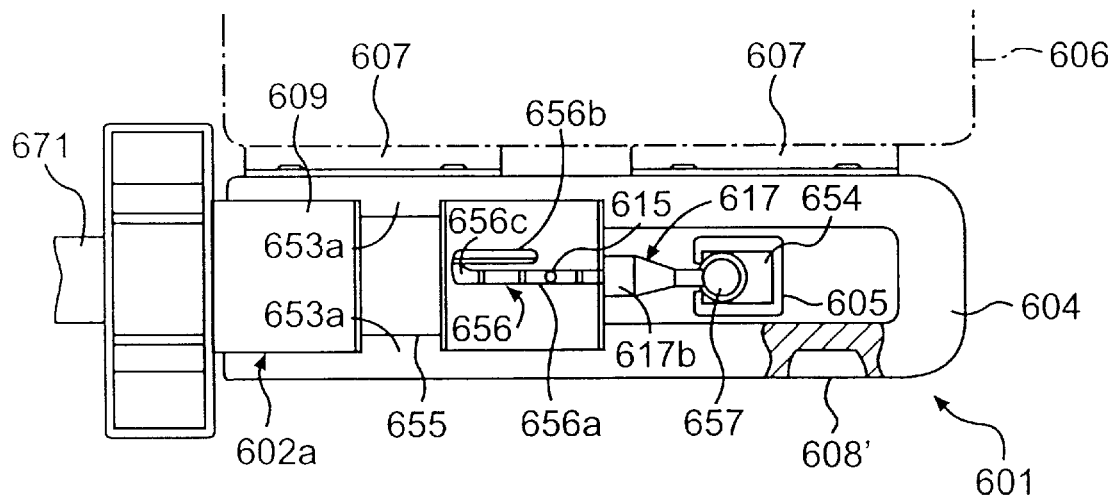
Figure 113A:
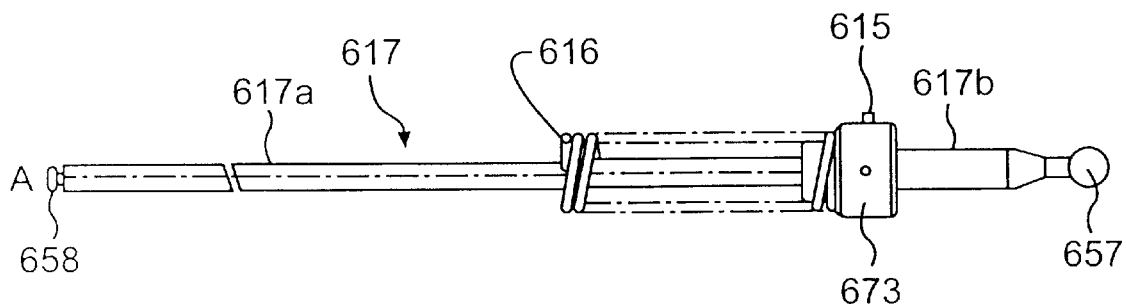
Figure 113B:
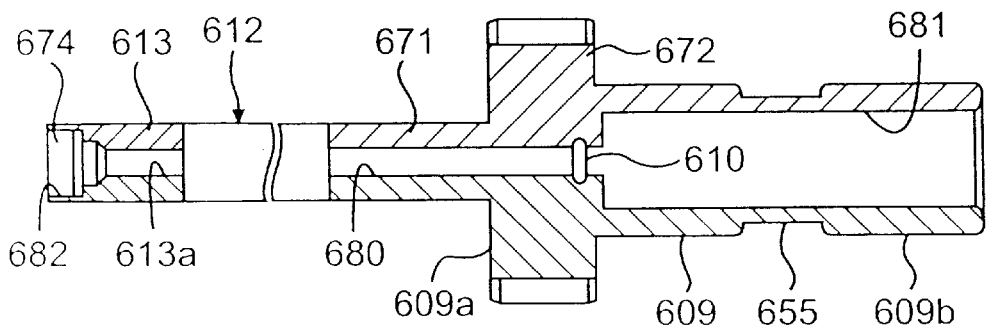
Figure 114A:
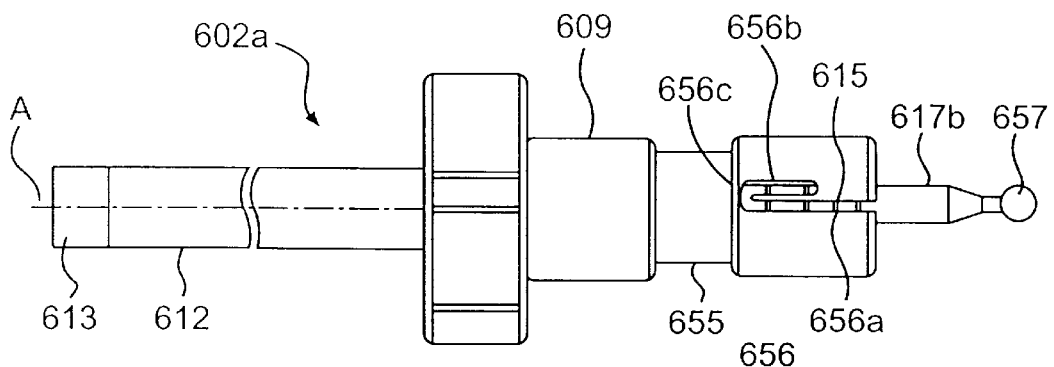
Figure 114B:
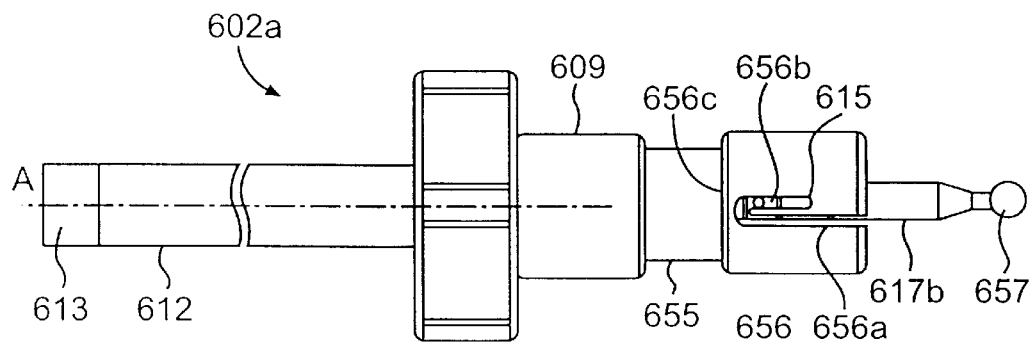
Figure 115:
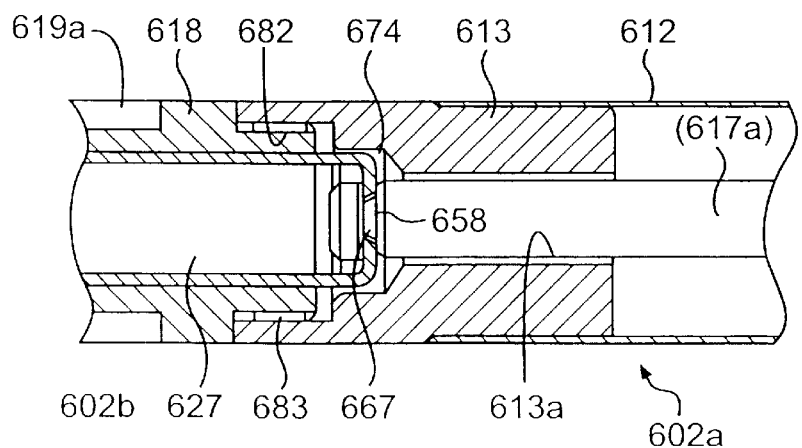
Figure 117:
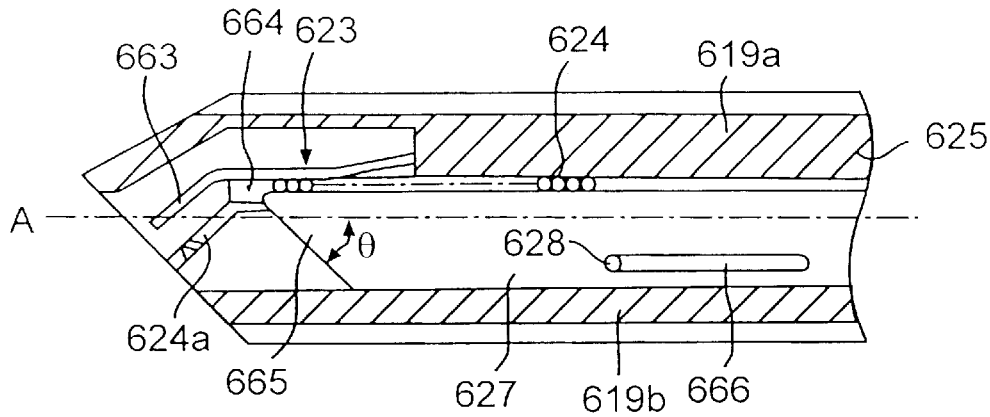
Figure 118:
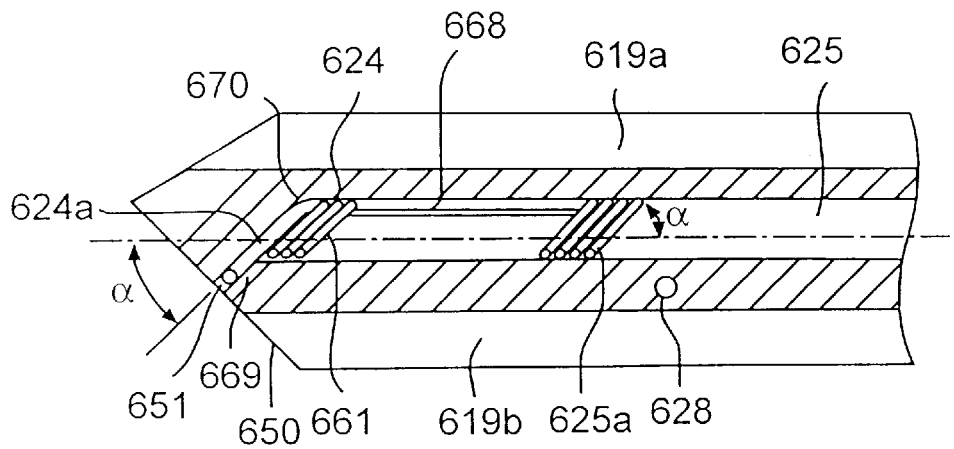
Figure 119:
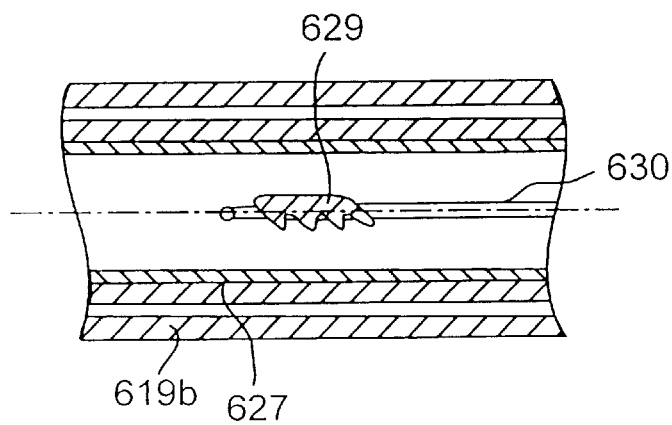
Figure 120:
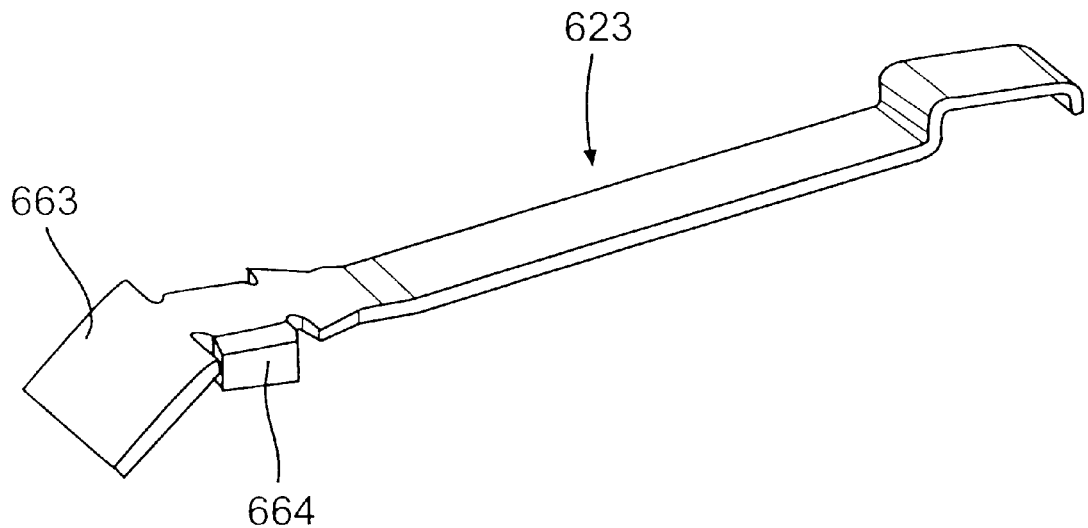
Figure 121:
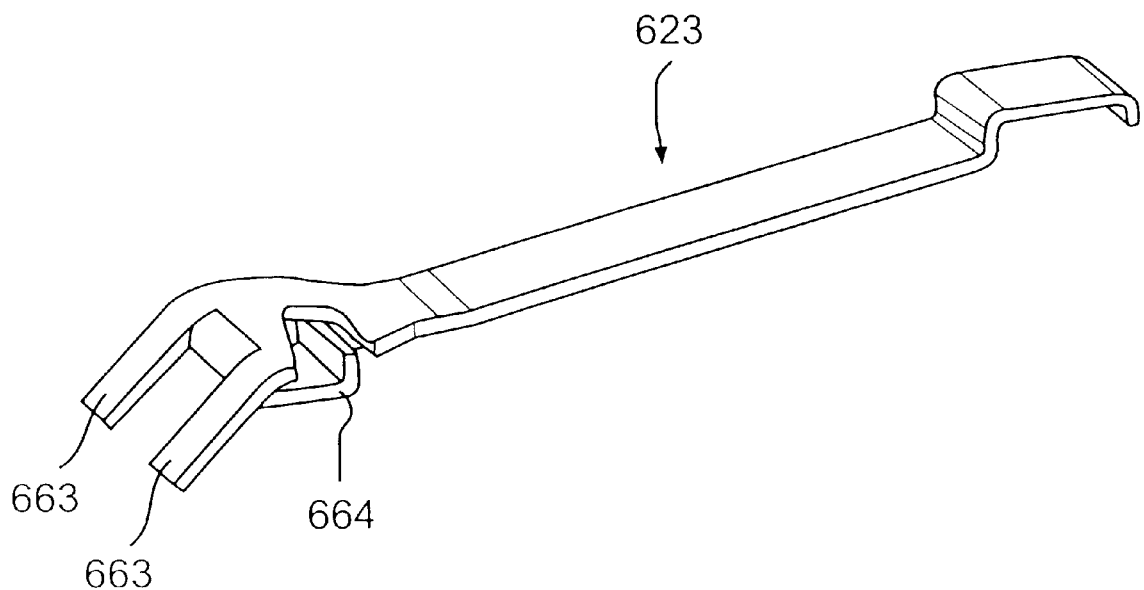
Figure 122:
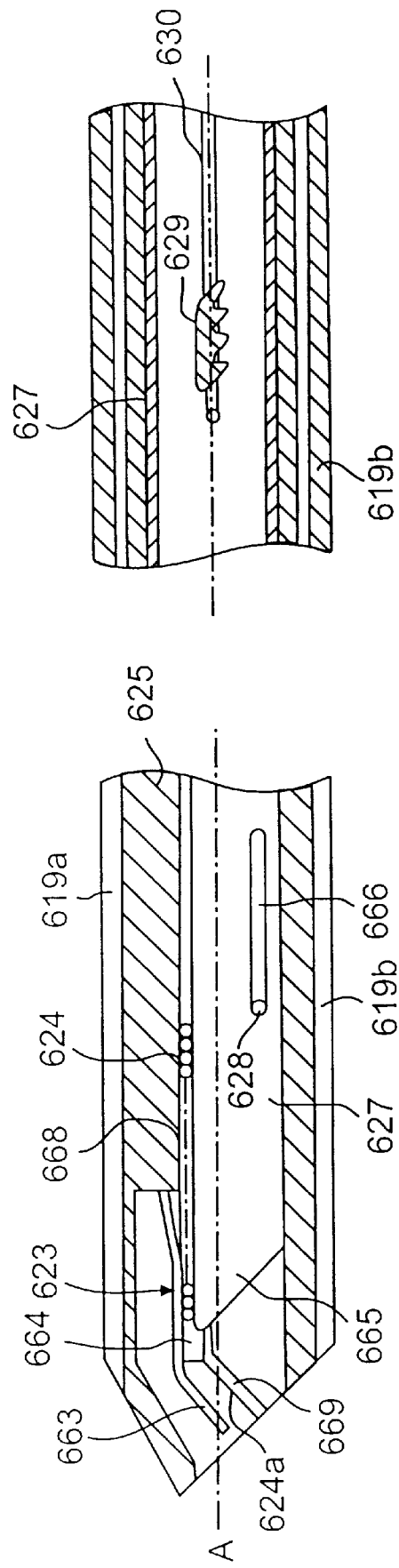

FIGS. 105A and 105B show a suturing instrument of a thirtieth embodiment of the present invention, wherein FIG. 105A is a longitudinally cross-sectional view showing the chief elements of the suturing instrument when a cutter of jaws of the suturing instrument is switched to an excisable state and FIG. 105B is a longitudinally cross-sectional view showing the chief elements of the suturing instrument when the cutter is switched to an unexcisable state;

FIGS. 106A and 106B show a suturing instrument of a thirty-first embodiment of the present invention, wherein FIG. 106A is a longitudinally cross-sectional view showing the chief elements of the suturing instrument when a cutter of jaws of the suturing instrument is switched to an excisable state and FIG. 106B is a longitudinally cross-sectional view showing the chief elements of the suturing instrument when the cutter is switched to an unexcisable state;

FIG. 107 is a cross-sectional view of the suturing instrument taken across line L1—L1 shown in FIG. 106A;

FIG. 108 is a perspective view showing a spacer of a suturing instrument of the thirty-first embodiment;

FIGS. 109A and 109B show a suturing instrument of a thirty-second embodiment of the present invention, wherein FIG. 109A is a longitudinally cross-sectional view showing the chief elements of the suturing instrument when a cutter of jaws of the suturing instrument is switched to an excisable state and FIG. 109B is a longitudinally cross-sectional view showing the chief elements of the suturing instrument when the cutter is switched to an unexcisable state;

FIG. 110A is a side view of a stapler of a thirty-third embodiment of the present invention;

FIG. 110B is an illustration showing an insertion section of the stapler when it has been rotated through 90 degrees with respect to an operating section from the state shown in FIG. 110A;

FIG. 111 is an exploded view of the stapler shown in FIGS. 110A and 110B which shows the stapler is disassembled into the operating section, a main body, and a cartridge;

FIG. 112 is a plan view of the stapler when viewed in the direction designated by B—B shown in FIGS. 101A and 111, the view showing the main body of the insertion section attached to the operating section while an upper cover is open;

FIGS. 113A and 113B show a disassembled state of a main body of an operating section, wherein FIG. 113A is a side view of the actuation rod and FIG. 113B is a side view showing a rotary knob and a support shaft;

FIGS. 114A and 114B are illustrations of the operating section main body when it is assembled;

FIG. 115 is a cross-sectional view of the stapler which is taken across line C—C shown in FIG. 110A and shows a detailed structure of a joint between the main body of the insertion section and the cartridge;

FIG. 116A is a longitudinally cross-sectional view of the cartridge;

FIG. 116B is a cross-sectional view of the cartridge taken across line D—D shown in FIG. 116A, or along a staple track for guiding the feeding travel of a staple;

FIG. 116C is a cross-sectional view of the cartridge taken across line E—E shown in FIG. 116A, or along a guide pin;

FIG. 117 is a cross-sectional view of the cartridge taken across line F—F shown in FIG. 116C, or along a staple feed closing member;

FIG. 118 is a cross-sectional view of the cartridge taken across line G—G shown in FIG. 116C, or along a pusher;

FIG. 119 is a cross-sectional view of the cartridge taken across H—H shown in FIG. 116A;

FIG. 120 is a perspective view of a feed leaf spring;

FIG. 121 is a perspective view showing a modification of the feed leaf spring;

FIG. 122 is a longitudinally cross-sectional view of the cartridge showing one example of the operation of the cartridge;

FIG. 123A is a longitudinally cross-sectional view of the cartridge showing one example of the operation of the cartridge;

FIG. 123B is an enlarged view of a circled area I shown in FIG. 123A;

FIG. 124A is a longitudinally cross-sectional view of the cartridge showing one example of the operation of the cartridge; and FIG. 124B is a cross-sectional view taken across line J—J shown in FIG. 124A.

DETAILED DESCRIPTION OF THE PREFERRED EMBODIMENTS

With reference to the accompanying drawings, the preferred embodiments of the present invention will be described in detail hereinbelow.

Figure 1:
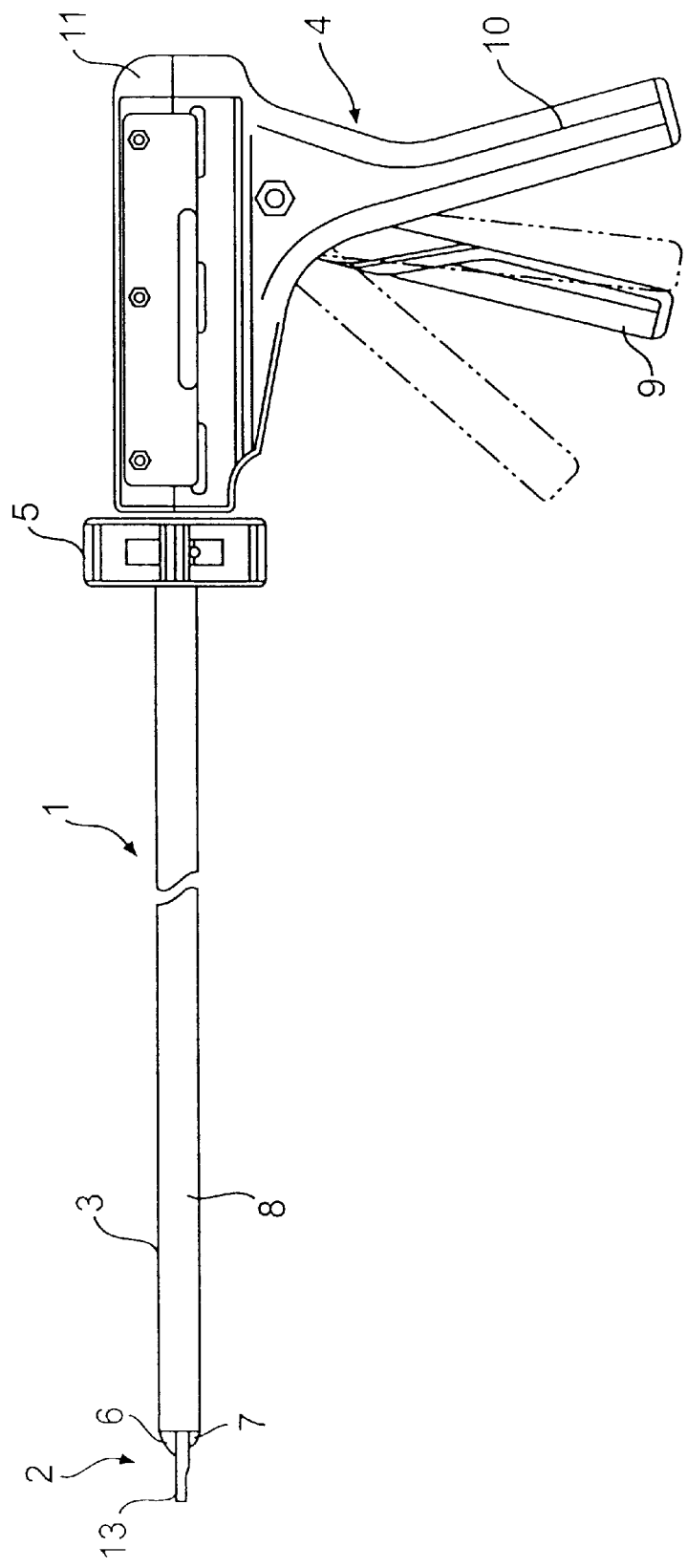
FIG. 1 is a side view of the entirety of an applier according to a first embodiment of the present invention.
Figure 3:
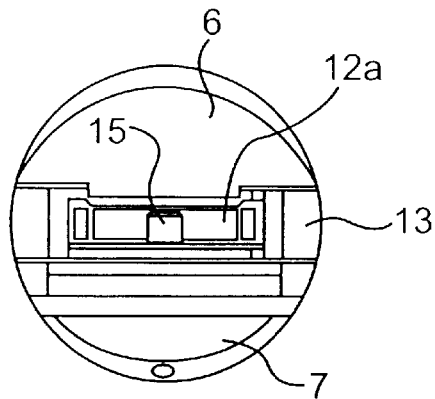
FIG. 3 is a front view of the attaching section when viewed in the direction designated by arrow X shown in FIG. 2B.
Figure 4:
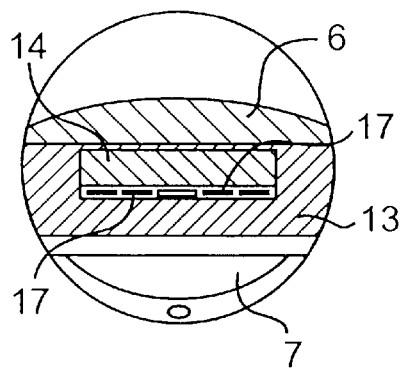
FIG. 4 is a cross-sectional view of the attaching section taken across line A–A' shown in FIG. 2B.
Figure 5:
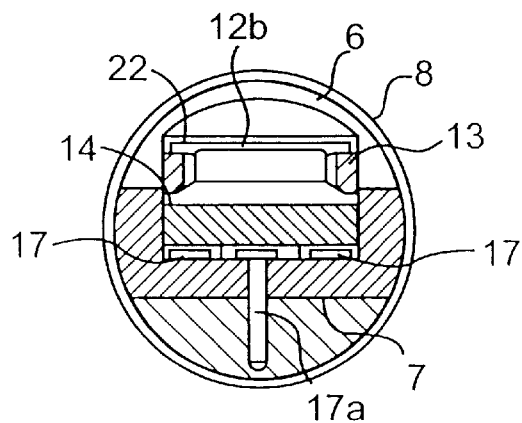
FIG. 5 is a cross-sectional view of the attaching section taken across line B–B' shown in FIG. 2B.
Figure 6:
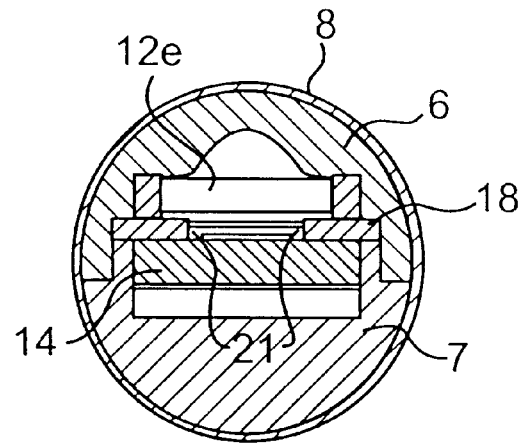
FIG. 6 is a cross-sectional view of the attaching section taken across line C–C' shown in FIG. 2B.

FIGS. 1 through 16 show a first embodiment of the present invention. FIG. 1 shows an applier 1 which serves as a medical treatment instrument for use in attaching a suturing and ligating element; e.g., a clip or staple, as will be described later, to tissue. The applier 1 comprises attaching section 2, which serves as medical treatment section for clinching the suturing and ligating element, an insertion section 3 for inserting the attaching section 2 into tissue through an unillustrated trachea, or the like, and operating section 4 for actuating the attaching section 2. The insertion section 3 is rotatable with respect to the operating section 4. A knob 5 for rotating the insertion section 3 is fitted around a joint between the proximal side of the insertion section 3 and the operating section 4.

As shown in FIGS. 2A and 2B, the insertion section 3 is split into an upper portion and a lower portion; namely, an upper insertion member 6 and a lower insertion member 7. An outer sheath tube 8 is formed from a transparent thermally-contractive tube so as to permit visual check of the inside of the insertion section 3.

As shown in FIG. 1, the operating section 4 is made up of a movable handle 9 and a fixed handle 10. The attaching section 2 can be actuated by moving the movable handle 9 with respect to the fixed handle 10.

A closure 11 which serves as a cover as will be described later, is provided on the top of the fixed handle 10 of the operating section 4. It is possible to remove or attach the insertion section 3 from or to the operating section 4, and to wash and sterilize the inside of the operating section 4 by opening and closing the closure 11.

FIGS. 2A and 2B through 6 show the structure of the attaching section 2. A guide member 13 is provided at the tip end of the attaching section 2 so as to guide the attaching section 2 when the suturing and ligating element 12 is attached. The suturing and ligating elements 12 are loaded in the guide member 13. A pusher 14 carries out loading of the suturing and ligating elements 12 in the guide member 3 and attachment of the same to tissue, as will be described later.

The guide member 13 is provided with a guide pin 15 for supporting the suturing and ligating element 12 during attachment of the suturing and ligating element 12. The guide pin 15 prevents the suturing and ligating element 12 from falling out toward the front by supporting it. Conventional attaching section 2 does not have any device such as a guide member 13, and therefore the attaching section are provided with two support pins 15 to reliably retain the suturing and ligating element 12. The interval between legs 12a of the suturing and ligating element 12, is relatively wider than the entire length of the legs 12a. However, since the attaching section 2 is provided with one support pin 15 in the first embodiment, it is possible to render the interval between the legs 12a relatively narrower. This narrower interval of the legs 12a is not only very effective at ligating a vessel but also effective from the viewpoint of minimum invasive surgery because the size of the guide member 13 and the outer diameter of the insertion section 3 can be reduced as well.

The insertion section 3 of the applier 1 for attaching the suturing and ligating element 12 to tissue, normally has an outer diameter of 10 to 12 mm. In contrast, by virtue of the previously-described simple structure of the insertion section 3, 7 mm is sufficient to house the suturing and ligating elements 12 to be used in the present embodiment. The thickness of each of the upper insertion member 6 and the lower insertion member 7 is 0.5 mm, and the outer diameter of the insertion section 3 is 8 mm$\phi$. According to the conventional art, the support pins 15 project from the tip end of the attaching section 2. In contrast, the support pin 15 is housed in the guide member 13 in the present embodiment, and therefore there is no risk of the support pin 15 coming into contact with tissue.

Further, the guide member 13 does not require much strength aside from the area where the support pin 15 is provided. The guide member 13 may be made at least partially transparent so as to allow easy visual check of suturing and ligating operations, which contributes to more safe and reliable suturing and ligating operations. As a result, the safety of the applier 1 is improved.

To clinch the suturing and ligating element 12 into a predetermined shape when attaching it to tissue with help of the support pin 15, the pusher 14 is provided with an indentation 16. An ejector 17 is provided in the guide member 13, below the suturing and ligating elements 12. This ejector 17 ejects the suturing and ligating element 12 from the applier 1 after the suturing and ligating element 12 has been attached to tissue.

The guide member 13 is fixed on the lower insertion member 7 which is a part of the insertion section 3 with pins 17a. A partition 18 is attached on the top of the lower insertion member 7, and storage section 19 is formed on the partition 18 so as to store the suturing and ligating elements 12. A press spring 22 is attached to the upper insertion member 6 so as to press the suturing and ligating elements 12 downwardly. The overall insertion section 3 is covered with the outer sheath tube 8. Of these constituent elements of the insertion section 3, the outer sheath tube 8, the upper insertion member 6, and the lower insertion member 7 are formed from transparent resin so that the state of the attaching section 2 and the storage section 19 can be visually checked, as previously described.

The pusher 14 has a hook 20 which serves as the transfer section for feeding the suturing and ligating element 12 positioned at the forefront of a line of suturing and ligating elements 12. The storage section 19 has a one-way clutch 21 to prevent the suturing and ligating element 12 from going backward. A plurality of suturing and ligating elements; for example, twenty suturing and ligating elements 12a to 12t, are housed in the applier 1 from its front end to the rear end. The number of suturing and ligating elements 12 initially housed in the applier 1 is not particularly limited. Any number of suturing and ligating elements may be housed in the applier 1 depending on intended manipulation.

Figure 9:
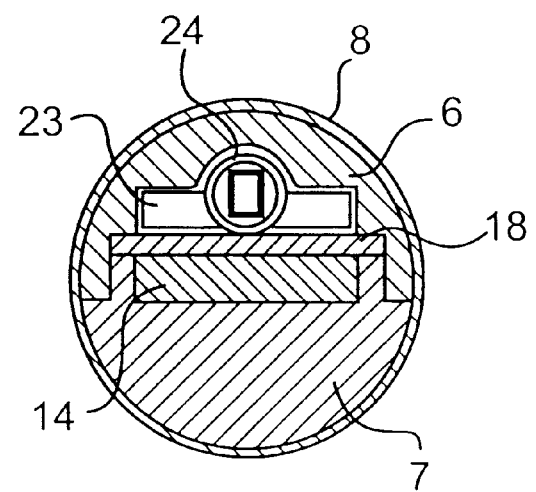
FIG. 9 is a cross-sectional view of the storage section taken across line E–E' shown in FIG. 7.

FIGS. 7 through 9 show the structure of the area of the insertion section 3 ranging from substantially the middle to the proximal end of the insert. A plate buffer 23 for thrusting the suturing and ligating element forwardly, meshes with the rear of the suturing and ligating element 12t positioned at the rearward end of the line of the suturing and ligating elements 12 stored in the storage section 19. The buffer 23 is also forwardly forced by a clip push spring 24. The rear of the clip push spring 24 is fixed to the proximal end of the insertion section 3 by means of a spring holder 25. The buffer 23 is formed in a color which is easy to see; e.g., a fluorescent color. The number of remaining suturing and ligating elements 12 can-be determined due to the forward movement of the buffer 23 which is carried out every time the suturing and ligating element 12 is ejected.

The number and type of suturing and ligating elements 12 stored in the storage section 19 may be displayed by arbitrarily setting the color of the buffer 23. Alternatively, they may be displayed by arbitrarily setting the color of each of the components forming the insertion section 3. In such a case, for example, it is possible to indicate that the number of remaining twenty suturing and ligating elements 12 is 20 if the guide member 13 is blue-colored, and that the number of remaining suturing and ligating elements 12 is 10 if the guide member 13 is red-colored. The number and type of remaining suturing and ligating elements may also be indicated by a combination of more than two colors. Assistants normally select equipment to be used in surgery in accordance with instructions of the doctor who performs the operation. In this case, the assistants do not identify target equipment by reading words printed thereon but identify the equipment by easily-recognizable elements such as the appearance of equipment; e.g., the shape and color of the equipment. Color identification is very effective because it contributes to prevention of erroneous selection of equipment and improves the efficiency of manipulation.

The pusher 14 is provided with a ratchet arm 26. The ratchet arm 26 forms a ratchet mechanism 28 together with ratchet teeth 27 fixed to the lower insertion member 7. The ratchet mechanism 28 prevents the suturing and ligating element 12 from blocking the inside of the attaching section 2, as a result of the return of the pusher 14 during its operation. In a conventional ratchet mechanism, a specially designed thin blade-like component is normally used as a counterpart which meshes with the ratchet teeth 27. Such a component becomes expensive when it is designed, so as to ensure the required resilient force. The ratchet arm 26 used in the present embodiment is formed by bending a round rod. The resilient force is ensured by increasing the effective length of the rod. In this way, the ratchet arm 26 can be easily and inexpensively formed.

FIGS. 10A and 10B show the proximal side of the insertion section 3. The knob 5 is fitted around the rear end of the insertion section 3 and is split into upper and lower portions. A main spring 29 is provided in the knob 5 and normally forces an actuation rod 30, connected to the pusher 14, toward an operator. The main spring 29 makes it possible to return the overall applier 1, including the attaching section 2 and the operating section 4, to its initial state after a sequence of clipping operations have been completed.

The rear of the actuation rod 30 is formed into a ball 32, and this ball 32 engages with an engaging slot 31 formed in an upper part of the movable handle 9. The rear of the actuation rod 30 and the knob 5 are sealed by an O-ring 33. In common endoscopic treatment, treatment is performed while the abdominal cavity called pneumoperitoneum is bulged with $CO_2$ gas. The medical treatment instrument used in the treatment, such as the applier 1, needs to be designed so as to prevent the gas from escaping from the abdominal cavity. The inside of the applier 1 is completely sealed by the O-ring 33, or a gas leak is suppressed to such an extent so as not to cause any practical problems.

The pusher 14 and the actuation rod 30 connected thereto, are provided along the longitudinal center of the insertion section 3. Therefore, when the insertion section 3 is rotated with respect to the operating section 4 by operating the knob 5, the pusher 14 and the actuation rod 30 can rotate without the aid of conventional special conversion member to connect the pusher 14 to the actuation rod 30 in order to correspond to a rotating operation, because the pusher 14 and the actuation rod 30 are positioned along the center of the rotating operation.

Figure 11:
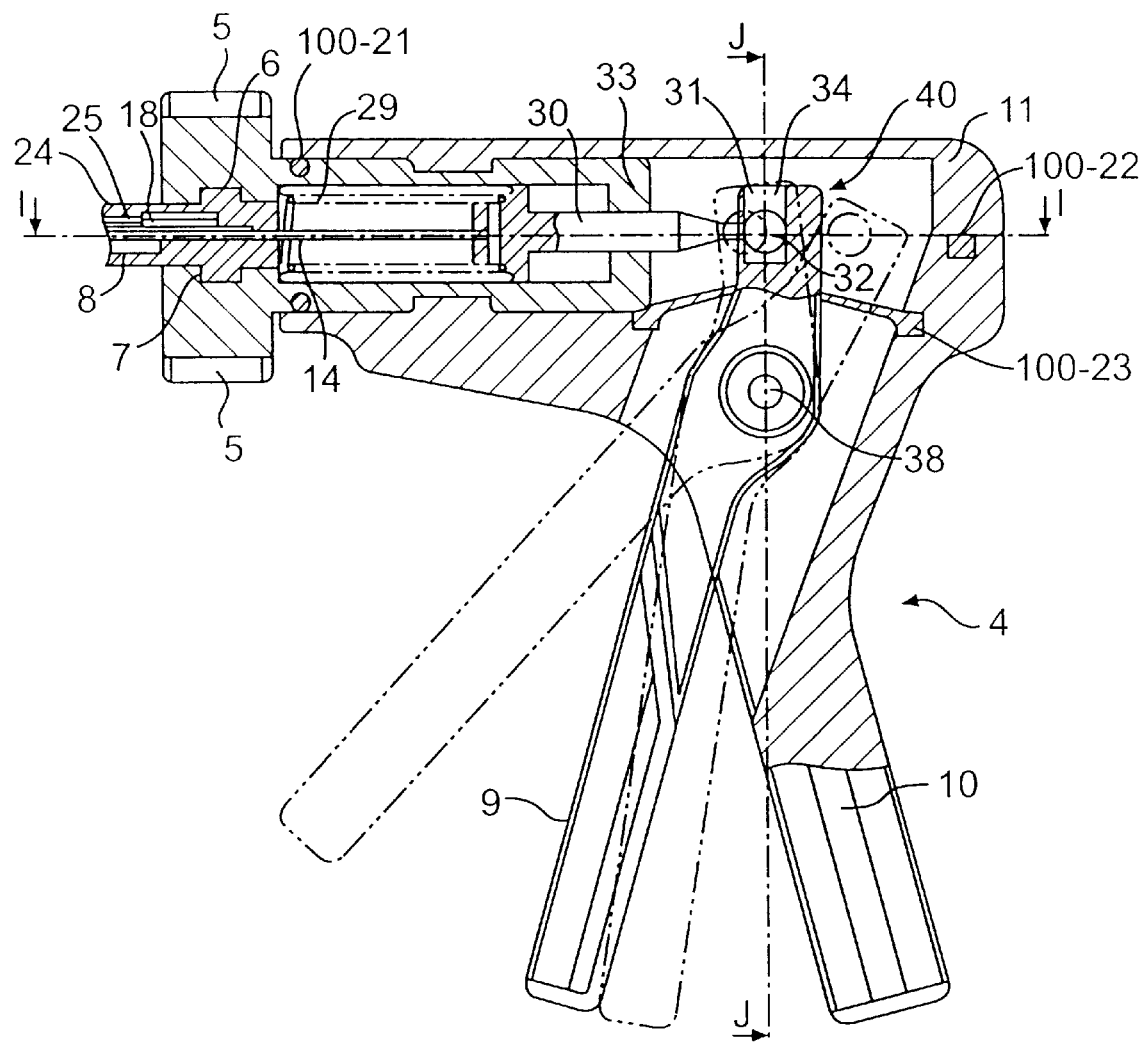
FIG. 11 is a longitudinal side view of the operating section of the applier of the first embodiment.
Figure 12:
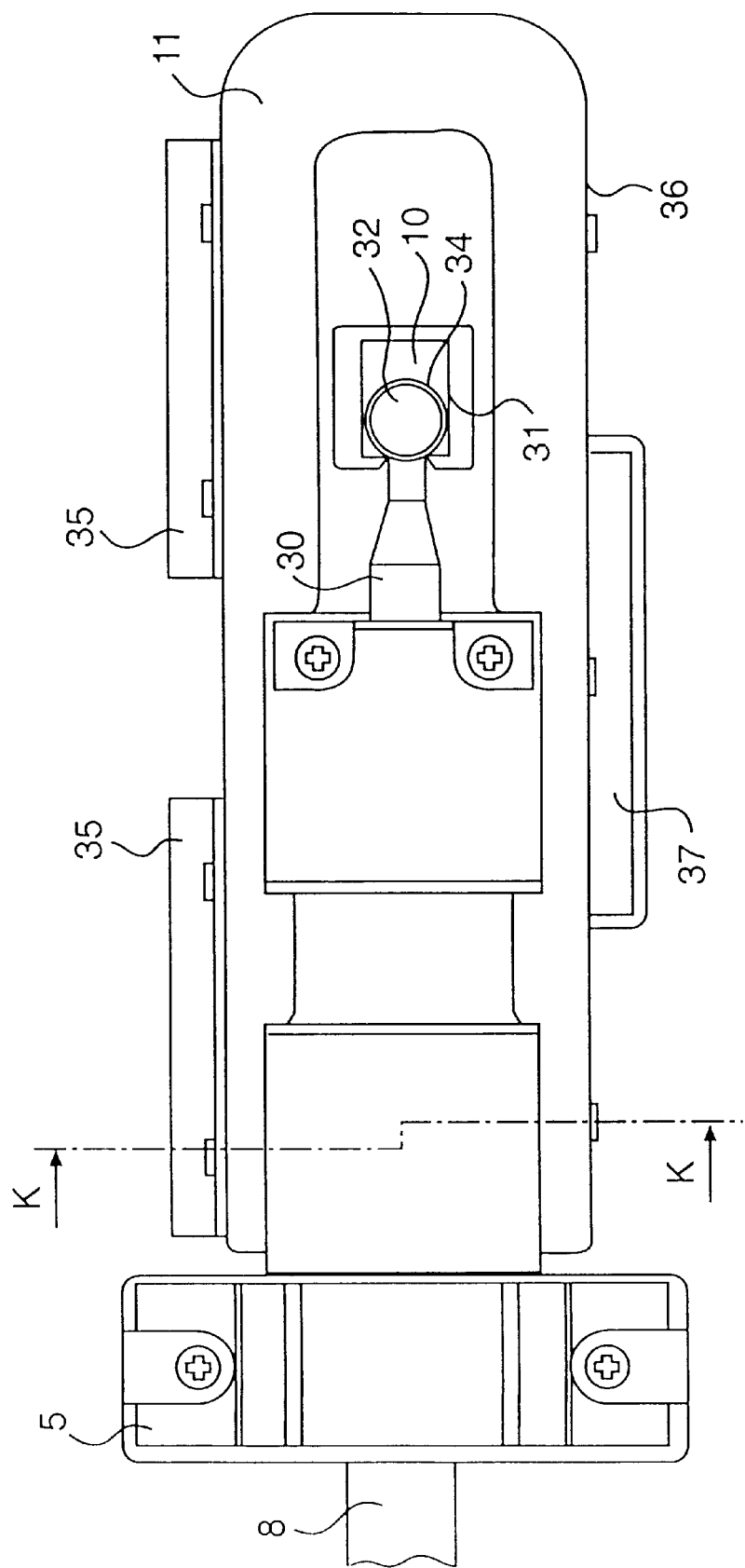
FIG. 12 is a cross-sectional view of the operating section taken across line I–I' shown in FIG. 11.
Figure 13:
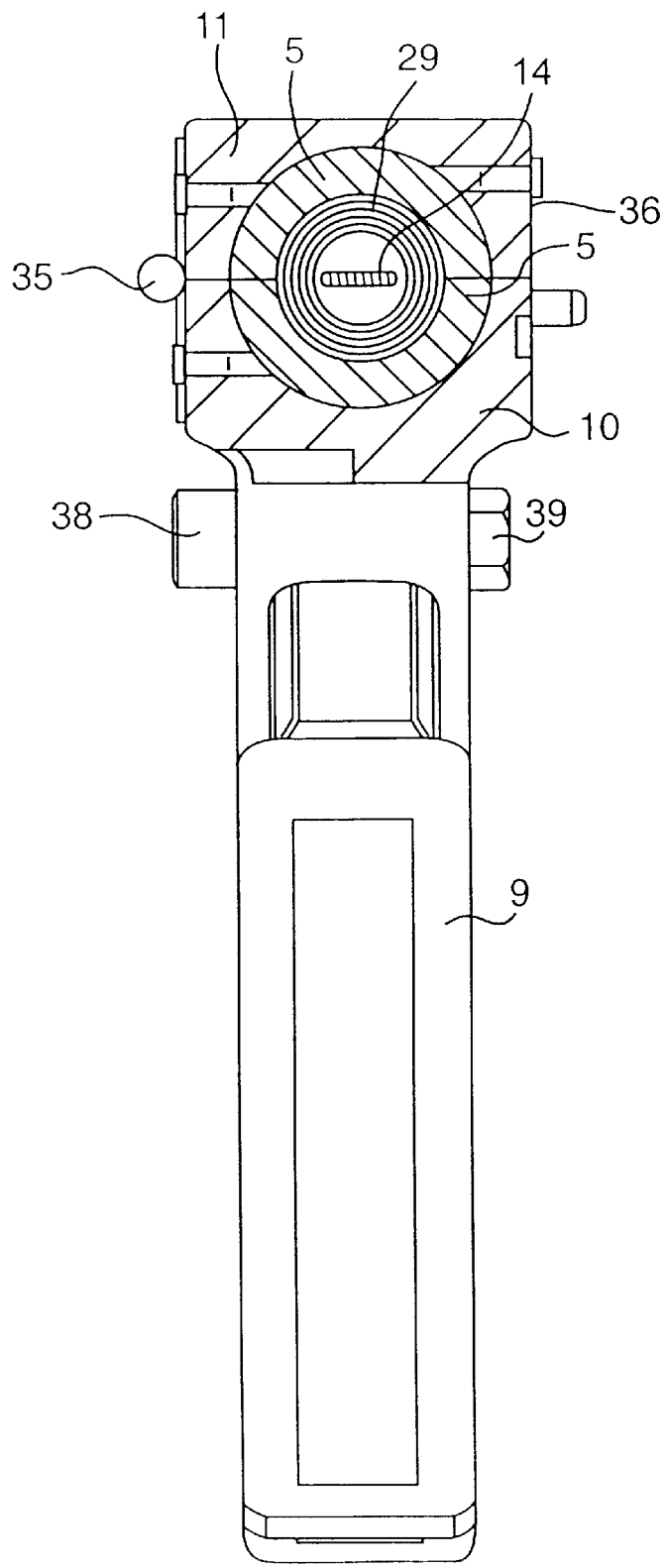
FIG. 13 is a cross-sectional view of the operating section taken across line K–K' shown in FIG. 12.

FIGS. 11 to 13 show the operating section 4. As has been described above, the operating section 4 is made up of the movable handle 9, the fixed handle 10, and the closure 11 provided on the top of the fixed handle 10. A drive mechanism 40 is provided in the operating section 4.

A description of the drive mechanism 40 is as follows: The knob 5 of the insertion section 3 is rotatably attached to the fixed handle 10. The ball 32 of the actuation rod 30 rotatably engages with a washer 34 provided in the engaging slot 31 of the upper portion of the movable handle 9, in a slidable fashion.

The closure 11 is attached to the fixed handle 10 by hinges 35 so as to make it possible to be opened and closed. The closure 11 is fixed by a snap fit 36 when it is closed. To open the closure 11, a tab 37 fixed to the snap fit 36 is forcibly moved to the outside. As a result, the fixed handle 10 disengages from the snap fit 36, whereby the closure 11 becomes open by the hinges 35.

The fixed handle 10 of the operating section 4 has a space formed herein so as to permit insertion of a wash and sterilizing gas for washing and sterilizing purposes, a high-temperature steam, or a washing tool, such as a washing brush. The upper portion of the fixed handle 10 can be thoroughly washed and sterilized along with the inside of the drive mechanism 40 by opening the closure 11, as previously described. Thus, the operating section 4 is reusable. It goes without saying that each of the constituent components of the operating section 4 is made of metal or resin having durability to withstand washing and sterilization processes.

The ball 32 of the actuation rod 30 rotatably engages with the engaging slot 31 formed in the upper portion of the movable handle 9, in a slidable fashion. The engaging slot 31 has its top opened, and the ball 32 engages with the engaging slot 31 by being inserted into the upper end of the engaging slot 31 from top. Conversely, the ball 32 disengages from the engaging slot 31 by reversing the engaging procedure.

The insertion section 3 can be removed from the operating section 4 by disengaging the ball 32 from the engaging slit 31 after having opened the closure 11 in the manner as previously described. The insertion section 3 can be attached to the operating section 4 by reversing the aforementioned order. As described above, the insertion section 3 can be very easily attached to and removed from the operating section 4. For example, if several inserts 3, each of which stores a different number of suturing and ligating elements 12 therein, are previously prepared, an insertion section 3 which stores the number of suturing and ligating elements 12 required by intended manipulation, can be used. Alternatively, the insertion section 3 with the suturing and ligating elements 12 consumed up can be replaced with a new insertion section 3.

Further, if several inserts 3, each of which stores the suturing and ligating elements 12 having a different shape, are previously prepared, the insertion section 3 can be replaced according to conditions. In general, the inside of the applier 1 similar to the present invention has such a complicated shape as not permit washing and sterilization. Further, the insertion section 3 can not be removed from the operating section 4. Therefore, the overall applier 1 is disposable. In contrast, in the case of the applier 1 of the present embodiment, the insertion section 3 is removable from the operating section 4. As previously described, the inside of the operating section 4 can be thoroughly washed and sterilized, and hence the applier 1 of the present embodiment is reusable. Only the insertion section 3 is disposable, but the operating section 4 can be repeatedly used. Accordingly, the amount of the portion of the applier 1 which is to be wasted is reduced. Therefore, in addition to cost reduction, environmental protection, energy conservation, prevention of waste of resources can be achieved.

The movable handle 9 is attached to the fixed handle 10 by a pivot screw 38 and a nut 39. The applier 1 is actuated by closing the movable handle 9 from its original position.

Figure 14:
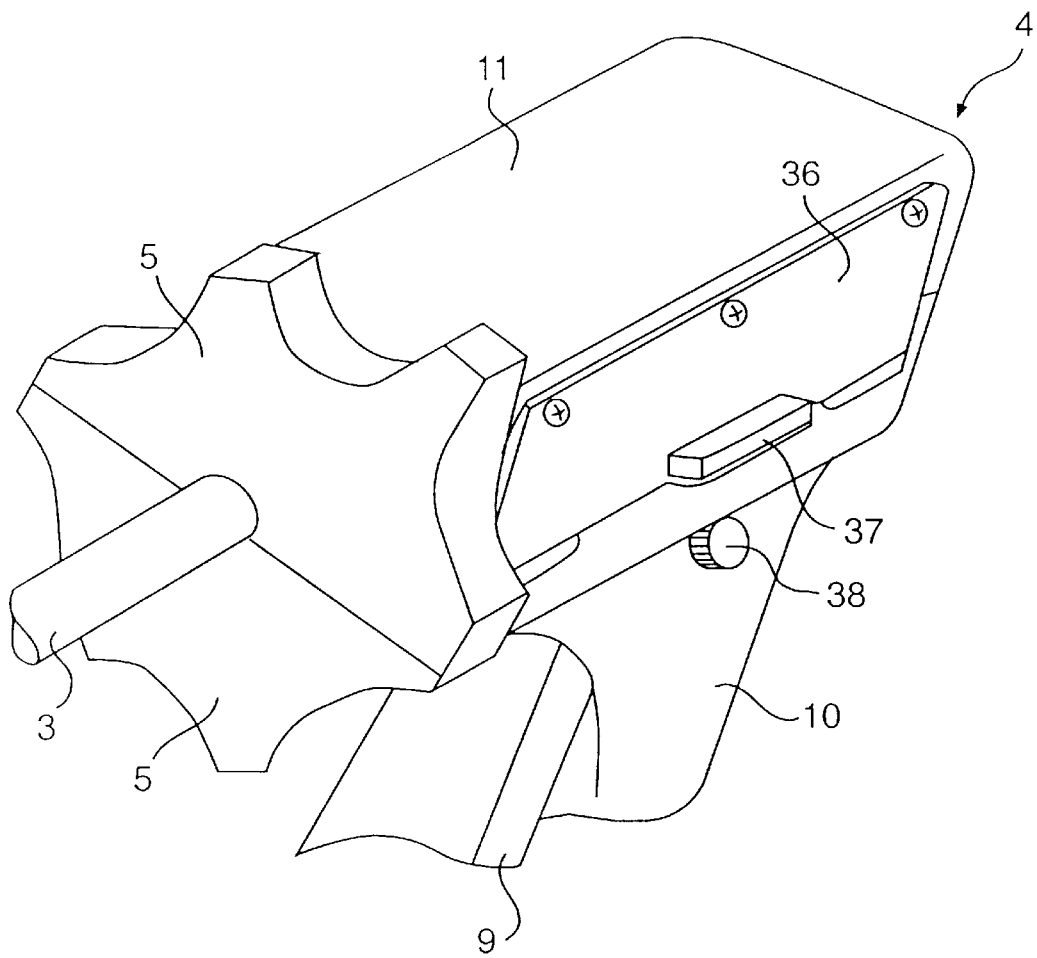
FIG. 14 is a perspective view showing a closed state of a cover of the operating section of the first embodiment.

The assembly and disassembly of the insertion section 3 and the operating section 4 will be described with reference to FIGS. 14 to 16. FIG. 14 shows the insertion section 3 attached to the operating section 4. At this time, the closure 11 is closed with respect to the fixed handle 10. The applier 1 is ready to be used in this state.

Figure 15:
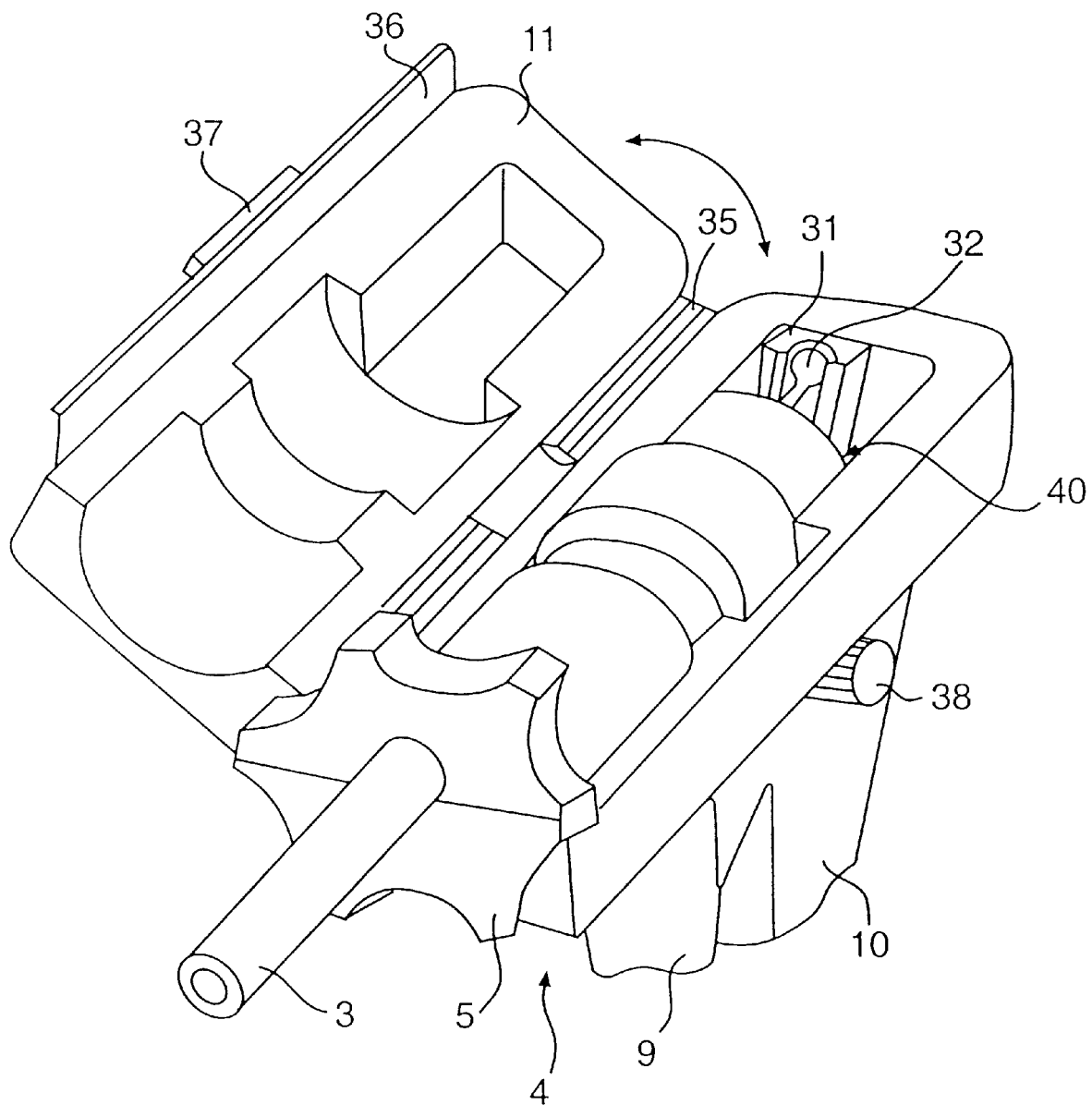
FIG. 15 is a perspective view showing an open state of the cover of the operating section of the first embodiment.

FIG. 15 shows the closure 11 in an open state. The snap fit 36 attached to the closure 11 disengages from the fixed handle 10 by pulling and raising the tab 37 fixed to the snap fit 36. Subsequently, the closure 11 is opened along the hinges 35, whereby the inside of the operating section 4 is exposed.

Figure 16:
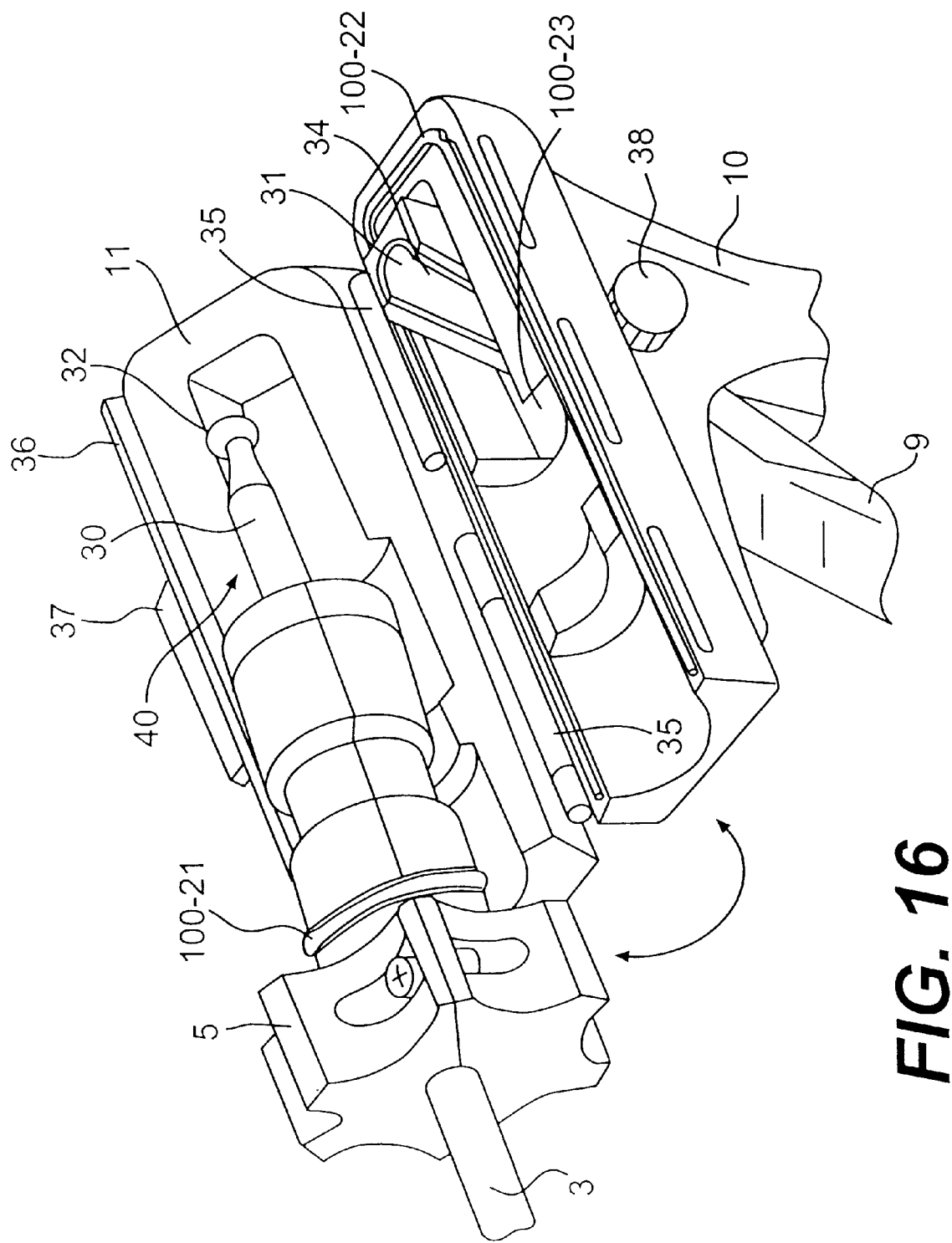
FIG. 16 is a perspective view of a drive mechanism of the first embodiment.

FIG. 16 shows the insertion section 3 removed from the operating section 4. The knob 5 of the insertion section 3 is placed simply on the top of the fixed handle 10. Further, the insertion section 3 engages with the movable handle 9 by fitting only the ball 32 in the washer 34 of the engaging slit 31 of the upper portion of the movable handle 9. In this arrangement, the insertion section 3 can be removed upwardly easily. In this state, the insertion section 3 and the operating section 4 can be easily assembled into a single unit in reverse order when a new insertion section 3 is attached to the operating section 4. For example, if further use of the suturing and ligating elements 12 is desired even after the insertion section 3 has been emptied of the suturing and ligating elements 12; if the use of the suturing and ligating elements 12 having a different size is desired, if the use of the insertion section 3 storing a different number of suturing and ligating elements 12 is desired; if the use of the operating section 4 having a different shape is desired; or if any one of the attaching section 2, the insertion section 3, and the operating section 4 has become broken, the insertion section 3 and the operating section 4 can be easily disassembled/reassembled or replaced.

Consequently, the insertion section 3 and the operating section 4 can be disassembled/reassembled or replaced without any problems during the course of surgery.

In addition to the insertion section 3 and the operating section 4 which can be disassembled and reassembled in the manner as previously described, the drive mechanism 40 stored in the operating section 4, can be uncovered by opening the closure 11. With this structure, the insertion section 3 is treated as being disposable, like a cartridge, and the operating section 4 is handled as being reusable. As a result, the disposable portion of the applier 1 can be reduced, compared with a conventional applier. Further, the ease of wash and sterilization of the applier is improved, and it becomes possible to selectively use the applier I suitable for surgery. Since the drive mechanism 40 of the operating section 4 is covered, fingers and hands are prevented from being injured as a result of coming into contact with the drive mechanism 40.

Moreover, even if the applier 1 has become broken, it can be fixed by a minimum number of replacement parts.

As described above, the insertion section 3 and the operating section 4 cannot be limited to any particular structure or shape so long as there are achieved the downsizing of disposable parts, improving ease of disassembly and reassembly, use of an applier suitable for surgery and objectives, improving ease of wash and sterilization, and improving safety for the doctor who performs the operation.

The medical treatment instrument of the present embodiment is provided with a first sealing member 100-21 provided at the area where the circumference of the cylindrical portion of the knob 5 contacts the closure 11, a second sealing member 100-22 provided at the area where the upper surface of the operating section 4 contacts the closure 11, and a third membrane-like sealing member 100-23 provided between the movable handle 9 and the fixed handle 10. If the closure 11 is closed, the inside of the operating section 4 is shielded from the outside by means of the above-described sealing members. As a result, the inside of the operating section 4 can be safely sealed, which in turn makes it possible to effectively maintain the medical treatment instruments hermetic sealing. If the medical treatment instrument is provided with the above-described sealing members, the O-ring 33 will become unnecessary.

If the insertion section 3 is repetitively used, it is necessary to wash the inside of the insertion section 3, using sterilizing gas used in a sterilizing operation or high-temperature steam. The sealing members are effective in simply and thoroughly washing the inside of the insertion section 3. If the treatment section 2 is forceps, a simply-covered drive mechanism may result in a leak of high-frequency electric current for treatment purposes caused by moisture adhering to the inside of the operating section 4, which results in an operator experiencing an electrical shock. However, if the operating section 4 is sealed by use of the sealing members 100-21, 100-22, and 100-23, as provided in the present embodiment, such shock hazards can be eliminated.

Figure 17:
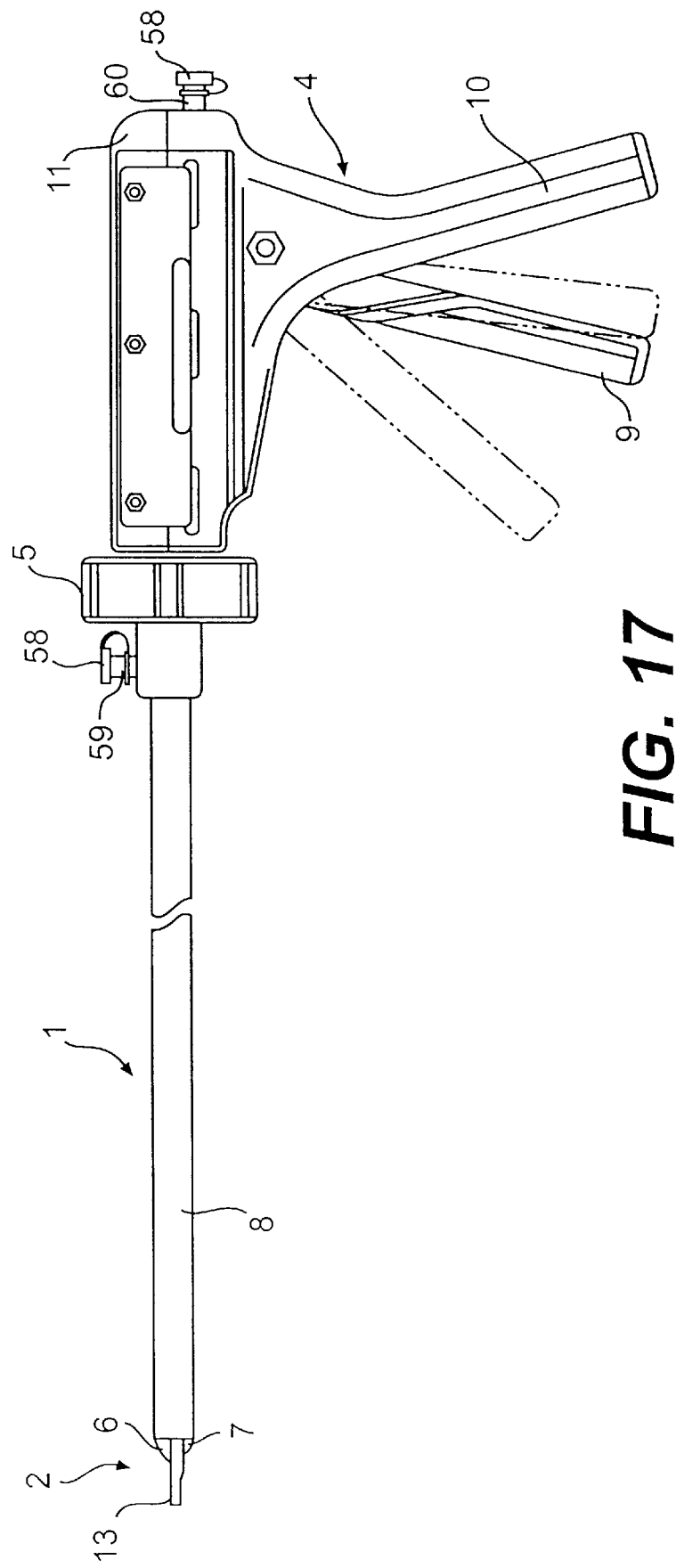
FIG. 17 is a side view of an applier of a second embodiment of the present invention.

FIG. 17 shows a second embodiment of the present invention. The applier 1 of the present embodiment is substantially the same as that of the first embodiment. Cocks 59 and 60 are respectively provided on the proximal side of the insertion section 3 and the rear end of the operating section 4 so that a fluid can flow through the insertion section 3 and the operating section 4. The opening of each of the cocks 59 and 60 is provided with a cap 58. As in the first embodiment, the insertion section 3 of the second embodiment is provided with the O-ring 33 to maintain the airtightness of the insertion section 3.

The equipment such as an applier 1 is normally used in a pneumoperitoneum. At this time, the gas used in bulging the pneumoperitoneum is apt to escape to the outside under the pressure of the pneumoperitoneum. If equipment like the applier 1 is inserted into the pneumoperitoneum, the gas tries to flow into the inside of the equipment. In some cases, blood and so on enters the inside of the applier I through the attaching section 2 along with the gas. The thus-entered blood sticks to the attaching section, which in turn hinders the operation of the applier 1. If this is the case, the applier 1 must be replaced with a new one even if the applier 1 still stores many suturing and ligating elements therein.

To prevent this problem, the insertion section 3 is provided with the cock 59 which communicates with the inside of the insertion section 3. A wash such as a physiological salt solution or air is supplied to the inside of the insertion section 3 through the cock 59, whereby sticks are easily eliminated from the inside of the insertion section 3 during the course of surgery. Consequently, the applier 1 can be used until it becomes empty of all the suturing and ligating elements 2. If it is not necessary to wash the applier 1, the cap 58 is covered with the cock 59 to prevent the gas from escaping from the pneumoperitoneum.

Similarly, an operating condition of the operating section 4 often becomes worse as a result of blood and so on sticking to the operating section 4. Even in such a case, there is no other alternative but to replace the applier 1 with a new one in the conventional art.

The operating section 4 can be washed by opening the closure 11 in the present embodiment. However, it is troublesome to disassemble the operating section 4 during the course of surgery by opening the closure 11. To prevent such a troublesome washing operation, the cock 60 is provided on the rear end of the operating section 4 so as to communicate with the inside of the operating section 4, whereby the inside of the operating section 4 can be easily washed in the same manner as previously described. As a result, the applier 1 can be used until it becomes empty of all the suturing and ligating elements 12 stored therein. Like the cock 59, the cock 60 is also covered with the cap 58.

If a connecting portion of each of these cocks 59 and 60 is designed like a lure-lock mouthpiece so that it can be easily connected to a tube used in supplying water or sucking fluid from a patient during the course of surgery, it will be very effective because the washing of the applier 1 can be washed more easily.

As a matter of course, the cocks 59 and 60 can be used in normal washing and sterilizing of the applier after use. Particularly, if the inside of the applier 1 is previously washed by utilization of the cock 60, dirt is removed to a certain extent when compared with a case where the inside of the applier is directly brushed from the beginning. Therefore, a risk of splashing of dirty water as a result of brushing is reduced accordingly, which contributes to improving safety for staffs engaging in washing and sterilizing the medical treatment instrument.

As previously described above, the applier 1 is not limited to a particular structure so long as the objects of the present invention are achieved; namely, down-sizing of disposable portions, improving ease of disassembly and reassembly, use of an applier suitable for the operator and the type of surgery, improving safety for the operator, improving ease of washing and sterilization, and use of a conduit for washing and sterilizing the inside of the applier.

Figure 18:
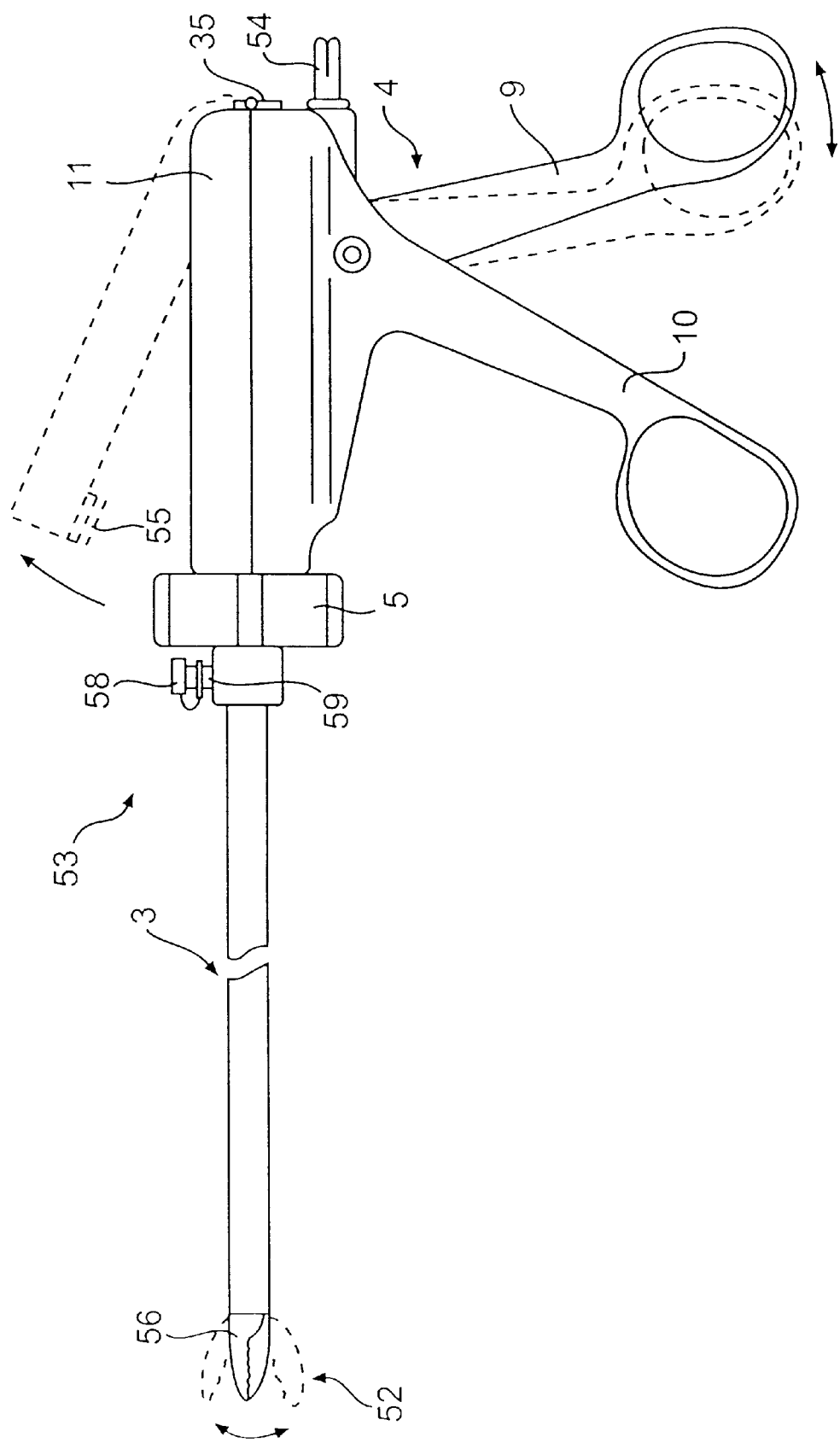
FIG. 18 is a side view of an applier of a third embodiment of the present invention.
Figure 19:
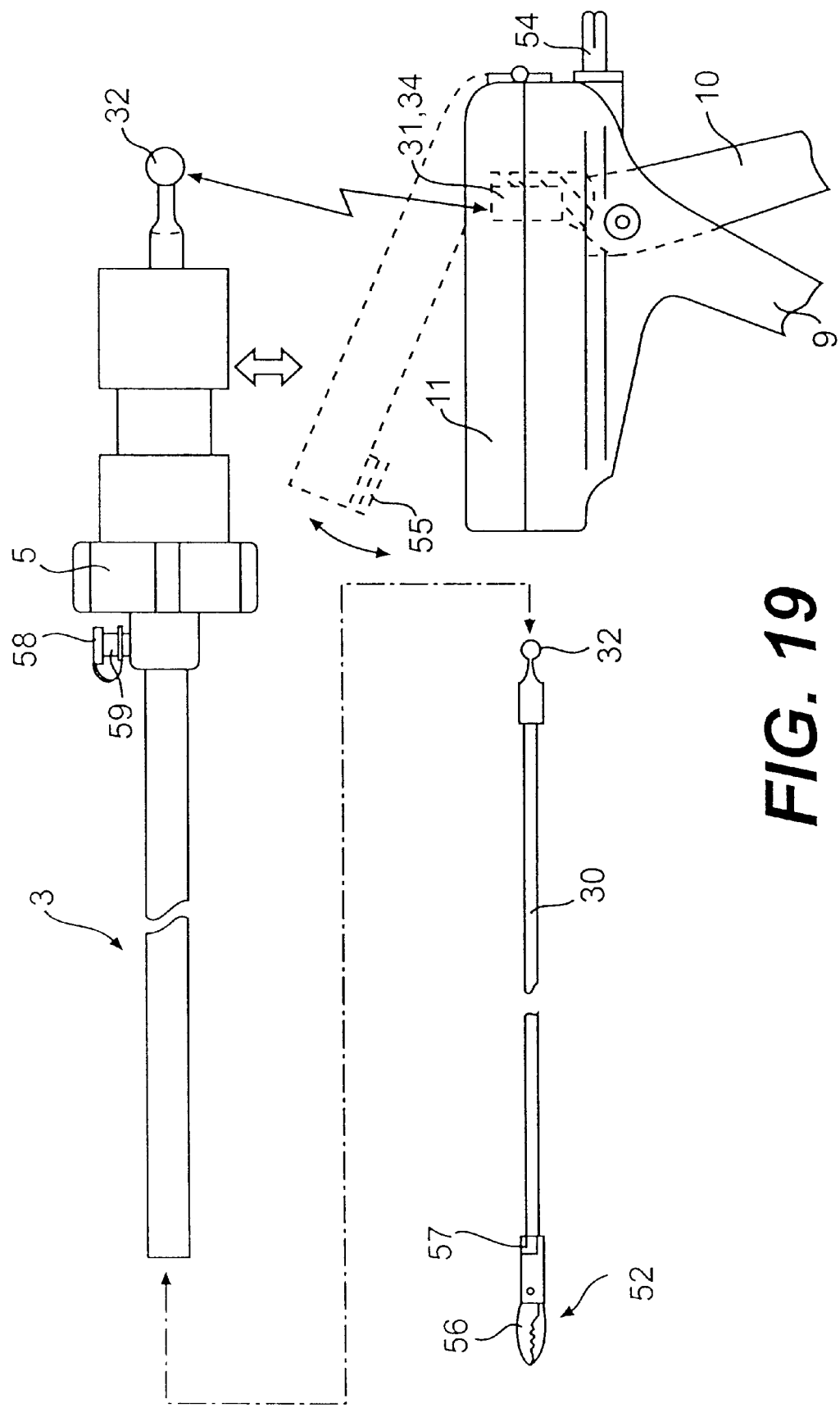
FIG. 19 is a side view of a disassembled state of the applier of the third embodiment.

FIGS. 18 and 19 show a third embodiment of the present invention. FIG. 18 shows the overall structure of a forceps 53. The forceps 53 is provided with a treatment section 52 for grasping, peeling, or cutting tissue. The treatment section 52 comprises a pair of jaws 56 capable of opening and closing so as to carry out grasping and peeling actions. The forceps 53 has the insertion section 3 for guiding the treatment section 52 to the inside of the tissue.

The operating section 4 is provided on the proximal side of the insertion section 3 for opening and closing the jaws 56. Any type of jaws can be used as the jaws 56. If the jaws are in the shape of, e.g., scissors, they can cut tissue.

The insertion section 3 is rotatable with respect to the operating section 4 and can be rotated by actuating the knob 5. The knob 5 is provided with the cock 59 as in the second embodiment.

A live pin 54 electrically connected to the jaws 56 is provided on the back of the operating section 4. It is possible to supply a high-frequency current to the jaws 56 by connecting the live pin 54 to an unillustrated RF power supply.

The closure 11 is provided on the top of the operating section 4, and the hinge 35 is attached to the rear end of the closure 11. Further, an engaging claw 55 is provided on the front end of the closure 11. Like the snap fit 36 of the first embodiment, the engaging claw 55 engages with the fixed handle 9, whereby the closure 11 is fixed to the fixed handle 10. The closure 11 can freely open and close around the hinge 35 with respect to the fixed handle 10. As a result of opening of the closure 11, the drive mechanism 40 within the operating section 4 can be uncovered, as well as the insertion section 3 being attached to or removed from the operating section 4.

The forceps 53 are designed such that the jaws 56 close by closing the movable handle 9. The jaws 56 grasp or peel tissue when opening or closing by the opening or closing action of the movable handle 9. Further, tissue can be cauterized or bleeding can be stopped by supplying a high-frequency electrical current to the jaws 56.

FIG. 19 shows a disassembled state of the forceps 53. The treatment section 52 can be attached to or removed from the distal end side of the insertion section 3 by means of a cam slit 57 and an unillustrated cam lock mechanism, or a cam pin, provided in the insertion section 3. An operation rod 30 for driving the jaws 56 extends as far as the proximal end of the insertion section 3. When the treatment section 52 and the insertion section 3 are assembled into a single unit, the operation rod 30 passes through the inside of the insertion section 3 so as to project from the proximal end of the insertion section 3. The ball 32 for engaging with the washer 34 of the engaging slit 31 formed in the handle 9 is formed on the tip end of the operation rod 30.

The insertion section 3 and the operating section 4 are disassembled and reassembled in the same way as in the first embodiment; namely, they are disassembled and reassembled by opening the closure 11. In practice, the treatment section 52 is fitted to the insertion section 3, and the insertion section 3 is then fitted to the operating section 4, whereby the forceps 53 is completed.

Airtightness is ensured while the treatment section 52 and the insertion section 3 are assembled into a single unit by combination of the treatment section 52 with the insertion section 3 in the present embodiment. For example, an elastic sealing member such as an O-ring may be provided in the insertion section 3, and the operation rod 30 may engage with the elastic sealing member. Further, the airtightness of the overall forceps 53 is ensured by attaching the insertion section 3 to the operating section 4 and closing the closure 11. In this case, the closure 11 and the engaging area between the insertion section 3 and the operating section 4 may be provided with sealing member such as a packing. Further, the insertion section 3 has a circular cross section, which prevents the gas from escaping from the pneumoperitoneum through the forceps 53 at the time of endoscopic treatment.

By virtue of the aforementioned arrangement, it is possible to arbitrarily use, e.g., different types of treatment section 52, insertion section 3, and operating section 4, in combination. Further, the treatment section 52, the insertion section 3, and the operating section 4 can be disassembled and reassembled, and the inside of the operating section 4 can be uncovered by opening the closure 11. As a result, each portion of the forceps 53 can be completely washed and sterilized. Therefore, the overall of the forceps 53 becomes reusable, which eliminates the necessity of disposable portions and enables replacement of only an impaired portion if the forceps is broken. Further, since a drive mechanism is stored in the operating section 4, injury to fingers and hands of an operator and a leak of a high-frequency current are prevented.

As described above, the forceps 53 are not limited to a particular structure so long as the objects of the present invention are achieved; namely, down-sizing of disposable portions, improving ease of disassembly and reassembly, use of a forceps suitable for the operator and the type of surgery, and improving safety for the operator.

Figure 20:
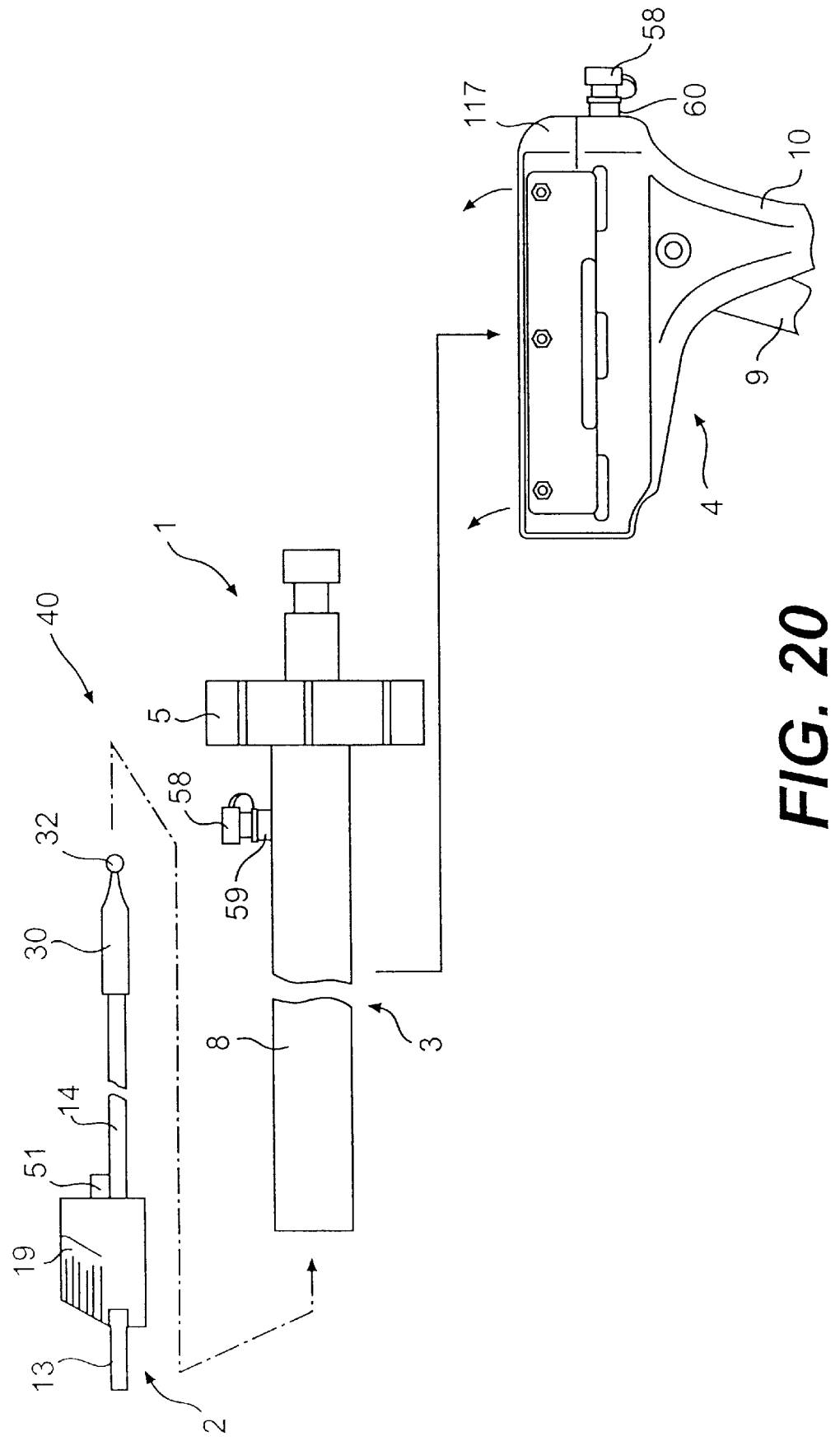
FIG. 20 is a side view of a disassembled state of an applier of a fourth embodiment of the present invention.

FIG. 20 shows a fourth embodiment of the present invention. The applier 1 of the present embodiment can be disassembled into and reassembled from the attaching section 2 which is integral with the pusher 14, the insertion section 3 which serves as endoscopic, and the operating section 4.

The attaching section 2 is provided with the storage section 19. The suturing and ligating elements 12 are vertically stacked in the storage section 19. The suturing and ligating elements 2 are fed one by one by the actuation of the operating section 4. An attachment claw 51 is provided on the back of the attaching section 2. The attaching section 2 is connected to the insertion section 3 by engaging the attachment claw 51 with the outer sheath tube 8 of the insertion section 3.

As described above, the suturing and ligating elements 12 are stored in the attaching section 2, and the attaching section 2 is removably attached to the insertion section 3 together with the pusher 14. As a result, the inside of the insertion section 3 can be thoroughly washed and sterilized.

In other respects, the applier 1 is the same as the applier 1 of the second embodiment in construction. Specifically, the applier 1 is the same as that of the first embodiment in that the insertion section 3 is attached to the operating section 4 from above by opening the closure 11. By virtue of this construction, a drive mechanism is housed in the operating section 4.

The airtightness of the areas between the attaching section 2, the insertion section 3, and the operating section 4 is ensured in the same manner as in the third embodiment, whereby a gas leak from the pneumoperitoneum during endoscopic treatment is prevented.

As previously described, the inside of both the insertion section 3 and the operating section 4 can be thoroughly washed and sterilized in the present embodiment. Therefore, the attaching section 2 can be replaced as a cartridge, whereas the insertion section 3 and the operating section 4 become reusable. When compared with a conventional applier which is totally disposable, the applier of the present embodiment leads to substantial reductions in costs and the amount of waste. In a case where there are prepared a plurality of attaching section 2 storing a different number of suturing and ligating elements or having different sizes, a plurality of inserts 3 which are curved or shorter, and a plurality of operating section 4 differing from each other in shape; e.g., having different in-line shapes, it is possible to construct the applier 1 suitable for the preference of an operator and a method of surgery. Further, in case of breakage, it is possible to minimize portions to be wasted by solely replacing broken portions.

As described above, the applier 1 is not limited to a particular structure so long as the objects of the present invention are achieved; namely, down-sizing of disposable portions, improving ease of washing and sterilization, use of an applier suitable for the operator and the type of surgery, improving safety for the operator, and improving ease of disassembly and reassembly.

Figure 21:
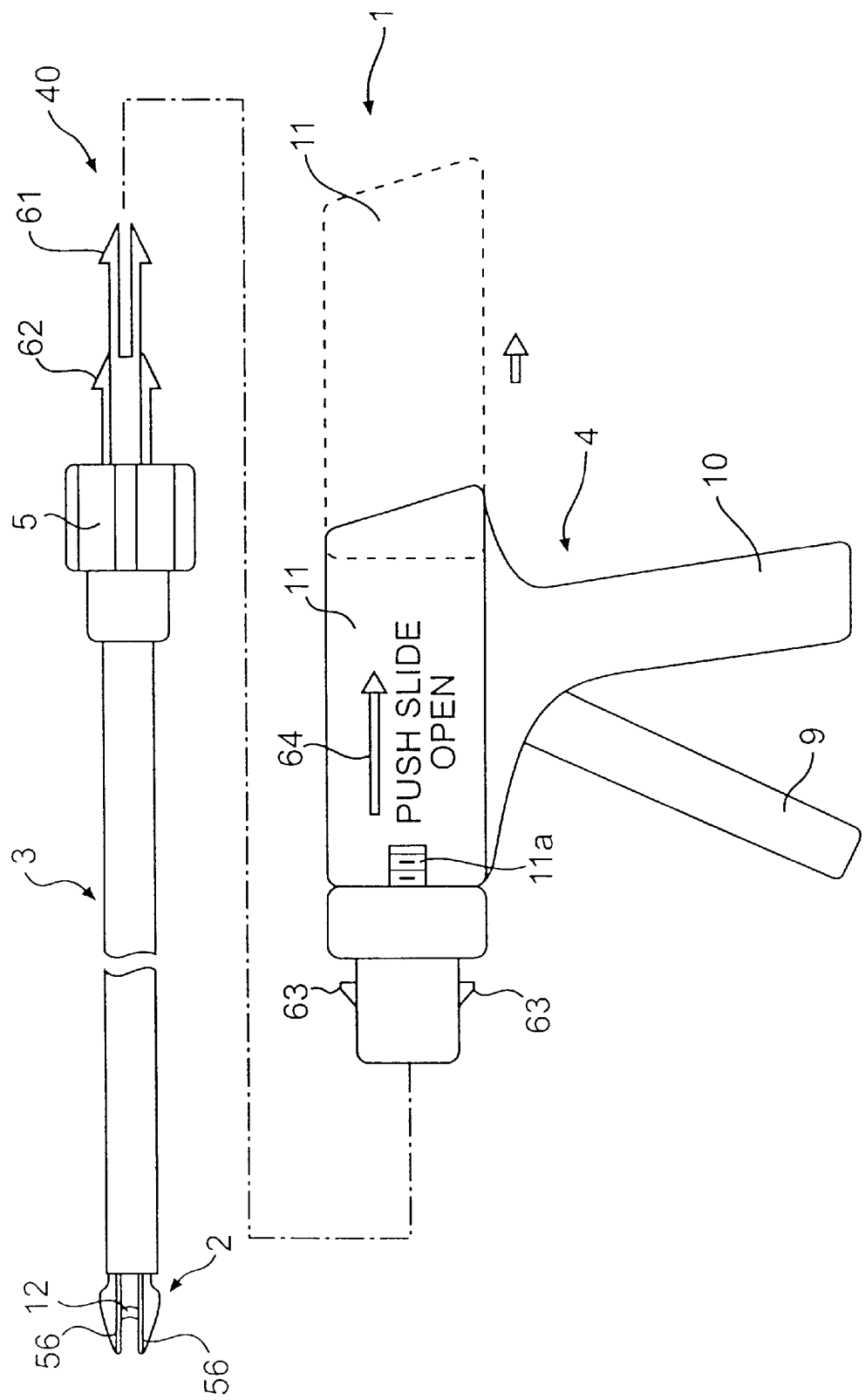
FIG. 21 is a side view of a disassembled state of an applier of a fifth embodiment of the present invention.
Figure 22:
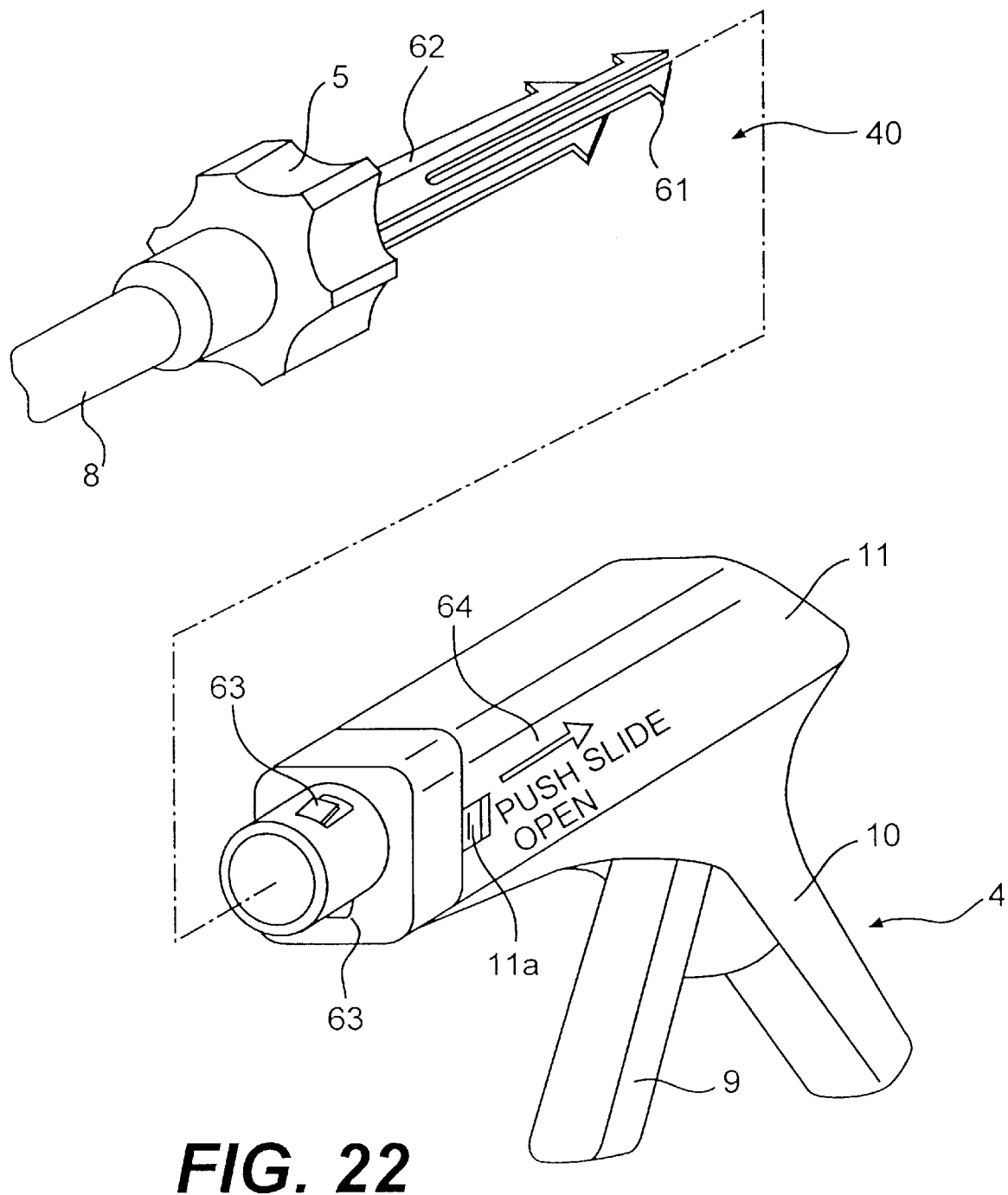
FIG. 22 is a perspective view of the exploded applier of the fifth embodiment.
Figure 23:
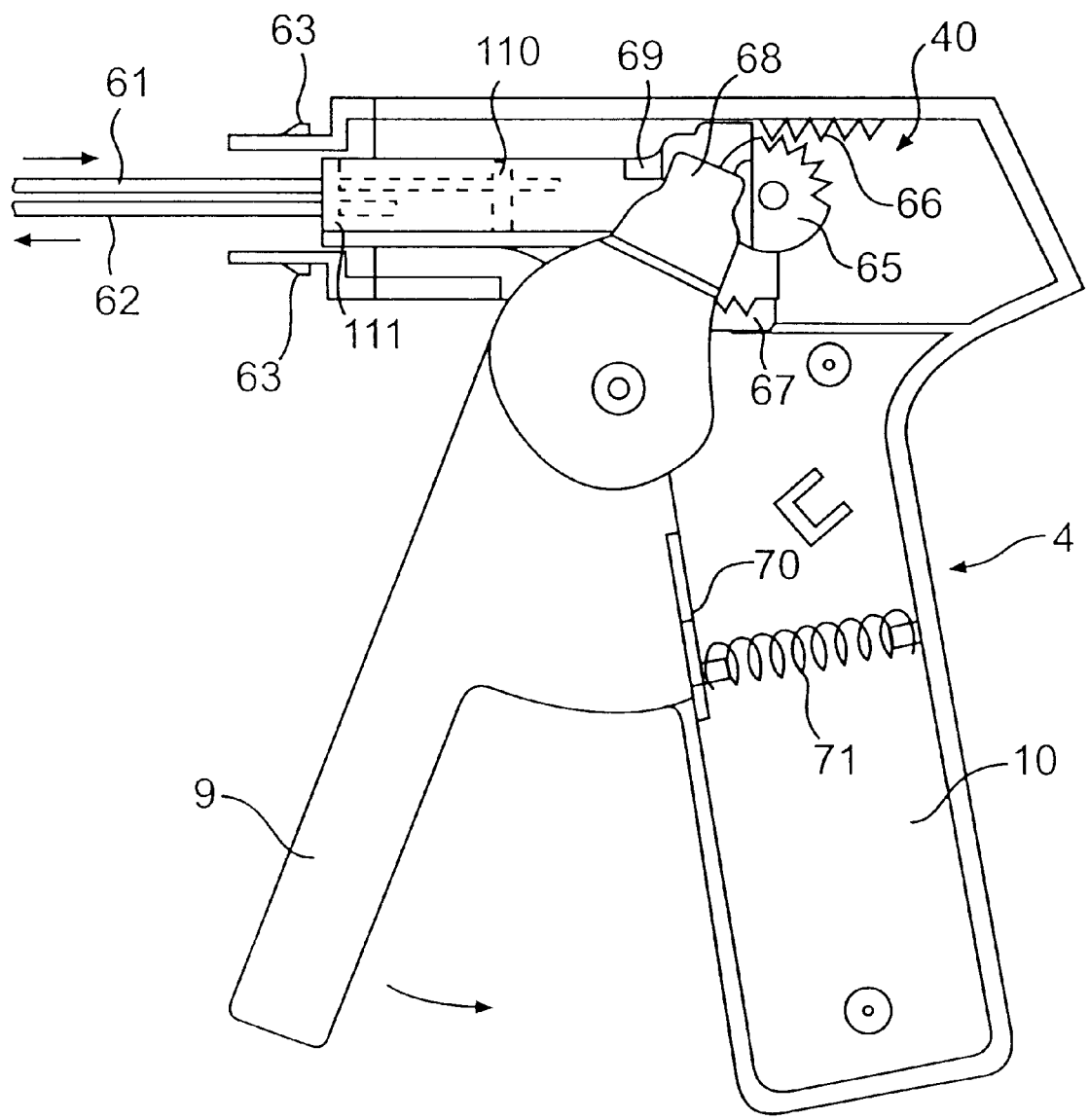
FIG. 23 is a longitudinal side view of the drive mechanism of the applier of the fifth embodiment.

FIGS. 21 to 23 show a fifth embodiment of the present invention. The applier 1 of the present embodiment comprises the insertion section 3 which is integral with the attaching section 2, as shown in FIGS. 21 and 22. A plurality of clips which are the suturing and ligating elements 12 are stored in the storage section 19 housed in the insertion section 3. The insertion section 3 can be removed from and attached to the operating section 4, and they are fastened to each other by engagement of the knob 5 with a knob attachment claw 63.

The closure 11 of the operating section 4 slides backwards with respect to the fixed handle 10 by backwardly drawing a slide stopper 11a in a pushing manner in accordance with the wording printed on an indication 64, whereby the drive mechanism 40 of the operating section 4 can be uncovered. Elastic claws on the tip ends of a bifurcated jaws closing member 62 for actuating the jaws 56 to close a clip of the attaching section 2, and elastic claws on the tip ends of a bifurcated clip feed member 61 for loading a clip into the jaws 56 engage with the drive mechanism 40. These members 61 and 62 can disengage from the drive mechanism 40 by opening the closure 11 with respect to the fixed handle 10. As a result, the insertion section 3 can be attached to or removed from the operating section 4.

The airtightness of the applier 1 is ensured by closing the closure 11 while the insertion section 3 and the operating section 4 are joined together in the present embodiment. Sealing member; e.g., an O-ring, may be provided in the area where the insertion section 3 engages with the operating section 4, and the closure 11 may be provided with a packing and so on. Coupled with the circular cross section of the insertion section 3, the sealing member prevents a leak of gas from the pneumoperitoneum through the applier 1 during endoscopic surgery.

With the foregoing arrangement, the inside of the operating section 4 can be washed and sterilized. Consequently, the insertion section 3 and the attaching section 2 of the applier 1 can be made replaceable like a cartridge, whereas the operating section 4 can be made reusable. As in the previous embodiments, if there are prepared a plurality of inserts 3 and operating section 4, they may be used in arbitrary combination. Further, in case of breakage of the applier 1, solely the broken portions can be replaced.

FIG. 23 shows the drive mechanism 40 of the operating section 4. The movable handle 9 is pressed in an opening direction by a return spring 71. An upper portion of the movable handle 9 is formed into a rotary arm 68, and a drive claw 69 formed on a jaws closing-and-actuating member 111 for driving the jaws closing member 62 meshes with the rotary arm 68. A first gear 66 is formed on the jaws closing-and-actuating member 111 and moves together with a third gear 67 via a second gear 65. The third gear 67 is formed on a clip feed-and-actuation member 110 and meshes with the clip feed drive member 61.

In terms of providing safety to the operator and preventing damage to the drive mechanism 40, with such a complicated arrangement, it is impossible to normally maintain the drive mechanism 40 of the operating section 4 exposed. For these reasons, the drive mechanism 40 of the conventional art cannot be washed and sterilized. In contrast, since the drive mechanism 40 can be uncovered by opening the closure 11 as required, it can be easily washed and sterilized in the present embodiment.

If the movable handle 9 is moved in a closing direction, the rotary arm 68 forces the drive claw 69 forwardly, whereby the jaws closing member 62 also moves forwards. As a result, the jaws 56 are closed. Associated with the closing action of the jaws 56, the first gear 66 travels forwardly, and the second gear 65 meshing with the first gear 66 rotated counterclockwise. Together with the counterclockwise movement of the second gear 65, the third gear 67 is driven backwardly, whereby the clip feed member 61 travels backwards.

When the movable handle 39 has completely closed, the jaws 56 are completely closed as well. Then, the clip loaded into the jaws 56 is attached to tissue. Concurrently, the clip feed member 61 travels to the rear of the clip to be subsequently loaded. The movable handle 9 is opened by means of the elastic force of the return spring 71, so that the jaws closing member 62 recedes. As a result, the jaws 56 are opened, and a clip is ejected. When the movable handle 9 has fully opened, the clip feed member 61 travels forwardly, and the next clip is loaded into the jaws 56. The clips are attached to tissue one after another through repetition of the aforementioned procedures.

As described above, the applier 1 is not limited to particular structure so long as the objects of the present invention are achieved; namely, down-sizing of disposable portions, improving ease of washing and sterilization of each section, improving safety for the operator, and use of the forceps suitable for the operator and the type of surgery.

Figure 24:
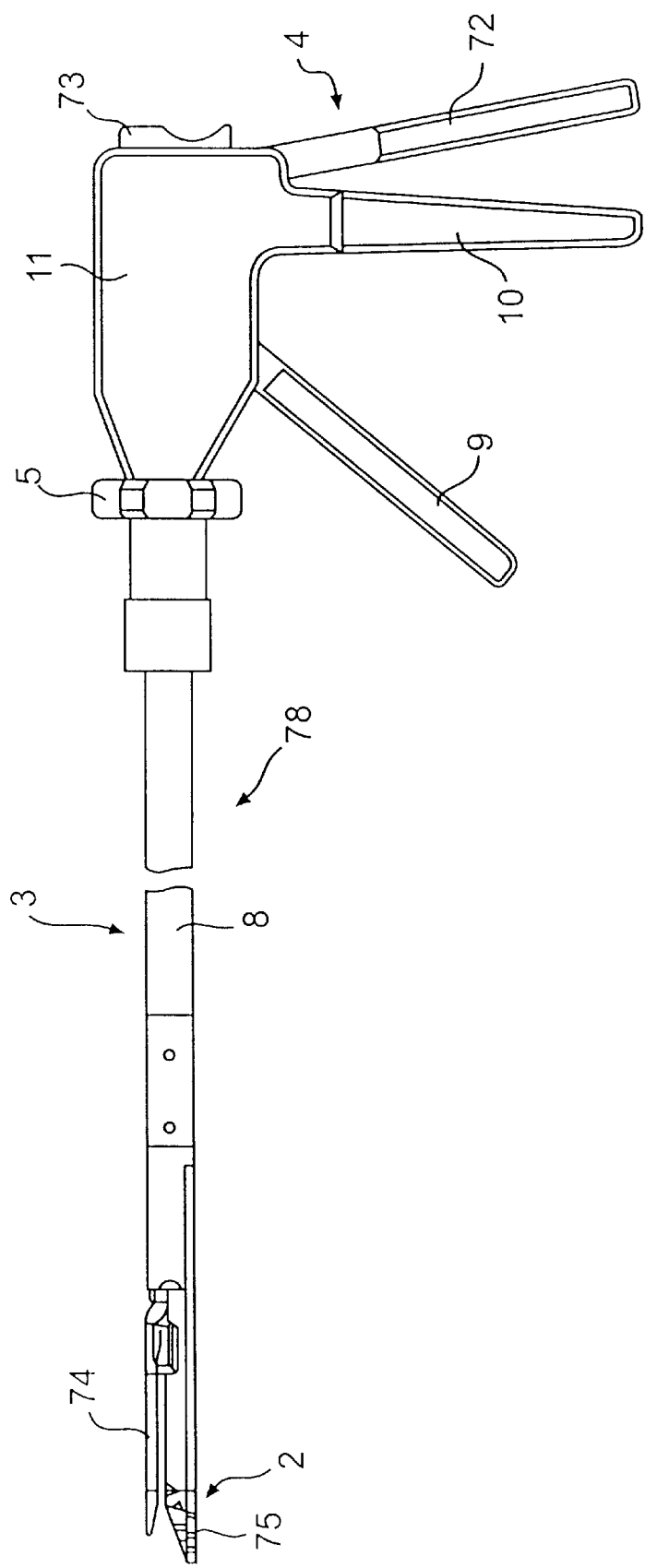
FIG. 24 is a side view of an automatic suturing instrument of a sixth embodiment of the present invention.
Figure 25:
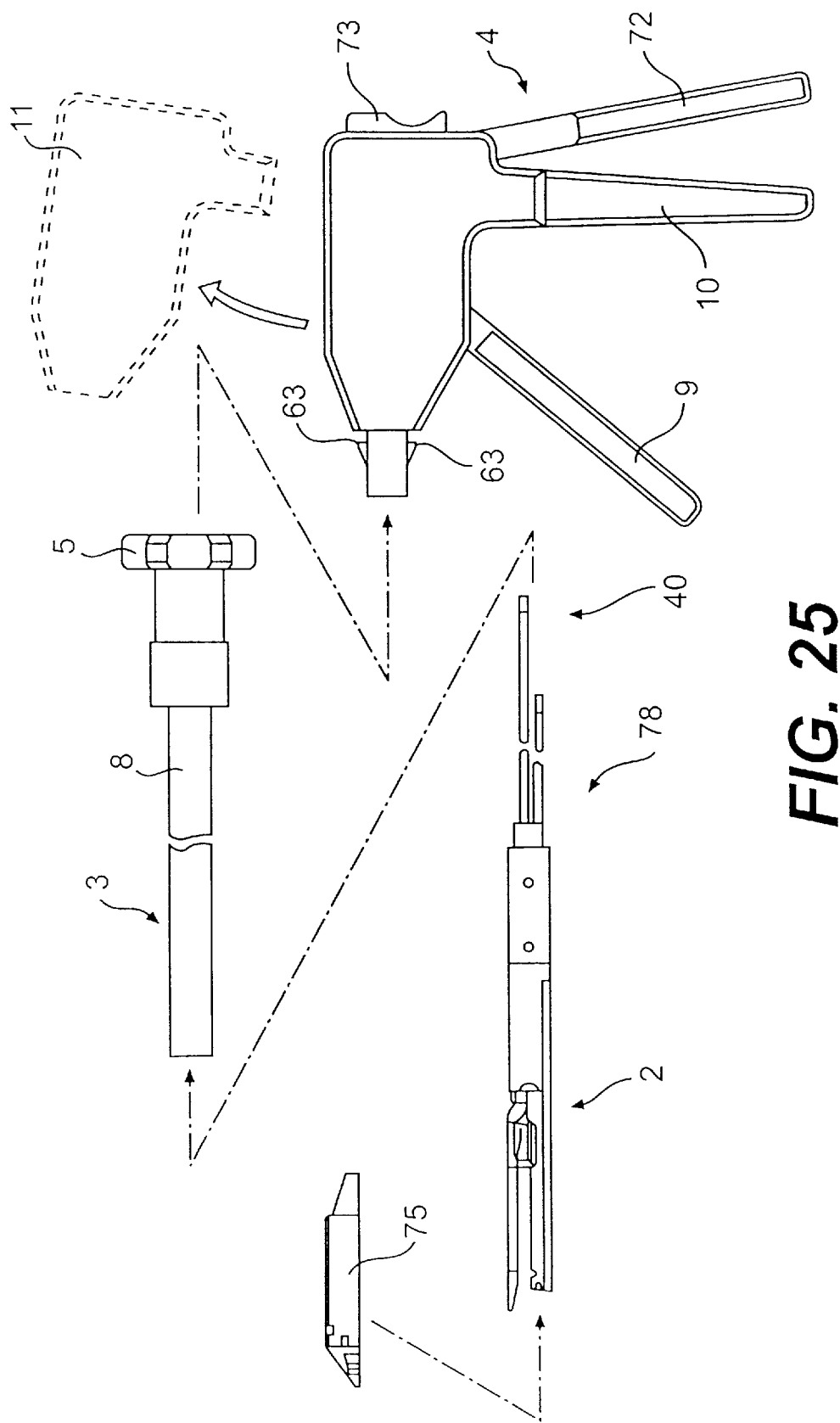
FIG. 25 is a side view of a disassembled state of the automatic suturing instrument of the sixth embodiment.

FIGS. 24 and 25 show a sixth embodiment of the present invention. The present embodiment shows an automatic suturing instrument 78. As shown in FIG. 24, the automatic suturing instrument 78 is made up of the attaching section 2, the insertion section 3, and the operating section 4. A cartridge 75 housing a plurality of staples for suturing purposes is fitted to the attaching section 2. An anvil 74 for clinching the staple is provided so as to open and close with respect to the cartridge 75.

The operating section 4 is provided with the movable handle 9 for actuating an unillustrated cutter by ejecting a staple, an anvil closing lever 72 for closing the anvil 74, and a release button 73 for releasing the anvil closing lever 72.

To begin with, the automatic suturing instrument 78 grasps tissue between the anvil 74 and the cartridge 75. Subsequently, the anvil closing lever 72 is closed, whereby the anvil 74 is closed so as to fix the tissue. The movable handle 9 is then closed, whereby a staple is ejected to suture the tissue. The cutter is then actuated to cut the tissue. The movable handle 9 is then released, and the release button 73 is pressed. As a result, the anvil 74 is opened again, thus completing the suturing and cutting of tissue. If it is desired to continue the same operation, the suturing and cutting of the tissue will be carried out again by replacing only the cartridge 75.

FIG. 25 shows a disassembled state of the automatic suturing instrument 78 before it is assembled. The automatic suturing instrument 78 can be disassembled into and reassembled from the cartridge 75, the attaching section 2, the insertion section 3, and the operating section 4. Unillustrated sealing member are provided in the attaching section 2. Coupled with the circular cross section of the insertion section 3, the sealing member prevents gas from escaping from the pneumoperitoneum through the automatic suturing instrument 78 during the course of endoscopic treatment. The closure 11 is provided on one side of the operating section 4. The drive mechanism 40, housed in the operating section 4, can be uncovered by removing the closure 11. At the same time, the attaching section 2 can be removed from and attached to the operating section 4. As previously discussed in the fifth embodiment, it was necessary to store the complicated drive mechanism 40 in the operating section 4 in the conventional art. However, it is impossible to wash the inside of the operating section 4, and therefore there is no other alternative but to render the overall automatic suturing instrument disposable. The inside of the operating section 4 can be washed and sterilized by removing the closure 11 in the present embodiment. Further, the disassembly and reassembly of each part of the automatic suturing instrument are possible. For example, since the inside of the insertion section 3 and the attaching section 2 can be thoroughly washed and sterilized, the automatic suturing instrument, except for the cartridge, can be reused. Consequently, the user can significantly reduce costs and wastes, which in turn contributes to the reduction of medical expenditures and of resources.

Each part of the automatic suturing instrument of the present embodiment can be disassembled and reassembled. As in the previous embodiments, the present embodiment provides the same effects; namely, if a plurality of cartridges 75 are prepared, attaching section 2, inserts 3, and operating section 4, they can be used in arbitrary combination. Further, only the broken portions of the automatic suturing instrument can be replaced.

As previously described, the automatic suturing instrument 78 is not limited to a particular structure so long as the objects of the present invention are achieved; namely, down-sizing of disposable portions, improving ease of washing and sterilization, improving ease of disassembly and reassembly, improving safety for the operator, and use of an applier suitable for the operator and the type of surgery.

Figure 26:
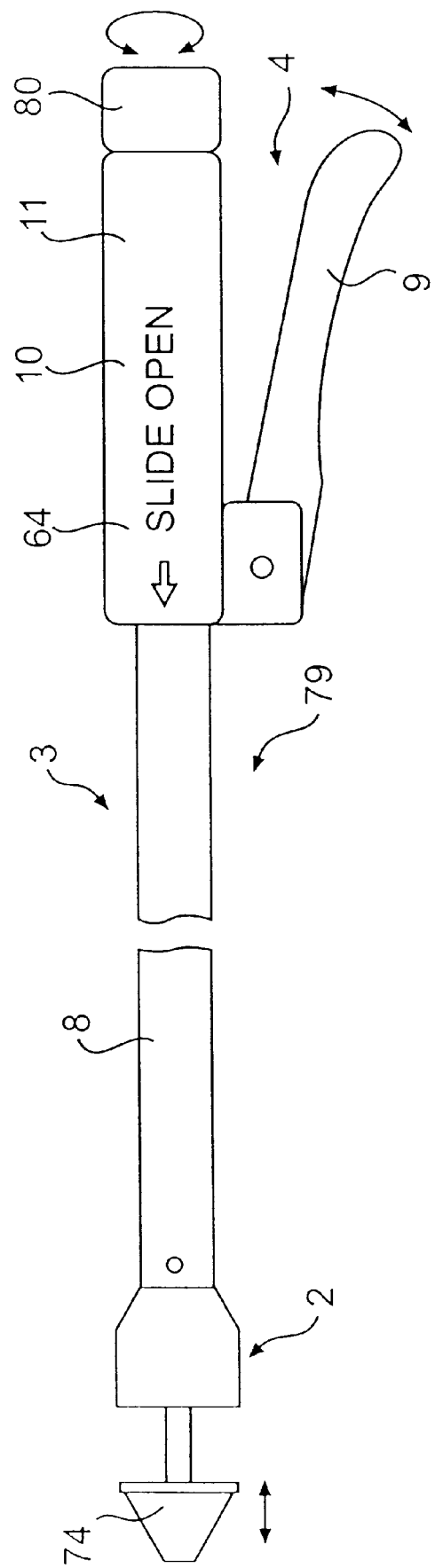
FIG. 26 is a side view of an anastomosing instrument of a seventh embodiment of the present invention.
Figure 27:
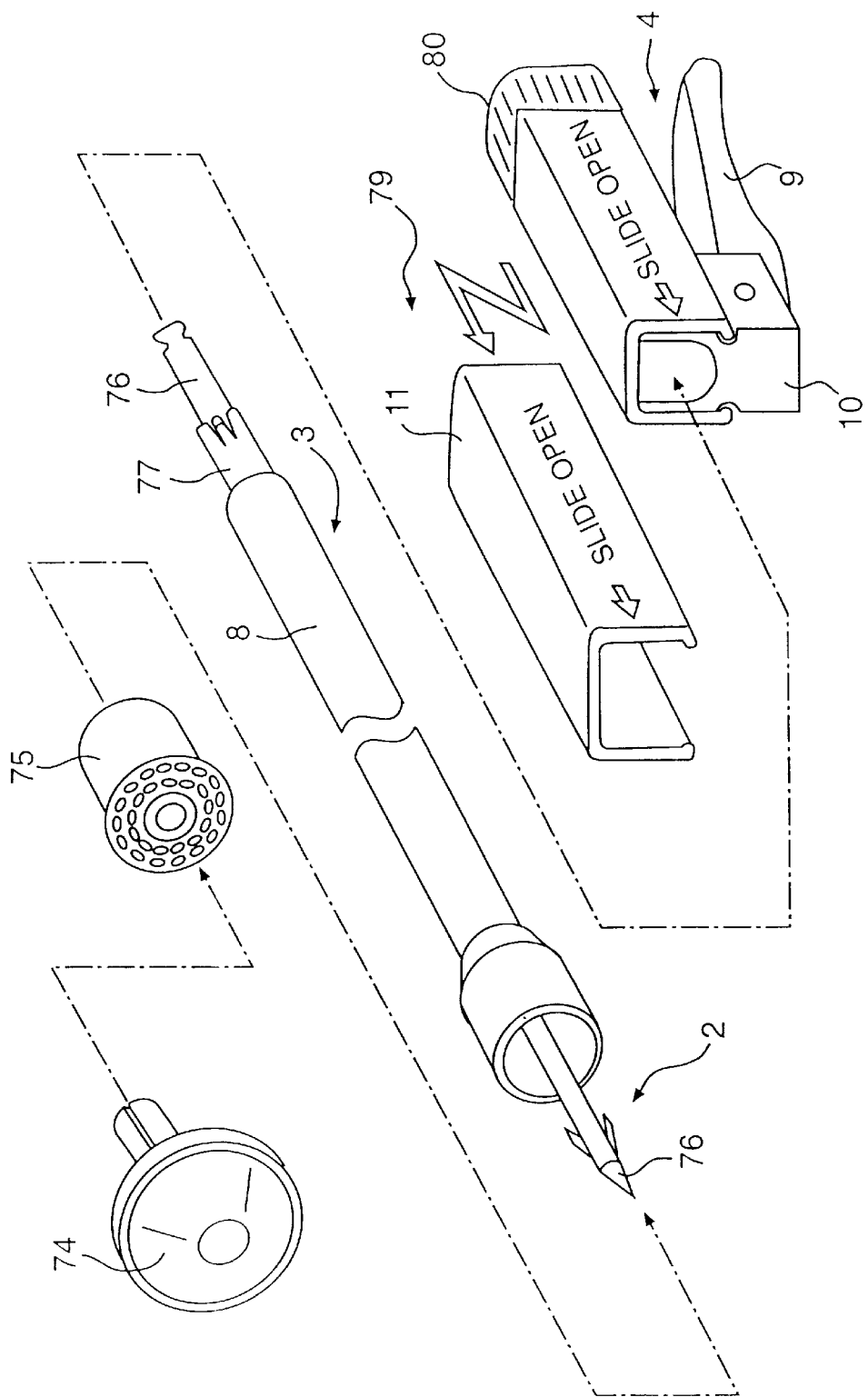
FIG. 27 is a perspective exploded view of the anastomosing instrument of the seventh embodiment.

FIGS. 26 and 27 show a seventh embodiment of the present invention. As shown in FIG. 26, an anastomosing instrument 79 of the seventh embodiment is made up of the attaching section 2, the insertion section 3, and the operating section 4. The attaching section 2 comprises the anvil 74, which receives and clinches a staple, and the cartridge 75 which stores a plurality of staples. The operating section 4 is comprised of the fixed handle 10, the movable handle 9, and a gap control knob 80 provided back of the fixed handle 10 used for opening and closing the anvil 74 with respect to the cartridge 75. A drive mechanism 41 is housed in the fixed handle 10 for ejecting a staple and cutting tissue. The drive mechanism is covered with the closure 11, and this closure 11 is opened when it is forwardly slid in accordance with the indication 64. As a result, the drive mechanism 40 is externally uncovered, and hence it is possible to thoroughly wash and sterilize the inside of the operating section 4.

FIG. 27 shows a disassembled state of the anastomosing instrument 79 before it is assembled. The anastomosing instrument 79 can be disassembled into and reassembled from the anvil 74, the cartridge 75, the insertion section 3, the operating section 4, and the closure 11. The anvil 74 is attached to an anvil drive member 76 and moves to and from associated with rotation of the gap control knob 80, as previously described. The cartridge 75 is attached to the tip end of the insertion section 3. The insertion section 3 is attached to the operating section 4 by insertion. Simultaneously, a fire member 77 and the anvil drive member 76 are connected to the inside of the drive mechanism 40. An unillustrated circular cutter is attached to the rear end of the cartridge provided on the tip end of the insertion section 3.

With the above-described arrangement, the anastomosing instrument 79 can be disassembled into or reassembled from the previously-described components. Further, the inside of the operating section 4 can be uncovered, and therefore each part of the anastomosing instrument 79 can be thoroughly washed and sterilized. The anastomosing instrument 79 is reusable except for the cartridge. In consequence, as in the previous embodiments, systematization of the anastomosing instrument 79 and replacement of only the broken portions can be realized in addition to the reduction in costs, and prevention of wastes and wasted resources.

A description of operation of the anastomosing instrument 79 is as follows: To begin with the anvil 74 is opened by rotating the gap control knob 80. Target tissue is grasped between the anvil 74 and the cartridge 75. The movable handle 9 is moved in a closing direction, whereby the fire member 77 is actuated. A staple stored in the cartridge 75 is ejected to anastomoze tissue. If the movable handle 9 is closed further, the previously-described cutter travels forwardly to cut the tissue. Subsequently, the movable handle 9 is released, and the gap control knob 80 is controlled so as to release the anvil 74, which completes the anastomosing and cutting of tissue.

As described above, the anastomosing instrument 79 is not limited to a particular structure so long as the objects of the present invention are achieved; namely, down-sizing of disposable portions, improving ease of washing and sterilization, improving ease of disassembly and reassembly, improving safety for the operator, and use of an applier suitable for the operator and the type of surgery.

Figure 28:
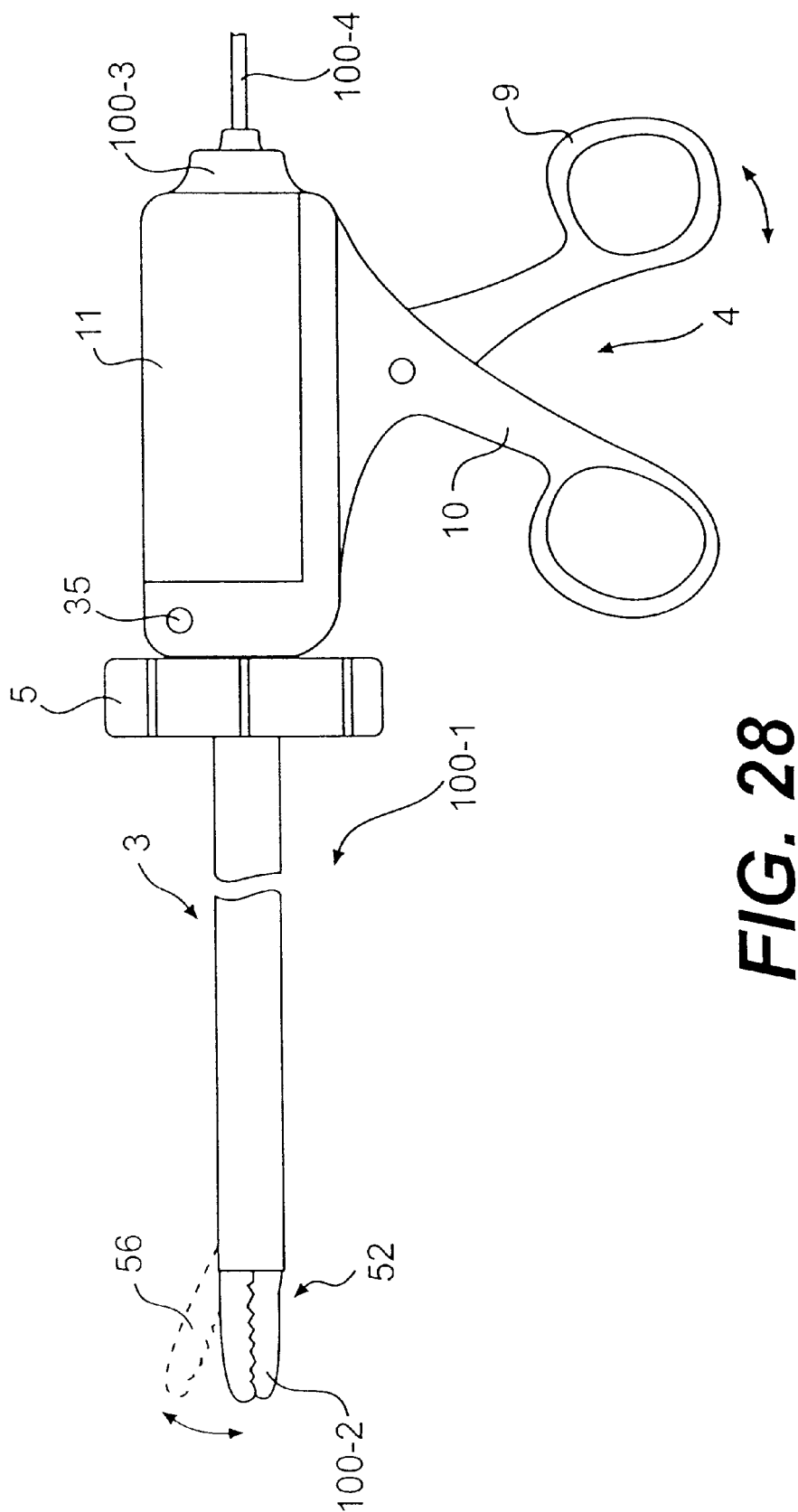
FIG. 28 is a side view of an ultrasonic clotting and incising instrument of an eighth embodiment of the present invention.
Figure 29:
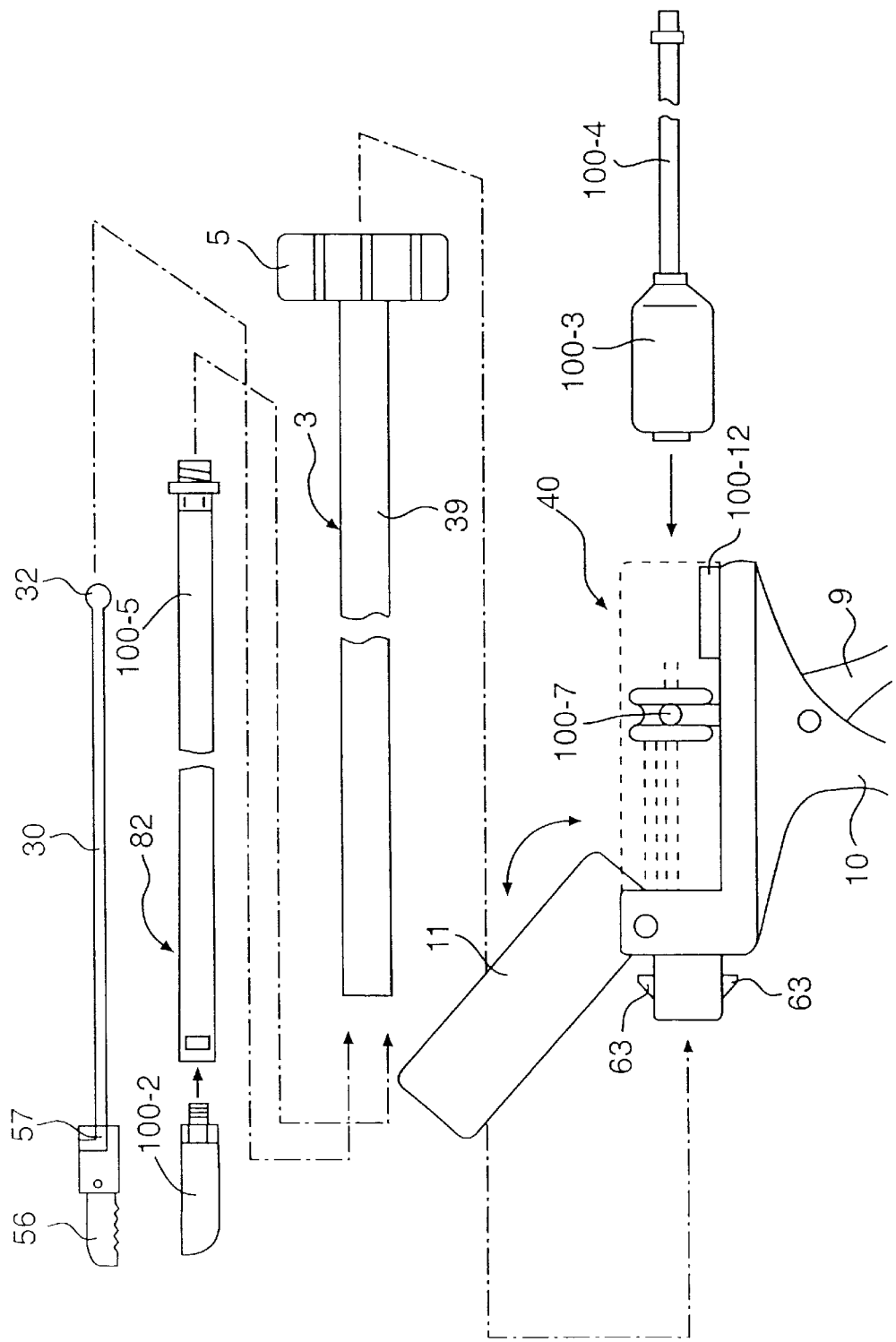
FIG. 29 is a side view of the ultrasonic clotting and incising instrument of the eighth embodiment when it is exploded.

FIGS. 28 and 29 show an eighth embodiment of the present invention. As shown in FIG. 28, an ultrasonic clotting and incising instrument 101 of the present embodiment is made up of the treatment section 52, the insertion section 3, and the operating section 4. The treatment section 5 comprises a tip 102 for providing tissue with ultrasonic vibrations, and the jaws 56 which open and close freely with respect to the tip 102. Tissue is grasped between the tip 102 and the jaws 56, and the thus-grasped tissue is subjected to ultrasonic vibrations, whereby the tissue can be cut or clotted without bleeding.

The jaws 56 are designed so as to open and close by opening and closing the movable handle 9 of the operating section 4. The insertion section 3 has a circular cross section suitable for endoscopic treatment and is rotatable with respect to the operating section 4 by rotating the knob 5. An ultrasonic transducer 103 is housed in an upper part of the operating section 4 and supplies ultrasonic vibrations to the tip 102. Further, the closure 11 is provided in an upper part of the operating section 4 and opens and closes around the hinge 35. The drive mechanism 40 housed in the operating section 4 and the ultrasonic transducer 103 can be uncovered by opening the closure 11. A cord 104 extends from the ultrasonic transducer 103 so as to be connected to an unillustrated power supply for driving purposes.

FIG. 29 shows a disassembled state of an ultrasonic clotting and incising instrument 101 before it is reassembled. The jaws 56 can be disassembled and reassembled as a forceps unit 82 with respect to the insertion section 3 by means of the cam slit 57 and a cam lock mechanism made of an unillustrated cam pin housed in the insertion section 3. The operation rod 30 is connected to the jaws 56 by a link mechanism or a cam mechanism. The ball 32 formed at the rear end of the operation rod 30 engages with the unillustrated engaging slit 31 of a ring 100-6 which is rotatably connected to the movable handle 9 of the operating section 4 by a drive pin 100-7 in a slidable manner. With this arrangement, the jaws 56 can open and close by opening and closing the movable handle 9 in the manner as previously described.

A tip 100-2 is screwed into a probe 100-5, and they are further screwed into an ultrasonic transducer 100-3. A cord 100-4 extends from the ultrasonic transducer 100-3 and is also provided with a connector 100-8 in the manner as previously described. The connector 100-8 is connected to an unillustrated drive power. These elements are provided along with the longitudinal center of the insertion section 3. As previously described, the forceps unit 82 is also rotatably connected to the operating section 4 by means of the ring 100-6. Therefore, the forceps unit 82 can rotate with respect to the operating section 4 in conjunction with the insertion section 3. At this time, rotation of the ultrasonic transducer 100-3 prevents the cord 100-4 from being twisted. To this end, the cord 100-4 is electrically and rotatively connected to the ultrasonic transducer 100-3 by; e.g., a slidable contact.

The insertion section 3 is rotatably connected to the operating section 4 by the knob attachment claw 63, and the previously-described ultrasonic transducer 100-3 is also rotatably connected to the operating section 4 by a transducer receiver 100-12. The ultrasonic transducer 100-3 and the operation rod 30 can be attached to or removed from the operating section 4 by opening the closure 11. In the present embodiment, the drive mechanism 40 and the probe 100-5 are completely housed in the ultrasonic clotting and incising instrument 100-1. Consequently, hands or fingers of an operator are prevented from erroneously touching the drive mechanism 40 and the probe 100-5. Further, a risk of a breakdown of the ultrasonic clotting and incising instrument from external factors becomes lower.

Such an ultrasonic transducer 100-1 is particularly effective for use in endoscopic treatment. For this reason, the cross section of the insertion section 3 is set to a circular pattern in the present embodiment, and unillustrated sealing member are provided in the insertion section 3, whereby the airtightness between the forceps unit 82 and the probe 100-5 is ensured. In this way, gas is prevented from escaping from a pneumoperitoneum through the ultrasonic clotting and incising instrument 100-1 during the course of endoscopic treatment.

Particularly, medical treatment instruments used in endoscopic treatment are difficult to disassemble and reassemble because the constituent parts of them are very small. The disassembly and reassembly of such medical treatment instruments put a heavy burden particularly on an assistant in charge of equipment. The disassembly and reassembly of the constituent parts of the ultrasonic clotting and incising instrument are very simple in the present embodiment, which makes it possible to reduce such a burden on the assistant.

As described above, the ultrasonic clotting and incising instrument can be disassembled into or reassembled from the constituent parts in the present embodiment. Since the inside of the operating section 4 can be uncovered by opening the closure 11, it is possible to thoroughly wash and sterilize the constituent parts including the parts which are particularly difficult to wash and sterilize; for example, a joint between the jaws 56 of the forceps unit 82 and the operation rod 30, the inside of the insertion section 3, and the drive mechanism 40 of the operating section 4. Consequently, the ultrasonic clotting and incising instrument 100-1 can be made completely reusable, which makes it possible to realize substantial reductions in costs and wastes and prevention of waste of resources.

By virtue of the fact that the constituent parts of the ultrasonic clotting and incising instrument are capable of being disassembled and reassembled in the way as previously described, various types of ultrasonic clotting and incising instrument 100-1 can be constituted by combination of a plurality of forceps units 82 and inserts 3; for example, the forceps units 82 and inserts 3 having different effective lengths, the different-shaped jaws 56 and tips 102, the different-shaped operating section 4, or the ultrasonic transducers 100-3 having different oscillation frequencies. As a result, it is possible to provide the ultrasonic clotting and incising instrument 100-1 suiting preferences of an operator or corresponding to a method of surgery. In the event of a trouble, it is possible to fix or replace only the broken parts.

As described above, the ultrasonic clotting and incising instrument is not limited to a particular structure or shape so long as the objects of the present invention are achieved; namely, down-sizing of disposable portions, ensuring safety for the operator, improving ease of washing and sterilization, improving ease of disassembly and reassembly, and providing an ultrasonic transducer suitable for the operator and the type of surgery.

Figure 30:
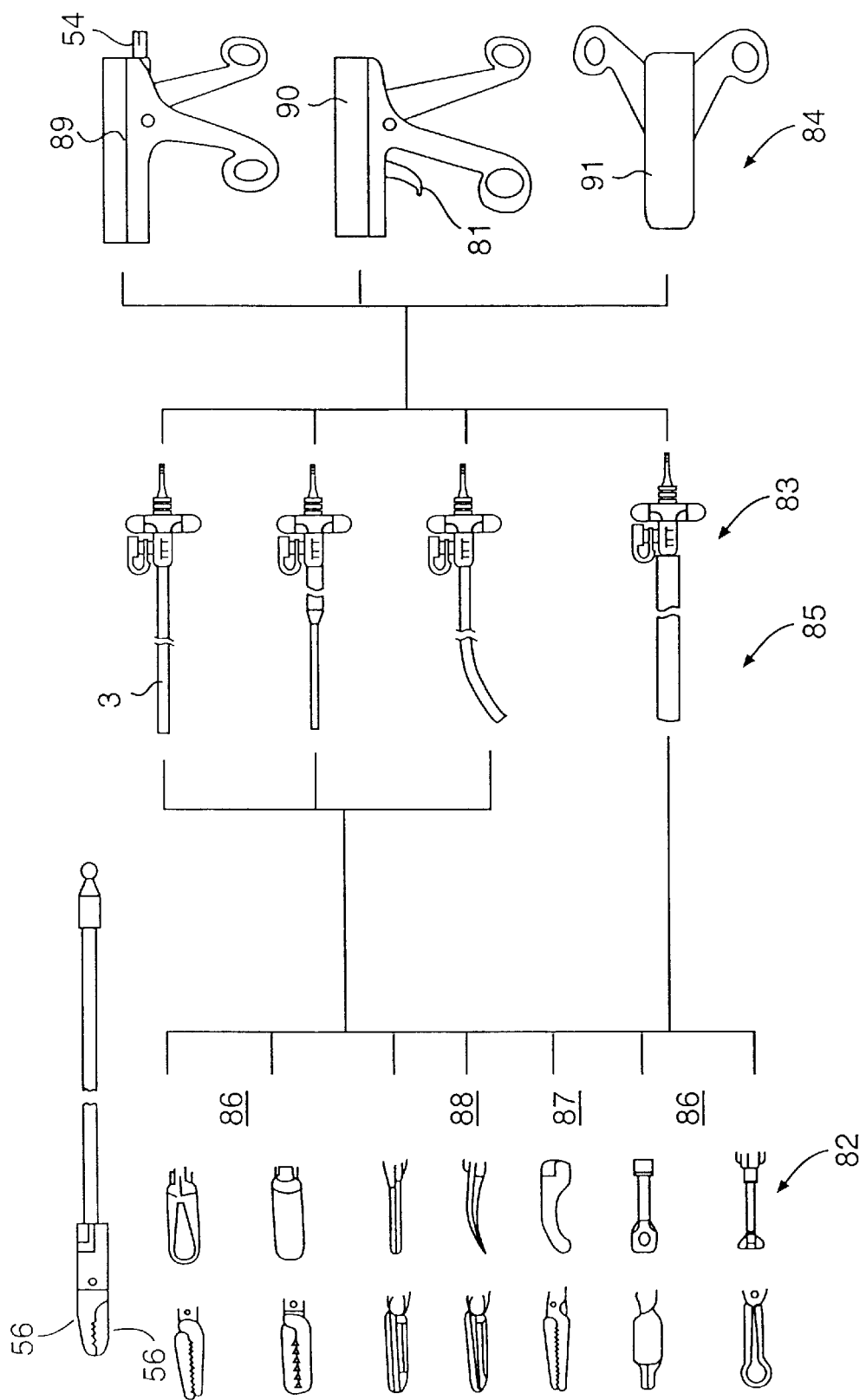
FIG. 30 is a side view of a forceps system of a ninth embodiment of the present invention which shows combination of attachments for use with the forceps system.

FIG. 30 shows a ninth embodiment of the present invention. The forceps system 85 is made up of a forceps unit 82, a sheath unit 83, and a handle unit 84. The forceps unit 82 further comprises various types of grasping forceps 86, release forceps 87, and scissors forceps 88, all of which have various shapes. The sheath unit 83 is combined with the inserts 3 having different diameters. For example, inserts of a trachea for endoscopic surgery purposes commonly have diameters of 5, 10, and 12 mm. Therefore, the sheath unit 83 is used with the inserts 3 having cross sections corresponding to these diameters or the curved insertion section 3.

The handle unit 84 is comprised of a live handle 89 which is provided with the live pin 54 so as to permit feeding of a high-frequency current to the jaws 56 from an unillustrated high-frequency power source, a ratchet handle 90 housing a ratchet mechanism, and an in-line handle 91.

In the case of such a forceps system, it will become difficult for an operator to decide available combinations. In this case, the constituent units of the forceps system should preferably be colored for identification. For instance, the forceps unit 82 with the scissors forceps 88 is painted red, or the forceps unit 82 with the grasping forceps 86 is painted blue. Like color-coded electrical resistance, the sheath unit 83 is provided with colors of the forceps capable of being combined with the sheath unit so as to allow an operator to easily acknowledge available combinations.

With this arrangement of the forceps system, it is possible for an operator to use the forceps 53 assembled by selecting units in accordance with a method of surgery and operators preferences. In the event of a trouble, only the broken parts can be replaced. Further, the advantages associated with the disassembly and reassembly of the closure 11 as described in the third embodiment will be obtained.

As described above, the forceps system is not limited to any particular structure, shape, or details so long as the objects of the present invention are achieved; namely, down-sizing of disposable portions, ensuring safety for the operator, improving ease of washing and sterilization, improving ease of disassembly and reassembly, and providing a forceps system suitable for the operator and the type of surgery.

Figure 31:
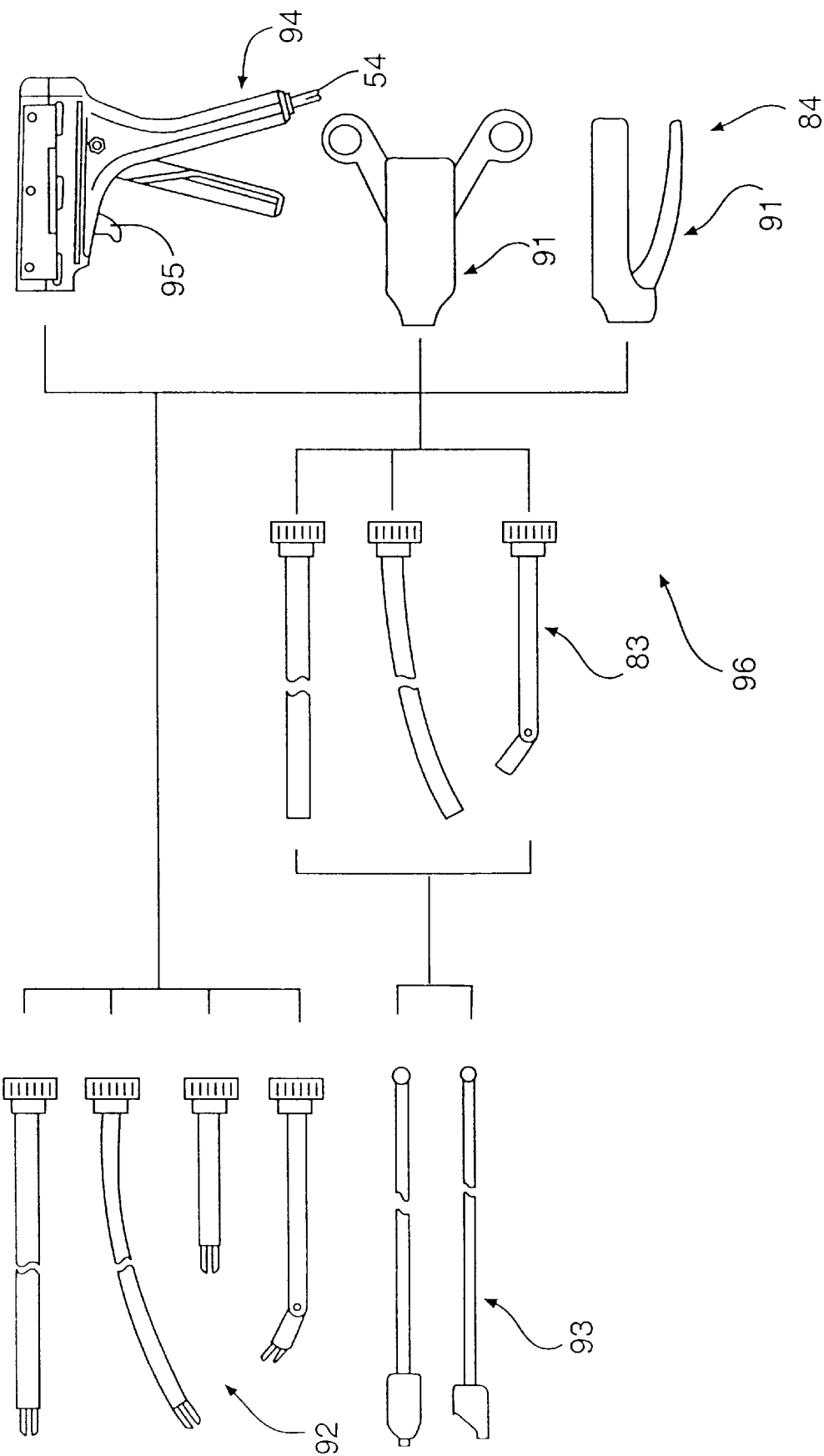
FIG. 31 is a side view of an applier system of a tenth embodiment of the present invention which shows combination of attachments for use with the applier system.

FIG. 31 shows a tenth embodiment of the present invention. An applier system 96 is made up of a clip unit 92, a stapler unit 93, the sheath unit 83, and the handle unit 84 as illustrated in the first, second, fourth, and sixth embodiments. The clip unit 92 comprises the attaching section 2 integral with the insertion section 3. A plurality of types of clip unit 92 are available according to the size of the clip, the number of clips stored in the applier, whether or not the insertion section 3 can bend, or the diameter of the insertion section 3. Similarly, there are provided a plurality of types of stapler unit. However, these stapler units are used with the separate inserts 3. Further, several types of sheath unit 83 are available.

For the handle unit to be connected to these units, there are provided several types of handle unit such as a pistol grip 94 and an in-line handle 91. For example, in the case of the pistol grip 94, the handle unit may be provided with an auxiliary lever 95 for use in feeding a clip or releasing a ratchet.

With this arrangement of the applier system, it is possible for an operator to use an applier assembled by selecting units in accordance with a method of surgery and operators preferences. In the event of a trouble, only the broken parts can be replaced. If the suturing and ligating elements 12 have run out, the clip unit 92 or the stapler unit 93 can be replaced with a new one. The other units of the applier system can be made reusable by replacement of the clip unit 92 and the stapler unit 93 as cartridges. Moreover, the advantages associated with the disassembly and reassembly of the closure 11 as described in the first, second, fourth, and fifth embodiments will be obtained.

As described above, the applier system is not limited to any particular structure, shape, or details so long as the objects of the present invention are achieved; namely, down-sizing of disposable portions, ensuring safety for the operator, improving ease of washing and sterilization, improving ease of disassembly and reassembly, and providing an ultrasonic transducer suitable for the operator and the type of surgery.

Figure 32:
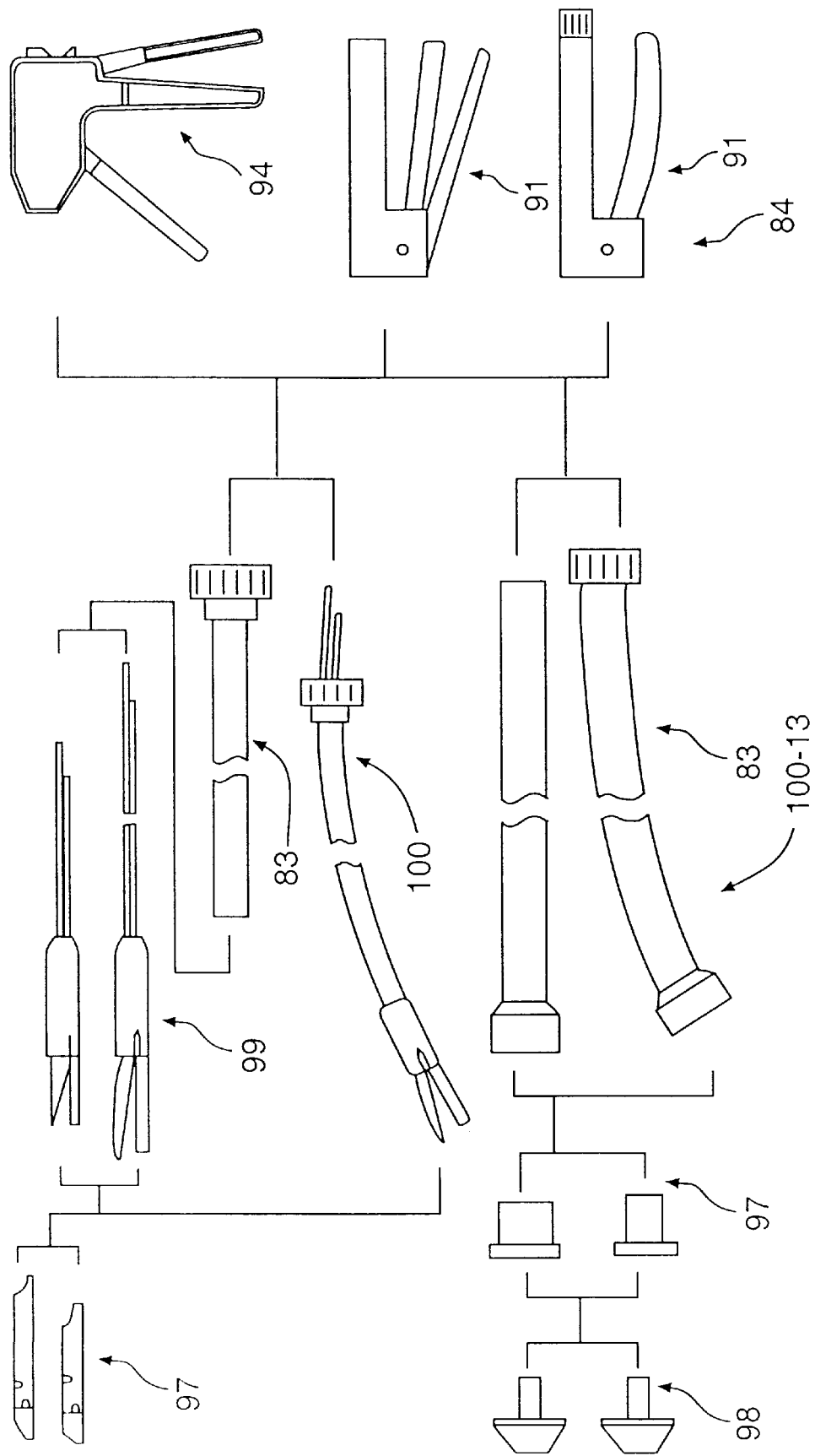
FIG. 32 is a side view of a suturing and anastomosing system of an eleventh embodiment of the present invention which shows combination of attachments for use with the suturing and anastomosing system.

FIG. 32 shows an eleventh embodiment of the present invention. The automatic suturing instrument 78 of the suturing and anastomosing system 100-13 is made up of a cartridge unit 97, a jaws unit 99, a sheath unit 83, and a jaws sheath unit 110 which are the same as those of the sixth embodiment. An anastomosing instrument 79 is made up of an anvil unit 98, the cartridge 97, and the sheath unit 83 which are the same as those of the seventh embodiment. A handle unit 84 is connected to these units. For examples, these units are available in many types according to the number of staples loaded in the cartridge unit 97, an effective length of the cartridge unit 97, an effective length of the sheath unit 83, the curved shape of the sheath unit 83, and the shape of the handle unit 84. It is possible to use the units in combination according to a method of surgery and operators preferences.

With this arrangement of the suturing and anastomosing system, in the event-of a trouble, only the broken parts can be replaced. Suturing and anastomosing operations can be repetitively carried out by replacement of the cartridge unit 97. The suturing and anastomosing system can be disassembled into and reassembled from constituent parts, and the inside of the operating section 4 can be also opened, whereby the constituent parts can be thoroughly washed and sterilized. The other units of the suturing and anastomosing system can be made reusable by handling only the cartridge 97 as being disposable. Moreover, the advantages associated with the disassembly and reassembly of the closure 11 as described in the sixth and seventh embodiments will be obtained.

As described above, the suturing and anastomosing system is not limited to any particular structure, shape, or details so long as the objects of the present invention are achieved; namely, down-sizing of disposable portions, improving safety for the operator, improving ease of washing and sterilization, improving ease of disassembly and reassembly, and providing an ultrasonic transducer suitable for the operator and the type of surgery.

Figure 33:
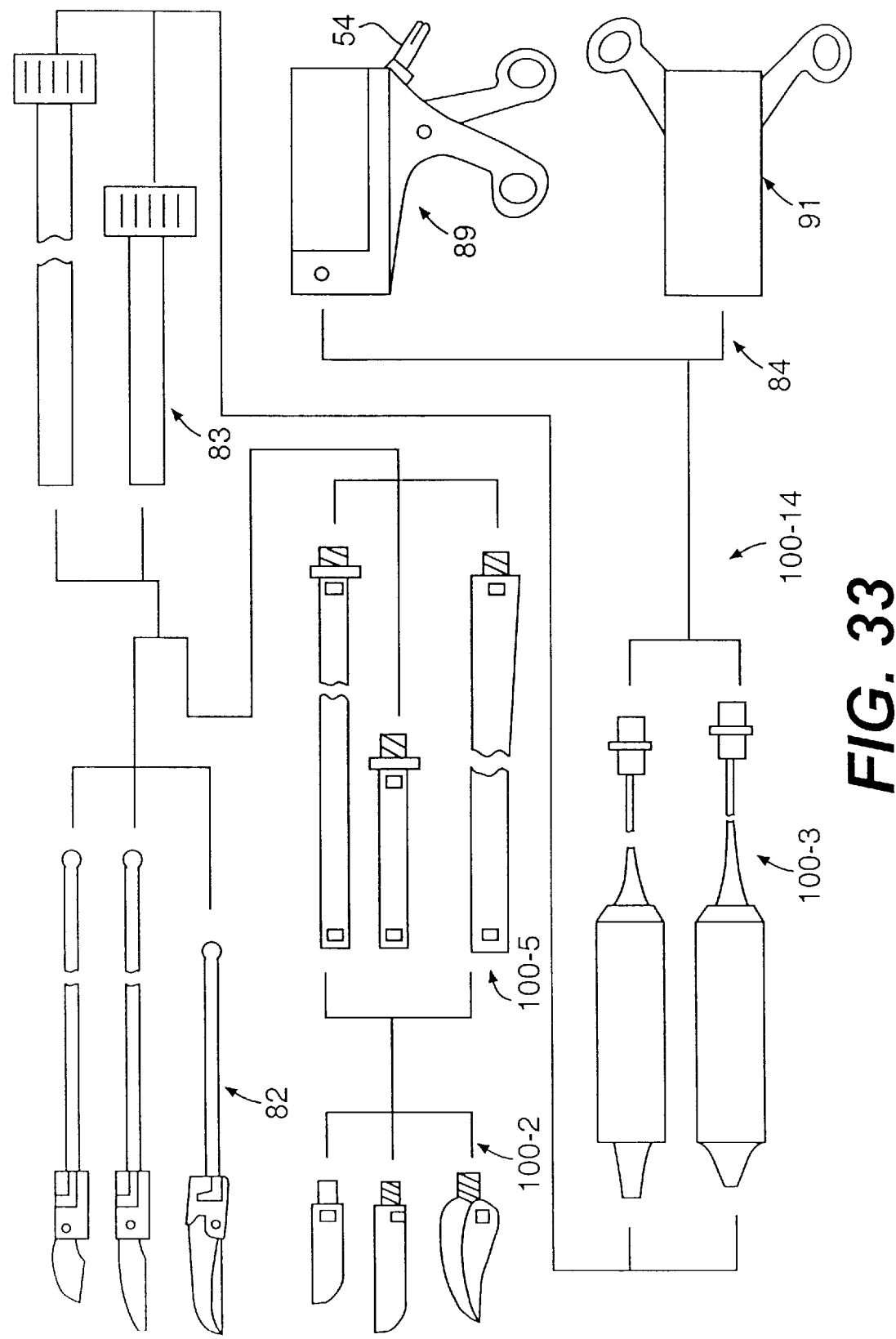
FIG. 33 is a side view of an ultrasonic clotting,and incising system of a twelfth embodiment of the present invention which shows combination of attachments for use with the ultrasonic clotting and incising system.

FIG. 33 shows a twelfth embodiment of the present invention. An ultrasonic clotting and incising instrument 114 of the present embodiment is made up of the forceps unit 82, the tip 100-2, the probe 100-5, the sheath unit 83, the ultrasonic transducer 100-3, and the handle unit 84. The ultrasonic clotting and incising instrument is provided with many types of units; for example, the forceps units 82 having the differently-shaped jaws 56, the tips 102 corresponding to the shapes of these forceps units 82, the probes 100-5 having different effective lengths and amplification factors of ultrasonic vibration, the sheath units 83 having different effective lengths, the ultrasonic transducer 103 having different frequencies and outputs, and the handle units 84 which have different shapes or are capable of using high-frequency currents in combination. It is possible to use the units in arbitrary combination.

With this arrangement of the ultrasonic clotting and incising system, in the event of a trouble, only the broken parts can be replaced in addition to the advantage of use of the units in arbitrary combination. Moreover, the advantages associated with the disassembly and reassembly of the closure 11 as described in the eighth embodiment will be obtained.

As described above, the clotting and incising system is not limited to any particular structure, shape, or details so long as the objects of the present invention are achieved; namely, down-sizing of disposable portions, improving safety for the operator, improving ease of washing and sterilization, improving ease of disassembly and reassembly, and providing an ultrasonic transducer suitable for the operator and the type of surgery.

FIGS. 34 and 35 show the shape of a suturing and ligating element 112 and the engagement between the suturing and ligating element 112 and a pusher 114. The suturing and ligating element 112 of a thirteenth embodiment is formed from titanium such as a titanium alloy as will be described later. The suturing and ligating element 112 comprises substantially parallel two legs 112-1 and a base 112-2 connecting these legs 112-1 and is substantially shaped like a letter C.

A ridge 140 having a substantially semi-circular cross section is longitudinally formed along the internal edge of a recess 116 of the pusher 114. An engaging slit 141 is formed in the base 112-2 of the suturing and ligating element 112 so as to engage with the ridge 140 when the suturing and ligating element 112 is deformed. If the suturing and ligating element 112 disengages from a guide member 113 during the . course of deformation, the engagement between the ridge 140 and the suturing and ligating element 112 prevents the suturing and ligating element 112 from becoming dislodged or changing in direction due to external interference. In general, it is easy to manufacture the suturing and ligating element 112 from a wire by pressing if it has the same cross section over the entire length of the wire. In such a case, the engaging slit 141 may be formed over the entire outer surface of the suturing and ligating element 112 (over the outer surface of the legs 112-1).

The titanium from which the suturing and ligating element 112 is formed is known to be very hard and to possess a high strength. Extremely large strength is needed to elastically deform such a suturing and ligating element 112. To make it easy for the suturing and ligating element 112 of the present embodiment easy to be deformed into a desired shape when the suturing and ligating element 112 is deformed by the pusher 114, notches 142 are formed in the legs 112-1 and the base 112-2. The suturing and ligating element 112 is to be bent along these notches 142. Since the notches 142 are only expected to be easily bent compared with the other portions of the suturing and ligating element 112, the following processing of the legs and the base will also be feasible. Specifically, only the areas of the legs and base where the notches 142 are to be formed are locally subjected to processing of material such as annealing so as to make Young's modulus comparatively larger than that of the other areas, so that the areas become apt to be bent. Alternatively, the areas may be formed such that a section modulus of the areas becomes comparatively smaller than that of the other areas in the direction in which the areas are bent.

Figure 36A:
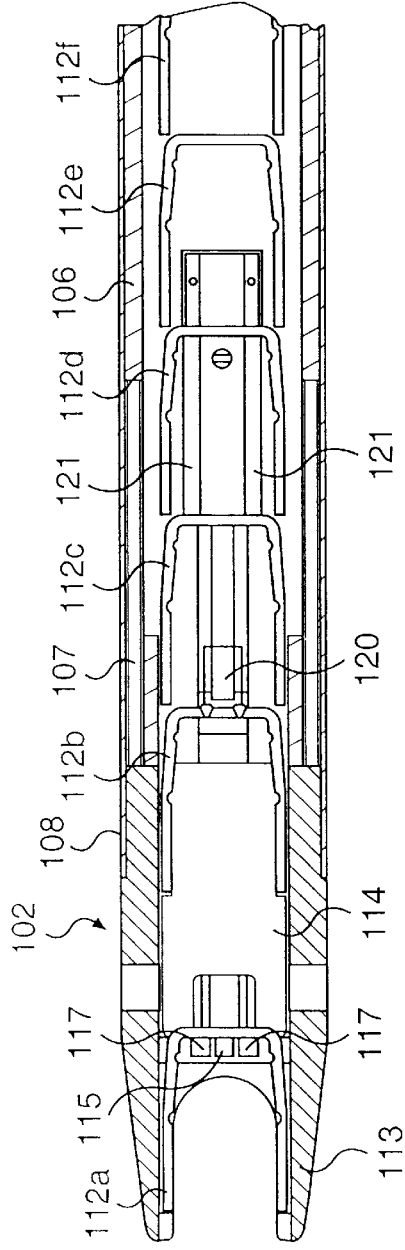
FIGS. 36A and 36B are longitudinally cross-sectional plan and side views showing the operation of an applier of the thirteenth embodiment.
Figure 36B:
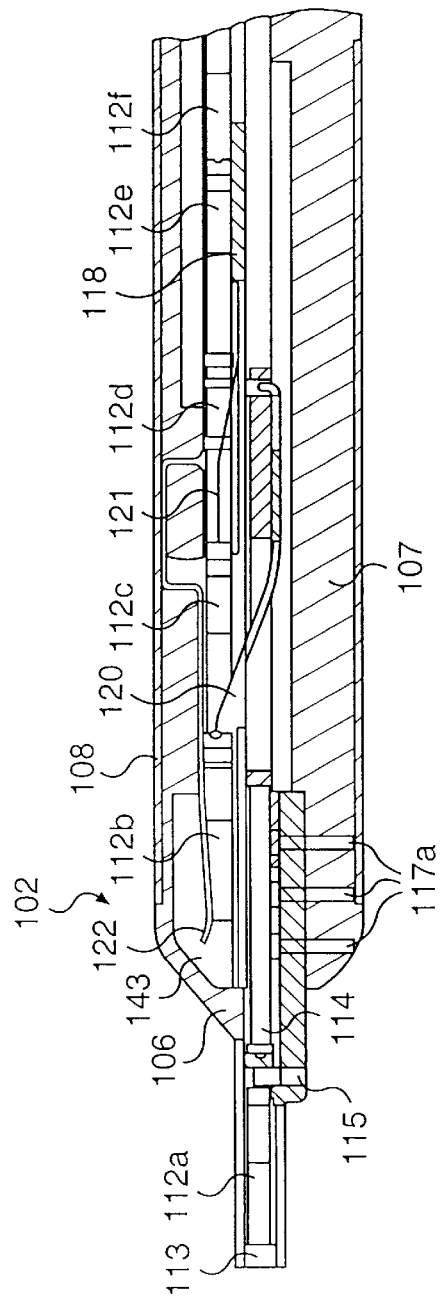

With reference to FIGS. 36A and 36B through FIG. 41, the operation of an applier 101 will be described. FIGS. 36A and 36B show the suturing and ligating elements 112 which are loaded in the guide member 113 and the movable handle 109 which is actuated to the first stage. At this time, the movable handle 109 is situated at the position designated by a solid line in FIG. 1. In this state, the pusher 114 holds a suturing and ligating element 112a using a support pin 115. The suturing and ligating element 112a is vertically retained by means of the guide member 113. Of the suturing and ligating elements 112, a suturing and ligating element 112b is in the course of travel to an opening 143 in front of a partition 118 by means of a hook 120 provided on the pusher 114, opposing a clip press spring 122. In the line of the suturing and ligating elements 112, a suturing and ligating element 112c following the suturing and ligating element 112b moves to a position across a one-way clutch 121 as a result of the suturing and ligating elements 121 next to a suturing and ligating element 121d of being forced by a buffer 123. The one-way clutch 121 is formed from elastic metal. Combined with its shape, the one-way clutch 121 is capable of forwardly pushing the suturing and ligating elements 112. However, once having passed across the one-way clutch 121, the suturing and ligating element cannot return to its original position.

Figure 37A:
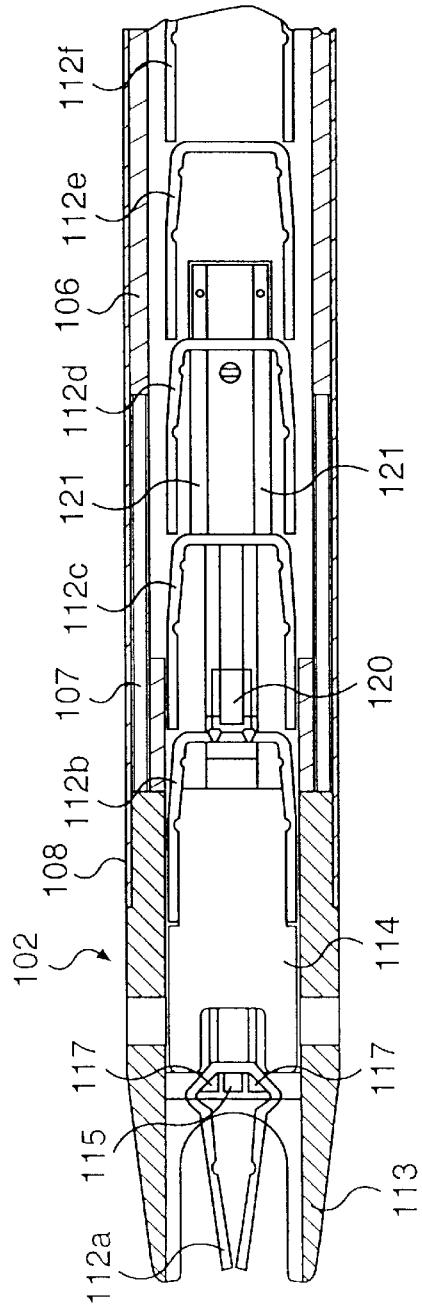
FIGS. 37A and 37B are longitudinally cross-sectional plan and side views showing the operation of the applier of the thirteenth embodiment.
Figure 37B:
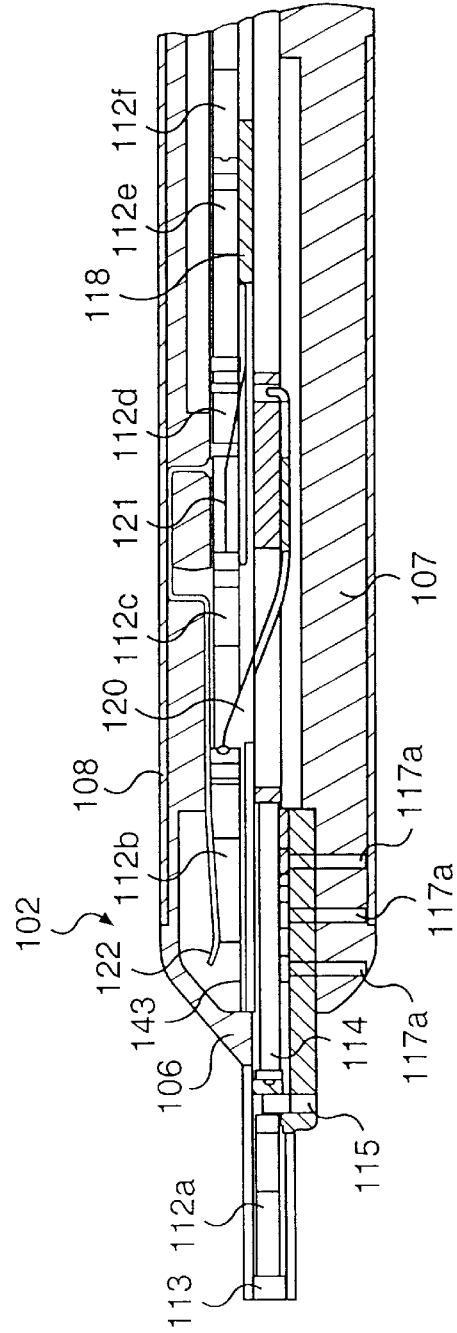
Figure 39A:
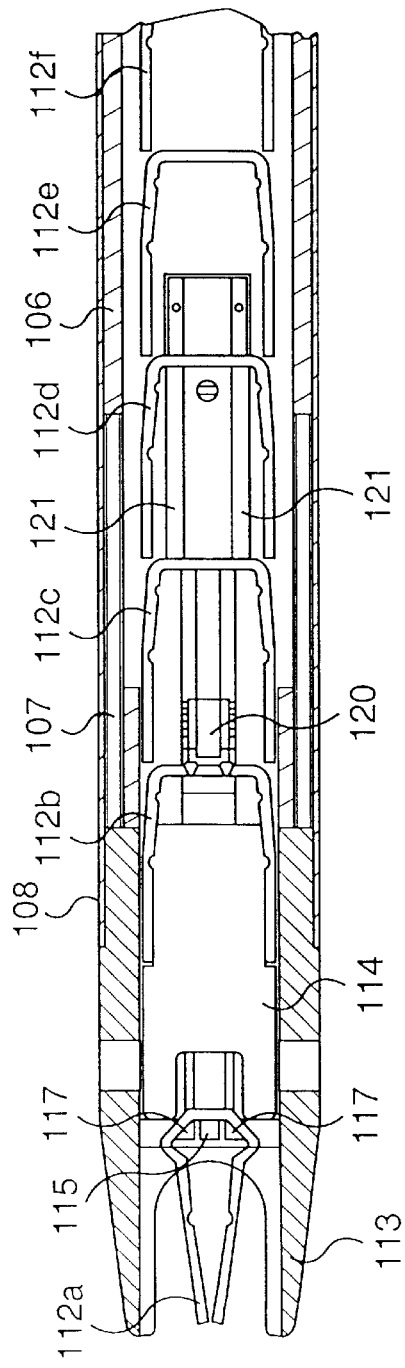
FIGS. 39A and 39B are longitudinally cross-sectional plan and side views showing the operation of the applier of the thirteenth embodiment.
Figure 39B:
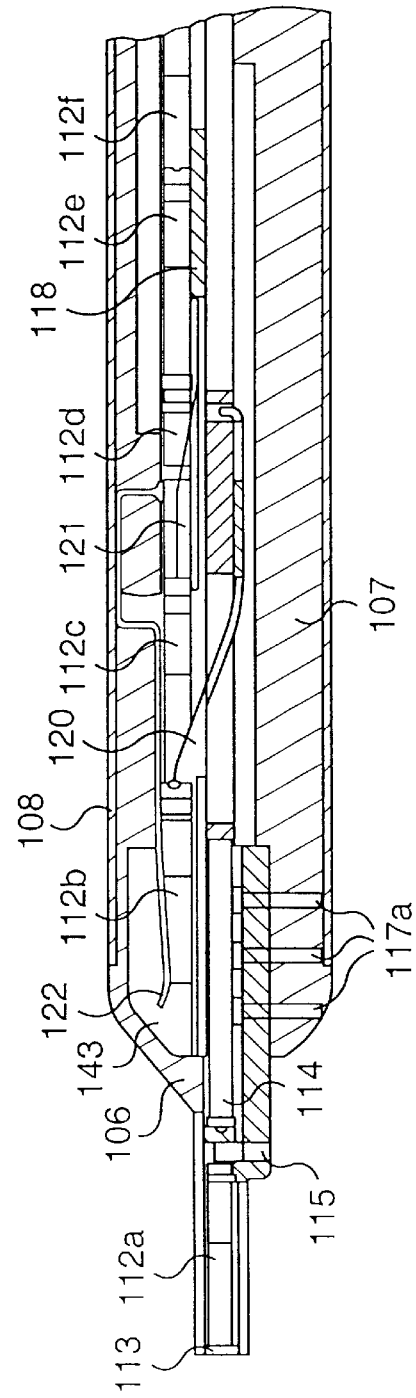

FIGS. 37A and 37B show a second actuating state of the applier. In this state, the movable handle 109 is further actuated in a closing direction from its first state, so that the pusher 114 forwardly travels further. The suturing and ligating element 112a is pushed forwardly by means of the ridge 140 of the recess 116. Since the suturing and ligating element 112a is supported by the support pin 115, the portions of the suturing and ligating element 112a pushed by the pusher 114 are bent forwardly. By virtue of the notches 142, the suturing and ligating element 112a is deformed into a given shape, whereby the edges of the suturing and ligating element 112a come into contact with each other. The suturing and ligating element 112a departs from the guide member 113. As the suturing and ligating element 112a becomes deformed, the ridge 140 of the pusher 114 comes into engagement with the engaging slit 141 of the suturing and ligating element 112a. As a result, the suturing and ligating element will not become dislodged from attaching section 102 during the course of an attaching operation.

At this time, the suturing and ligating elements 112 loaded in storage section 119 further move forwardly with the help of a forcing action of the clip press spring 124 as a result of forward movement of the suturing and ligating element 112b caused by the hook 120.

As shown in FIGS. 38A and 38B through FIGS. 40A and 40B, as the movable handle 109 is closed, the pusher 114 travels forwardly, and the suturing and ligating element 112a is gradually deformed. Further, the suturing and ligating elements 112 stored in the storage section 119 are also carried forwardly. The movable handle 109 completely arrives at a closed position in the stage shown in FIGS. 40A and 40B, and the pusher 114 moves to the foremost position. As a result, the suturing and ligating element 112a changes to a finally-deformed state.

The suturing and ligating element 112b moves to the position above an opening 143 of the partition 118 in this stage and is loaded on an upper surface of the pusher 114 within the opening 143 by means of the clip press spring 122. The remaining suturing and ligating elements 112 travel forwardly so as to follow the suturing and ligating element 112b.

The final shape of the suturing and ligating element 112 obtained at this time is set such that the lengths of the substantially proximate and parallel portions of the two legs 112-1 are more than about twice the length of the portion of the suturing and ligating element 112 surrounding the support pin 115. In this way, the length of the final shape of the suturing and ligating element 112 is set so as not to become unnecessarily long.

The applicator then proceeds to a stage shown in, FIGS. 41A and 41B. A series of operation of the movable handle 109 are completed in this stage, and the movable handle 109 fully moves to a release position by means of a main spring provided on the rear edge of the insertion section 103.

Subsequently, the suturing and ligating element 112a disengages from the pusher 114, and the suturing and ligating element 112a is horizontally ejected to the outside of the guide member 113 by means of a resilient force of an ejector 115 provided in the guide member 113. In general, in a case where a vessel 150 is ligated, one suturing and ligating element 112 is attached to the area of the vessel 150 to be cut, and two suturing and ligating elements 112 are attached to the area of the vessel 150 to be left. In this case, according to the conventional art, it is impossible for the applicator 101 to eject the suturing and ligating element 112 without detaching the applier 101 from the vessel 150 every time a ligating operation is carried out. In contrast, according to the present embodiment, the ligating operations can be carried out one after another only by horizontally moving the guide member 113 in order. For this reason, there is no risk of losing of the vessel 150 once it has been caught.

The pusher 114 moves backward further than the opening 143, and hence the suturing and ligating element 112b travels to the front of the pusher 114 by means of the elastic force of the clip press spring 122. The suturing and ligating element 112b is now ready for the next ligating operation. The suturing and ligating elements 112 following the suturing and ligating element 112b move to the position where the suturing and ligating element 112b comes into contact with the clip press spring 122 by means of the elastic force of the clip press spring 124. As a result, the overall applier 101 returns to its original state.

If the movable handle 109 is closed again from this state, the series of operations shown in FIGS. 36A and 36B to FIGS. 41A and 41B are repeated, whereby the suturing and ligating elements 112 are ejected in a continuous fashion. When the last suturing and ligating element 112t has been ejected, the storage section 119 becomes empty of the suturing and ligating elements 112. At this time, the buffer 123 moves to the forefront as previously described. By virtue of the easily-recognizable color of the buffer 123, it is acknowledged that the suturing and ligating elements 112 have run out. If the applier 101 is further actuated while the suturing and ligating elements 112 have run out, it does not have any movable portion to which the suturing and ligating elements 112 are attached. Therefore, only the pusher 114 moves back and forth, which may not injure tissue.

If the ligating operation is continued after the suturing and ligating elements 112 have run out, the insertion section 103 is removed from the operating section 104 by opening a closure 111 of the operating section 104 in the way as previously described. A new insert 103 is attached to the operating section 104, and the closure 111 is closed. New suturing and ligating elements 112 are now loaded into the applier 101.

Figure 48:
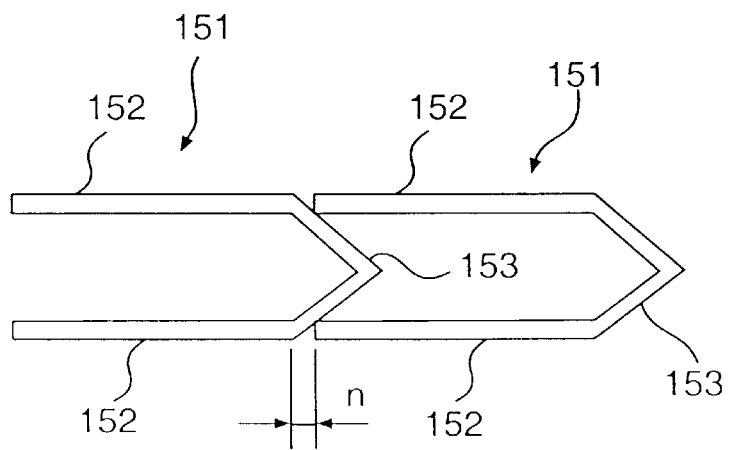
FIG. 48 is an illustration of the conventional suturing and ligating instrument.
Figure 47:
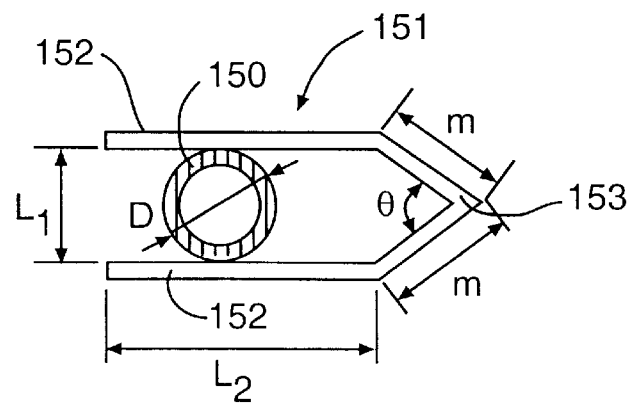
FIG. 47 is an illustration of a conventional suturing and ligating instrument.

If the suturing and ligating element 112 of the present embodiment is compared with a conventional suturing and ligating element 151 shown in FIGS. 47 and 48, the length of legs 152 of the suturing and ligating element 151 must be about twice the length of the portion of the suturing and ligating element surrounding the vessel in order to ligate the vessel 150 having a diameter D. A distance $L_1$ between the two legs 152 must satisfy the following relationship $L_1 \geq D$.

In the conventional art, a base 153 of the conventional suturing and ligating element 151 is formed into a substantial square having an angle θ in order to cause the suturing and ligating element to be easily deformed. To this end, the entire length of the suturing and ligating element 151 becomes $L_2 + m \cos θ$. In this way, the conventional suturing and ligating element 115 is longer than the conventional suturing and ligating element 112 by m cos θ.

As shown in FIG. 48, in a case where the suturing and ligating elements 151 are sequentially loaded in the applier, every pair of adjacent suturing and ligating elements 151 require a useless length n. As the number of suturing and ligating elements 151 increases, the useless length n becomes longer. As a result, the number of suturing and ligating elements 151 capable of being stored in a storage section becomes smaller. In contrast, the suturing and ligating elements of the present embodiment become free of such a useless length n. For example, in a case where 20 suturing and ligating elements are loaded in the applier, a length corresponding to 19n can be ensured. Since four suturing and ligating elements 151 can be additionally loaded into the applier, the problems of the conventional suturing and ligating elements can be solved.

If the suturing and ligating element 151 is deformed into a predetermined shape, its entire length becomes $L_2 + m$ according to the conventional art. In contrast, the entire length of the suturing and ligating element becomes $L_2 + 1/2$ in the present embodiment. Therefore, the size of a substance remained in tissue can be reduced by the difference between ($L_2 + m$) and ($L_2 + 1/2$); namely, (m−1)/2. As described above, the applier 101 and the suturing and ligating element 112 are not limited to any particular shape or structure so long as the objects of the present invention are achieved; namely, use of the safe and simple applier 101, an increase in the number of suturing and ligating elements 112 capable of being loaded in the applier 101 as a result of reduction in the size of the suturing and ligating elements 112, prevention of unnecessarily large residues in tissue.

Figure 42:
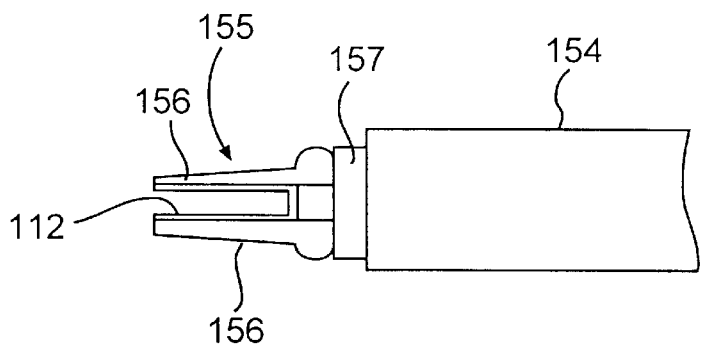
FIG. 42 is a plan view showing attaching section of an applier of a fourteenth embodiment of the present invention.

FIG. 42 shows a fourteenth embodiment of the present invention. The shape of the suturing and ligating element 112 of the present embodiment is the same as that of the suturing and ligating element 112 of the third embodiment. Further, they are characterized by the same fact that the portions of the suturing and ligating element which would become angles at the time of deformation are formed so as to be easily bent. Jaws 156 of attaching section 155 of an applier 154 are closed and opened through forward and backward movements of a jaws closing member 157. As a result, the suturing and ligating element 112 loaded into the jaws 156 is deformed into a desired shape, whereby a target tissue can be sutured and ligated.

As in the previously-described thirteenth embodiment, a large number of suturing and ligating elements 112 can be loaded into the applier 101 in the fourth embodiment because the suturing and ligating element 112 is small. Further, the present embodiment has the advantage of prevention of unnecessarily large residuals in tissue.

As described above, the suturing and ligating element 112 is not limited to any particular structure or material so long as the objects of the present invention are achieved; namely, storage of a large number of suturing and ligating elements 112 in the applier 101, and prevention of leaving of unnecessarily large residues in tissue.

Figure 43A:
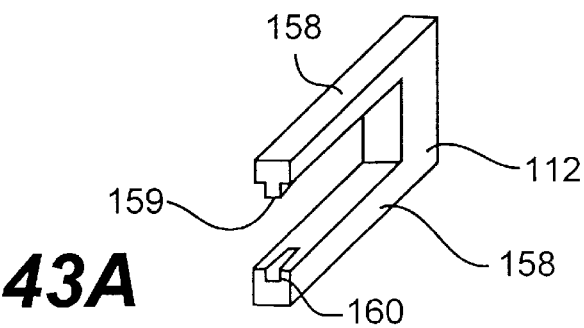
FIG. 43A is a perspective view of a suturing and ligating instrument of a fifteenth embodiment of the present invention.
Figure 43B:
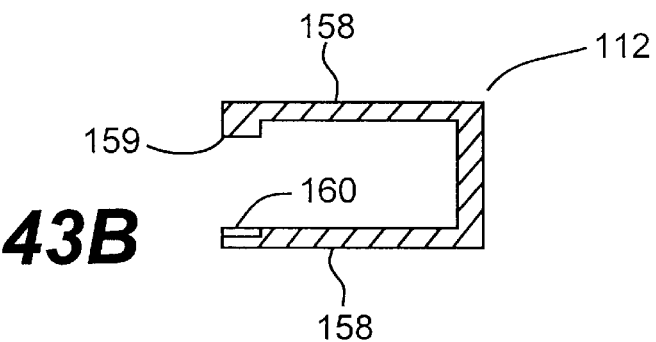
FIG. 43B is a longitudinally cross-sectional view of the suturing and ligating instrument of the fifteenth embodiment.
Figure 44A:
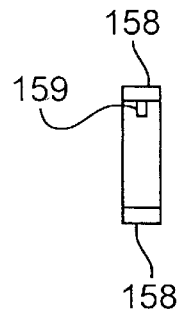
FIG. 44A is an end view of the suturing and ligating instrument of the fifteenth embodiment.
Figure 44B:
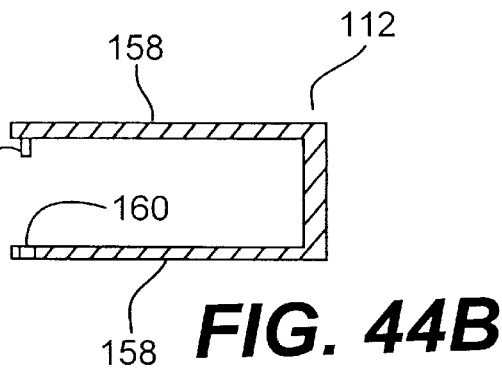
FIG. 44B is a longitudinally cross-sectional view of the suturing and ligating instrument of the fifteenth embodiment.

FIGS. 43 and 44 show a fifteenth embodiment of the present invention. The basic configuration of the suturing and ligating element 112 of the present embodiment is substantially the same shape as that of the suturing and ligating element 112 of the thirteenth embodiment. As shown in FIG. 43, a protuberance 159 and a recess 160 are provided at the ends of the respective internal surfaces of two legs 158 which are opposite to each other, in such a way as to engage with each other. FIG. 44 shows the protuberance 159 made of a pin-shaped member and the recess 160 formed into a hole formed in the leg 158. If the suturing and ligating element 112 is deformed into a predetermined shape as a result of the protuberance 159 engaging with the recess 160, the legs 158 can reliably come into parallel to and close proximity to each other without misalignment, which in turn enables execution of a reliable suturing and ligating operation.

As described above, the suturing and ligating element 112 is not limited to any particular structure and material so long as the object of the present invention is achieved; namely, execution of reliable suturing and ligating operations.

Figure 45:
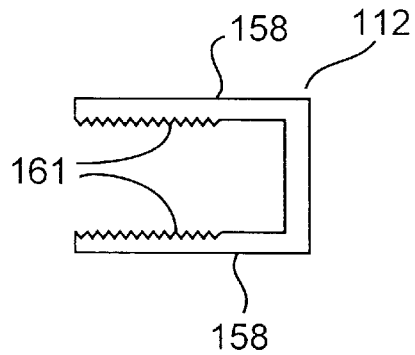
FIG. 45 is a side view of a suturing and ligating instrument of a sixteenth embodiment of the present invention.

FIG. 45 shows a sixteenth embodiment of the present invention. The suturing and ligating element 112 of the present embodiment basically has the same shape as that of the suturing and ligating element 112 of the thirteenth embodiment. As shown in FIG. 45, non-slip areas 161 are provided on the respective internal surfaces of the two legs 158 in order to prevent tissue from slipping from the clip when the suturing and ligating element 112 is attached to the tissue. In the present embodiment, the internal surfaces which are opposite to each other are partially knurled to prevent the tissue from slipping from the suturing and ligating element 112.

Figure 46A:
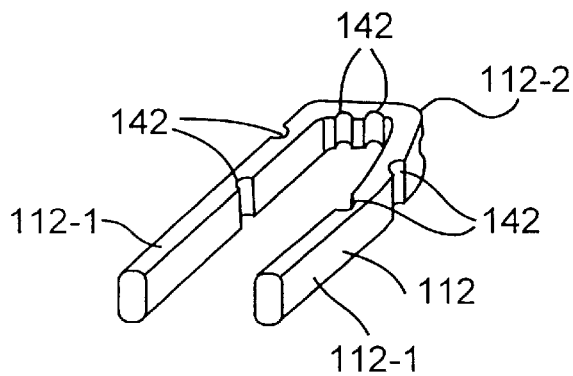
FIG. 46A is a perspective view of a suturing and ligating instrument of a-seventeenth embodiment of the present invention when viewed from an open end of the suturing and ligating instrument.
Figure 46B:
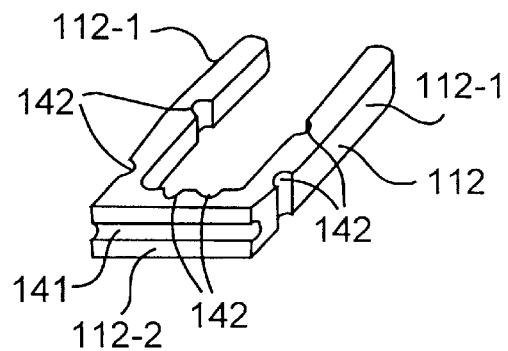
FIG. 46B is a perspective view of the suturing and ligating instrument of the seventeenth embodiment when viewed from a closed end of the suturing and ligating instrument.

FIG. 46 shows a seventeenth embodiment of the present invention. The basic structure of the suturing and ligating element 112 of the present embodiment is substantially the same as that of the suturing and ligating element 112 of the thirteenth embodiment. Recesses such as notches 142 are formed in the internal surface of the areas ( legs 112-1 and a base 112-2) of the suturing and ligating element 112 which are to become angular when the suturing and ligating element 112 is deformed into a predetermined shape. As a result, the suturing and ligating element 112 is apt to deform.

The non-slip areas 161 may be also formed by, for example, satin-finishing the internal surfaces of the two legs 158 that are opposite to each other. In this event, the non-slip areas 161 can be formed by sand blasting or chemical surface treatment.

As described above, the suturing and ligating element 112 is not limited to particular structure and material so long as the object of the present invention is achieved; namely, execution of reliable suturing and ligating operations.

Figure 49:
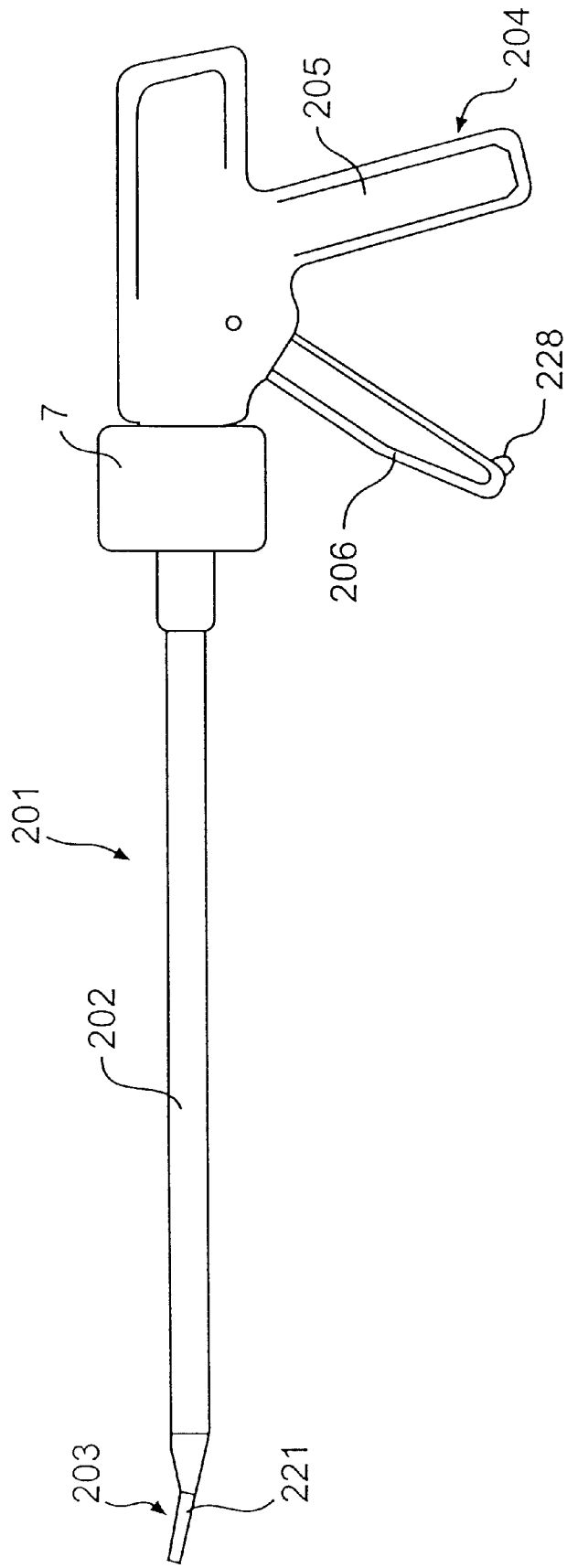
FIG. 49 is a side view of the entirety of a clip applier of an eighteenth embodiment of the present invention.

FIGS. 49 to 56 show an eighteenth embodiment of the present invention. As shown in FIG. 49, a clip applier 201 has an insertion section 202 which is inserted into a body cavity through a trachea, or the like, during endoscopic surgery. The insertion section 202 has at the proximal end operating section 204 for operating the clip applier 201 as well as at the distal end clip attaching section 203 for attaching a clip to tissue. The operating section 204 comprises a fixed handle 205 and a movable handle 206 which is rotatably attached to the fixed handle 205.

The insertion section 202 is rotatably connected to the operating section 204 through a knob 207. Clip attaching section 203 can be rotated with respect to the operating section 204 by rotating the knob 207.

Figure 50:
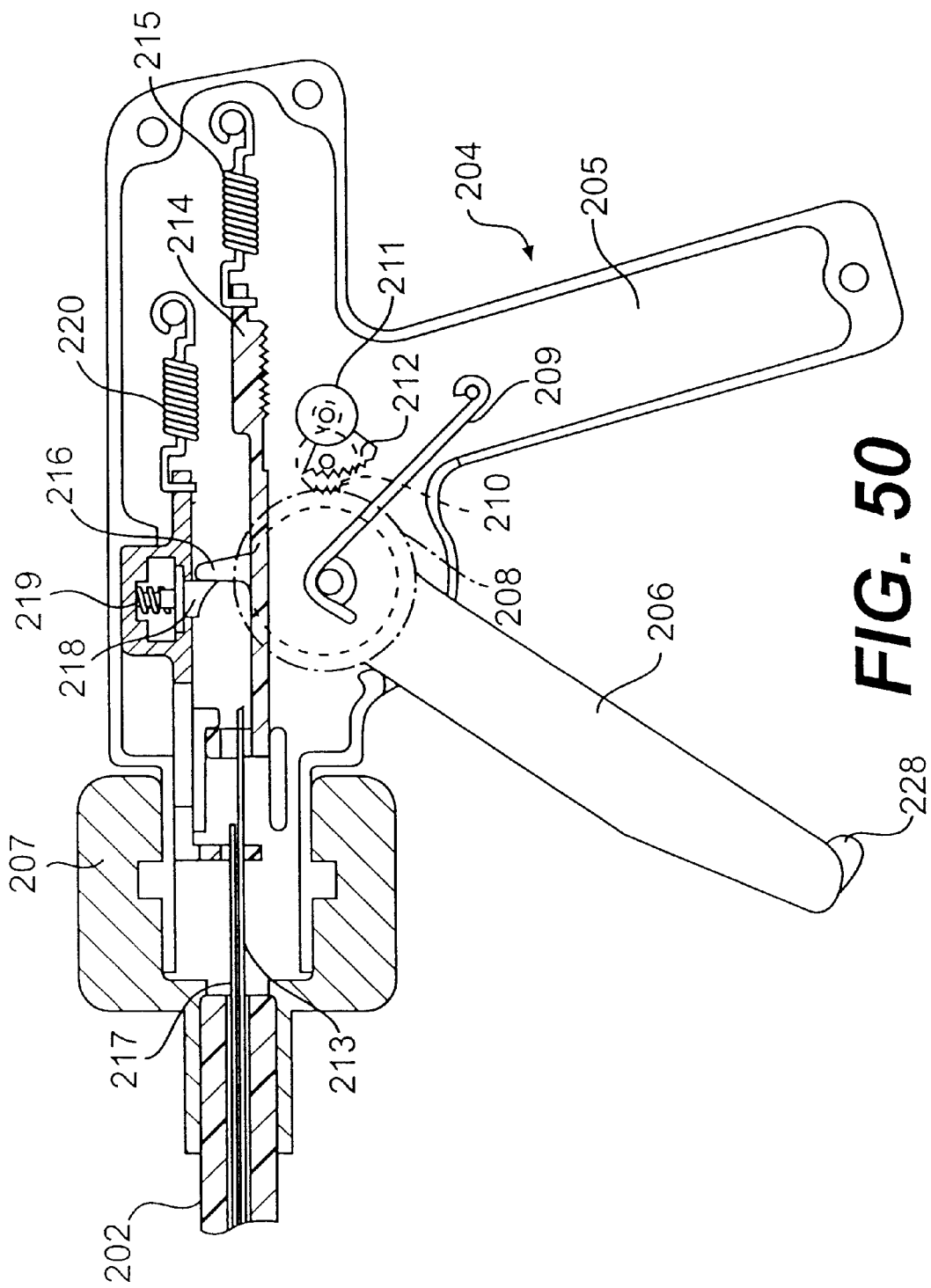
FIG. 50 is a cross-sectional view showing an initial state of operating section of the eighteenth embodiment.

FIG. 50 shows the initial state of the operating section 204. A first gear 208 is provided at the pivot of the movable handle 206 and is normally forced in an opening direction by means of a first spring 209. The first gear 208 meshes with an adjacent second gear 210. A third gear 211 meshes with the second gear 210. A fan-shaped fourth gear 212 is further attached to the third gear 211. A jaws closing-and-operating member 213 is provided above the gears 208, 210, 211, and 212. The jaws closing-and-operating member 213 has at its proximal end a fifth gear 214 and a second spring 215 for normally drawing the jaws closing-and-operating member 213 toward the proximal end of the clip applier 201.

A flange 216 is attached to the movable handle 206. The flange 216 meshes with a claw 218 provided at the proximal end of a clip feed drive member 217 which serves as clip feed member. The claw 218 is normally forced downward by a third spring 219. The clip feed drive member 217 has at its proximal end a fourth spring 220, and this fourth spring 220 normally draws the clip feed drive member 217 toward the proximal end of the clip applier 201.

Figure 51A:
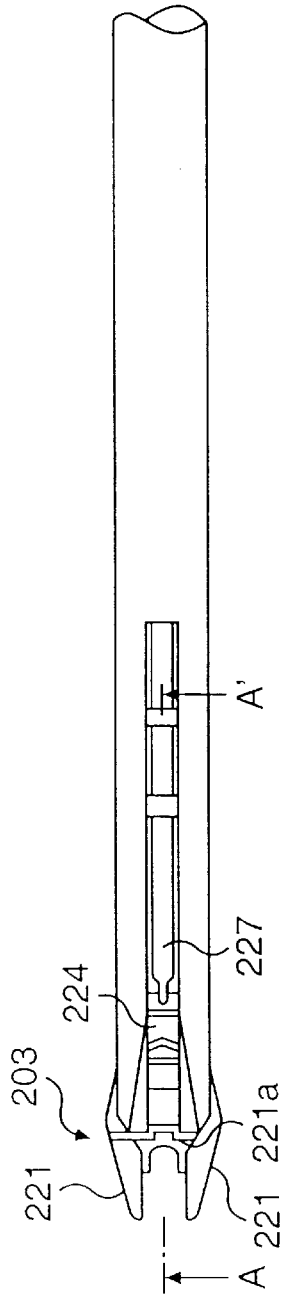
FIG. 51A is a plan view of attaching section of the eighteenth embodiment when it is in an initial state.
Figure 51B:
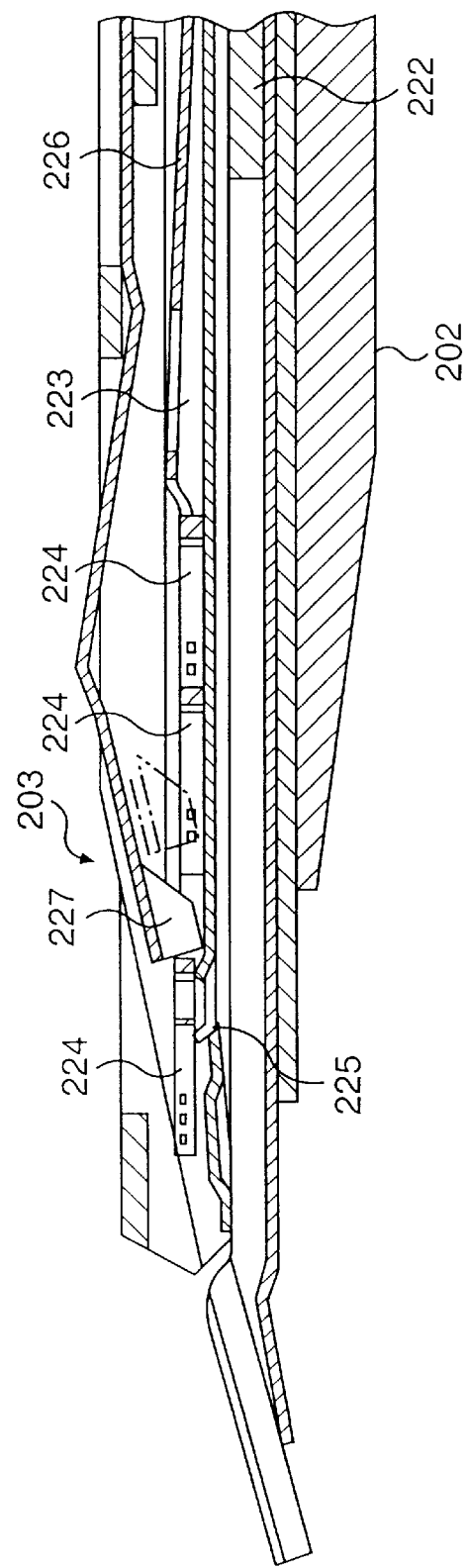
FIG. 51B is a longitudinally cross-sectional view of the attaching section taken across line A–A' shown in FIG. 51A.

FIGS. 51A and 51B show the initial state of the clip attaching section 203. The clip attaching section 203 has jaws 221 which are opened within an identical plane, a jaws closing member 222 for operating the jaws 221, and a blood vessel protective member 221a. The jaws 221 are bifurcated and normally forced in an opening direction by virtue of elastic force of themselves. Clip storage section 223 is provided above the jaws 222, and a plurality of substantially U-shaped clips 224 are stored in the clip storage section 223 in order such that openings of the clips are directed to the front end of the clip attaching section 203.

The clip 224 positioned at the distal end of the line of clips 224 is pressed by a clip press spring 225 so as not to drop from the front end of the clip attaching section 203. On the other hand, the clip 224 positioned at the proximal end of the line of clips 224 is normally forced toward the distal end by means of a buffer 226 forced to the distal end of the clip applier 201 by means of an unillustrated spring. Consequently, the clips 224 are kept in the state shown in FIGS. 51A and 51B in spite of the fact that they are normally forced to the distal end, because the force with which the clip press spring 225 presses the clips 224 is greater than the pressing force of the buffer 226. A pusher 227 connected to the clip feed drive member 217 engages with the back of the clip 224 situated at the distal end of the line of clips 224.

Figure 52:
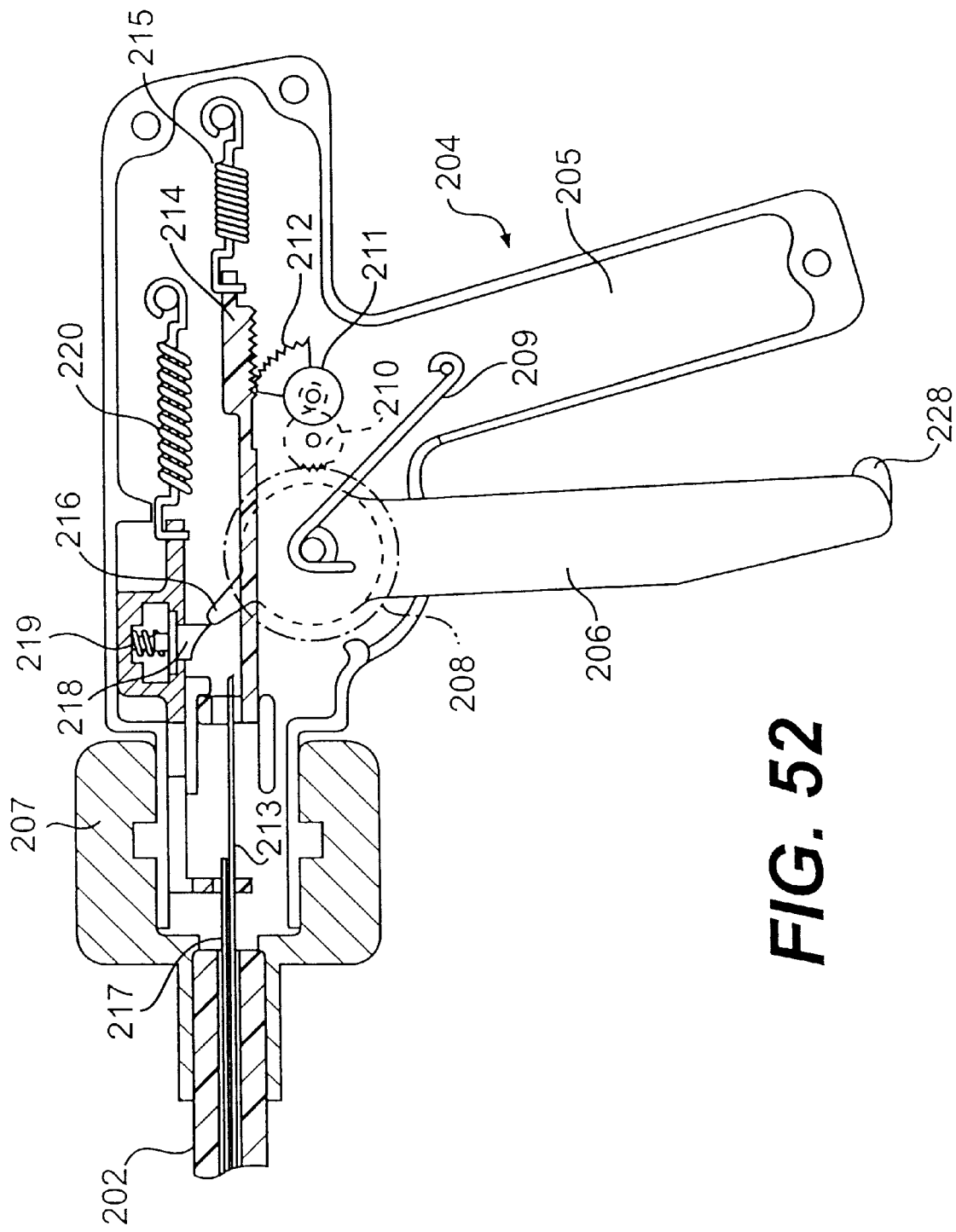
FIG. 52 is a cross-sectional view of the operating section of the eighteenth embodiment when it is in a first actuating state.

FIG. 52 shows the operating section 203 having been actuated to the first stage. Associated with actuation of the movable handle 206 up to the first stage in a closing direction, the flange 216 pivots and forces the claw 218 toward the distal end of the clip applier 201. As a result, the clip feed drive member 217 is actuated toward the distal end of the clip applier 201, and the fourth spring 220 is concurrently expanded, whereby elastic energy is stored in the fourth spring 220. Further, the pivotal movement of the movable handle 206 results in rotation of the first gear 208, so that the second and third gears 210 and 211 rotate together with the rotation of the first gear 208. The fourth gear 212 also rotates in conjunction with the rotation of the second and third gears 210 and 211, as a result of which the edge of the fourth gear 212 meshes with the end of the fifth gear 214.

As shown in FIGS. 53A and 53B, the pusher 227 travels toward the distal end of the clip applier 201 as a result of movement of the clip feed member 217 toward the distal end of the clip applier 201. Then, the clip 224 provided at the distal end of the line of clips 224 is loaded into the jaws 221. The remaining clips 224 are fed toward the distal end of the clip applier 201 by means of the buffer 226 until the clip 224 at the distal end engages with the clip press spring 225.

Figure 54:
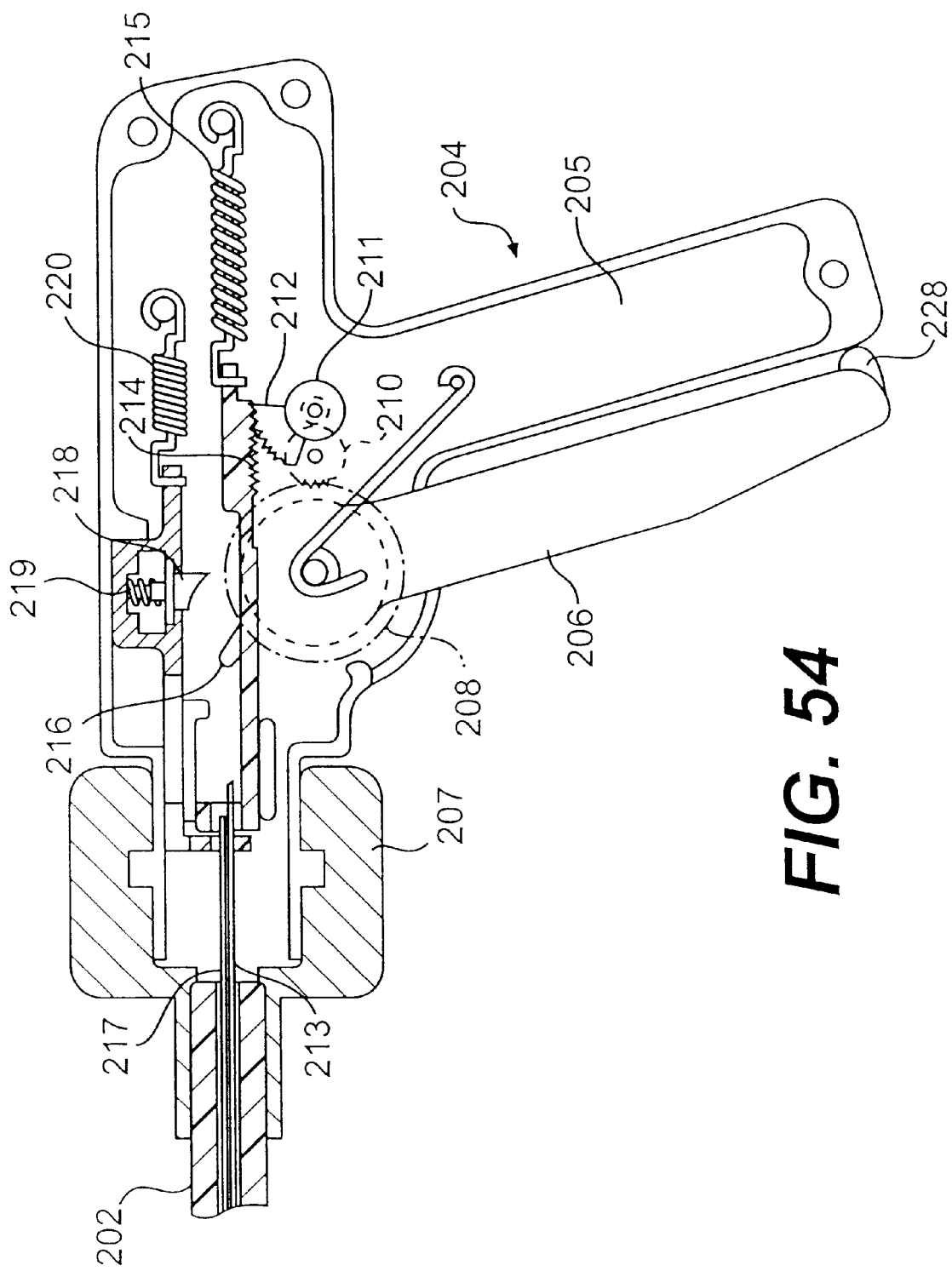
FIG. 54 is a side cross-sectional view of the operating section of the eighteenth embodiment when it is in a fully-actuating state.

FIG. 54 shows the operating section 204 having been actuated to the second stage. If the movable handle 206 is rotated up to the second stage in a closing direction, a stopper 228 provided at the end of the movable handle 206 comes into contact with the fixed handle 205 so as to prevent further pivotal movement of the movable handle 206. As a result of further pivotal movement of the flange 216 from the first stage, the flange 216 disengages from the claw 218. The clip feed drive member 217 is forced toward the proximal end of the clip applier 201 by virtue of the elastic energy stored in the fourth spring 220 and finally returns to its original state.

As a result of rotation of the first gear 208 associated with the action of the movable handle 206, the fourth gear 212 in mesh with the fifth gear 214 in the first stage further rotates, so that the fifth gear 214 is carried toward the distal end of the clip applier 201. As a result, the jaws closing-and-operating member 213 travels toward the distal end of the clip applier 201, and the second spring 215 is concurrently expanded, whereby elastic energy is stored in the second spring 215.

Figure 55A:
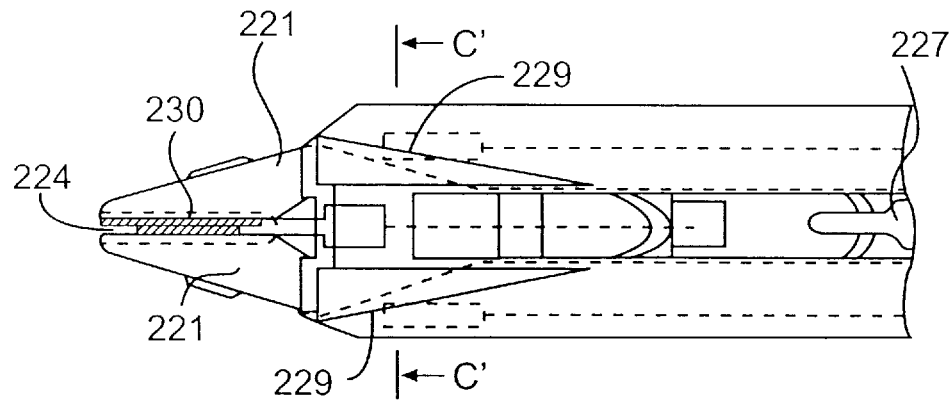
FIG. 55A is a plan view of the attaching section of the eighteenth embodiment when it is in a fully-operating state.
Figure 55B:
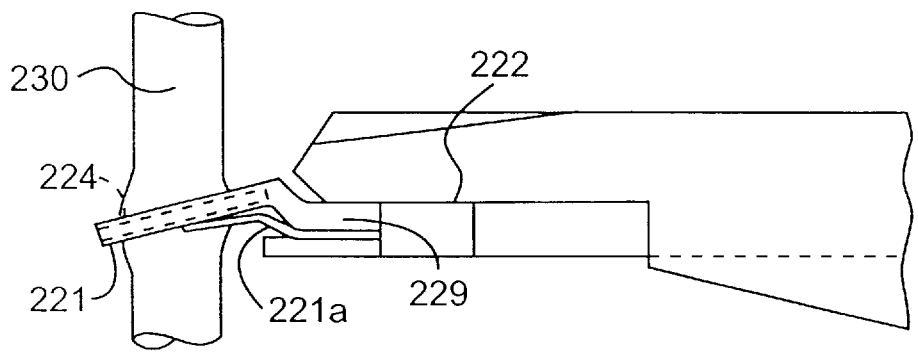
FIG. 55B is a side view of the attaching section of the eighteenth embodiment when it is in the fully-operating state.
Figure 56:
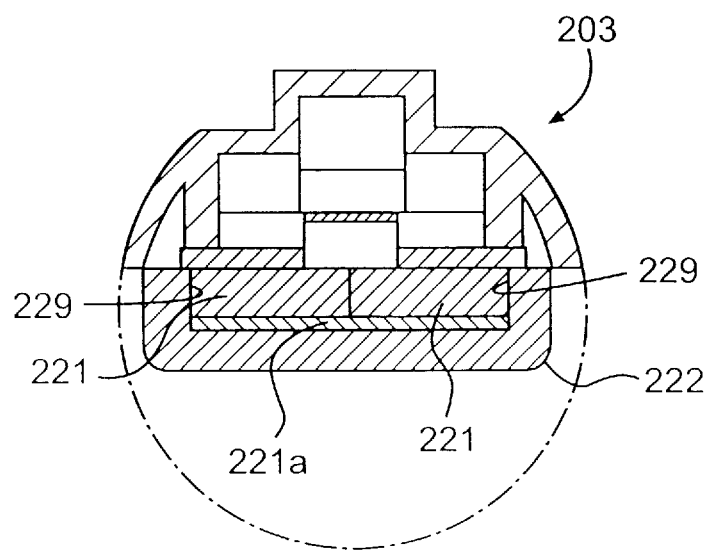
FIG. 56 is a cross-sectional view of the attaching section of the eighteenth embodiment when it is in a fully-operating state and is taken across line C–C' shown in FIG. 55A.

As shown in FIGS. 55A and 55B, together with returning action of the clip feed drive member 217 to its original state, the pusher 227 moves toward the distal end of the clip applier 201 and returns to its original state; namely, it is situated behind the distal-end clip 224 of all the clips 224 remaining in the clip storage section 223. At the same time, the jaws closing member 222 moves toward the distal end of the clip applier 201 together with the action of the jaws closing-and-operating member 213. The jaws closing member 222 is shaped into a letter C as shown in FIG. 56. The jaws 221 are operated so as to become close to each other by means of a cam mechanism constituted of the internal wall surface of the jaws closing member 222 and cam surfaces 229 of the jaws 221, so that the clip 224 is closed. The clip 224 is attached to tissue, such as a vessel 230, previously grasped by the clip 224, which allows the vessel 230 to be ligated.

If the movable handle 206 is opened after the previously-described series of operations, the movable handle 206 returns to its original state by means of the elastic energy stored in the first spring 209. At that time, the jaws closing-and-operating member 213 returns to its original state by means of the elastic energy stored in the second spring 215. During the course of returning to the original state, the flange 216 passes across the claw 218 by temporarily raising it against the third spring 219. The claw 218 is then lowered by the elastic force of the third spring 219, so that the flange 216 engages with the back of the claw 218. The flange 216 now returns to its original state as shown in FIGS. 50, 51A, and 51B.

As described above, the present embodiment is characterized by the clip applier 201 that operates in the following manner. Namely, the pusher 227 is directly and manually moved by operating the operating section 224, so that the clip 224 is loaded into the jaws 221. Then, the jaws are operated so as to attach the clip 224 to tissue such as the vessel 230. The clip applier 201 returns to its original state by means of the energy stored in its constituent elements after a series of operations. The clip applier 201 is not limited to any particular mechanism so long as the above-described feature of the present embodiment is ensured.

FIGS. 57 to 63A and 63B show a nineteenth embodiment of the present invention. The same elements as those of the eighteenth embodiment are assigned the same reference numerals.

The clip applier 201 is substantially the same as that of the eighteenth embodiment with regard to the overall structure; namely, the clip applier 201 has at the distal end the clip attaching section 203 and at the proximal end the operating section 204.

Figure 57:
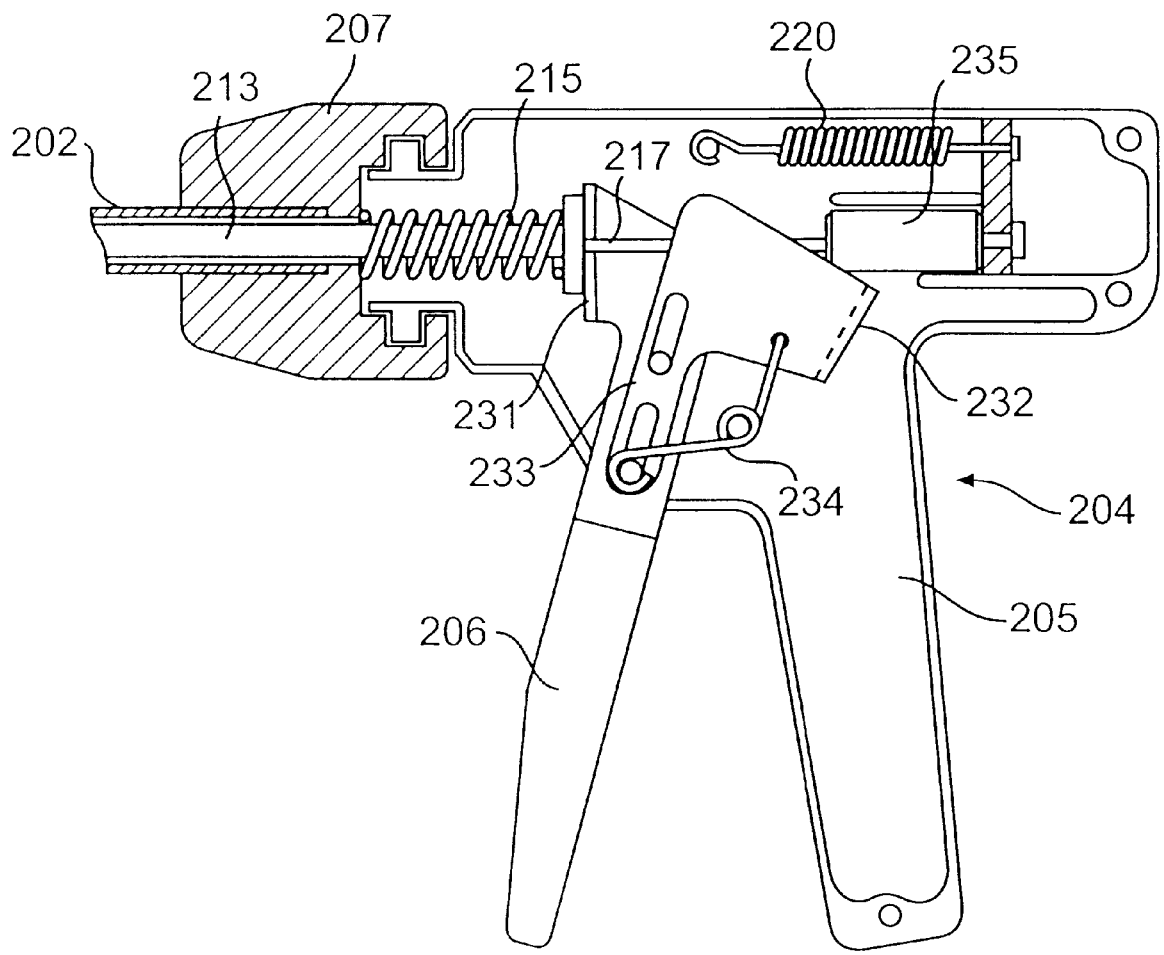
FIG. 57 is a side cross-sectional view of operating section of a nineteenth embodiment when it is in an initial state.

FIG. 57 shows the operating section 204 which is in its original state. The movable handle 206 is rotatably attached to the fixed handle 205. The upper part of the movable handle 206 engages with the jaws closing-and-operating member 213 via a press section 231. The jaws closing-and-operating member 213 is normally forced toward the proximal end of the clip applier 201 by the second spring 215. The second spring 215 also forces the movable handle 206 in an opening direction.

The movable handle 206 constitutes a slide mechanism 233 in cooperation with a flange 232. The flange 232 is slidable with respect to the movable handle 206 by virtue of this slide mechanism 233 and is normally forced upward by means of a fifth spring 234. The clip feed drive member 217 is provided in line with the jaws closing-and-operating member 213. An engaging section 235 for engaging with the flange 232 is provided at the proximal end of the clip feed drive member 217. The clip feed drive member 217 is normally forced toward the distal end of the clip applier 201 by means of the second spring 215.

Figure 58A:
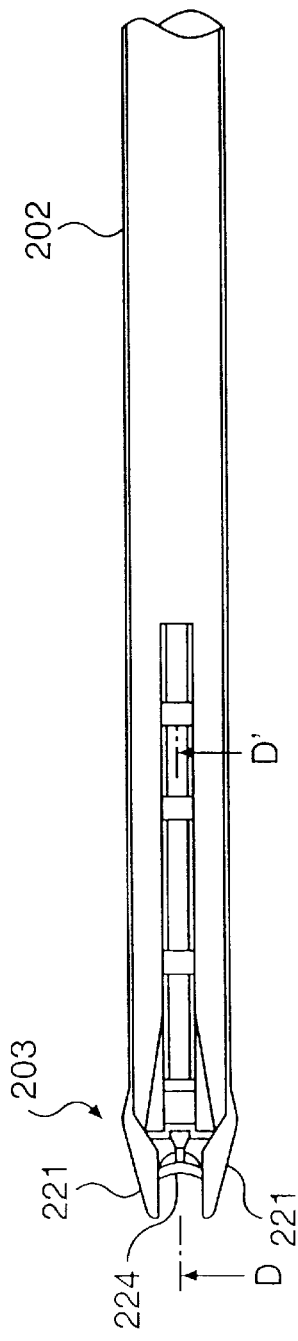
FIG. 58A is a plan view of attaching section of the nineteenth embodiment when it is in an initial state.
Figure 58B:
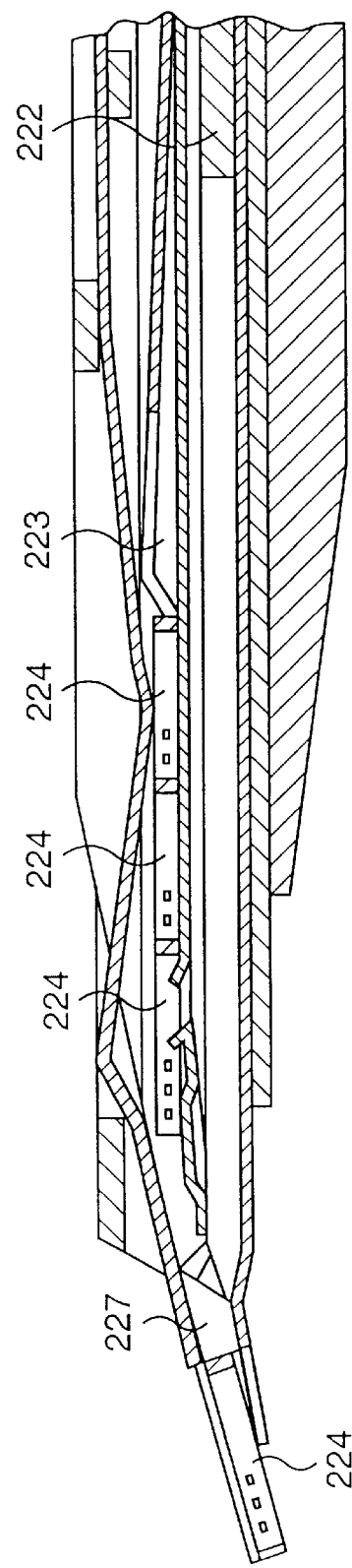
FIG. 58B is a cross-sectional view of the attaching section taken across line D–D' shown in FIG. 58A.

FIGS. 58A and 58B show the initial state of the clip attaching section 203. The basic structure of the clip attaching section 203 of the present embodiment is substantially the same as that of the clip attaching section 203 of the eighteenth embodiment shown in FIGS. 51A and 51B. In the initial state, the clips 224 are already loaded into the jaws 221. The pusher 227 is also placed in the position in which the clip 224 is loaded into the jaws 221 as a result of the clip feed drive member 217 being forced toward the distal end of the clip applier 201. The jaws 221 are designed so as not to grasp the pusher 227 or not to interfere with the pusher 227 during the course of clip-closing operations which will be described later.

Figure 59:
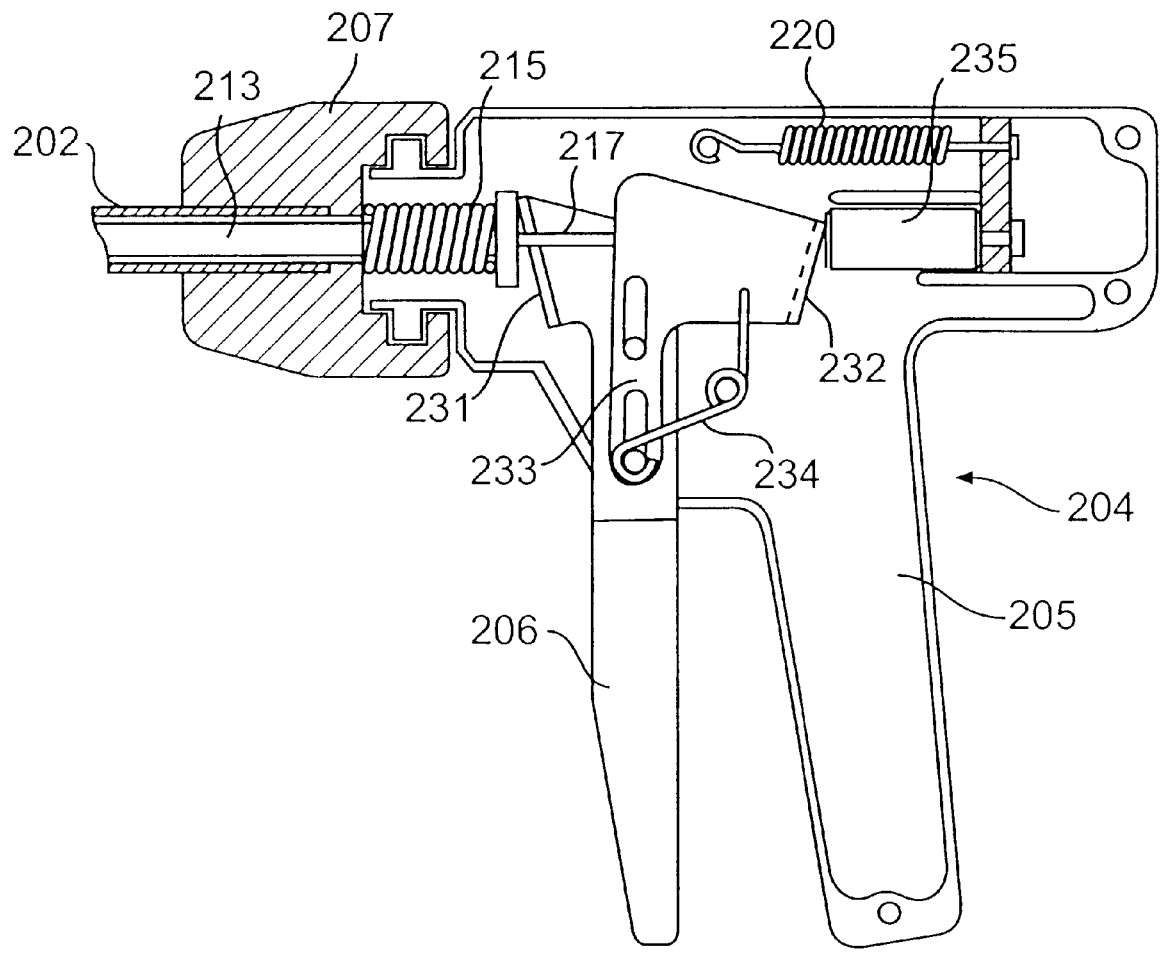
FIG. 59 is a side cross-sectional view of the operating section of the nineteenth embodiment when it is in a fully-actuating state.

FIG. 59 shows the operating section 204 that is in a fully-operated state. If operated up to the first stage in a closing direction, the movable handle 206 is pressed against the press section 231, thereby moving the jaws closing drive member 213 toward the distal end of the clip applier 201. At this time, the second spring 215 is compressed, whereby the elastic energy is stored in the second spring 215. The flange 232 pivots toward the distal end of the clip applier 201 together with the operation of the movable handle 206. During the course of the pivotal movement, the flange 232 temporarily moves downward by means of the slide mechanism 233 so as to pass across the engaging section 235. As a result, the flange 232 moves to the front of the engaging section 235.

Figure 60A:
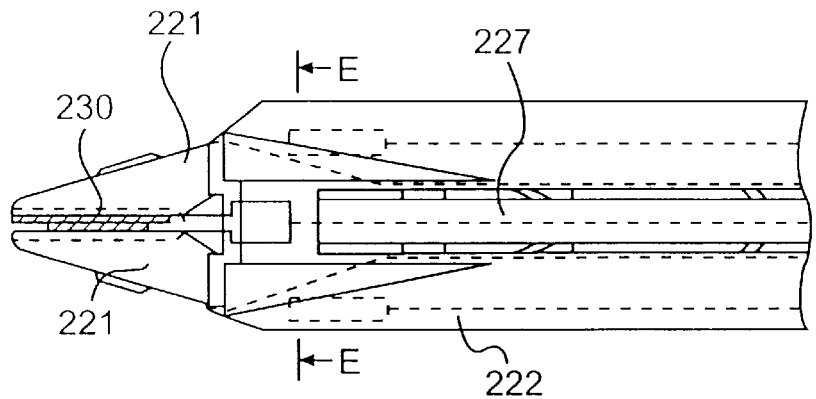
FIG. 60A is a plan view of the attaching section of the nineteenth embodiment when it is in a fully-operating state.
Figure 60B:
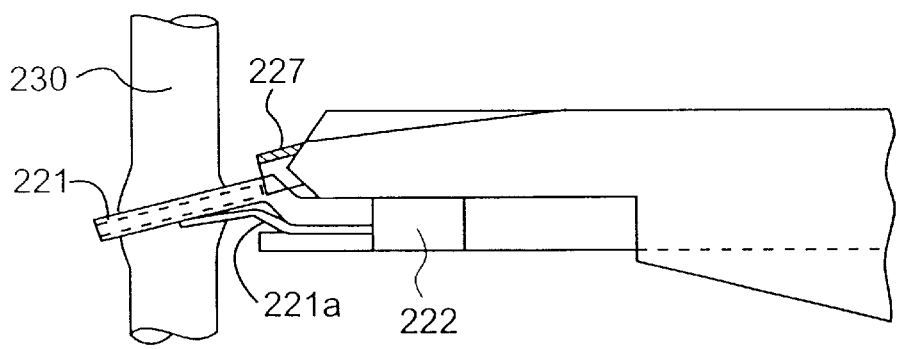
FIG. 60B is a side view of the attaching section of the nineteenth embodiment when it is in a fully-operating state.
Figure 61:
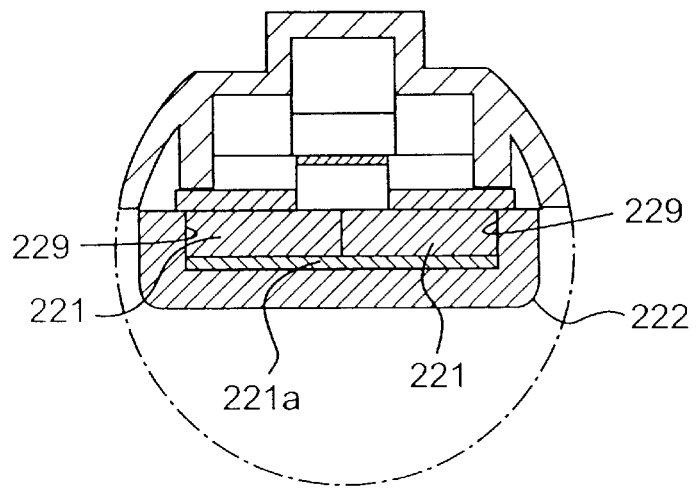
FIG. 61 is a cross-sectional view which shows the attaching section of the nineteenth embodiment when it is in a fully-operating state and is taken across line E–E' shown in FIG. 60A.

FIGS. 60A, 60B, and 61 show the fully-operated state of the clip attaching section 203. As previously described, as a result of operation of the jaws closing-and-operating member 213 toward the distal end, the jaws closing member 222 travels toward the distal end of the clip applier 201. As in the eighteenth embodiment, the clip 224 is attached to tissue, such as the vessel 230, previously grasped by the clip 224.

Figure 62:
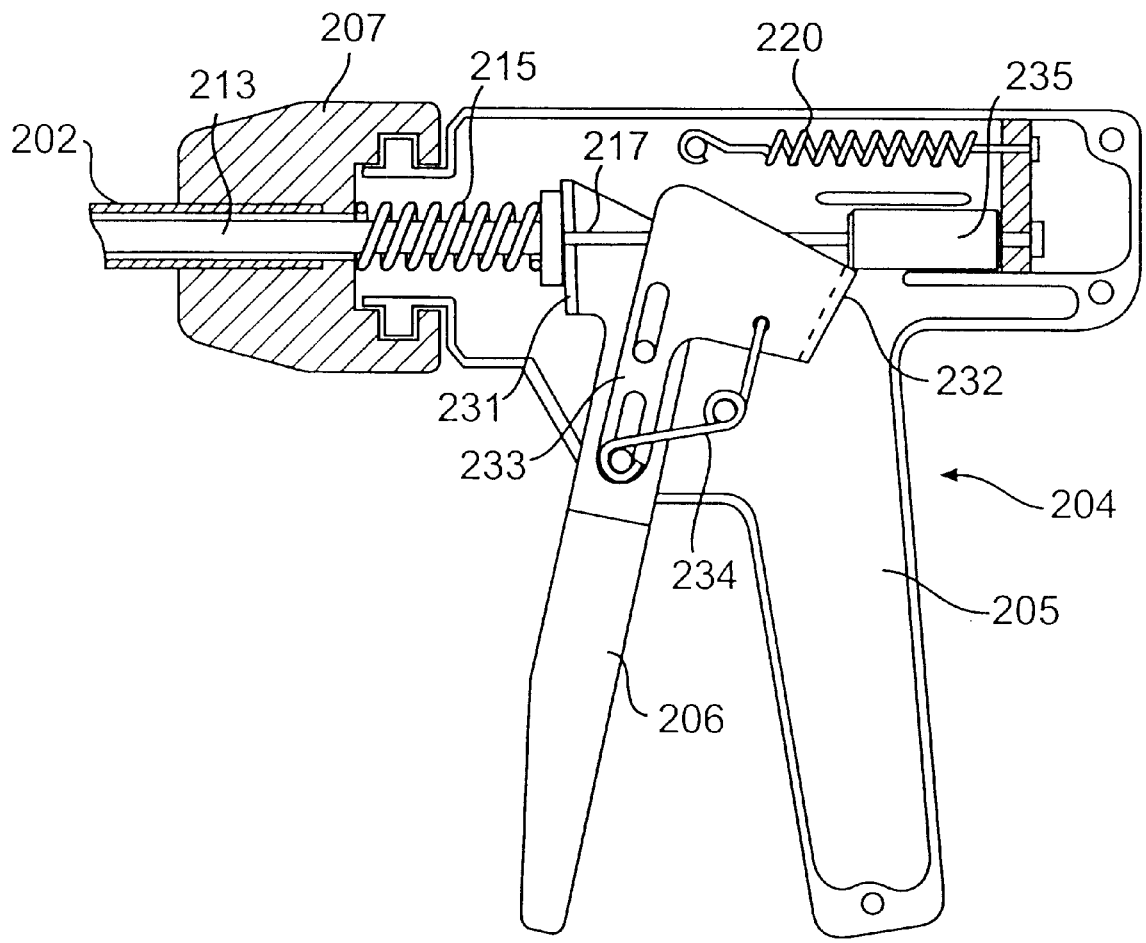
FIG. 62 is a side cross-sectional view showing the operating section of the nineteenth embodiment when it is in the course of returning to its initial state.

FIG. 62 shows the operating section 204 when it is in the course of returning to its original state. In this state, the movable handle 206 moves in an opening direction by means of the elastic energy of the fifth spring 234. At this time, the engaging section 235 is pushed toward the distal end of the clip applier 201 by means of the flange 232, and the clip feed drive member 217 also moves toward the distal end. Associated with this movement of the clip feed drive member 217, the second spring 215 is expanded, whereby elastic energy is stored in the second spring 215. If the movable handle 206 is opened further, the flange 232 disengages from the engaging section 235. The disengaging section 235 returns to its original state by means of the elastic energy of the fourth spring 220. Together with the returning action of the disengaging section 235, the clip feed mechanism 217 also returns to its original state. Subsequently, the movable handle 206 fully returns to its original state, whereupon the overall clip applicator 201 returns to its original state as shown in FIG. 59.

As described above, the present embodiment is characterized by the clip applier 201 that operates in the following manner. Namely, energy is stored in clip feed member when a clip applier 201 returns to its original state after the clip 224 has been attached to tissue, and the next clip 224 is supplied to the jaws by discharging the energy stored when the clip applier has fully returned to its original state. The clip applier 201 is not limited to any particular structure so long as the above-described feature of the present embodiment is ensured.

Figure 64:
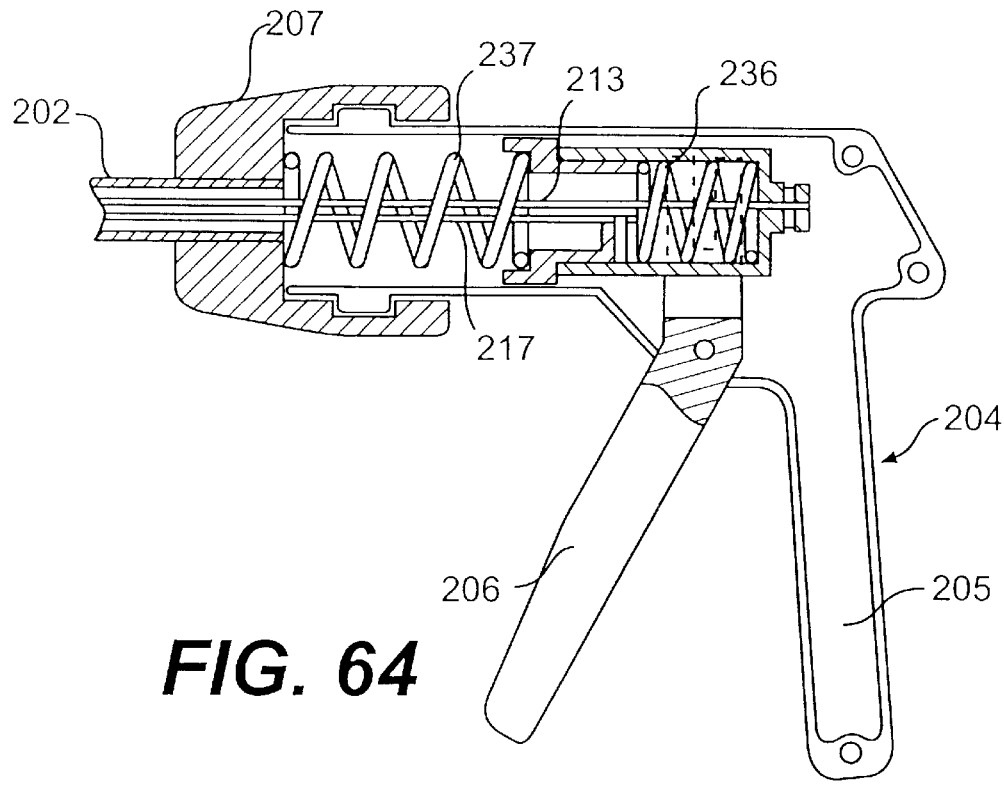
FIG. 64 is a side cross-sectional view of operating section of a twentieth embodiment when it is in an initial state.
Figure 65:
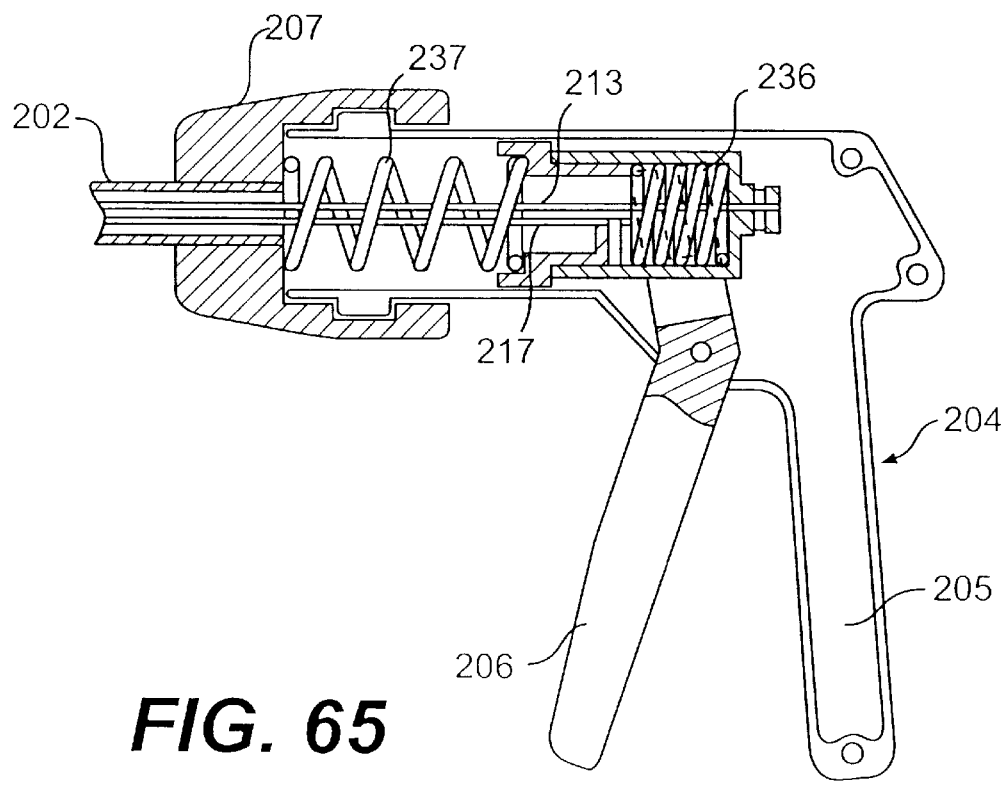
FIG. 65 is a side cross-sectional view of the operating section of the twentieth embodiment when it is in a first actuating state.
Figure 66:
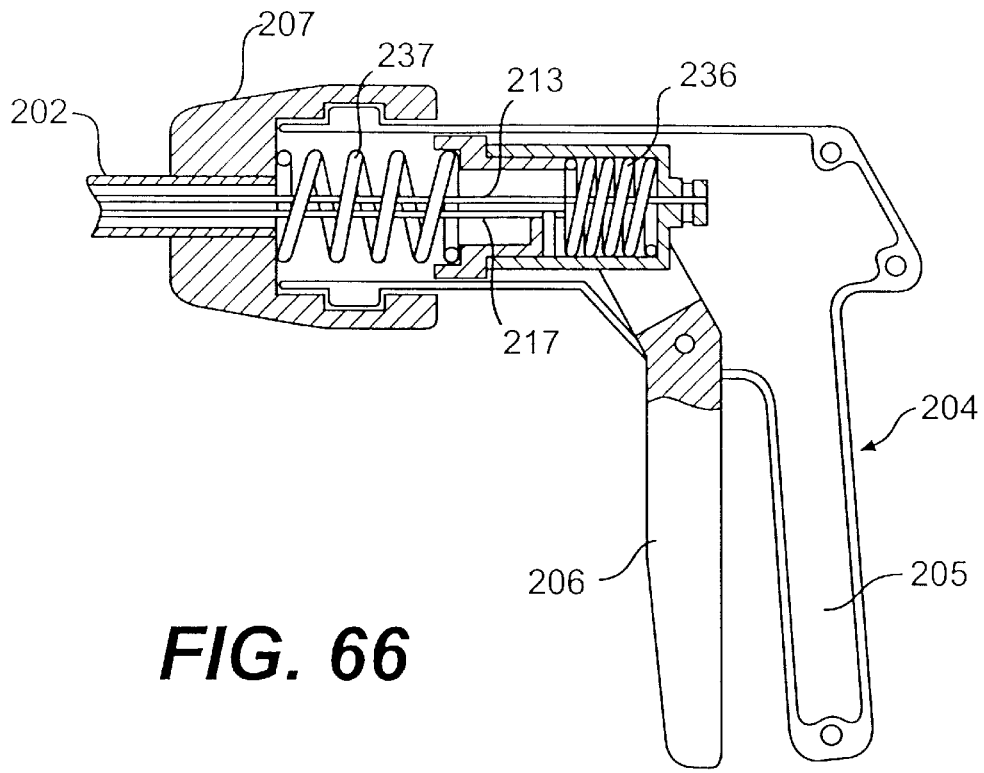
FIG. 66 is a side cross-sectional view of the operating section of the twentieth embodiment when it is in a fully-actuating state.

FIGS. 64 to 66 show a twentieth embodiment of the present invention. The same elements as those of the eighteenth and nineteenth embodiments are assigned the same reference numerals.

As in the previously-described eighteenth and nineteenth embodiments, the movable handle 206 is rotatable with respect to the fixed handle 205 in the present embodiment. An upper part of the movable handle 206 is rotatably connected to the jaws closing-and-operating member 213 in a slidable manner. The jaws closing-and-operating member 213 and the clip feed member 217 are connected substantially in line with each other by means of a sixth spring 236 having a comparatively small spring constant. The clip feed member 217 is further connected to the distal end of the operating section 204 by means of a seventh spring 237 having a comparatively large spring constant. At this time, in the clip attaching section 203 having substantially the same structure as that of the clip attaching section 203 of the second embodiment, the jaws 221 are opened, and the pusher 227 is positioned behind the clip 224 at the distal end of the line of clips 224 stored in the clip storage section 223.

FIG. 65 shows the operating section 204 which has been actuated to the first stage. As a result of closing action of the movable handle 206 up to the first stage, the jaws closing-and-operating member 213 advances to the first stage. As a result, the sixth spring 236 is compressed, whereby elastic energy is stored. At this time, the jaws closing member 222 advances to the first stage, whereby the attaching section 203 partially closes the jaws 221. As a result, tissue such as the vessel 230 previously grasped by the jaws 221 is slightly grasped so as not to slip from the jaws.

FIG. 66 shows the operating section 204 that is in a fully-operated state. If the movable handle 206 is completely operated from the first stage, the clip feed member 217 and the jaws closing-and-operating member 213 are simultaneously actuated toward the distal-end of the clip applier 201 because the sixth spring 213 is already compressed. As a result, a seventh spring 237 is compressed, whereby elastic energy is stored in the seventh spring 237. At this time, the clip attaching section 203 loads the distal-end clip 224 into the jaws 221, and the jaws 221 are simultaneously closed, whereby the clip 224 is attached to tissue such as the vessel 230. Subsequently, the movable handle 206 is opened by means of the elastic force of the sixth and seventh springs 236 and 237. As in the eighteenth embodiment, the jaws 221 are opened, and the pusher 227 returns to the rear of the clip 224 at the distal end of the line of clips 224 remaining in the clip storage section 223. The overall clip applier 201 returns to its original state.

As described above, the present embodiment is characterized by the clip applier 201 that operates in the following manner. Namely, the jaws 221 are partially closed so as to prevent target tissue from slipping away. Next, the clip 224 is loaded into the jaws 221, and the jaws 221 are closed, whereby the clip 224 is attached to the tissue. The clip applier 201 is not limited to any particular structure so long as the above-described feature of the present embodiment is ensured.

FIGS. 67 to 69A and 69B show a twenty-first embodiment of the present invention. The same elements as those of the eighteenth to twentieth embodiments are assigned the same reference numerals.

Figure 67A:
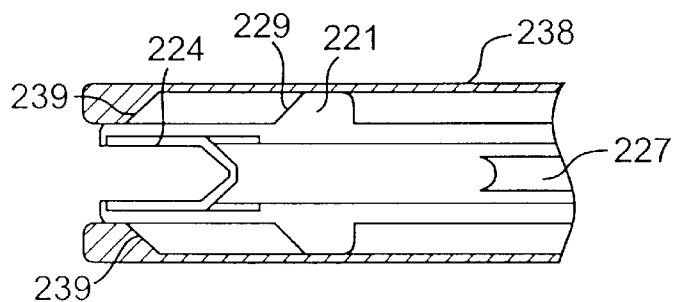
FIG. 67A is a longitudinally cross-sectional plan view of attaching section of a twenty-first embodiment of the present invention.
Figure 67B:
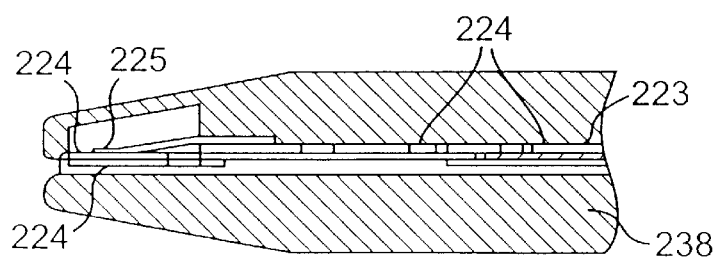
FIG. 67B is a longitudinally cross-sectional view of the attaching section.
Figure 69A:
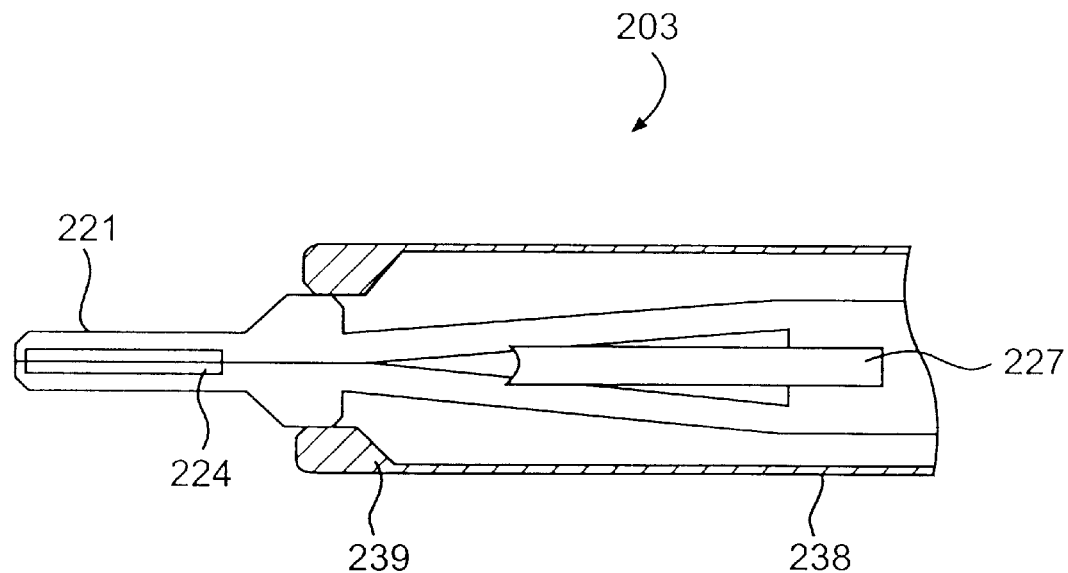
FIG. 69A is a longitudinally cross-sectional plan view of the attaching section of the twenty-first embodiment when it is in a fully-operating state.
Figure 69B:
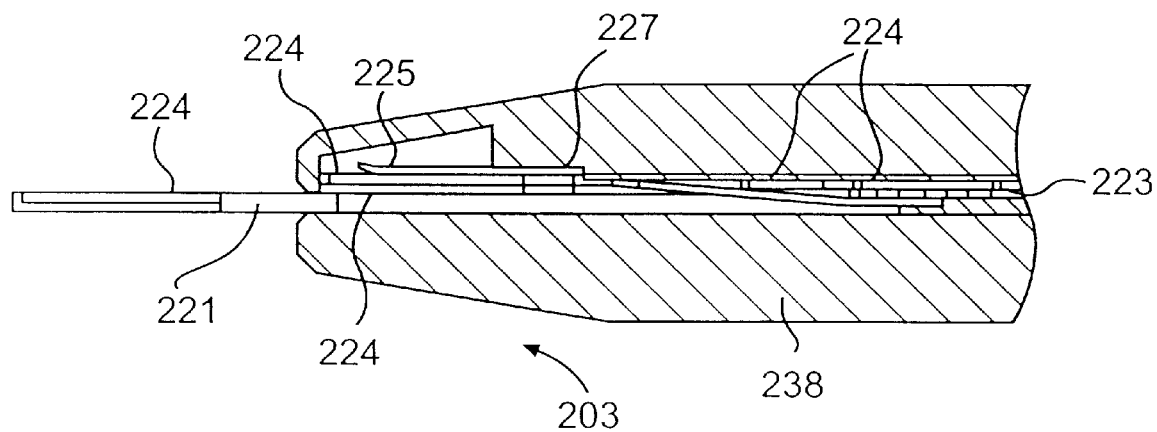
FIG. 69B is a longitudinally cross-sectional view of the attaching section of the twenty-first embodiment when it is in a fully-operating state.

FIGS. 67A and 67B show the initial state of the clip attaching section 203. As shown in FIGS. 69A and 69B, the jaws 221 are bifurcated as are the jaws 221 of the eighteenth embodiment. The jaws 221 are covered with and stored in a sheath 238. The clip 224 is loaded in the distal end of the jaws 221, and the other clips 224 are stacked on the clip 224 at the distal end of the line of clips 224. The clip 224 at the distal end of the line of clips 224 is pressed by the clip press spring 225. In this state, the jaws 221 are provided with the pusher 227, and this pusher 227 is stored in the jaws 221.

Figure 68A:
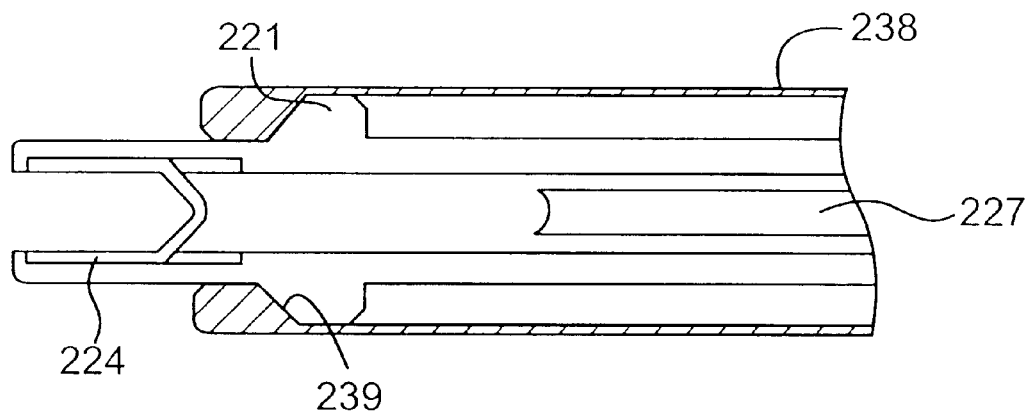
FIG. 68A is a longitudinally cross-sectional plan view of the attaching section of the twenty-first embodiment when it is in a first operating state.
Figure 68B:
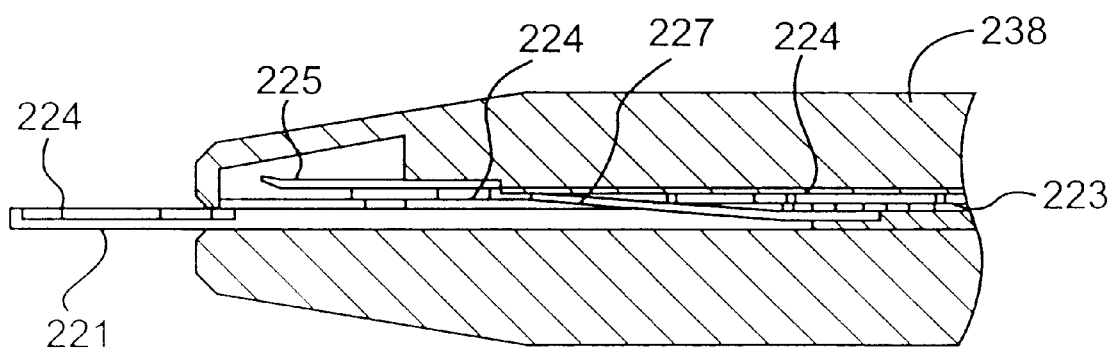
FIG. 68B is a longitudinally cross-sectional view of the attaching section of the twenty-first embodiment when it is in the first operating state.

FIGS. 68A and 68B show the operating section 204 which has been actuated to the first stage. In this state, the jaws 221 themselves advance forward, so that cam surfaces 229 provided on the jaws 221 are joined to tapered surfaces of protuberances 239 formed along the internal surface of the sheath 238. Concurrently, the pusher 227 also travels forward and rises by virtue of its elasticity. As a result, the clip 224 positioned at the distal end of the line of clips 224 stored in the storage section 223 is carried toward the distal end of the clip applier 201 against the clip press spring 225.

FIGS. 69A and 69B show the clip attaching section 201 which is in a fully-operated state. In this state, the jaws 221 further advance and are closed by the protuberances 239 of the sheath 238, whereby the loaded clip 224 is closed and attached to the target tissue. In this event, after having moved the previously-described clip 224 to a specified position, the pusher 227 returns to its initial state, whereupon the jaws 221 return to their initial state. As a result, the jaws 221 are opened. Of the two clips 224 positioned above the jaws 221, a lower clip 224 is loaded into the jaws 221 by means of the clip press spring 225, whereas an upper clip 224 is carried to a standby position for the next loading operation. Simultaneously, the pusher 227 also recedes to the inside of the jaws 221 so as to be situated in a standby position for carrying the clip 224 at the distal end of the line of clips 224 stored in the jaws 221. In this way, the overall clip applier 201 returns to the initial state.

As described above, the present embodiment is characterized by the clip applier 201 that has a simple structure and operates in the following manner. Namely, the clips 224 are loaded into the jaws 221 from above, and the jaws 221 are normally filled with the clips 224. The jaws 221 project only when attaching the clip 224. The clip applier 201 is not limited to any particular structure so long as the above-described feature of the present embodiment is ensured.

FIGS. 70A and 70B to 73 show a twenty-second embodiment of the present invention. The same elements as those of the eighteenth to twenty-first embodiments are assigned the same reference numerals.

FIGS. 70A and 70B show an initial state of the clip attaching section 240. The clip applier 201 has the same overall structure as that of the clip applier 201 of the eighteenth to twenty-first embodiments. The jaws 221 are normally closed, and the clips 224 are sequentially stored in the clip storage section 223 so as to follow the jaws 221. In the present embodiment, a total of twenty clips 224a to 224t are stored in the clip storage section 223. The last clip 224t is forced forward by a clip press spring 241. As a result, the line of clips 224a to 224t as a whole are also forced forward. For this reason, the forefront clip 224a is pressed by the clip press spring 225 so as not to drop forward.

The sheath 238 connected to the insertion section 202 is connected to the back of the clip attaching section 240, and the jaws 221 are fixed to the sheath 238 by jaws fixing pins 242. The jaws 221 are bifurcated as are the jaws 221 of the eighteenth to twenty-first embodiments of the present invention. As previously described, the jaws 221 are normally closed by their elasticity. A jaws closing member 243 is provided so as to house the jaws 221, and a jaws drive pin 244 connected to the jaws closing member 243 is provided between the bifurcated jaws 221. The jaws 221 have the cam surfaces 229, second cam surfaces 245, and third cam surfaces 246 formed thereon in order to constitute a cam mechanism which engages with the jaws drive pins 244. As will be described later, the cam mechanism open and close the jaws 221.

Figure 71:
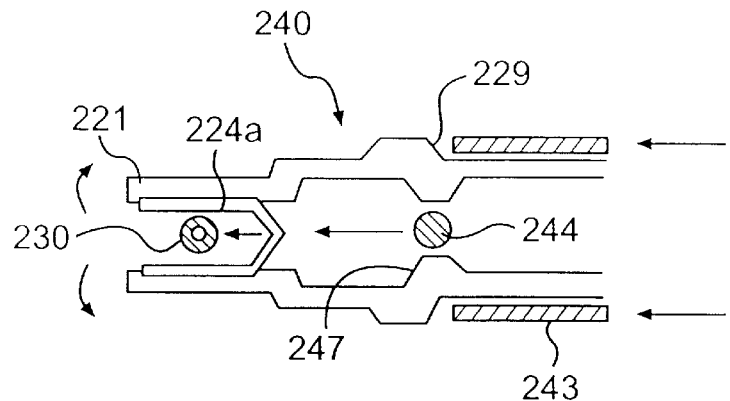
FIG. 71 is a side cross-sectional view of attaching section of the twenty-second embodiment when it is in a first operating state.
Figure 72:
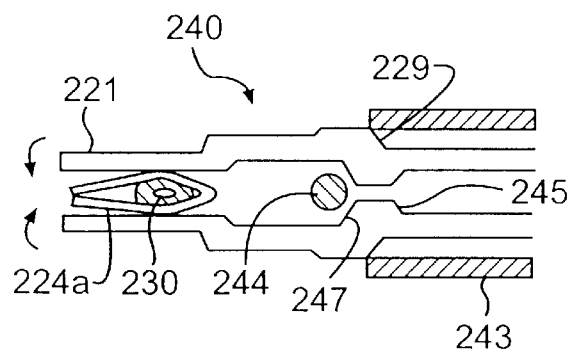
FIG. 72 is a side cross-sectional view of the attaching section of the-twenty-second embodiment when it is in a fully-operating state.
Figure 73:
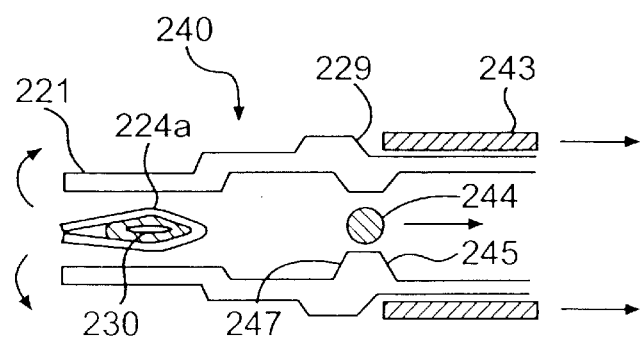
FIG. 73 is a side cross-sectional view of the attaching section of the twenty-second embodiment when it is in the course of returning to its initial state.

FIG. 71 shows the clip attaching section 240 which is in the first operated state. If the movable handle 206 of the operating section 204 of the eighteenth embodiment shown in FIG. 49 is operated to the first stage, the jaws closing member 243 advances, and the jaws drive pins 244 simultaneously travel forwardly. As a result, the jaws drive pins 244 and the second cam surfaces 245 mesh with each other, whereby the jaws 221 are opened. Concurrently, the clip press spring 225 is forced downwardly by the end face of the jaws closing member 243. The clips 224a to 224t are carried forwardly by the clip press spring 241, and the forefront clip 224a is loaded into the jaws 221.

Next, if the movable handle 206 is further actuated until it enters a fully-operated state, the jaws closing member 243 advances further together with the operation of the movable handle 206. The end face of the jaws closing member 243 and the cam surfaces 229 mesh with each other, whereby the jaws 221 are forcibly closed. Consequently, the clip 224a loaded in the jaws 221 is closed and can be attached to the vessel 230 previously grasped between the jaws 221.

As the movable handle 206 is opened from the previously-described state, the jaws closing member 243 accordingly recedes. The jaws closing member 243 disengages from the cam surfaces 229, and the jaws drive pins 244 and the third cam surfaces 247 engage with each other. As a result, the jaws 221 are forcibly opened. The clip 224a is ejected in this state, so that the clip attaching section 203 is removed from the vessel 230. By opening the movable handle 206 further, the clip attaching section 240 return to its original state as shown in FIGS. 70A and 70B.

As described above, the clip applier 201 is not limited to any particular structure so long as the object of the present invention; namely, opening of the normally-closed jaws 221 only when necessary, is achieved.

FIGS. 74 to 77 show a twenty-third embodiment of the present invention. In the drawings, reference numeral 301 designate a clip 301 for use as a suturing and ligating element for ligating tissue, particularly, vessels such as blood vessels. The clip 301 is manufactured from metallic material, particularly, non-magnetic titanium metal or plastic material having bio-absorbency. The clip 301 is made up of a pair of legs 302 and a joint 303 for connecting the legs 302 to each other.

Figure 77:
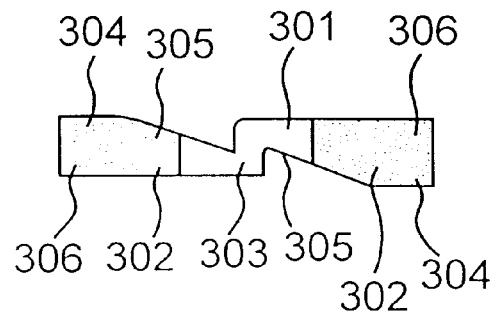
FIG. 77 is a developed view of the clip of the twenty-third embodiment when it is in the manufacturing phase.

The clip 301 has such a configuration as can be seen from a development elevation shown in FIG. 77 when it is in a material phase. In a case where the clip 301 is made of metallic material, the clip will be punched by pressing. In contrast, where the clip 301 is made of resin, it will be made by injection molding. In order to prevent tissue from slipping from the clip 301, serrations 306 are formed on grip surfaces 304 of the clip 301 by which the clip 301 comes into contact with and grasps tissue. The serrations 306 may be formed from a satin-finished surface by sand-blasting or may be formed by grooving the clip when it is pressed or ejection-molded. The serrations 306 may be formed in any shapes so long as they improve friction between the clip 301 and tissue.

Figure 74:
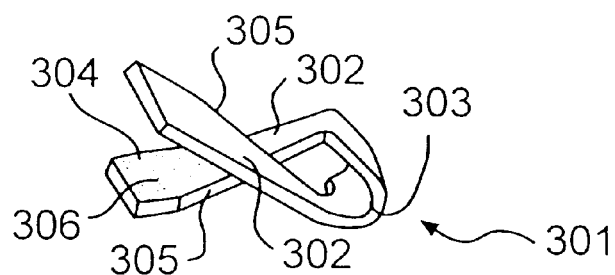
FIG. 74 is a perspective view of a clip of a twenty-third embodiment of the present invention which shows the initial shape of the clip when it is in a manufacturing phase.
Figure 75:
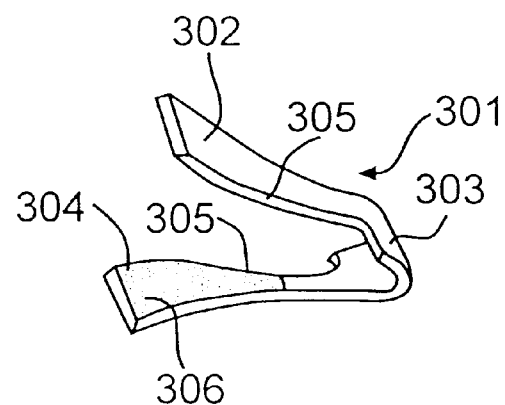
FIG. 75 is a perspective view of the clip of the twenty-third embodiment when the legs of the clip crossing each other are released from each other during the manufacturing phase.
Figure 76:
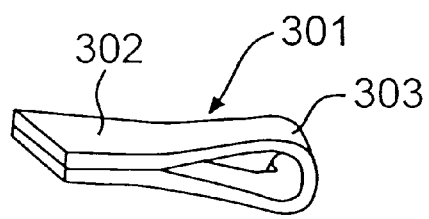
FIG. 76 is a perspective view of the initial shape of the clip of the twenty-third embodiment when it is practically used.

The shape shown in FIG. 74 is the initial state of the clip 301 in the present embodiment. The clips 301 are loaded into a clip applier as they are. The clip 301 is attached to tissue by being resiliently clinched by the clip applier the order as shown in FIGS. 74 to 76. At this time, tapered portions 305 are formed in legs 302 as can be seen from the development elevation shown in FIG. 77, and hence the legs 302 are apt to be released from a twist. Further, the legs 302 are prone to be released from the crossed state during the course of deforming processes shown in FIGS. 74 and 75.

By virtue of the above-described structure, a ligating force of the clip is improved when compared with a conventional resilient clip.

As described above, the clip 301 is not limited to any particular structure so long as the object of the present invention; namely, improvements in a ligating force of a resilient clip when it is in an initial state, is achieved.

FIGS. 78 to 81 show a twenty-fourth embodiment of the present invention. A method and materials used for forming a clip of the present embodiment are substantially the same as those used in the twenty-third embodiment. In the drawings, reference numeral 301 designates a suturing and ligating element for ligating tissue and, particularly, vessels such as blood vessels. The clip 301 comprises a pair of legs 302 and a joint 303 connecting the legs 302.

Figure 81:
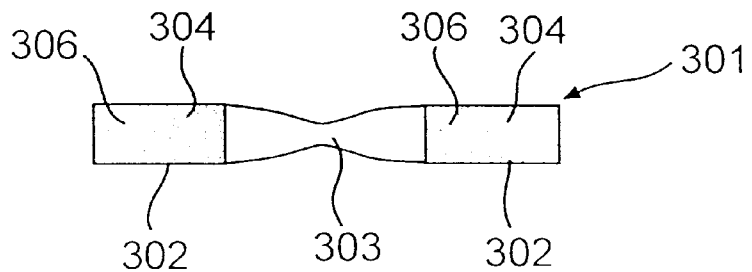
FIG. 81 is a developed view of the clip of the twenty-fourth embodiment when it is in the manufacturing phase.

The clip 301 has such a configuration as can be seen from a development elevation shown in FIG. 81 when it is in a material phase. In a case where the clip 301 is made of metallic material, the clip will be punched by pressing. In contrast, where the clip 301 is made of resin, it will be made by injection molding. In order to prevent tissue from slipping from the clip 301, the serrations 306 are formed on the grip surfaces 304 of the clip 301 by which the clip 301 comes into contact with and grasps tissue. The serrations 306 may be formed from a satin-finished surface by sand-blasting or may be formed by grooving the clip when it is pressed or ejection-molded. The serrations 306 may be formed in any shapes so long as they improve friction between the clip 301 and tissue.

The joint 303 is formed to become narrower than the legs 302 so as to prevent from interfering with the legs 302 when the legs 302 are opened and closed by means of, e.g., a guide of the clip applier which acts as a suturing and ligating instrument for attaching the clip 301 to tissue and will be described later.

Figure 78:
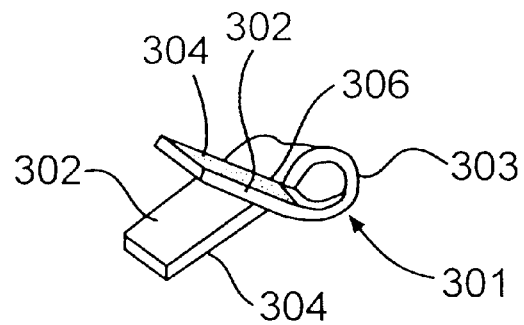
FIG. 78 is a perspective view of a clip of a twenty-fourth embodiment of the present invention showing the initial shape of the clip when it is in the manufacturing phase.

After having been formed into such a configuration as can be seen from the development elevation shown in FIG. 81, the material is resiliently deformed into the shape as shown in FIG. 78. During the resiliently deforming action, the clip 301 is formed by slightly twisting the legs 302; namely, the clip 301 is formed by opening the legs 302 once having crossed them.

Figure 79:
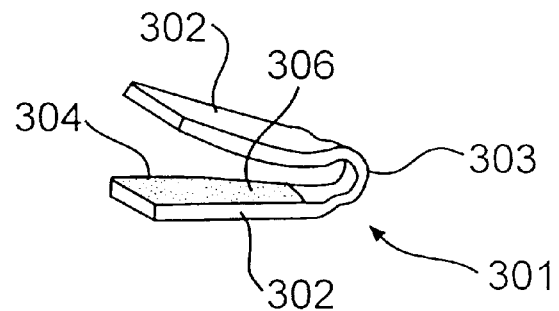
FIG. 79 is a perspective view of the clip of the twenty-fourth embodiment when the legs of the clip crossing each other are released from each other during the manufacturing phase.
Figure 80:
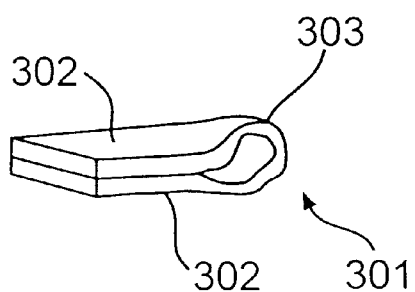
FIG. 80 is a perspective view of the initial shape of the clip of the twenty-fourth embodiment when it is practically used.

Then, the legs 302 are released from a twistedly crossed state in order to transform the clip 301 into such a shape as shown in FIG. 79. The legs 302 are then opened, whereupon the clip 301 assumes such a shape as shown in FIG. 80. By virtue of the previously-described series of manufacturing processes, it is possible to provide the clip 301 with an effective grasping force in its initial configuration as shown in FIG. 80 when the clip 301 is used.

More specifically, the conventional clips of the conventional art have been resiliently clinched into the shape as shown in FIG. 80 from the beginning. As a result, in a case where tissue which is in its initial state; i.e., in the state in which it is thin, soft, and fragile, is ligated using the clip, there is a risk of dropping of the clip 301 as a result of its insufficient effective ligating force. In contrast, the clip 301 of the present embodiment has already been resiliently clinched from its original state shown in FIG. 79. Consequently, an effective resilient force acts on the legs 302 when the clip 301 is in its initial and practical configuration shown in FIG. 80. Therefore, an effective ligating force acts on tissue which is thin, soft, and fragile, which in turn eliminates the risk of dropping of the clip 301.

As described above, the clip 301 is not limited to any particular material, structure, and shape so long as the object of the present invention; namely, improvements in a ligating force of a resilient clip when it is in an initial state, is achieved.

Figure 82:
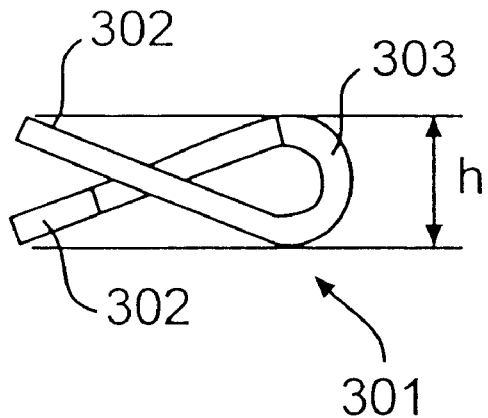
FIG. 82 is a side view of a clip of a twenty-fifth embodiment of the present invention.

FIG. 82 shows a twenty-fifth embodiment of the present invention. The clip 301 of the present embodiment is the same as that of the twenty-third embodiment with regard to a structure and material. The clip 301 of the present embodiment is characterized by the fact that the width of an opening formed between the legs 302 is identical with the height h of the joint 303 in the initial state of the clip 301. As the width of the opening between the legs 302 increases, a force for ligating tissue becomes stronger. However, if the width of the opening is excessively increased, the advantage of the clip 301; namely, the advantage of compactness compared to the conventional resiliently deformable clip, will be impaired. To prevent this problem, the width of the opening formed between the legs 302 is made so as to substantially equal the height h of the joint 303, whereby assurance of a ligating force of and compactness of the clip 301 are achieved.

As described above, the clip 301 is not limited to any particular material and structure so long as the objects of the present invention; namely, compactness of and assurance of a ligating force of a clip, are achieved.

Figure 83:
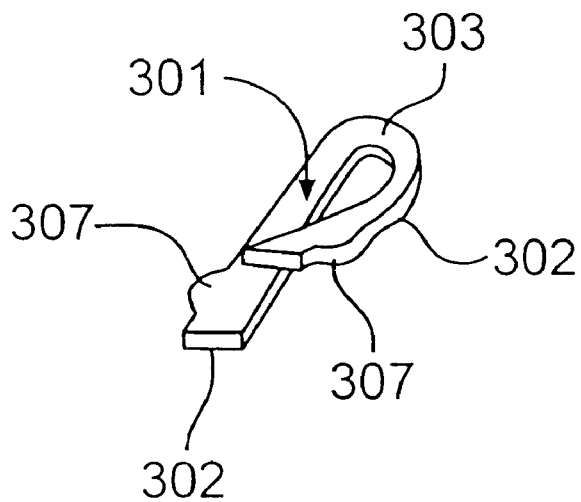
FIG. 83 is a perspective view of a clip of a twenty-sixth embodiment of the present invention.

FIG. 83 shows a twenty-sixth embodiment of the present invention. The clip 301 of the present embodiment is the same as that of the twenty-third embodiment with regard to a structure and material. The clip 301 is formed so that the legs 302 and the joint 303 have the same width. Engaging tabs 307 which are wider than the width of the joint 303 are formed in a part of the legs 302 and are used when engaging with a clip applier for attaching the clip 301 to tissue. The clip 301 of the present embodiment is the same as the clip 301 of the twenty-fourth embodiment with regard to its operation and effects.

As described above, the clip 301 is not limited to any particular structure so long as the object of the present invention; namely, improvements in a ligating force of a resilient clip when it is in an initial state, is achieved.

Figure 84:
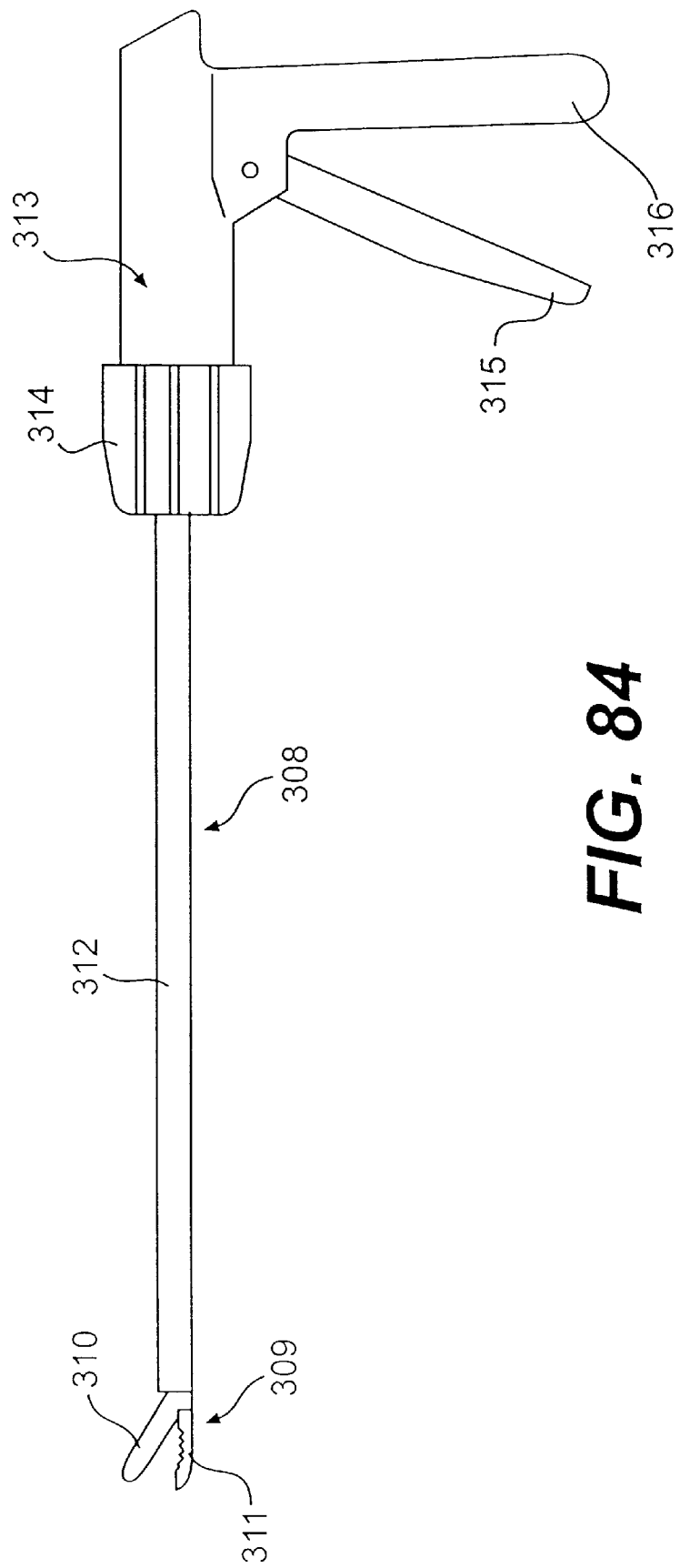
FIG. 84 is a side view showing the entirety of a clip applier of a twenty-seventh embodiment of the present invention.

FIGS. 84 to 96 show a twenty-seventh embodiment of the present invention. FIG. 84 shows the overall structure of a clip applier 308 for attaching a clip 301 of the present embodiment to tissue 324 (see FIG. 86). The clip applier 308 comprises attaching section 309 for attaching the clip 301 to the tissue 324, an insertion section 312 for guiding the attaching section 309 to the tissue 324, and operating section 313 for actuating the clip applier 308.

The attaching section 309 is made up of a fixed jaw 311 fixed to the insertion section 312, and a movable jaw 310 which can open and close with respect to the fixed jaw 311. It is possible to retain the tissue 324 by opening and closing the movable jaw 310.

A rotary ring 314 is attached to the proximal end of the insertion section 312. The insertion section 312 can be rotated around its axis with respect to the operating section 313 by rotating the rotary ring 314.

The operating section 313 is made up of a fixed handle 316 and a movable handle 315 which can open and close with respect to the fixed handle 316. The clip 301 can be attached to the tissue 324 by closing the movable 315.

Figure 85:
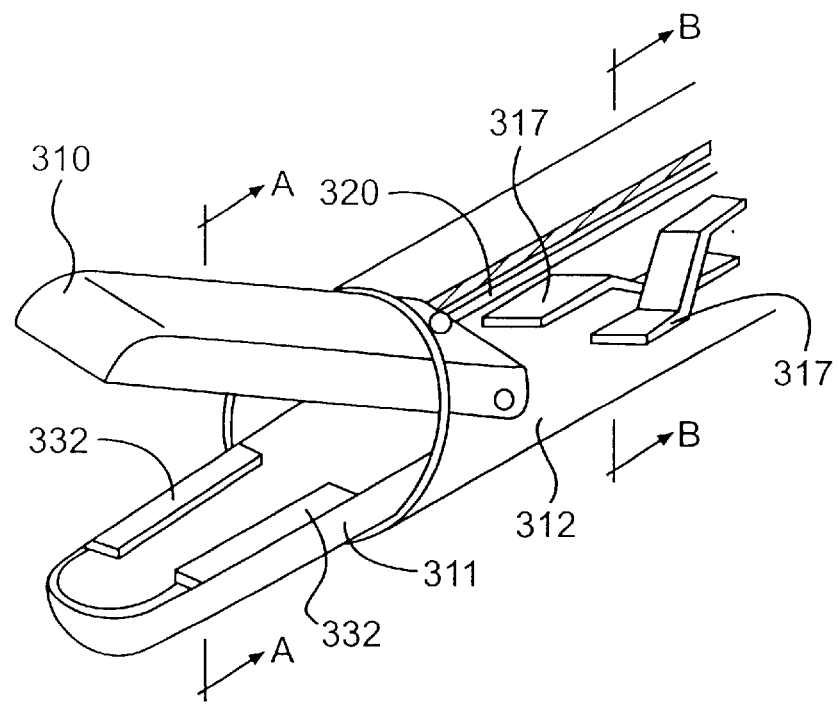
FIG. 85 is a perspective view of attaching section of the twenty-seventh embodiment.
Figure 86:
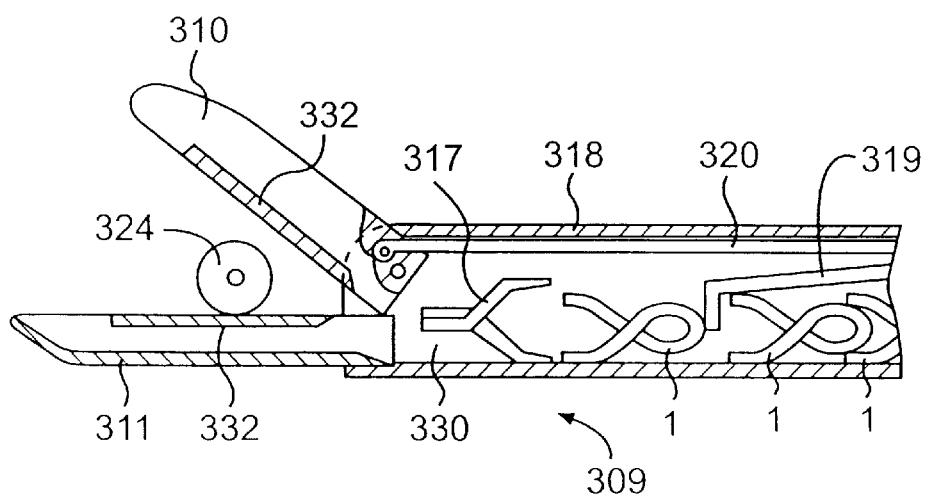
FIG. 86 is a longitudinal cross-sectional view of the attaching section of the twenty-seventh embodiment.

FIGS. 85 to 89 show the internal structures of the attaching section 309 and storage section 329. As shown in FIGS. 85 and 86, the fixed jaw 311 and the movable jaw 310 are provided at the front end of the attaching section 309. An operation rod 320 is connected to the rear end of the movable jaw 310. The operation rod 320 moves in conjunction with the action of the movable handle 315 of the operating section 313.

The movable jaw 310 opens and closes by opening and closing the movable handle 315.

Figure 88:
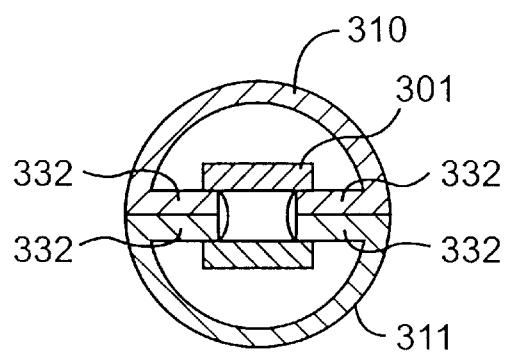
FIG. 88 is a cross-sectional view of the attaching section taken across line A–A' shown in FIG. 85.

As shown in FIG. 88, a space is formed between the movable jaw 310 and the fixed jaw 311 so as to permit passage of the clip 301. Guides 332 are provided in this space for engaging with the legs 302 of the clip 301.

Figure 89:
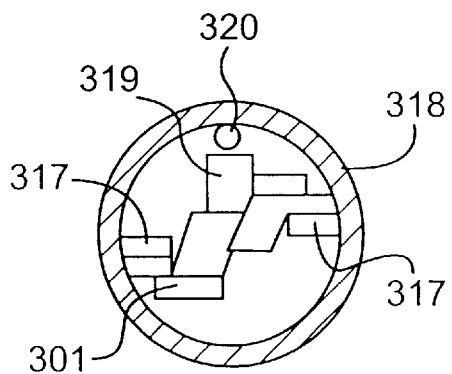
FIG. 89 is a cross-sectional view of the attaching section taken across line B–B' shown in FIG. 85.

Guides 317 are provided in the insertion section 312 in the vicinity of the rear end of the attaching section 309 for canceling the cross between the legs 302 of the clip 301. As shown in FIG. 89, the cross of the legs 302 is canceled when the clip 301 passes through the insertion section 312.

A pusher 319 is also provided in the insertion section 312 in order to supply the clips 301 one by one. This pusher 319 is designed so as to supply the forefront clip 301 of the line of clips 301 stored in the storage section 329 by actuation of the movable handle 315.

Figure 87:
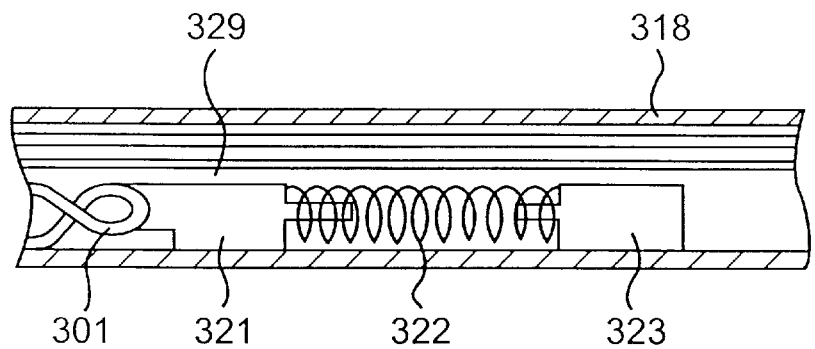
FIG. 87 is a longitudinally cross-sectional view of storage section of the twenty-seventh embodiment.

The storage section 329 is provided in the insertion section 312. The rear end of the storage section 329 is shown in FIG. 87. As shown in this drawing, a coil spring 322 attached to a base 323 fixed on the internal surface of the insertion section 312 forces the clip 301 at the end of the line of clips 301 toward the front end of the clip applier 308 via a buffer 321. In this way, the clips 301 sequentially stored in the storage section 329 are thrust to the tip end of the clip applier 308.

Figure 90:
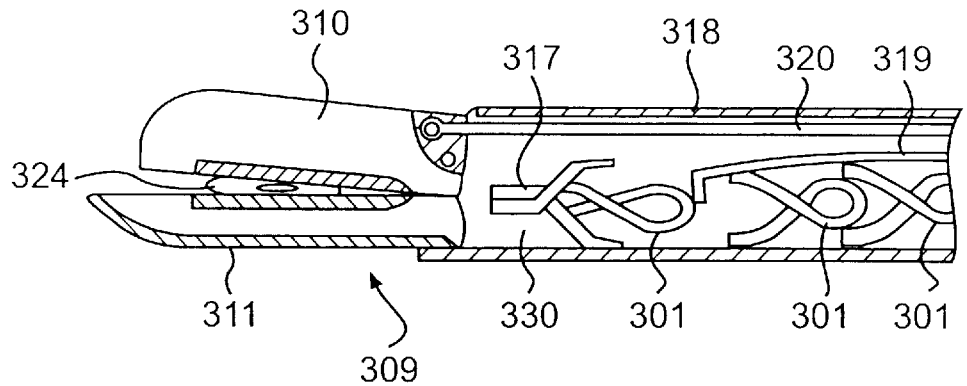
FIG. 90 is a longitudinally cross-sectional view of the attaching section of the twenty-seventh embodiment when it is in an initial state.
Figures 93, 94:
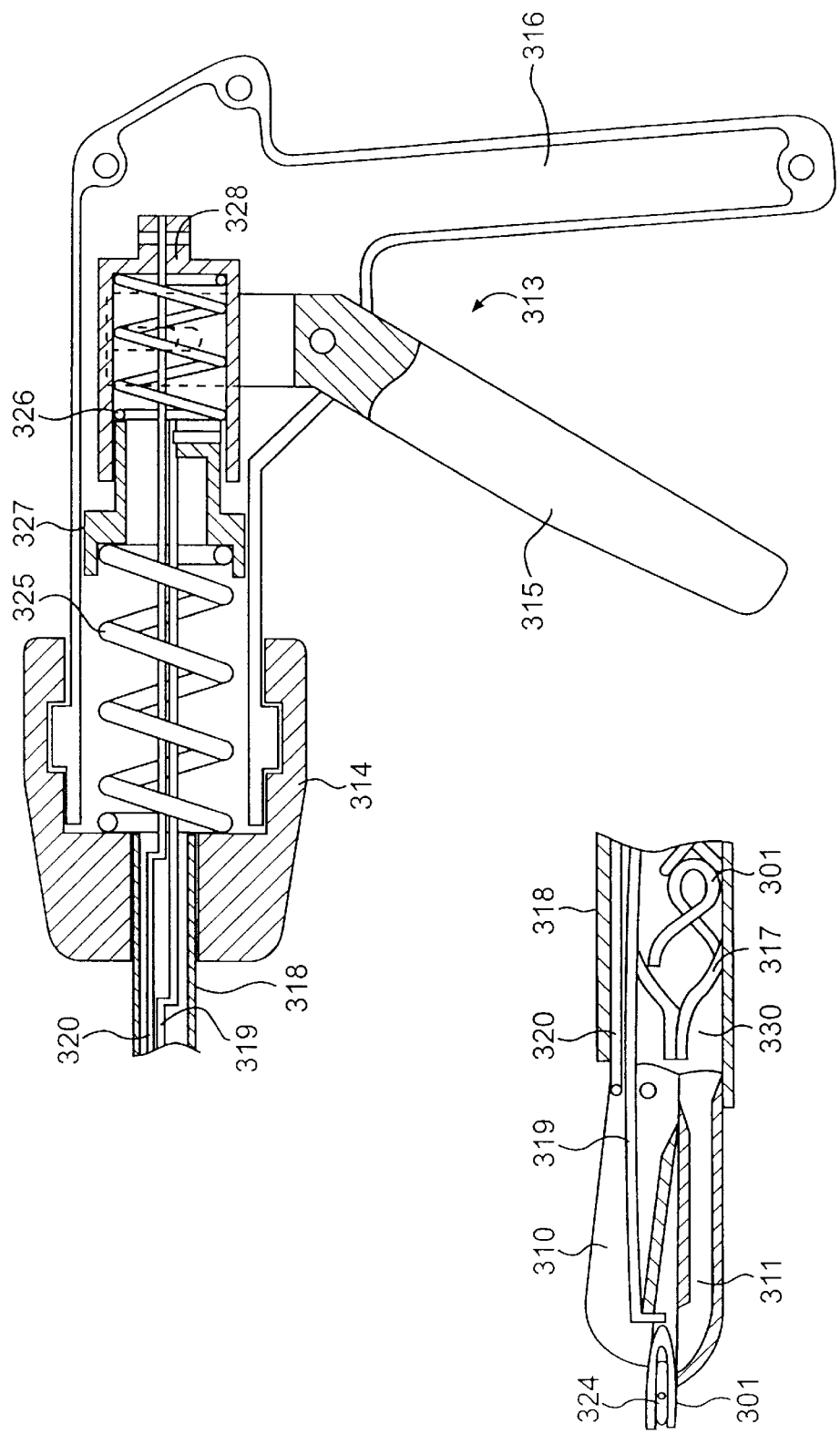
FIG. 93 is a longitudinally cross-sectional view of the attaching section of the twenty-seventh embodiment when it is in the end of an ligating operation.
FIG. 94 is a longitudinally cross-sectional view of operating section of the twenty-seventh embodiment when it is in an initial state.

FIGS. 90 to 96 show the operation of the clip applier 308 of the present embodiment. FIG. 90 shows an initial state of the clip applier 308. In this state, the pusher 319 is situated behind the forefront clip 301. At this time, the operating section 313 is in such a state as shown in FIG. 94.

The movable handle 315 is opened with respect to the fixed handle 316, and the pusher 319 is in a rearwardly drawn state by means of coil springs 325 and 326 together with the operation rod 320. The movable jaw 310 is open with respect to the fixed jaw 311.

The coil springs 325 and 326 are set such that the coil spring 325 becomes larger than the coil spring 326 with regard to a spring constant. The coil spring 325 is not compressed unless the coil spring 326 is fully compressed.

Figure 95:
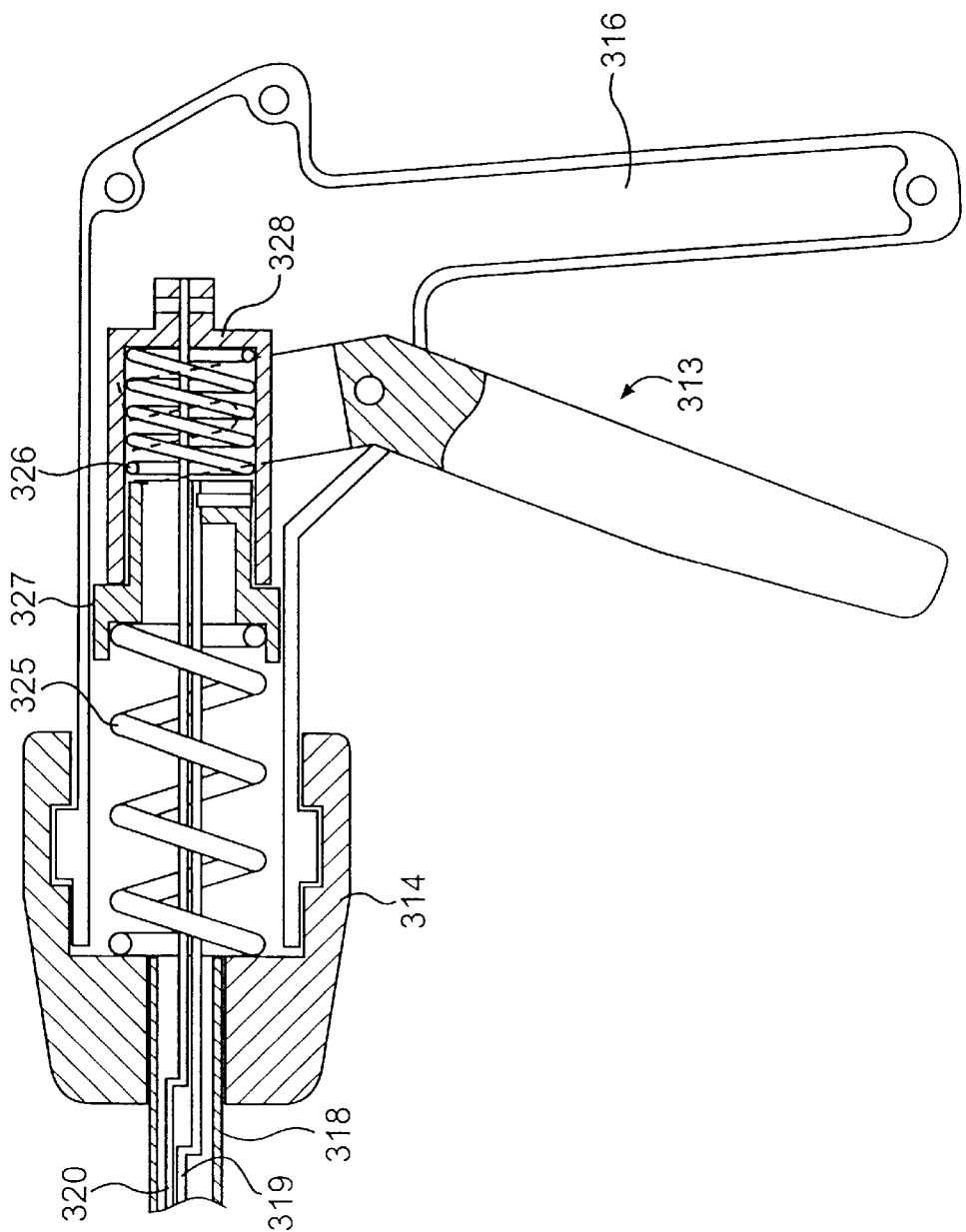
FIG. 95 is a longitudinally cross-sectional view of the operating section of the twenty-seventh embodiment when it is in second through third stages.

Next, the movable handle 315 is slightly moved to the closing direction, whereby the movable handle 315 enters a state shown in FIG. 95. At this time, the attaching section 309 enters a state shown in FIG. 90. The coil spring 326 is compressed when the spring holder 328 is actuated by the movable handle 315, so that the operation rod 320 is moved forward. As a result, the movable jaw 310 is closed with respect to the fixed jaw 311, and hence the tissue 324 previously positioned between the movable jaw 310 and the fixed jaw 311 can be grasped.

Figure 91:
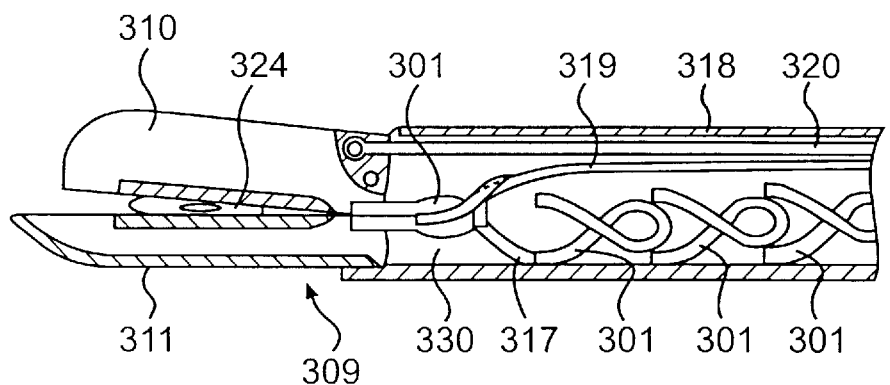
FIG. 91 is a longitudinally cross-sectional view of the attaching section of the twenty-seventh embodiment when it is in a second stage.
Figure 92:
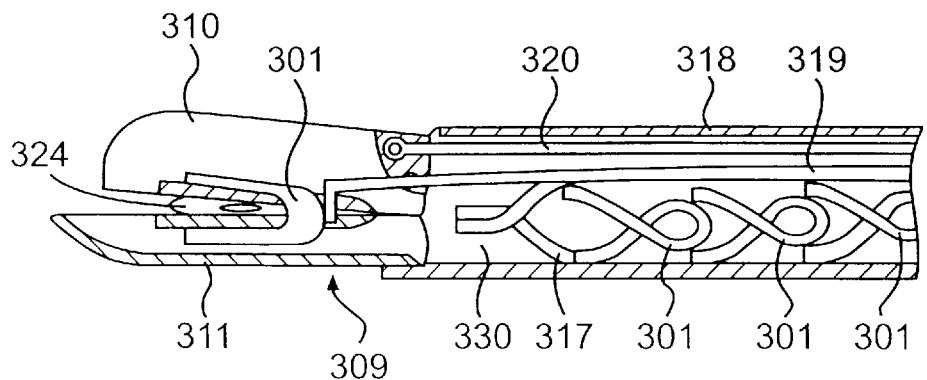
FIG. 92 is a longitudinally cross-sectional view of the attaching section of the twenty-seventh embodiment when it is in a third stage.

Further, the coil spring 326 is fully compressed by actuating the movable handle 315 in a closing direction. If the movable handle 315 is actuated further in the closing direction, the coil spring 325 starts to be compressed. As a result, the pusher 319 travels forward so as to push the clip 301 into the guides 317 as shown in FIG. 91. At this time, the cross between the legs 302 of the clip 301 is canceled by the guides 317. Through further continuous execution of the operations, the clip 301 engages with the guides 322 of the movable jaw 310 and the fixed jaw 311 by means of the pusher 319. The legs 302 are opened by the guides 322, and the clip 301 is attached to the tissue 324. As a result of further forward movement of the pusher 319, the clip 301 is ejected so as to pass through the inside of the movable jaw 310 and the fixed jaw 311 while ligating the tissue 324. The ligation of the tissue 324 is now completed.

Figure 96:
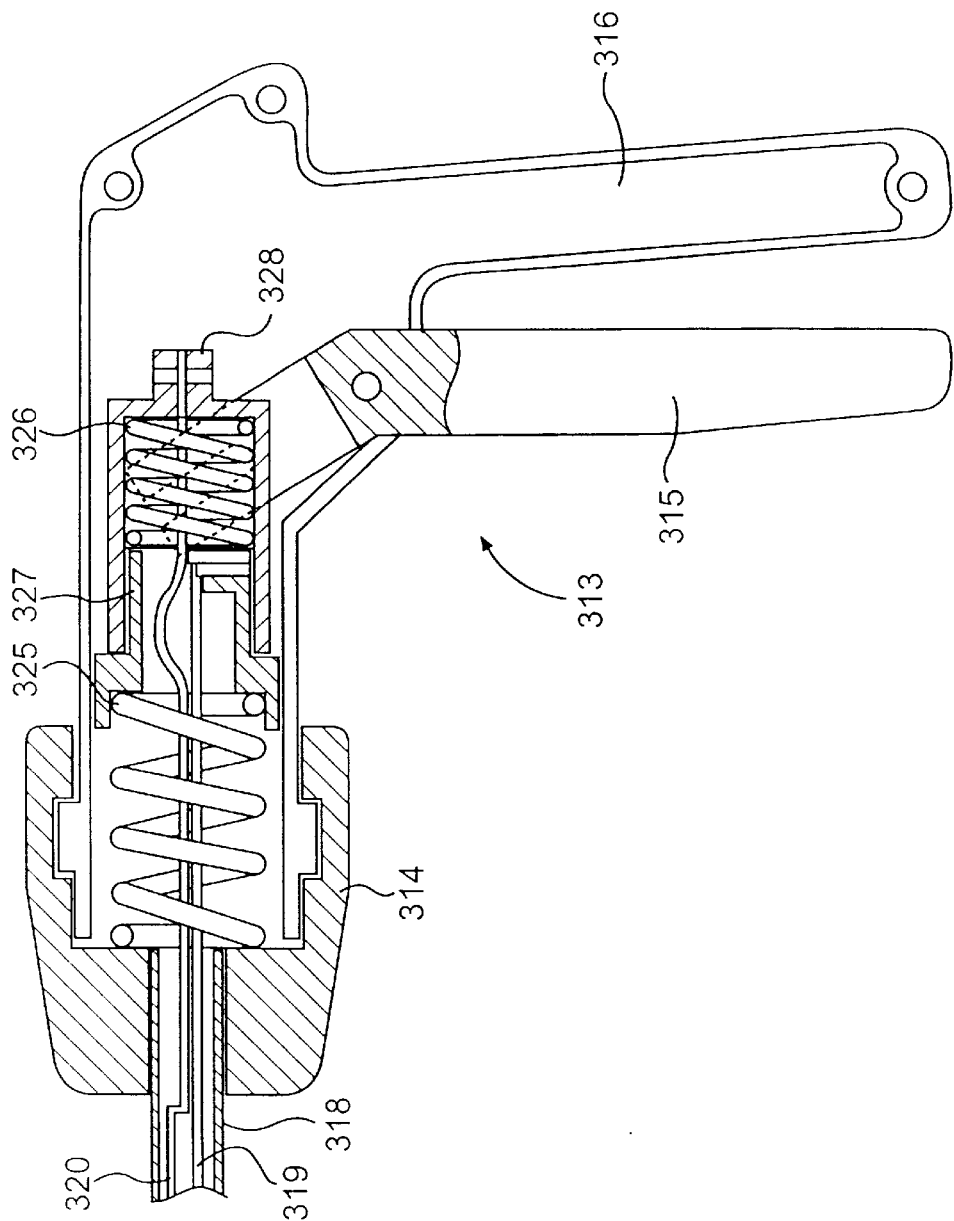
FIG. 96 is a longitudinally cross-sectional view of the operating section of the twenty-seventh embodiment when the ligating operation of the operating section is completed.

At this time, the operating section 313 is in a state as shown in FIG. 96. The operation rod 320 cannot move forward any further after the movable jaw 310 has been fully closed. As a result, the operation rod 320 itself elastically deflects, which absorbs the actuating force exerted on the movable handle 315. By virtue of the foregoing mechanism, a grasping force of the clip 301 is improved by the elastic force, which makes it possible to reliably grasp the tissue 324.

If the movable handle 315 is opened after the ligating operation has been completed, the pusher 319 will recede to the back of the guides 317 by means of the coil spring 322. As a result, the pusher 319 engages with the next clip 301, and the operation rod 320 also recedes, whereby the movable jaw 310 is also opened. The clip applier 308 eventually recovers its original state. If the ligating operation is performed further, the foregoing operations are repeated carried out. As a result, it is possible to perform the ligating operations so as to correspond to the number of clips 301 through repeated execution of the foregoing operations.

By virtue of the previously-described structure, the clip 301 for use with the clip applier 308 becomes more compact than a clip applier for attaching a conventional resiliently deformable clip to tissue with regard to an initial shape. Therefore, the outside diameter of the insertion section 312 could be reduced, and the clip applier 308 could be manufactured less expensively because of its simple structure. Further, the clip 301 has the advantage of a stronger ligating force due to the crossed legs 302 of the clip 301 when it is in the initial state. It is also possible to reliably ligate tissue using the conventional resilient clip.

As described above, the clip 301 is not limited to any particular structure so long as the objects of the present invention are achieved; namely, provision of an inexpensive and simple clip applier with a narrow-insertion section, and reliable execution of a ligating operation.

Figure 97:
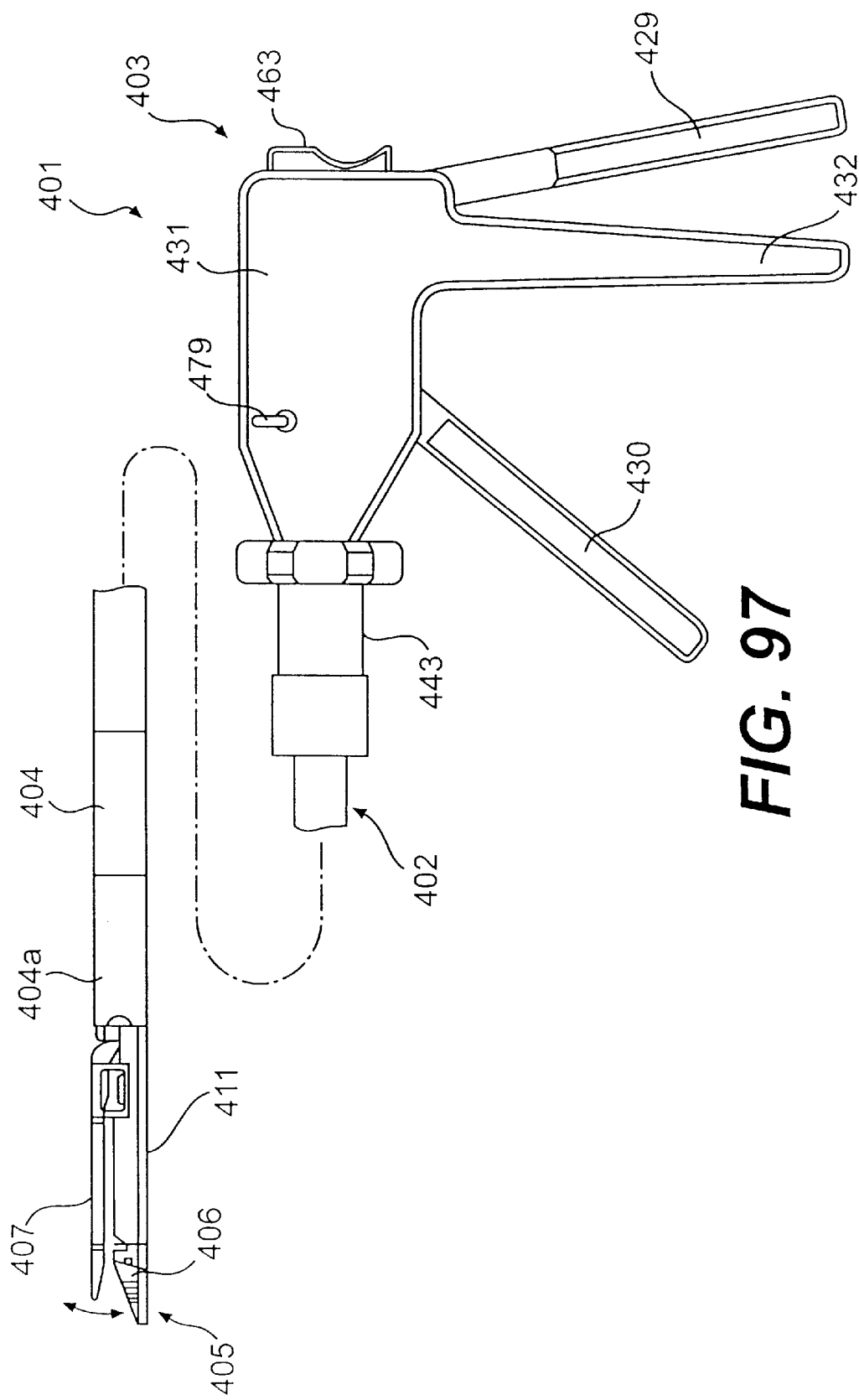
FIG. 97 is a side view schematically showing the entirety of a suturing instrument of a twenty-eighth embodiment of the present invention.

With reference to FIGS. 97 to 103, a twenty-eighth embodiment of the present invention will now be described. FIG. 97 schematically shows the overall structure of a suturing instrument 401 of the present embodiment. A gun-grip-shaped operating section 403 of the suturing instrument 401 which is provided at the proximal end of the suturing instrument 401 is connected to the base of a narrow insert 402 to be inserted into a body.

The insertion section 402 is provided with; e.g., a narrow-pipe-shaped insert sheath 404 having a circular cross section of about 12 mm in diameter. A front end cover 404a is provided at the front end of the insertion section sheath 404.

Jaws 405 which can open and close are provided at the front end of the insertion section 402 in order to grasp tissue. The jaws 405 are provided with a staple cartridge 406 and an anvil 407 which is connected to the staple cartridge 406 so as to be able to open and close.

Figure 98:
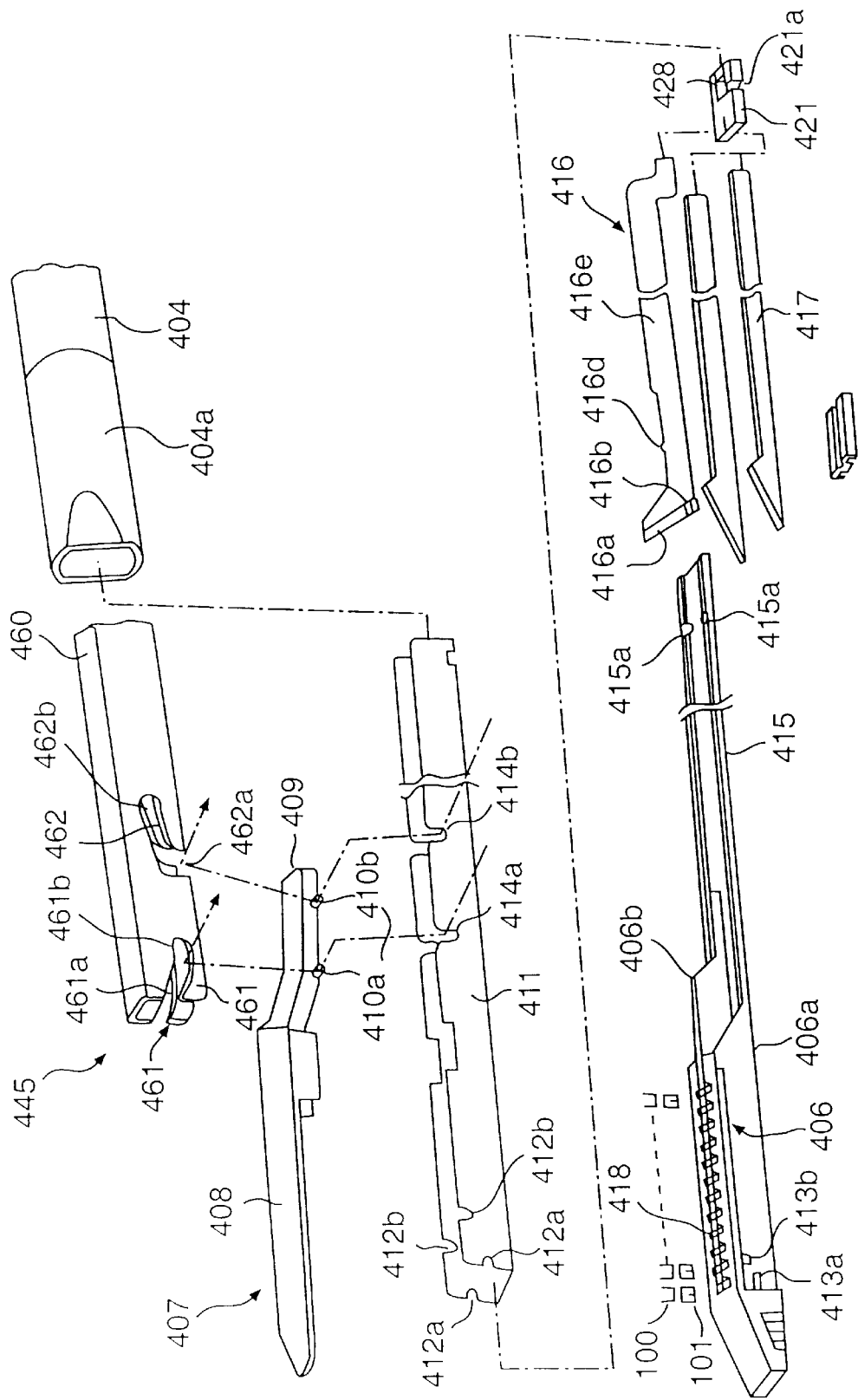
FIG. 98 is an exploded perspective view showing an anvil open-close mechanism of the suturing instrument and the structure of a stapling mechanism of the twenty-eighth embodiment.

As shown in FIG. 98, a staple storage section 406a is formed at the front end of the cartridge 406. A plurality of substantially U-shaped staples 500 made of biologically compatible titanium or stainless steel are stored in the staple storage section 406a with both edges upward so as to be ejected to the anvil 407. The staples 500 to be stored in the staple storage section 406a of the cartridge 406 should preferably be arranged into; e.g., four to six lines.

Substantially rectangular parallelepiped staple drive members 501 are provided below the respective staples 500 within the staple storage section 406a. A tapered surface is formed below the staple drive members 501 in order to eject the staples 500 toward the anvil 407. The staple drive members 501 are supported so as to be able to slide toward the anvil 407 when the staple drive members 501 come into contact with the staple 500.

As shown in FIG. 98, the anvil 407 is provided with a staple clinching section 408 for clinching the staples 500, and a rearwardly-extending section 409 which extends from the staple clinching section 408. A pair of cam pins 410a and 410b project from both sides of the rearwardly-extending section 409.

As shown in FIGS. 99A to 99C, a cartridge holder 411 is provided below the anvil 407 so as to removably support the cartridge 406. This cartridge holder 411 is formed so as to have a substantially U-shaped cross section by bending. A pair of notches 412a and 412b are formed in the front edge and upper edge on each side of the front end of the cartridge holder 411. In this case, a pair of projections 413a and 413b project from the front end on each side of the cartridge 406 so as to removably engage with the notches 412a and 412b. In a state in which the cartridge 406 is fitted into the cartridge holder 411, the engagement projections 413a and 413b of the cartridge 406 removably engage with the notches 412a and 412b of the cartridge holder 406. Here, the shape of a removable portion between the cartridge 406 and the cartridge holder 411 is not limited to the structure of the present embodiment. A collet chuck may also be used.

A pair of guide slots 414a and 414b are formed in the upper edge on each side of the cartridge holder 411 so as to engage with the cam pins 410a and 410b of the anvil 407.

An extension 415 extends backward from the back of the staple storage section 406a of the cartridge 406. Engaging protuberances 415a inwardly project from both side edges in the vicinity of the rear end of the extension 415. A cutter 416 which serves as excising member for excising tissue grasped by the jaws 405, and cam plates 417 having their front edges tapered so as to push the staples 500 on a line-to-line basis are provided on the extension 415.

Figure 100:
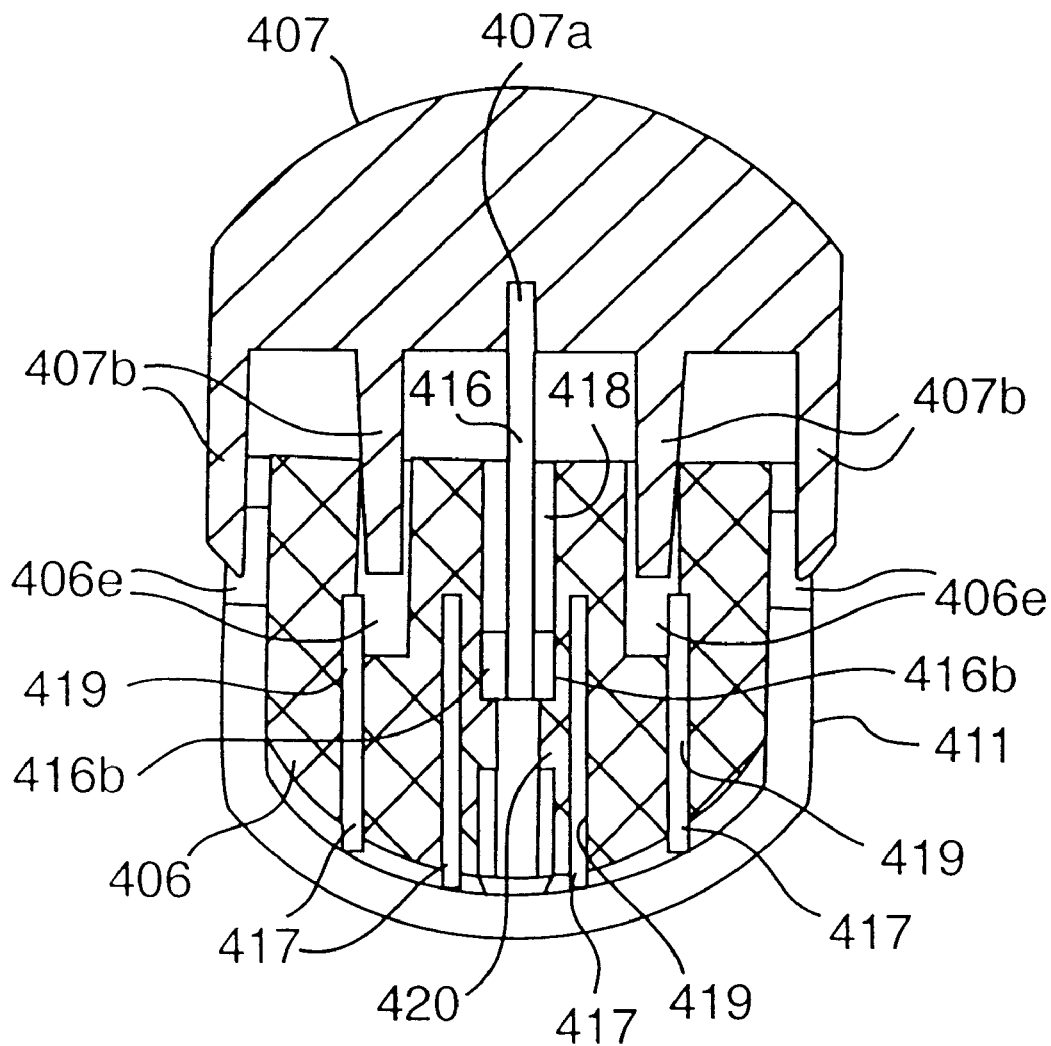
FIG. 100 is a cross-sectional view of the anvil taken across line L1—L1 shown in FIG. 99C.

As shown in FIG. 100, a cutter slot 418 is formed between the staple lines within the staple storage section 406a of the cartridge 406 in order to guide the sliding action of the cutter 416. Further, guide slits 419 are formed below the staple lines in order to guide the travel of the cam plates 417.

As shown in FIG. 100, a rib-shaped rail (or a slide passage) 420 inwardly projects along the longitudinal center of each internal surface of the cutter slot 418 so as to make the width of the slot 418 narrow. The cutter slot 418 is divided into upper and lower sections by means of the rails 420; namely, upper slots 418a and lower slots 418b.

As shown in FIGS. 101A and 101B, obliquely cut sections (or switching member) 420a are formed in the rear of the rails 420. The upper and lower slots 418a and 418b separated by the rails 420 are connected to each other through the obliquely cut sections 420a.

The rails 420 are different from each other in height across the obliquely cut sections 420a. Front areas 420b are set so as to become lower than rear areas 420c in relation to the obliquely cut sections 420a. In the cutter slot 418, the rear ends of the lower slots 418b are positioned in front of the rear ends of the upper slots 418a. Further, a bridge 406b for connecting together the tops of both sides of the cutter slot 418 is formed in the vicinity of the rear end of the staple storage section 406a of the cartridge 406.

As shown in FIGS. 101A and 101B, an edge 416a which serves as a cutting blade is formed on the front end of the cutter 416. A protuberance 416b sideward projects from a lower portion on each side of the cutting edge 416a. A rear end 416c of each protuberance 416b is tapered.

As shown in FIG. 98, a claw 416d and a plateau-like shoulder 416e are raised from the rear portion of the cutter 416 behind the edge 416a. When the cutter 416 is in its initial state before actuated, the claw 416d of the cutter 416 removably engages with the bridge 406b of the cartridge 406.

The rear ends of the cam plates 417 and the rear end of the cutter 416 are connected to each other by a holder 421. Recesses 421a which engage with the engaging protuberances 415a of the cartridge 406 are formed in both sides of the holder 421. Further, slits are formed in the front end of the holder 421 so as to permit fitting of the rear ends of the cutter 416 and the cam plates 417.

As shown in FIGS. 101A and 101B, the holder 421 is removably connected to the front end of a narrow joint rod 422 provided in the insertion section sheath 404 via a connector 423. In this case, the joint rod 422 is provided in line with the insertion section 402. The joint rod 422 and the connector 423 are connected with each other so as to rotate around the axis of the insertion section 402 by means of a C link 424 or the like. The rear end of the joint rod 422 extends to the operating section 403.

A resilient hook 425 is provided at the front end of the connector 423. The resilient hook 425 comprises an arm 426 projecting from the front end surface of the connector 423, and an engaging claw 427 provided on the front end of the arm 426 for engaging with the holder 421.

An engaging hole 428 for engaging with the connector 423 is formed in the vicinity of the rear end of the holder 421. When the holder 421 is connected to the connector 423, as shown in FIG. 101A, the engaging claw 427 of the resilient hook 425 is removably connected to the engaging hole 428 of the holder 421. The engaging hole 428 of the holder 421 may be an indentation or a bridge.

As shown in FIG. 100, a guide slit 407a for use with the cutter 416 is formed along the longitudinal center of the opposite surface of the anvil 407 with respect to the cartridge 406. A plurality of protuberances 407b for positioning purposes downwardly project from the surface on the both side edges of the guide slit 407a. Protuberance receiving sections 406e such as indentations or holes are formed in the opposite surface of the cartridge 406 with respect to the anvil 407 so as to correspond to the protuberances 407b of the anvil 407. In this case, the protuberances 407b of the anvil 407 extend so as to protrude through a tissue grasping plane.

When the anvil 407 is closed with respect to the cartridge 406, the protuberances 407b of the anvil 407 removably engage with the protuberance receiving sections 406e of the cartridge 406. As a result, slots formed in the cartridge 406 for retaining the staples 500 and staple forming slits formed in the anvil 407 are appropriately corrected (aligned to each other), whereby the staples 500 can be correctly clinched.

As shown in FIG. 97, the operating section 403 of the suturing instrument 401 is provided with an anvil open/close lever (i.e., a jaws open/close lever) 429 for opening and closing the anvil 407 of the jaws 405, and a staple ejection lever 430 which ejects the staple 500 and also doubles as an excising lever for operating the cutter 416. A gun-grip 432 for use as a handgrip is integrally mounted on the main body (or a casing) 431 of the operating section 403. The anvil open/close lever 429 is provided behind the grip 432, whereas the staple ejection lever 430 is provided in front of the grip 432. In other words, the grip 432 is interposed between the anvil open/close lever 429 and the staple ejection lever 430.

Figures 102A, 102B:
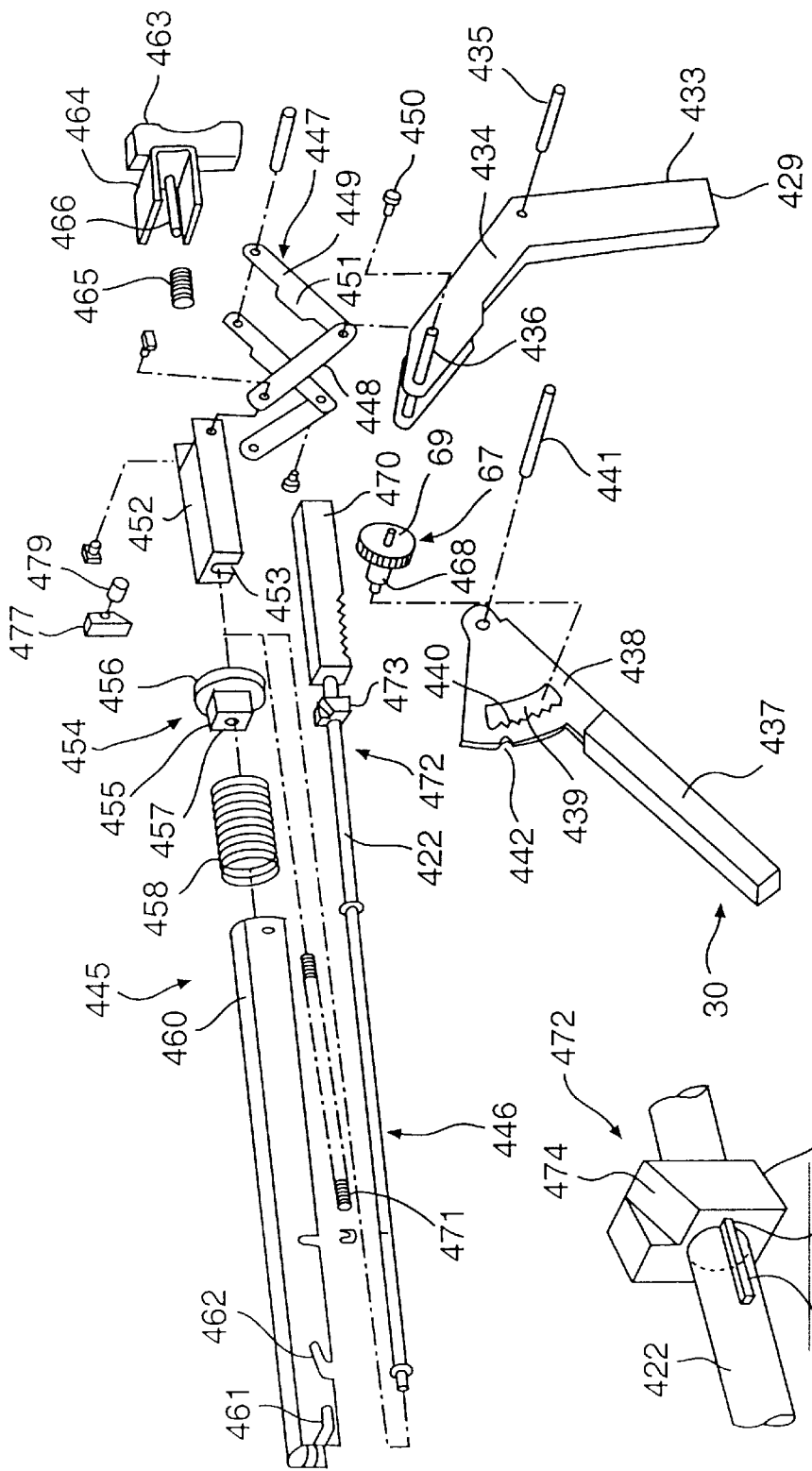
FIG. 102A is an exploded perspective view showing the internal structure of the suturing instrument of the twenty-eighth embodiment.

The anvil open/close lever 429 is formed into a doglegged shape as shown in FIG. 102A. A lower portion of the thus-doglegged anvil open/close lever 429 forms a hold 433, and an upper portion of the same forms a joint arm 434.

Figure 103:
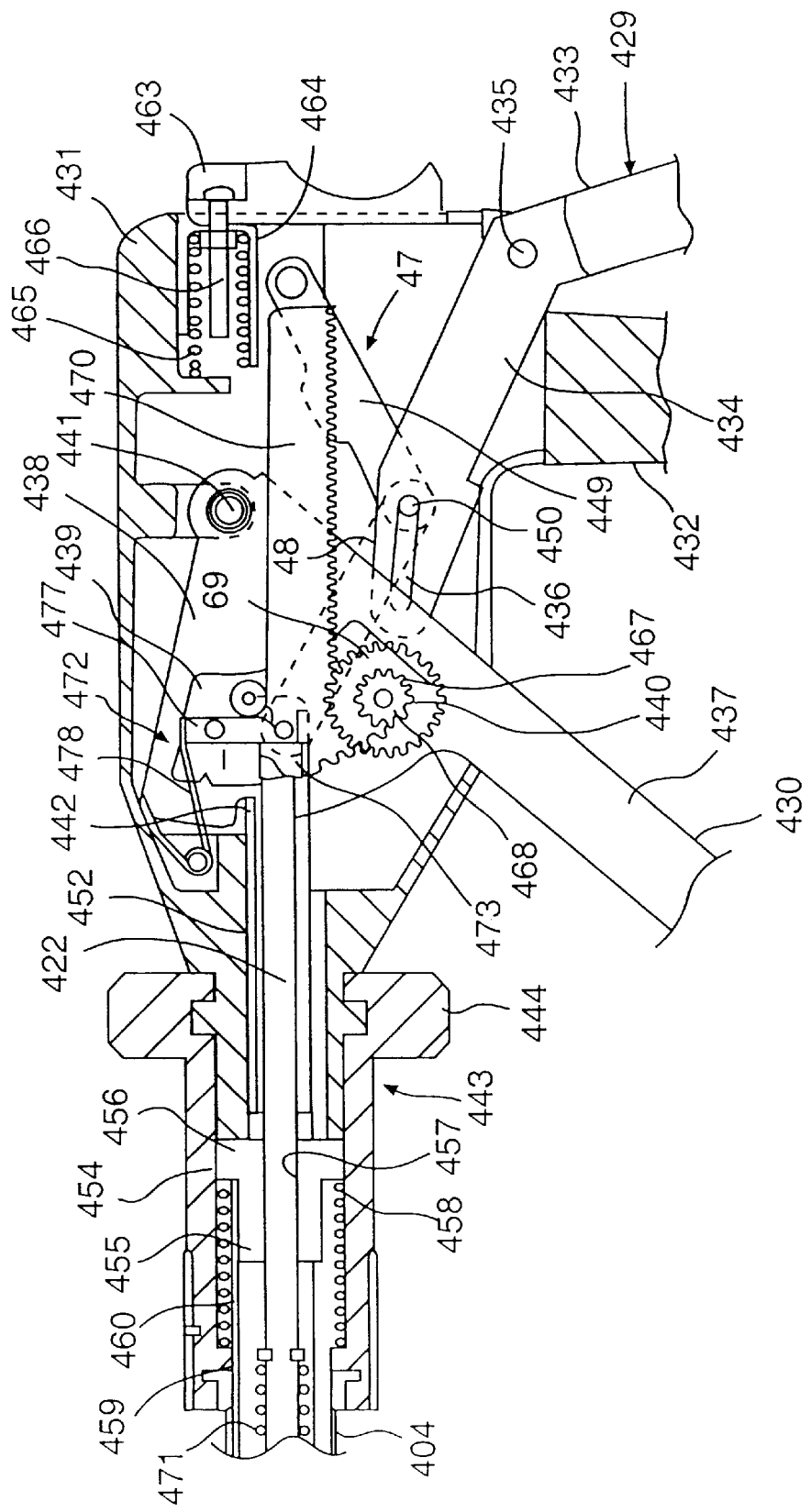

Further, as shown in FIG. 103, the angular area between the hold 433 and the joint arm 434 of the anvil open/close lever 429 is pivotally connected to the operating section main body 431 via a pivot pin 435. The anvil open/close lever 429 is supported so as to open and close in a rearward direction of the grip 432. An elongated cam groove 436 is formed in the vicinity of the upper end of the joint arm 434 of the open/close lever 429. The pivot pin 435 of the anvil open/close lever 429 is positioned below the axial center of the insertion section 402.

A hold 437 is formed in a lower portion of the staple ejection lever 430, and a substantially fan-shaped section 438 is formed in an upper portion of the same. Further, a substantially circular-arc elongated hole 439 is formed in the vicinity of the outer periphery of the fan-shaped section 438. A gear 440 having a plurality of teeth is formed along the distal-end circular-arc internal periphery of the elongated hole 439.

The innermost end of the fan-shaped section 438 (i.e., the pivot of the fan) is pivotally connected to the operating section main body 431 via the pivot pin 441. The staple ejection lever 430 is supported so as to open and close in a forward direction of the grip 432. A notch 442 is formed in the outer edge of the fan-shaped section 438 of the staple ejection lever 430. The pivot pin 441 of the staple ejection lever 430 is positioned above the axial center of the insertion section 402.

As shown in FIG. 103, a substantially cylindrical rotating member 443 is rotatably connected to the front end of the operating section main body 431. The base of the insertion section sheath 404 is fitted on the front end of the rotating member 443. A rotating knob 444 is integrally provided on the rear end of the rotating member 443. The insertion section 402 is rotated around its longitudinal center with respect to the operating section main body 431 as a result of rotation of the rotating knob 414.

An anvil open/close mechanism (i.e., a jaws open/close mechanism) 445 for opening and closing the anvil 407 of the jaws 405 in response to actuation of the anvil open/close lever 429, and a staple ejection mechanism 446 for ejecting the staple 500 of the cartridge 406 in response to operation of the staple ejection lever 430, and a mechanism for operating the cuter 416 are provided within the suturing instrument 401.

As shown in FIG. 103, the anvil open/close mechanism 445 comprises a pair of link mechanisms 447 housed in the operating section main body 431. Each link mechanism 447 comprises a first link 448 and a second link 449 provided behind the first link 448.

The second link 449 has its rear end rotatably connected to the operating section main body 431 and has its front end rotatably connected to the rear end of the first link 418 by caulking or press-fitting of pins. In this case, a joint pin 450 between the first link 448 and the second link 449 of the link mechanism 447 is fitted into the cam groove 436 of the anvil open/close lever 429. A protuberance 451 is raised from the upper edge of the second link 449.

The front end of the first link 448 is rotatably connected to the rear end of a substantially box-shaped first slider 452 positioned in front of the link mechanism 447. The rear end surface of the slider 452 is opened, and a lit 453 is formed in the front end surface of the slider 452 for passage of the joint rod 422. This slider 452 is provided so as to be slidable along the axis of the insertion section 402 with respect to the operating section main body 431. In the initial state of the suturing instrument 401, the upper rear edge of the first slider 452 engages with the notch 442 of the staple ejection lever 430.

A second slider 454 is provided in front of the front end of the first slider 452 and is inserted into the rotating member 443. The second slider 454 has a substantially cubic portion 455 provided on the front end, and a flange 456 is provided on the back of the cubic portion 455. A through hole 457 is formed in the center of the second slider 455 for passage of the joint rod 422. The second slider 454 is retained in the rotating member 443 so as to be slidable along the longitudinal axis of the insertion section 402 along the joint rod 422.

A coil spring 458 is provided in line with the joint rod 422 within the rotating member 443 for forcing the second slider 454 in a rearward direction. In this case, a spring receiver 459 inwardly projects along the internal surface of the area in the vicinity of the front end of the rotating member 443. The coil spring 458 is interposed between the spring receiver 459 and the flange 456 of the second slider 454.

An anvil open/close member 460 having a substantially U-shaped cross section has its rear end fixedly fitted to the cubic portion 455 of the second slider 454. A pair of cam slits 461 and 462 are formed in each side surface of the vicinity of the front end of the anvil open/close member 460. In this case, the cam slit 461 comprises a tapered portion 461*a* which is tapered downwardly toward its rear end, and a horizontal portion 461*b* connected to the rear end of the tapered portion 461*a*. The front edge of the tapered portion 461*a* of the cam slit 461 is opened in the front end of the anvil open/close member 460. Similarly, the cam slit 462 comprises a tapered portion 462*a* which is upwardly tapered toward its rear end, and a horizontal portion 462*b* connected to the rear end of the tapered portion 462*a*. The front end of the tapered portion 462*a* of the cam slit 462 is opened in the lower side edge of the anvil open/close member 460. The horizontal portion 462*b* of the cam slit 462 is set so as to become higher than the horizontal portion 461*b* of the cam slit 461.

The cam pins 401*a* and 410*b* of the anvil 407 are fitted into the cam slits 461 and 462 of the anvil open-close member 460. In this case, since the front ends of the tapered portion 461*a* of the cam slit 461 and the tapered portion 462*a* of the cam slit 462 are opened, it is easy to fit the cam pins 410*a* and 410*b* of the anvil 407 into the cam slits 461 and 462. As a result, it is easy to assemble the anvil open/close member 460 and the anvil 407 into one piece.

A release button 463 is provided on the back of the operating section main body 431. This release button 463 is placed at a rearwardly elevated position with respect to the link mechanism 447 of the anvil open/close mechanism 445. The release button 463 is supported by the operating section main body 431 so as to be slidable toward the insertion section 402.

A press member 464 made by bending a plate so as to be substantially U-shaped is fitted on the internal surface of the release button 463. A coil spring 465 is fitted in the press member 464 for pressing the release button 463 rearward. In this case, a spring guide pin 466 for guiding the spring 465 projects from the inner bottom of the press member 464 toward the insertion section 402. The release button 463 is normally forced so as to project to the outside of the operating section main body 431 by means of a spring force of the coil spring 465.

The staple ejection mechanism 446 is provided with a gear unit 467 which is rotatably supported by a shaft within the operating section main body 431. This gear unit 467 comprises a first gear 468 having a small diameter and a second gear 469 having a large diameter, both of which are coaxially aligned. A ratio of the first gear 468 to the second gear 469 with regard to the number of teeth is set to about 1:2.

The first gear 468 of the gear unit 467 is in mesh with the gear 440 of the staple ejection lever 430, and the second gear 469 is in mesh with a rack 470 provided above the gear unit 467. The rack 470 is connected to the base of the joint rod 422 and is supported so as to be slidable along the longitudinal axis of the insertion section 402.

One end of a coil spring 471 butts against the joint rod 422 by an E ring or the like. The other end of the coil spring 471 is fixed in the anvil open/close member 460 or the insertion section sheath 404.

A plastic stopper 473 of a double-ejection preventive mechanism 472 for preventing double-ejection of the staple 500 is provided in front of the rack 470 so as to be slidable over the joint rod 422. As shown in FIG. 102B, a tapered surface 474 having a down slope toward the front is formed in an upper portion of the stopper 473. To fit the stopper 473 to the joint rod 422, a key slit 475 is formed in the stopper 473, and a key 476 is formed so as to mesh with the key slit 475 of the stopper 473. The stopper 473 is prevented from rotating around the joint rod 422 by the engagement between the key slot 475 of the stopper 473 and the key 476 of the joint rod 422. The stopper 473 is pressed against the rack 470 by means of an unillustrated forcing member such as a spring.

A substantially cubic slide member 477 which is capable of sliding in the direction perpendicular to the sliding direction of the rack 470 is provided in the operating section main body 431 so as to butt against the front end surface of the rack 470. The upper end of the slide member 477 is fixed to a spring member 478 and is forced downward by this spring member 478. Further, the slide member 477 is connected to a knob 479 provided outside the operating section main body 431.

The operation of the suturing instrument 401 having the previously-described construction will now be described.

First, when the suturing instrument 401 of the present embodiment is used, the second slider 454 is pushed toward the operating section 403, or in the rightward direction in FIG. 103, by means of the spring force of the coil spring 458 provided in the rotating member 443. A rearward pushing force is normally exerted on the area between the first link 448 and the second link 449 of the link mechanism 447 via the first slider 452, whereby the first and second links 448 and 449 are retained in a substantially doglegged state. The anvil open/close lever 429 of the operating section 403 is retained in a predetermined position spaced apart from the grip 432. The joint rod 422 is pushed toward the operating section 403, or in the rightward direction of FIG. 103, by means of the spring force of the coil spring 471 of the joint rod 422, whereby the staple ejection lever 430 is also retained in a predetermined location spaced apart from the grip 432.

The anvil open/close member 460 is retained in a predetermined location close to the operating section 403 together with the second slider 454. In this state, the cam pins 410a and 410b of the anvil 407 are restricted by the cam slits 461 and 462. As shown in FIG. 99A, the anvil 407 is retained in an open position spaced apart from the cartridge 406. Similarly, while the joint rod 422 is retained in the predetermined location close to the operating section 403, the cutter 416 and the cam plates 417 are also retained in their predetermined locations close to the operating section 403.

While the anvil open/close lever 429 and the staple ejection lever 430 of the operating section 430 are retained in the positions spaced away from the grip 432, the upper rear edge of the first slider 452 engages with the notch 442 of the staple ejection lever 430. As a result, the staple ejection lever 430 is prevented from pivoting.

When the suturing instrument 401 is used, the insertion section 402 of the suturing instrument 401 is inserted into the body of a patient by endoscopic observation such that the jaws 405 provided at the front end of the insertion section 402 are guided to the vicinity of tissue to be treated in the body. After the tissue has been grasped between the anvil 407 situated in an open position and the cartridge 406, the anvil open/close lever 428 is closed until it comes into contact with the grip 432.

At this time, the anvil open/close mechanism 445. operates in the following manner in response to the closing action of the anvil open/close lever 429. More specifically, when the anvil open/close lever 429 is closed, the joint arm 434 of the anvil open/close lever 429 pivots on the pivot pin 435. In conjunction with this pivotal movement of the joint arm 434, the joint pin 450 is operated, and the link mechanism 447 are operated via the joint pin 450. As a result, the first link 448 and the second link 449 of the link mechanism 447 which are downwardly bent are raised upwardly until they become substantially linear. Since a rearwardly pushing force normally acts on the first and second links 448 and 449 of the link mechanism 447, the first and second slits 448 and 449 are locked in substantially a linear state.

In conjunction with the action of the link mechanism 447, the first and second sliders 452 and 454, and the anvil open/close member 460 are slid toward the insertion section 402 opposing the spring force of the coil spring 458 provided within the rotating member 443. At this time, together with the sliding action of the anvil open/close member 460, a force vertically acts on the cam pins 410a and 410b of the anvil 407 by means of the cam slits 461 and 462 of the anvil open/close member 460 in the area of the front end of the insertion section 402. The front end of the anvil 407 is closed toward the cartridge 406.

As a result of movement of the first slider 452 associated with the closing action of the anvil open/close lever 429, the upper rear edge of the first slider 452 disengages from the notch 442 of the staple ejection lever 430, whereby the staple ejection lever 430 is switched to a rotatable state.

Next, the staple ejection lever 430 is closed toward the grip 432. At this time, as shown in FIG. 103, the staple ejection lever 430 pivots counterclockwise around the pivot pin 441. In conjunction with the pivotal movement of the staple ejection lever 430, the first gear 468 rotates in the same direction in which the staple ejection lever 430 pivots, by means of the gear 440. Then, the rack 470 is slid toward the insertion section 402 via the second gear 469. As a result, the cutter 416 and the cam plates 417 are pushed and slid toward the cartridge 406 via the joint rod 422.

Together with the sliding action of the cam plates 417, the staples 500 loaded in the cartridge 406 are sequentially pushed to the anvil 407 via the staple operating member 501 by means of the cam plates 417. Further, together with the ejection of the staple 500, the cutter 461 slides over the upper slot 418a of the cutter slot 418 along the rails 420. The edge 416a of the cutter 416 then cuts the tissue positioned between the lines of staples.

After completion of the ejection of the staple and the cutting of the tissue carried out by the cutter 416, the joint rod 422 is pushed back to its original position by means of the spring force of the coil spring 471 when the staple ejection lever 430 is released. As a result, the lever 430 is opened together with the sliding action of the joint rod 422, and the cam plates 427 and the cutter 416 recede.

When the cutter 416 slides from the front end of the cutter slot 418 to the back of the staple storage section 406a of the cartridge 406, the shoulder 416e of the cutter 416 comes into slidable contact with the bridge 406b of the cartridge 406, so that the cutter 416 receives a downward force. In consequence, the protuberances 416b of the cutter 416 enters the lower slot 418b of the cutter slot 418 from the obliquely cut sections 402a of the rails 420.

As shown in FIG. 101B, if the ejection lever 430 is closed again in this state, the protuberances 416b of the cutter 416 slide forwardly through the lower slot 418b. Therefore, the edge 416a of the cutter 416 is retained so as to be hidden behind the surface of the cartridge 406 (i.e., the edge 416a of the cutter 416 is not projected outside from the cartridge 406).

The rear end of the lower slots 418b of the cutter slot 418 is set in front of the rear end of the upper slots 418a. The cutter 416 moves to the rear end of the lower slots 418b during the course of its returning action. When the returning action of the cutter 416 is stopped, the returning action of the connection rod 422 is still continued. For this reason, as shown in FIG. 101B, the engaging claw 427 of the connector 423 disengages from the engaging hole 428 of the holder 421 as a result of the returning action of the joint rod 422 carried out after the cutter 416 has returned to the rear end of the lower slots 418b and stopped there, and the holder 421 disengages from the connector 423.

Finally, the front end of the press member 464 of the release button 463 comes into collision with the protuberance 451 of the second link 449 of the link mechanism 447 by pressing the release button 463. As a result, the second links 449 are pressed downward, whereby the first and second links 448 and 449 of the link mechanism 447 are bent into a doglegged shape; i.e., their original state (or the original positions), by means of the spring force of the coil spring 458. The anvil open/close lever 429 returns to its original position spaced apart from the grip 432 as a result of the action of the joint pin 450 of the link mechanism 447.

Together with the action of the link mechanism 447, the first slider 452, the second slider 454 and the anvil open/close member 460 are simultaneously drawn toward the operating section 403 by means of the coil spring 458. In conjunction with the action of the anvil open/close member 460, the cam pins 410a and 410b of the anvil 407 are moved along the cam slits 461 and 462 of the anvil open/close member 460 in the area of the front end of the insertion section 402. As shown in FIG. 99A, the anvil 407 returns to the open position spaced away from the cartridge 406.

Descriptions of operations of the stopper 473 and the slide member 477 of the double-ejection preventive mechanism 472 of the suturing instrument 401 are as follows: First, the stopper 473 is spaced apart from the front end of the rack 470 while the anvil open/close lever 429 and the staple ejection lever 430 of the operating section 403 are retained in the predetermined locations spaced apart from the grip 432.

If the staple ejection lever 430 is closed after the anvil open/close lever 429 has been closed, the rack 470 and the stopper 473 move toward the front end of the suturing instrument 401. At this time, the stopper 473 moves while raising the slide member 477 against the spring force of the spring member 478, by means of the tapered surface 474 formed on the front of the stopper 473.

When the staple ejection lever 430 is opened after the ejection of the staple and the cutting of tissue carried out by the cutter 416 have been completed, the upper surface of the stopper 473 is situated above the upper surface of the rack 470. Consequently, the slider 477 is positioned between the front end of the rack 470 and the stopper 473. Even if an attempt is made to close the staple ejection lever 430 again in this state, the rack 470 cannot slide because the slider 477 and the front end of the rack 470 engage with each other. The pivotal movement of the staple ejection lever 430 is eventually prohibited, and double-ejection of the staple is prevented.

In a case where the cartridge 406 is exchanged, the cartridge 406, and the cutter 416, the cam plates 417 and the holder 421 incorporated in the cartridge 406 are removed from the front end of the insertion section 402 in the form of one replacement unit. Then, a virgin cartridge 406 is attached to the replacement unit. In this case, it is easy to replace the cartridge 406 because the joint rod 422 disengages from the holder 421.

The suturing instrument 401 having the previously described construction provides the following advantages.

In the suturing instrument 401 of the present embodiment, the obliquely cut portions 420a are formed in the rear of the rails 420 for guiding the cutter 416 which are formed in the cartridge 406 of the jaws 405. When the cutter 416 advances, the protuberances 416b of the cutter 416 are guided by the upper slot 418a above the rails 420. As a result, the cutter 416 is retained in the position where it is possible to cut tissue grasped between the cartridge 406 and the anvil 407 of the jaws 405. In contrast, during the course of return of the cutter 416 to its original position after the cutter 416 has cut the tissue, the protuberances 416b of the cutter 416 are guided to the lower slot 418b of the cutter slot 418 through the obliquely cut portions 420a of the rails 420. Consequently, it is possible to switch the cutter 416 to the position where it is impossible to cut tissue. By virtue of the above-described arrangement, once having been moved forward, the cutter 416 can be retained while it is switched to the position where the cutter cannot cut tissue. Even if the spent cartridge 406 is loaded in the suturing instrument 401, the cutter 416 can be prevented from advancing again in the position where it can cut tissue. Therefore, there is no risk of unnecessarily damaging tissue with the cutter 416, and the safety of the suturing instrument 401 can be improved.

While the anvil open/close lever 429 and the staple ejection lever 430 of the operating section 403 are retained in the positions spaced apart from the grip 432, the upper rear edge of the first slider 452 engages with the notch 442 of the staple ejection lever 430. Consequently, since the staple ejection lever 430 is prevented from pivoting, it is impossible to cut tissue by pivoting the staple ejection lever 430 unless the anvil 407 is closed together with the closing action of the anvil open/close lever 429.

As a result of each opening-and-closing action of the staple ejection lever 301, the staple ejection lever 430 is locked by means of the double-ejection preventive mechanism 472 for preventing double ejection of the staple 500. Therefore, it is possible to acknowledge whether or not the staple 500 has been ejected without withdrawing the cartridge 406 from the suturing instrument 401.

Once the cutter 416 has advanced to the front end of the cutter slot 408 together with the closing action of the staple ejection lever 430, the edge 416a of the cutter 416 is hidden behind the cartridge 406. Since the edge 416a is prevented from projecting from the surface of the cartridge 406, there is no risk of the cutter 416 cutting tissue while the staple 500 is not retained in the cartridge 406 after the staple 500 retained by the cartridge 406 has been ejected.

Even in a case where the cartridge 406 is exchanged, the edge 416a of the cutter 416 is hidden behind the surface of the cartridge 406. Therefore, it is easy to remove the cartridge 406 from the front end of the insertion section 402, which in turn enables quick and safe exchange of the cartridge 406 of the insertion section 402 of the suturing instrument 401.

It is also possible to enable application of the suturing instrument 401 to a case where cutting of tissue is not required, by use of a structure which causes the edge 416a of the cutter 416 to be hidden as a result of a light touch on the staple ejection lever 430.

If the cartridge 406 is constructed such that the cutter 416 and the cam plates 417 do not slide even when undergoing a certain degree of vibration and shock, the safety of the cartridge 406 when it is transported as a single unit is improved.

Figure 104:
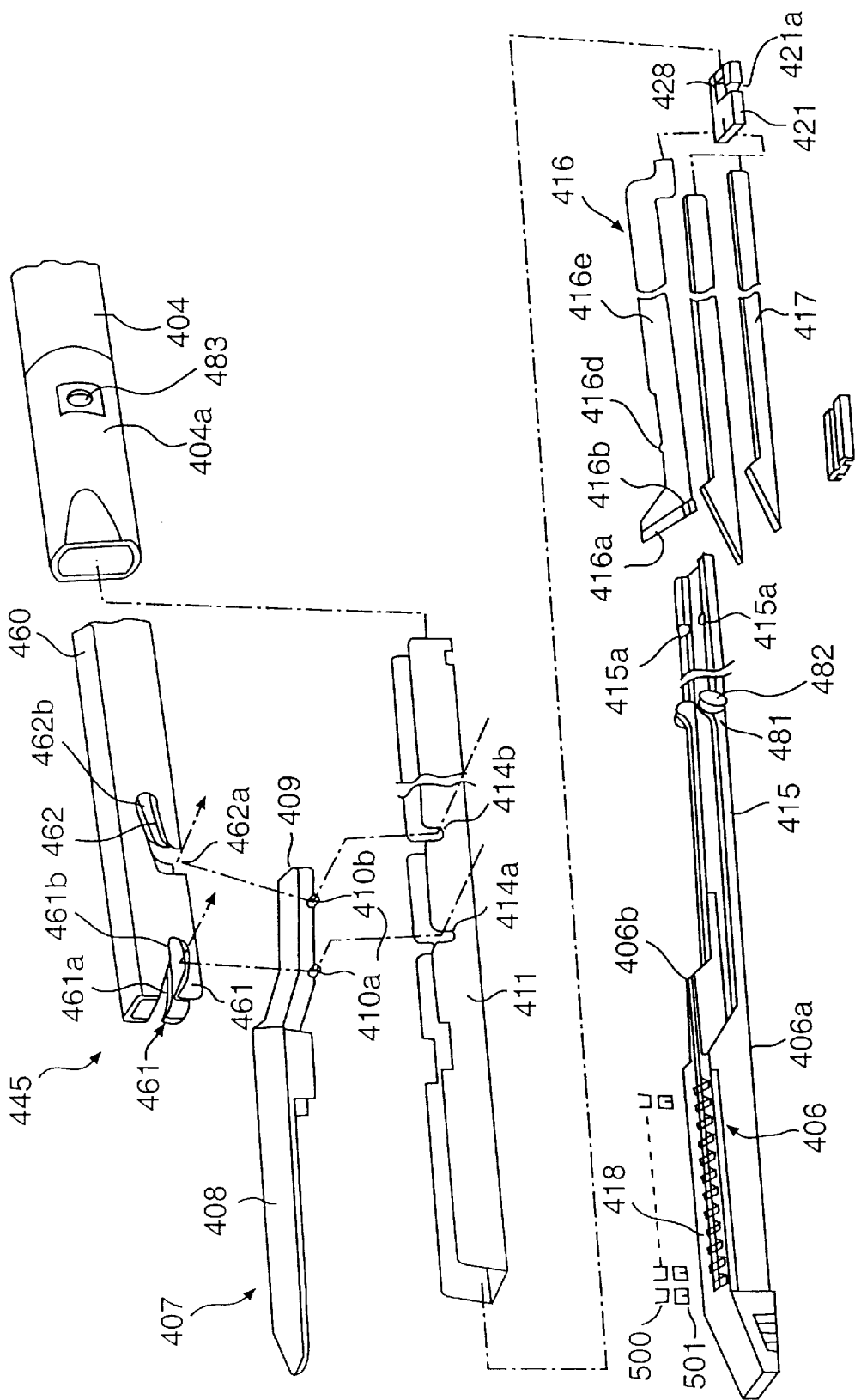

FIG. 104 shows a twenty-ninth embodiment of the present invention. Contrasted with the twenty-eighth embodiment, the present embodiment is modified with regard to removal and attachment of the cartridge 406 from and to the cartridge holder 410 of the suturing instrument 401 in the manner as will be described below. More specifically, leaf springs 481 whose front ends are elastically deformable are provided on both sides of the extension 415 of the cartridge 406 in the twenty-ninth embodiment. A removal button 482 is provided on the front end of each leaf spring 481, and holes 483 which engage with the removal buttons 482 of the cartridge 406 are formed in the front end cover 404a of the insertion section sheath 404.

In a modification of this embodiment, the removal buttons 482 of the cartridge 406 fit to the holes 483 of the insertion section sheath 404 from inside while the cartridge 411 is attached to the cartridge 406. If the removal buttons 482 are inwardly pressed from outside of the insertion section sheath 404, the removal buttons 482 of the cartridge 406 disengage from the holes 483 of the insertion section sheath 404. As a result, the cartridge 406 can be removed from the cartridge holder 411.

FIGS. 105A and 105B show a thirtieth embodiment of the present invention. Contrasted with the twenty-eighth embodiment, the present embodiment is modified with regard to the construction of the member for switching the cutter 416 of the suturing instrument 401. Specifically, in the present embodiment, an elastic latch 491 is formed on a lower surface of the edge 416a of the cutter 416, and a rectangular spacer 493 which is pivotal on a support pin 492 is formed on a lower portion in the vicinity of the rear end of the cutter slot 418 of the cartridge 406. The spacer 493 is made from polycarbonate or ABS resin. In the present embodiment, the bottom of the cutter slot 418 of the cartridge 406 is closed by a bottom plate 418c.

As shown in FIG. 105A, the spacer 493 is disposed with its longitudinal sides upward. In this case, the edge of the bottom plate 418c of the cutter slot 418 is in contact with one side of the spacer 493, so that the spacer 493 cannot pivot toward the front end of the cutter 416.

Further, an opening 494 is formed in the bottom plate 418c of the cutter slot 418 below the spacer 493. As shown in FIG. 105B, when the spacer 493 rotates in a rearward direction of the cartridge 406, the spacer 493 is set so as to be leveled with the bottom plate 418c of the cutter slot 418 of the cartridge 406.

In the present embodiment, a resilient member; e.g., a leaf spring or a spring, may be provided so as to push the cutter 416 against the bottom plate 418c of the cutter slot 418.

The operation of the suturing instrument of the present embodiment will now be described. In the present embodiment, the spacer 493 is retained with its longitudinal sides upward as shown in FIG. 105A in an initial state; namely, before the cutter 416 moves toward the front end of the cutter slot 418. At this time, the edge 416a of the cutter 416 is retained while it projects from the surface of the cartridge 406 toward the anvil 407.

When the cutter 416 advances toward the front end of the suturing instrument 401 through the cutter slot 418 together with the pivotal movement of the staple ejection lever 430, the spacer 493 is retained while it is in such an upright position as shown in FIG. 105A. In this case, the edge 416a of the cutter 416 slides toward the front end of the cutter slot 418 while being projected from the surface of the cartridge 406 toward the anvil 407, together with the ejection of the staple 500. As a result, the tissue grasped between the cartridge 406 and the anvil 407 is cut by the edge 416a.

When the staple ejection lever 430 is released, the cutter 416 returns from the front end to the base end of the cutter slot 418. During the returning action of the cutter 416, the spacer 493 comes into contact with the elastic latch 491 of the cutter 416. As shown in FIG. 105B, the spacer 493 rotates in the rearward direction of the cartridge 406. As a result, the edge 416a of the cutter 416 is switched so as to become hidden behind the surface of the cartridge 406 (i.e., so as not to project from the cartridge 406 outwardly).

In other respects, the suturing instrument 401 of the present embodiment is the same as that of the twenty-eighth embodiment with regard to structure and operation. Even in the case of the suturing instrument of the present embodiment having the previously-described construction, it goes without saying that the same advantageous results are obtained as those obtained in the twenty-eighth embodiment.

FIGS. 106A and 106B to 108 show a thirty-first embodiment of the present invention. Contrasted with the suturing instrument 401 of the twenty-eighth embodiment, the suturing instrument of the present embodiment is modified with regard to the structure of the member for switching the cutter 416. More specifically, a substantially wedge-shaped notch 511 is formed in a lower portion of the edge 416a of the cutter 416 in the present embodiment. Further, there is provided a spacer 512 as shown in FIG. 108 as a member for switching the cutter 416. As in the thirtieth embodiment, the bottom of the cutter slot 418 of the cartridge 406 is closed by the bottom plate 418c.

As shown in FIG. 107, the spacer 512 is provided with a substantially-plate-like butt portion 513 against which one side surface of the front end of the cutter 416 butts, and a substantially U-shaped spacer main body 514 which receives the cutter 416.

A hook-shaped engaging portion 515 which removably engages with the notch 511 of the cutter 416 is provided on the spacer main body 514. The height of the spacer main body 514 is set to retain the cutter 416 while the engaging portion 515 engages with the notch 511 of the cutter 416, and while the edge 416a of the cutter 416 projects; e.g., about 2 to 3 mm, from the surface of the cartridge 406 toward the anvil 407. A protuberance 516 downwardly projects from a lower surface of the spacer main body 514, thereby constituting an elastic hook or engaging portion.

A spacer stopper 517 in the form of an indentation or opening is formed in the front end of the bottom plate 418c of the cutter slot 418. In the cartridge 406, a rib 518 is longitudinally formed along the corner or edge of the internal upper surface of the cutter slot 418 so as to project to the inside of the cutter slot 418.

An elastic leaf spring 519 is fitted on the upper surface of the cutter 416 behind the edge 416a. The free end of the leaf spring 519 is pressed by the lower surface of the rib 518, so that the edge 416a of the cutter 416 is downwardly pressed.

A description of operation of the suturing instrument of the present embodiment is as follows: As shown in FIG. 107, in the present embodiment, one side surface of the front end of the cutter 416 is butted against the butt 513 of the spacer 512 in an initial state; namely, before the cutter 416 advances toward the front end of the suturing instrument 401 through the cutter slot 418. Further, as shown in FIG. 106A, the engaging portion 515 provided on the spacer main body 514 engages with the notch 511 of the cutter 416. At this time, the edge 416a of the cutter 416 is retained while projecting from the surface of the cartridge 406 toward the anvil 407.

When the cutter 416 travels through the cutter slot 418 toward its front end together with pivotal movement of the staple ejection lever 430, the cutter 416 slides toward the front end of the cutter slot 418 through the cutter slot 418 of the cartridge 406 along with the spacer 512. In this case, the tissue grasped between the cartridge 406 and the anvil 407 is cut by the edge 416a of the cutter 416 which slides toward the front end of the cutter slot 418 while projecting from the surface of the cartridge 406 toward the anvil 407, at the same time that the staple 500 is ejected.

When the edge 416a of the cutter 416 slides to the front end of the cutter slot 418, the elastic hook-shaped protuberance 516 of the spacer main body 514 engages with the spacer stopper 517 of the bottom plate 418c of the cutter slot 418. As a result, the spacer 512 is fixedly retained in the front end of the cartridge 406. If the staple ejection lever 430 is released in this state, only the cutter 416 travels through the cutter slot 418 from its front end to base end. Together with the returning action of the cutter 416, the engaging portion 515 of the spacer main body 514 disengages from the notch 511 of the cutter 416. At this time, the edge 416a of the cutter 416 is pressed downward by means of the leaf spring 519 provided on the cutter 416 behind the edge 416a. As a result, the edge 416a of the cutter 416 is switched so as to become hidden behind the surface of the cartridge 406 (i.e., so as not to project from the cartridge 406 outwardly).

In other respects, the suturing instrument 401 of the present embodiment is the same as that of the twenty-eighth embodiment with regard to structure and operation. Even in the case of the suturing instrument of the present embodiment having the previously-described construction, it goes without saying that the same advantageous results are obtained as those obtained in the twenty-eighth embodiment.

The cutter 416 disengages from the spacer 512 every time the ejection of a staple is completed in the present embodiment. If the staple ejection lever 430 is closed without replacement of the cartridge 406, the edge 416a of the cutter 416 slides toward the front end of the cartridge 406 while being hidden behind the surface of the cartridge 406. Therefore, even if the staple ejection lever 430 is erroneously closed while a spent cartridge 406 is loaded in the suturing instrument 401, the edge 416a of the cutter 416 slides while being hidden behind the surface of the cartridge 406, thereby ensuring safety by preventing cutting of tissue.

FIGS. 109A and 109B show a thirty-second embodiment of the present invention. Contrasted with the suturing instrument 401 of the twenty-eighth embodiment, the suturing instrument of the present embodiment is modified with regard to the structure of the member for switching the cutter 416. More specifically, the edge 416a provided on the front end of the cutter 416 is provided on a separated cutting blade 521 which is separated from the other portion of the cutter 416 in the present embodiment. The member for switching the cutter 416 is constituted by rotatably supporting the separated cutting blade 521 on the front end of a main body 522; namely, the other portion of the cutter 416.

In this case, an elongated cam slit 523 is formed in the front end of the main body 522 of the cutter 416. The separated cutting blade 521 is rotatably attached to the cam slit 523 of the main body 522 with a caulking pin 524. Further, a jaw-shaped protuberance 525 downwardly projects from a lower portion of the edge 416a of the separated cutting blade 521 past the bottom of the main body 522.

The bottom of the cutter slot 418 of the cartridge 406 is closed by the bottom plate 418c. A guide groove (or slide) 526 in which the protuberance 525 of the separated cutting blade 521 is inserted, is also formed in the bottom plate 418c. The front end of the guide groove 526 is positioned behind the front end of the cutter slot 418. In other respects, the suturing instrument 401 of the present embodiment is the same as that of the twenty-eighth embodiment.

The operation of the suturing instrument 401 of the present embodiment will now be described. As shown in FIG. 109A, the cutting blade 521 of the cutter 416 is retained in an upright position in an initial state; namely, before the cutter 416 advances through the cutter slot 418 toward its front end. At this time, the edge 416a of the separated cutting blade 521 of the cutter 416 is retained while projecting from the surface of the cartridge 406 toward the anvil 407, and the protuberance 525 is retained while being inserted in the guide groove 526.

When traveling through the cutter slot 418 toward its front end together with pivotal movement of the staple ejection lever 430, the cutter 416 slides through the cutter slot 418 of the cartridge 406 toward its front end while the separated cutting blade 521 of the cutter 416 is retained in an upright position. For this reason, in this case, the tissue grasped between the cartridge 406 and the anvil 407 is cut by the edge 416a of the cutter 416 which slides toward the front end of the cutter slot 418 while projecting from the surface of the cartridge 406 toward the anvil 407, at the same time that the staple 500 is ejected.

When the front end of the cutter 416 has slid to the front end of the cutter slot 418, the protuberance 525 of the separated cutting blade 521 butts against the front end of the guide groove 526, so that the separated cutting blade 521 rotates around the caulking pin 524. At this time, if the separated cutting blade 521 fully rotates, the edge 416a of the separated cutting blade 521 is switched so as to become hidden behind the surface of the cartridge 406 (i.e., so as not to project from the cartridge 406 outwardly).

If the staple ejection lever 430 is released in this state, the edge 416a of the separated cutting blade 521 travels through the cutter slot 418 to the base end of the cartridge 406 while being hidden behind the surface of the cartridge 406 as shown in FIG. 109B.

Even if the staple ejection lever 430 is closed while a spent cartridge 406 is loaded into the suturing instrument 401 of the present embodiment, the edge 416a of the separated cutting blade 521 of the cutter 416 slides while being hidden behind the surface of the cartridge 406, thereby ensuring safety by preventing cutting of tissue. Further, contrasted with the other embodiments, the present embodiment provides a suturing instrument having a simpler structure. In other respects, the suturing instrument 401 of the present embodiment is the same as that of the twenty-eighth embodiment with regard to structure and advantages.

It goes without saying that the present invention is not limited to the previously-described embodiments but may be variously modified within the scope of the purport of the present invention.

FIGS. 110A and 110B through 124A and 124B show a thirty-third embodiment of the present invention. As shown in FIG. 110A, a surgical stapler of the present embodiment is made up of an operating section 601, and a narrow insert 602a which is removably attached to the operating section 601. Further, the insertion section 602 is made up of a main body 602a which is removably attached to the operating section 601, and a cartridge 602b which is removably attached to the front end of the insertion section main body 602a. The insertion section main body 602a is capable of rotating around a longitudinal axis A of the insertion section main body 602a with respect to the operating section 601. A tapered surface 650 is formed on the front edge of the cartridge 602b so as to extend at an angle with respect to the longitudinal axis A of the insertion section 602.

FIG. 110B shows the insertion section 602 when it is rotated through 90 degrees with respect to the operating section 601 from the state shown FIG. 110A. As shown in FIG. 110B, an opening 651 is formed in the tapered surface 650 of the cartridge 602b for supplying a staple 624 (see FIG. 116), which will be described later, at an angle with respect to the longitudinal axis A of the insertion section 602.

FIG. 111 shows the surgical stapler when it is disassembled into the operating section 601, the insertion section main body 602a, and the cartridge 602b.

As shown in the drawing, the operating section 601 comprises a handle 604, an upper cover 606 hinged to the handle 604 with a hinge 607 so as to open and close, and a trigger 605 pivotally supported by the handle 604. FIG. 111 shows the surgical stapler with the upper cover 606 open. A latch 608 provided along the edge of the upper cover 606 engages with a counterpart latch 608 (see FIG. 112) provided along the edge of the handle 604, whereby the upper cover 606 is closed. As shown in the drawing, the above-described construction allows the upper cover 606 to rotate around the shaft of the hinge 607 parallel to the longitudinal axis A. However, the present invention is not limited to this construction. For example, the upper cover 606 may be arranged so as to rotate along the shaft of a hinge at right angles to the longitudinal axis A. Further, the upper cover 606 may be arranged so as to open and close in a slidable manner with respect to the operating section 601. The operating section 601 may be used as an operating section of an operation instrument such as a clip applier or a linear cutter as well as an operating section of the stapler as shown in the present embodiment.

The insertion section main body 602a is comprised of a rotating knob 609, a narrow support shaft 612 extending from the front end of the rotating knob 609, and an operation rod 617 inserted into the rotating knob 609 and the support shaft 612 in a slidable manner.

The cartridge 602b comprises a first housing 619a and a second housing 619b. A cartridge connector 618 to be removably attached to the cartridge holder 613 disposed at the front end of the support shaft 612 is provided at the base end of the cartridge 602b.

FIG. 112 shows the insertion section main body 602a attached to the operating section 601 while the upper cover 606 is open. As shown in the drawing, protuberances 653a project from both internal sides of the handle 604. These protuberances 653a engage with a retaining groove 655 formed along the outer circumference of the rotating knob 609 of the insertion section main body 602a so as to rotatably support the base end of the insertion section main body 602a. Further, as shown in FIG. 111, protuberances 653b project from both internal sides of the upper cover 606. These protuberances 653b also engage with the retaining groove 655 formed along the outer circumference of the rotating knob 609 of the insertion section main body 602a so as to rotatably support the base end of the insertion section main body 602a.

As shown in FIGS. 113A and 113B, a transmission groove 654 is formed in the trigger 605 of the operating section 601 in order to transmit an actuating force exerted on the trigger 605 to the operation rod 617 of the insertion section main body 602a. A trigger connector 657 formed at the base end of the operation rod 617 removably engages with the transmission groove 654. A substantially U-shaped cam slit 656 is formed in the base end of the rotating knob 609 of the insertion section main body 602a. A cam pin 615 projecting from a spring mount 673 (which will be described later) of the operation rod 617 engages with the cam slit 656. The cam slit 656 comprises a first linear slit 656a having one end open through the base end of the rotating knob 609, a second slit 656b extending in parallel to the first slit 656a, and a joint slit 656c for connecting the end of the second slit 656b to the base of the first slit 656a.

The insertion section main body 602a is disassembled into the operation rod 617 shown in FIG. 113A, the rotating knob 609 shown in FIG. 113B, and the support shaft 612 by disengaging the cam pin 615 from the cam slit 65.

These element will now be described in detail. As shown in FIG. 113A, the operation rod 617 comprises the narrow long rod portion 617a and a spring press 617b attached to the base end of the long rod portion 617a. An engaging slit 658 is formed along the outer periphery of the front end of the long rod portion 617a so as to engage with a pair of engaging claws 667 of a staple feed closing member 627 which will be described later. The spring mount 673 is formed around the spring press 617b. The cam pin 615 projects from the spring mount 673, and one end of a return spring 616 is fixed to the spring mount 673. The previously-described trigger connector 657 which engages with the transmission groove 654 of the operating section 601 is formed at the base end of the spring press 617b.

As shown in FIG. 113B, the rotating knob 609 comprises a front end portion 609a consisting of a shaft holder 671 and a knob 672, and a base end portion 609b. The base end portion 609b further comprises the previously-described retaining groove 655 which engages with the protuberances 653a and 653b of the operating section 601, and the cam groove 656 which engages with the cam pin 615. The support shaft 612 is fixedly connected to the shaft holder 671 of the front end portion 609a. A first small hole 680 having a small diameter is formed in the front end portion 609a so as to guide the rod portion 617a of the operation rod 617 in a slidable manner. A second hole 681 having a large diameter is formed in the base portion 609b so as to communicate with the first hole 680 and to permit slidable insertion of a return spring 616 and a spring press 617b of the operation rod 617. In this case, an O-ring 610 is attached to the first hole 680 for hermetically retaining the connection between the rotating knob 609 and the operation rod 617. The cartridge holder 613 attached to the front end of the support shaft 612 has a hole 613a in line with the first hole 680, and a connection port 674 to be connected to the cartridge connector 618 of the cartridge 602b.

To attach the operation rod 617 to the rotating knob 609 and the support shaft 612, all of which are in such a state as shown in FIGS. 113A and 113B, the front end of the operation rod 617 is initially inserted into the second hole 681 through the base end of the rotating knob 609. The long rod portion 617a of the operation rod 617 is guided toward the support shaft 612 through the first hole 680. As shown in FIG. 114A, the cam pin 615 of the operation rod 617 is guided into the cam groove 656 from the open end of the first slit 656a of the rotating knob 609. During the course of the guiding operation, the spring press 617b of the operation rod 617 is guided into the second hole 681 while the return spring 616 attached to the operating section 617 comes into compressed contact with the front end surface of the second hole 681. From this state, the cam pin 615 is pushed into the joint slit 656c from the first slit 656a against the thrusting force of the return spring 616. The operation rod 617 is rotated with respect to the rotating knob 609 at the joint slit 656c, so that the cam pin 615 becomes engageable with the second slit 656b. By releasing the pressing force acting on the operation rod 617, the cam pin 615 is pushed toward the inside of the second groove 656 by dint of the thrusting force of the return spring 616. As shown in FIG. 114B, the cam pin 615 eventually comes into collision with the end of the base of the second slit 656b. The attachment of the operation rod 617 to the rotating knob 609 is now completed.

In the reassembling state in which the cam pin 615 is guided to and engages with the second slit 656b, the operation rod 617 becomes unrotatable with respect to the rotating knob 609 and the support shaft 612 which is integral with the rotating knob 609. In this state, however, the cam pin 615 is guided so as to slide over a distance corresponding to the stroke necessary to feed and clinch a staple 612 (see FIG. 116), in a longitudinal direction of the insertion section main body 602a.

The spring press 617b is pressed into the second hole 681 from the state shown in FIG. 114B in excess of the stroke (or a staple feeding and clinching stroke) necessary to feed and clinch the staple 612 against the thrusting force of the return spring 616. As a result, the cam pin 615 arrives at the joint slit 656c, whereby the insertion section main body 602a can be disassembled into the state shown in FIGS. 113A and 113B in the reverse of assembly.

FIG. 115 shows the details of the structure of the joint between the insertion section main body 602a and the cartridge 602b. As shown in the drawing, a female screw 682 is cut on the internal surface of the connection port 674 of the cartridge holder 613 provided at the front end of the insertion section main body 602a. Further, a male screw 683 which can mesh with the female screw 682 is cut on the external surface of the base end of the cartridge connector 618 provided on the base end of the cartridge 602b. The cartridge 602b is fitted to the insertion section main body 602a by screwing the male screw 683 to the female screw 682. In this state, an engaging claw 659 of a staple feeding and clinching member 627 (which will be described later) passing through the cartridge connector 618, engages with the engaging slit 658 formed around the front end of the operation rod 617. The actuating force exerted on the trigger 605 of the operating section 601 is transmitted to the cartridge 602b via the operation rod 617. The insertion section main body 602a and the cartridge 602b can be fixedly connected to each other by utilization of; e.g., cam member or a collet chuck, instead of the screws.

FIGS. 116A, 116B, 116C through 119 show the details of structure of the cartridge 602b. FIG. 116A is a cross section of the cartridge 602b taken in a longitudinal direction, and FIGS. 116B is a cross section of the cartridge 602b taken across line D—D shown in FIG. 116A; namely, a staple track along which the staple 624 is guided. FIG. 116C is a cross section of the cartridge 602b taken across line E—E shown in FIG. 116A; namely, along a guide pin 628 which will be described later. FIG. 117 is a cross section of the cartridge 602b across line F—F shown in FIG. 116C; namely, along the staple feeding and clinching member 627 which will be described later. FIG. 118 is a cross section of the cartridge 602b taken across line G—G shown in FIG. 116C; namely, along a pusher 625 which will be described later. FIG. 119 is a cross section of the cartridge 602b across line H—H shown in FIG. 116A.

As shown in FIG. 116A, the previously-described two housings 619a and 619b are attached to the cartridge connector 618. As previously described, the front ends of the housings 619a and 619b constitute the tapered surface 650 at a predetermined angle with respect to the longitudinal axis A of the insertion section 602. The opening 651 is formed in the tapered surface 650 for supplying the staple 642.

As shown in FIG. 116B, the staple 624 is substantially U-shaped; namely, it consists of a base 660 and a pair of legs 661, 661 extending from both ends of the base 660. The staple 624 is usually made of biologically compatible metallic material such as stainless or titanium.

A staple track is formed in the housings 619a and 619b so as to constitute a feed passage of the staple 642. As shown in FIGS. 116B and 118, the staple track is comprised of a first rear 668 which extends in parallel to the longitudinal axis A of the insertion section 602, a second area 669 which extends at an angle α with respect to the longitudinal axis A, and a third area 670 which smoothly connects the first area 668 to the second area 669. The second area 669 communicates with the outside of the cartridge 602, thereby forming the opening 651 of the tapered surface 650.

The first area 668 houses a plurality of adjoining staples 624 arranged in a line in the longitudinal direction A. The pusher 625 is positioned behind the base end side of the line of staples 624 in the first area 668 in a slidable manner and is pressed against the base end side of the line of staples 624. More specifically, as shown in FIG. 116A, the coil spring 626 is compressedly inserted between the pusher 625 and the cartridge connector 618. The line of staples 624 is normally thrust toward its front end through the pusher 625 by dint of the thrusting force of the coil spring 626. The front end of the pusher 625 thrust toward the front end of the stapler by dint of the thrusting force of the coil spring 626 constitutes a tapered surface 625a at an angle α with respect to the longitudinal axis A. Consequently, the line of staples 624 forwardly thrust by the tapered surface 625a is arranged such that a pair of legs 661, 661 are inclined at only an angle α with respect to the longitudinal axis A in the first area 668. The front end of the forwardly-thrust line of staples 624 (i.e., the base 660 at the front end of the line of staples 624) is pressed against a finger 664 of the leaf spring 623 which will be described later (see FIGS. 116A, 116B, and 117).

As shown in FIG. 116A, the cartridge 602b is provided with the staple feeding and clinching member (i.e., the slide member) 627 that slides in parallel to the pusher 625. The staple feeding and clinching member 672 slides forward by dint of the actuating force exerted from the operation rod 617, whereby one piece of staple 624a which is separated from the front end of the line of staples 624 and is placed in a standby position in the second area 669, is ejected at an angle α with respect to the longitudinal axis A. Further, the staple feeding and clinching member 672 clinches the staple 624a in cooperation with the anvil 621 which will be described later. In other words, the staple feeding and clinching member 672 constitutes a member for feeding the staple 624 at an angle of α, in conjunction with the second area 669.

As shown in FIG. 117, the staple feeding and clinching member 627 is provided in the housings 619a and 619b so as to be slidable in a longitudinal direction. A pair of blades 665, 665 (see FIG. 116B) are formed at the front end of the staple feeding and clinching member 627. These blades 665, 665 are caught by both sides of the base 660 of the staple 624a situated at the standby position within the second area 669 and pushes the staple 624a downwardly (i.e., at an angle α with respect to the longitudinal axis A). The front ends of the blades 665 are formed into tapered surfaces at an angle 0 (=90 α) with respect to the longitudinal axis A so as to be square to the second area 669 of the staple track.

As shown in FIG. 117, the staple feeding and clinching member 627 has a guide slit 666 formed in the base end portion of the blade 665. The guide pin 628 (see FIGS. 116A and 116C) formed so as to pass through the second housing 619b engages with the guide slits 666. As a result of the, engagement between the guide pin 628 and the guide slit 666, the staple feeding and closing member 627 is prevented from interfering with the line of staples 624 disposed in the first area 668 of the staple track.

As shown in FIGS. 116A and 119, a ratchet 629 is provided inside of the base end portion of the staple feeding and clinching member 627. A latch pin 630 which is engageable with the ratchet 629 is provided in the second housing 619b. The latch pin 630 meshes with the ratchet 629, which axially slides together with the staple feeding and clinching member 627, at a predetermined location, whereby the sliding action of the staple feeding and clinching member 627 is limited.

As previously described, the pair of internally-bent engaging claws 667, 667 are formed at the base end of the staple feeding and clinching member 627 (see FIG. 115).

These engaging claws 667, 667 engage with the engaging slit 658 grooved in the front end of the operation rod 617 through the cartridge connector 618 and the cartridge holder 613 that connect the cartridge 602b to the insertion section main body 602a. With this arrangement, the actuating force exerted on the trigger 605 of the operating section 601 is transmitted to the staple feeding and clinching member 627 through the operation rod 617. As a result, the staple feeding and clinching member 627 can slide along the longitudinal axis A.

As shown in FIG. 116A, the anvil 621 is disposed at the front end of the second housing 619b. The anvil 621 has an anvil surface which is gently bent so as to partially block the opening 651. The anvil 621 butts against the base 660 of the staple 624a and clinches the staple 624a in cooperation with the staple feeding and clinching member 627.

As shown in FIG. 116B, the anvil 621 has a bifurcated front end. A removal spring 620 fixed to the second housing 619b is positioned between the bifurcated front of the anvil 621. A standby spring 622 is mounted on the front end portion of the second housing 619b so as to cover the second area 669 of the staple track.

Further, as shown in FIG. 116A, a feed leaf spring 623 is mounted on the first housing 619a for controlling the feeding of the staple 624 positioned in the first area 668 of the staple track to the second area 669. As shown in FIG. 120 in more detail, the feed leaf spring 623 is provided with a wing 663 extending toward the front end of the feed leaf spring 623, and fingers 664 faced toward the anvil 621. The wing 663 extends so as to block the path of the staple feeding and clinching member 627 so that the leaf spring 623 can be raised in the direction opposite to the anvil. The fingers 664 are formed so as to be able to supply the forefront staple 624 of the line of staples positioned in the first area 668 to the standby spring 622 when the feed leaf spring 623 is thrust by the anvil 621 in the manner as will be described later. The wing 663 and the fingers 664 may be formed into such shapes as shown in FIG. 121.

The operation of the surgical stapler having the previously-described configuration will now be described with reference to FIGS. 122 to 124A and 124B.

As previously described, the surgical stapler is used while the operating section 601, the insertion section main body 602a, and the cartridge 602b are assembled into one piece.

FIG. 120 is a cross section of the stapler taken along the second area 669 of the staple track, and FIG. 121 is an enlarge view of the second area 669 of the staple track.

First, the stapler is set into an initial state as shown in FIG. 122 by moving the stapler feeding and clinching member 627 back and forth. In this initial state, the staple 624a positioned in the forefront of the line of staples 624 within the first area 668 of the staple track is thrust to the standby spring 622 positioned so as to cover the second area 669, by the fingers 664 of the feed leaf spring 623. The thus-thrust staple 624 is temporarily held in the standby position spaced a predetermined distance away from the anvil 621. The standby position is set such that the legs 661 of the staple 624a do not project from the tapered surface 650 while the staple 624a is in the standby position. The legs 661 of the staple 624a will not project from the tapered surface 650, unless the trigger 605 is actuated in such a way as will be described later. Therefore, the legs 661 of the staple 624a do not injure tissue outside a target area.

Further, in this initial state, the staple feeding and clinching member 627 is thrust toward the base end of the cartridge 602b by dint of the thrusting force of the return spring 616 (see FIG. 113). The ratchet 629 mounted on the staple feeding and clinching member 627 is situated in the position spaced way from the latch pin 630 in the direction of the base end portion of the cartridge 602b.

As shown in FIG. 123A, where the trigger 605 of the operating section 601 is actuated as if it is slightly gripped, the staple feeding and clinching member 627 advances in the longitudinal direction of the insertion section 602 via the operation rod 617. The thus advanced staple feeding and clinching member 627 catches the staple 624a situated in the standby position in the second area 669 by means of the blades 665. At this time, as shown in FIG. 123B, a force $f_1$ resulting from the movement of the blades 665 acts on the staple 624a situated in the inclined second area 669 of the staple track in the form of component forces $f_r$, $f_t$. In this case, the legs 661 of the staple 624a are guided by the second area 669 of the staple track, and hence the staple 624a can freely move in the direction of the component force $f_r$, but not in the direction of the component force $f_t$. In short, the inclined angle of the front end of the blades 665 through which the staple 624a is supplied to the anvil 621 along the second area 669, is not necessarily set to the angle θ (=90−α) so long as it is an angle at which a component force capable of supplying the staple 624a to the anvil 621 along the second area 669 is developed in the direction of the angle α.

The staple feeding and clinching member 627 that advances while catching the staple 624a using the blades 665 raises the wing 663 positioned so as to block the path of the staple feeding and clinching member 627 by means of the blades 665. As a result, the overall feed leaf spring 623 is raised in the direction opposite to the anvil 621. At this time, the ratchet 629 meshes with the latch pin 630, and hence the staple feeding and clinching member 627 is prevented from returning to its original state opposing the return spring 616. Further, the staples 624 are prevented from entering the second area 669 from the first area 668.

If the trigger 605 of the operating section 601 is further actuated in this state as if it is gripped, the staple 624a is clinched as if the base 660 is pressed against the anvil 621 by the staple feeding and clinching member 627 as shown in FIG. 124A. FIG. 124B (i.e., a cross section of the cartridge 602b taken across line J—J shown in FIG. 124A) shows the staple 624a when it is clinched. As shown in the drawing, the blades 665 of the staple feeding and clinching member 627 that are in an advancing state clinch the staple 624a from a deformed state as designated by a two-dot chain line to a D-shaped state designated by a solid line in cooperation with the anvil 621. At this time, if a vector of the component force $f_r$ resulting from advancement of the blades 665 is out of alignment with the direction of the legs 661 of the staple 624a to be clinched, the legs 661 of the staple 624a will be bent in the longitudinal axis A, thereby resulting in insufficient clinching of the staple 624a. However, the vector of the component force $f_r$ is in alignment with the direction of the legs 661 of the clinched staple 624a in the present embodiment. Therefore, it is possible to sufficiently clinch the staple 624a.

In a step in which the staple 624a is clinched into the D-shaped form, the blades 665 raise the feed leaf spring 623 to such an extent that the staple 624 can advance toward the second area 669 below the fingers 664 that cover the first area 668 of the staple track. Further, the ratchet 629 disengages from the latch pin 630 in this state, and the latch pin 630 goes to the rear of the ratchet 629 by virtue of its elasticity (see FIG. 124A).

If the trigger 605 of the operating section 601 is released in this state, the staple feeding and clinching member 627 recedes by means of the return spring 616, thereby resulting in the initial state as shown in FIG. 122 again. When the staple feeding and closing member 627 returns to the initial state in this way, the feed leaf spring 623 raised by the blades 665 is released. At this time, the feed leaf spring 623 thrusts the staple 624 positioned in the forefront of the line of staples to the standby position within the second area 669 by means of the finger 664, so that the fingers 664 block the first area 668 again.

The staple 624a clinched into a D shape is automatically removed from the anvil 621 by the removal spring 620.

The structures of the operating section 601 and the insertion section main body 602a of the staple used in the previously-described manner can be made simple by arranging the elements having complicated structures, such as the ratchet 629, in the cartridge 602b in an concentrated manner. Further, the stapler can be disassembled into the operating section 601, the insertion section main body 602a, and the cartridge 602b. Therefore, the cartridge 602b having a complex structure is disposed after use of the stapler, and the remaining operating section 601 and the insertion section main body 602a having simpler structures can be sufficiently washed, disinfected, and sterilized. After the washing, disinfecting, and sterilizing operations, these sterilized components can be reassembled for reuse.

As has been described above, the stapler of the present embodiment is capable of supplying a staple at an angle with respect to the longitudinal axis of the insertion section 602 by advancing only the staple feeding and clinching member 627 without need of complex motion. As a result, it is possible to prevent faulty operations of the stapler as much as possible. More specifically, if the staples 624 are arranged at an inclined angle with respect to the longitudinal direction of the insertion section 602; namely, the direction in which the staple feeding and clinching member 627 advances and recedes, the stapler of the present embodiment is capable of supplying the staple 624-at an inclined angle from the second area 669 of the staple track which extends at an inclined angle substantially corresponding to the inclined angle of the staple 624, by advancing simply the staple feeding and clinching member 627 by means of the front-end tapered surface of the staple feeding and clinching member 627 that is substantially square to the legs 661 of the inclined staple 624. In short, contrasted with conventional staplers, the stapler of the present embodiment is capable of supplying the staple 624 at an angle with respect to the longitudinal direction of the insertion section 602 without need of complicated motion, such longitudinal movement of an insertion section or pivotal movement of the insertion section so as to mesh with an anvil. Consequently, in the event that body fluid or blood sticks to the inside of a feed path of the staple 624 during surgery, it is possible to reduce a risk of faulty operations of the staple 624 or the staple feeding and clinching member 627.

Further, as regards the stapler of the present embodiment, the structures of the operating section 601 and the insertion section main body 602a of the stapler can be made simple by arranging the elements having complicated structures, such as the ratchet 629, in the cartridge 602b in an concentrated manner. Further, the stapler can be disassembled into the operating section 601, the insertion section main body 602a, and the cartridge 602b. Moreover, the insertion section main body 602a can be disassembled into the rotating knob 609 and the operation rod 617, and the inside of the operating section 601 can be uncovered by opening the upper cover 606. Therefore, the cartridge 602b having a complex structure is disposed after use of the stapler, and the remaining operating section 601 and the insertion section main body 602a having simpler structures can be reused after having sufficiently washed, disinfected, and sterilized.

As regards conventional staplers disclosed in U.S. Pat. Nos. 5,381,943 and 5,289,963, staples and a feed spring, or an anvil and a staple clinching member are housed in a cartridge of the stapler. Further, a ratchet for controlling the feeding and clinching of the staple or a return spring for restoring the stapler to its original state are housed in an insertion section of the stapler. If members which are difficult to wash, such as an insertor a cartridge, are disposed in such random arrangements as previously described, it is very difficult to wash these members. For this reason, the overall stapler is usually disposed in case of endoscopic surgery. In other words, it can be said that the conventional staplers are designed provided that it should be disposed. However, disposal of the overall stapler results in a hike in medical expenditures. In contrast, if the stapler is reused in order to reduce the medical expenditures, it is necessary to carry out difficult washing and sterilizing operations, which in turn imposes a heavy burden on the user.

To solve the foregoing problems in the related art, as previously described, the structures of the operating section 601 and the insertion section main body 602a of the stapler of the present embodiment can be made simple and easy to wash by arranging the elements having complicated structures, such as the ratchet 629, in the cartridge 602b in an concentrated manner. Further, the stapler can be disassembled into the operating section 601, the insertion section main body 602a, and the cartridge 602b. In other words, the present invention is intended to reduce costs of operation instrument accounting for the medical expenditures by reducing the disposable components (such as the cartridge 602b) to as small an amount as possible, and by rendering the other components easy to wash so that they can be reused.

In the stapler of the present embodiment, the cartridge 602b may be inseparably integrated with the insertion section main body 602a. In this case, the overall insert 602 including the cartridge 602b is disposed after surgery, and the operating section 601 can be reused after having been washed, disinfected, and sterilized. In short, the operating section 601 may be used as a new stapler by attaching a new sterilized insert 602 thereto.

As has been described above, the present invention is capable of ensuring safety and ease of use by housing a drive mechanism in an operating section and providing the operating section with a cover capable of opening and closing so as to prevent hands and fingers from touching the drive mechanism. Further, it is possible to wash and sterilize the drive mechanism housed in the operating section by opening or removing the cover in a simple operation.

The above and other advantages, features, and additional objects of the present invention will be manifest, to those who are versed in the art, upon reference to the following detailed descriptions and the accompanying drawings illustrating preferred embodiments based on the principles of the present invention by way of illustrative examples.

What is claimed is:

1. A medical treatment instrument comprising:
   a treatment section for treating tissue;
   an insertion section which has at one end the treatment section;
   an operating section provided at the other end of the insertion section for operating the treatment section, the operating section comprising a fixed portion and a movable portion, with the treatment section being operated by operating the movable portion with respect to the fixed portion; and a drive mechanism disposed within the operating section for driving the treatment section in response to the operation of the operating section, and the operating section further comprising a main body and a cover which is displaceable between a first position in which the medical treatment instrument is used and a second position in which the inside of the operating section including the drive mechanism is uncovered.

2. The medical treatment instrument as defined in claim 1, wherein an engaging portion between the insertion section and the operating section is sheathed with the cover.

3. The medical treatment instrument as defined in claim 2, wherein the engaging portion between the insertion section and the operating section is defined by the main body and the cover of the operating section.

4. The medical treatment instrument as defined in claim 1, wherein the inside of the operating section is sealed from outside by closing the cover.

5. The medical treatment instrument as defined in claim 1, wherein the cover serves as a part of the operating section when being closed.

6. The medical treatment instrument as defined in claim 5, wherein an engaging section disposed in the insertion section removably engages with an engaging section of the operating section.

7. The medical treatment instrument as defined in claim 1, wherein a degree of opening of the cover is substantially set so as to permit sufficient washing of the inside of the operating section.

8. The medical treatment instrument as defined in claim 1, wherein the cover is disposed on the operating section in a position opposite to the movable portion.

9. The medical treatment instrument as defined in claim 1, wherein the treatment section, the insertion section, and the operating section can be separated from each other and reassembled into one piece.

10. The medical treatment instrument as defined in claim 1, wherein the insertion section is detachable from the operating section.

11. The medical treatment instrument as defined in claim 9, wherein the operating section, the insertion section, and the treatment section are respectively selected from an operating unit including a plurality of types of operating section, a sheath unit including a plurality of types of sheath, and a treatment unit including a plurality of types of treatment section, and the thus-selected operating section, insertion section, and treatment section are combined together.

12. The medical treatment instrument as defined in claim 11, wherein the treatment unit is a forceps unit comprising various types of forceps such as dissection type forceps grip-type forceps and scissors forceps.

13. The medical treatment instrument as defined in claim 11, wherein the treatment unit is an applier unit including various types of applier such as a clip unit and a stapler unit.

14. The medical treatment instrument as defined in claim 11, wherein the treatment unit is a suturing and purse string unit comprising various units such as a cartridge unit, a jaws unit, and an anvil unit.

15. The medical treatment instrument as defined in claim 11, wherein the treatment unit comprises various units such as a forceps unit, a tip unit, and a probe unit.

16. The medical treatment instrument as defined in claim 9, wherein the insertion section and the treatment section are replaceable in the form of a cartridge.

17. The medical treatment instrument as defined in claim 16, wherein the insertion section can be detached from the operating section by opening the cover, and the insertion section can be attached to the operating section by closing the cover.

18. The medical treatment instrument as defined in claim 16, wherein the insertion section is rotatable with respect to the operating section.

19. The medical treatment instrument as defined in claim 18, wherein the insertion section is restricted with respect to the movable section of the operating section in a longitudinal direction thereof by engaging with the operating section.

20. The medical treatment instrument as defined in claim 18, further comprising an operation rod disposed in the insertion section for driving the treatment section, the operation rod comprising a ball portion disposed at the end of the insertion section where the operating section is provided, the ball portion engaging slidably and rotatably with a groove formed in the operating section.

21. The medical treatment instrument as defined in claim 20, wherein a sealing member is disposed between the operation rod and rear of the insertion section.

22. The medical treatment instrument as defined in claim 16, wherein the insertion section is covered with a sheath.

23. The medical treatment instrument as defined in claim 22, wherein the treatment section and the insertion section comprise respective one of an attachment claw and an engaging part for coupling to each other.

24. The medical treatment instrument as defined in claim 16, wherein the insertion section is divided into an upper insert member and a lower insert member.

25. The medical treatment instrument as defined in claim 24, wherein at least one of the upper and lower insert members is formed from substantially transparent material.

26. The medical treatment instrument as defined in claim 16, wherein a sealing member is disposed between the inside of the insertion section and the treatment section.

27. The medical treatment instrument as defined in claim 16, wherein a packing member is disposed between the insertion section and the operating section and between the operating section and the cover.

28. The medical treatment instrument as defined in claim 16, wherein the insertion section has a circular cross section.

29. The medical treatment instrument as defined in claim 1, wherein a suturing and ligating element is loaded in the treatment section.

30. The medical treatment instrument as defined in claim 29, wherein the insertion section comprises a cartridge suturing and ligating instrument.

31. The medical treatment instrument as defined in claim 29, wherein the suturing and ligating element is substantially U-shaped in its initial state and comprises a base and two parallel legs extending from the base at right angles, and the surfaces of the two legs which face each other come into at least partial contact with each other after the suturing and ligating element has been clinched.

32. The medical treatment instrument as defined in claim 31, further comprising: at least one holding member for holding the suturing and ligating element; and a pusher for deforming the suturing and ligating element to shape desiredly by urging the base while sandwiching the suturing and ligating element between the pusher and the holding member.

33. The medical treatment instrument as defined in claim 29, wherein the suturin and ligating element comprises legs and a joint for connecting together the legs, and the legs cross each other when the suturing and ligating element is in its initial state but are clinched after having been released from the crossed state when the suturing and ligating element is deformed.

34. The medical treatment instrument as defined in claim 29, wherein the suturing and ligating element is substantially U-shaped in its initial state and comprises a base and two parallel legs extending from the base at right angles, and a space is formed in the vicinity of the base after the two legs have been clinched.

35. The medical treatment instrument as defined in claim 29, wherein the staples are stored and ejected in an inclined orientation.

36. The medical treatment instrument as defined in claim 35, wherein a tapered surface is formed at the front end of the treatment section, and an opening is formed in the tapered surface for supplying the suturing and ligating element at an angle with respect to the longitudinal direction of the insert.

37. The medical treatment instrument as defined in claim 1, wherein the cover rotates around a hinge attached to the operating section.

38. The medical treatment instrument as defined in claim 37, wherein the cover is openable and closeable around a hinge provided behind the cover.

39. The medical treatment instrument as defined in claim 37, wherein the hinge is provided along one side of the cover, and the cover becomes open around the hinge.

40. The medical treatment instrument as defined in claim 1, wherein the treatment section includes forceps having jaws.

41. The medical treatment instrument as defined in claim 40, wherein the operating section comprises a live pin electrically connected to the jaws.

42. The medical treatment instrument as defined in claim 1, wherein the treatment section has a storage member, and a plurality of suturing and ligating elements are loaded in the storage member.

43. The medical treatment instrument as defined in claim 42, wherein the treatment section is replaceable with a cartridge.

44. The medical treatment instrument as defined in claim 1, wherein the insertion section and the treatment section are integrated into one piece.

45. The medical treatment instrument as defined in claim 1, wherein the cover engages with the operating section in a slidable manner.

46. The medical treatment instrument as defined in claim 1, wherein the drive mechanism comprises:
 a pivotal arm formed in the movable portion of the operating section;
 a first treatment section drive member;
 a first actuation member engaging with the pivotal arm and actuating the first treatment drive member;
 a first gear formed in the first actuating member;
 a second gear fixed on the operating section;
 a second actuation member having a third gear which engages with the second gear; and
 a second treatment section drive member driven by the second actuation member.

47. The medical treatment instrument as defined in claim 1, wherein the treatment section comprises an automatic suturing instrument.

48. The medical treatment instrument as defined in claim 47, wherein the automatic suturing instrument comprises a cartridge housing a plurality of staples for suturing purposes, and an anvil for clinching the staples.

49. The medical treatment instrument as defined in claim 48, wherein a close lever for closing the anvil with the respect to the cartridge and a release button for releasing the close lever are provided on the operating section.

50. The medical treatment instrument as defined in claim 48, wherein the treatment section comprises an excising member which travels along a slide path, and a switch for switching the excising member between a position where it can excise tissue and a position where it cannot excise the tissue.

51. The medical treatment instrument as defined in claim 50, wherein the insertion section is provided with an insertion section sheath having a hole therein, and the cartridge has a removal button which fits into the hole.

52. The medical treatment instrument as defined in claim 1, wherein the treatment section comprises a cartridge housing therein a plurality of staples for anastomosing and an anastomosing instrument having an anvil for deforming the staples.

53. The medical treatment instrument as defined in claim 52, wherein a gap control knob for opening and closing the anvil with respect to the cartridge is disposed in the rear of the fixed portion of the operating section.

54. The medical treatment instrument as defined in claim 53, wherein the drive mechanism is housed in the fixed portion.

55. The medical treatment instrument as defined in claim 1, wherein the treatment section comprises an ultrasonic clotting and incising instrument for clotting and incising tissue by ultrasonic vibrations.

56. The medical treatment instrument as defined in claim 55, wherein the treatment section comprises a tip for affording ultrasonic vibrations to tissue, and jaws which is freely openable and closeable with respect to the tip.

57. The medical treatment instrument as defined in claim 56, wherein the operating section houses an ultrasonic transducer.

58. The medical treatment instrument as defined in claim 1, wherein the treatment section is provided with a first treatment member and a second treatment member, and the drive mechanism comprises a first treatment section drive member and a second treatment section drive member, both of which are manually operated.

59. The medical treatment instrument as defined in claim 58, wherein the treatment section has jaws, and wherein the drive mechanism comprises a spring-thrust clip feed member which is operated together with the movable portion of the operating section and is connected to a pusher, and a spring-thrust jaws closing member which is operated together with the movable portion of the operating section and is connected to the jaws of the treatment section.

60. The medical treatment instrument as defined in claim 58, wherein the second treatment section drive member is arranged in line with the first treatment section drive member, the movable portion of the operating section drives the first treatment section drive member, the drive mechanism comprising a flange formed in the movable portion of the operating section in a slidable manner, and an engaging section engaging with the flange and driving the second treatment section drive member.

61. The medical treatment instrument as defined in claim 58, wherein the first and second treatment section drive members are rotatably connected to the operating section in a slidable manner, and the drive mechanism comprises a first spring for connecting together the first and second treatment section drive members, and a second spring for connecting together the second treatment section drive member and a distal end of the operating section, and wherein the spring constant of the first spring is smaller than that of the second spring.

62. The medical treatment instrument as defined in claim 58, wherein the second treatment member comprises jaws which are normally stored in a sheath and project from the sheath only when the medical treatment instrument is used.

63. The medical treatment instrument as defined in claim 58, further comprising a spring for normally thrusting the second treatment section drive member forwardly, a sheath interposed between the treatment section and the insertion section, the sheath attaching to the first treatment member and housing the first treatment section drive member, a drive pin which is provided in the sheath and is connected to the first treatment section drive member, and a cam mechanism which is formed as a result of engagement of one end of the first treatment section with the drive pin.

64. The medical treatment instrument as defined in claim 48, further comprising a first handle for closing the anvil with respect to the cartridge and a second handle for ejecting the staples, said first and second handles being disposed in front-rear direction of the fixed portion of the operating section.

65. The medical treatment instrument as defined in claim 1, further comprising a first sealing member disposed in the area where the insertion section comes into contact with the operating section, a second sealing member disposed in the area where the operating section main body comes into contact with the cover, and a third sealing member disposed in the area between the fixed portion and the movable portion of the operating section.

66. The medical treatment instrument as defined in claim 65, wherein the first, second, and third sealing members are made of insulating material.

67. The medical treatment instrument as defined in claim 63, wherein the third sealing member is a membrane.

68. A medical treatment instrument comprising:

an insertion section;

a treatment section for treating tissue, the treatment section being at one end of the insertion section;

an operating section disposed at the other end of the insertion section for operating the treatment section, said operating section comprising a fixed portion and a movable portion, the treatment section being operated by moving the movable portion of said operating section relative to the fixed portion of said operating section, and said operating section further comprising a main body and a cover body; and a drive mechanism disposed within said operating section for driving the treatment section in response to the operation of said operating section, and the cover body is opened relative to the main body or removed from the main body to completely expose the inside of said operating section and the drive mechanism for cleaning and sterilizing.

69. A medical treatment instrument comprising:

an insertion section;

a treatment section for treating tissue, the treatment section being at one end of the insertion section; and an operating section disposed at the other end of the insertion section and being connected to a connecting portion that extends through the insertion section for operating the treatment section, said operating section comprising a fixed portion and a movable portion, the treatment section being operated by moving the movable portion of said operating section relative to the fixed portion of said operating section, and said operating section further comprising a main body and a cover body, wherein the cover body is opened relative to the main body or removed from the main body to completely expose the connection of said operating section and said connecting portion for cleaning and sterilizing.

\* \* \* \* \*

UNITED STATES PATENT AND TRADEMARK OFFICE
CERTIFICATE OF CORRECTION

PATENT NO. : 6,099,537  Page 1 of 1
DATED : August 8, 2000
INVENTOR(S) : Toshiya Sugai, Hiroyuki Nagamizu, Minoru Tsuruta, Yoshihito Shimuzu, Toshihiko Suzuta, Norikiyo Shibata, Shinichi Nishigaki, Naoki Uchiyama and Yoshinao Oaki It is certified that error appears in the above-identified patent and that said Letters Patent is hereby corrected as shown below:

Column 63,
Line 51, delete "dissection type forceps" and insert -- dissect-type forceps --.

Column 64,
Line 62, delete "suturin" and insert suturing --.

Signed and Sealed this

Ninth Day of July, 2002

Attest:

Attesting Officer

JAMES E. ROGAN
Director of the United States Patent and Trademark Office